US010065971B2

(12) United States Patent
Virgili-Bernado et al.

(10) Patent No.: US 10,065,971 B2
(45) Date of Patent: Sep. 4, 2018

(54) AMIDE DERIVATIVES OF 1-OXA-4,9-DIAZASPIRO UNDECANE COMPOUNDS HAVING MULTIMODAL ACTIVITY AGAINST PAIN

(71) Applicant: LABORATORIOS DEL DR. ESTEVE S.A., Barcelona (ES)

(72) Inventors: Marina Virgili-Bernado, Barcelona (ES); Monica Alonso-Xalma, Barcelona (ES); Carlos Alegret-Molina, Barcelona (ES); Carmen Almansa-Rosales, Barcelona (ES); Ramón Merce-Vidal, Barcelona (ES)

(73) Assignee: ESTEVE PHARMACEUTICALS S.A., Barcelona (ES)

( * ) Notice: Subject to any disclaimer, the term of this patent is extended or adjusted under 35 U.S.C. 154(b) by 0 days.

(21) Appl. No.: 15/315,095

(22) PCT Filed: Jun. 2, 2015

(86) PCT No.: PCT/EP2015/001114
§ 371 (c)(1),
(2) Date: Nov. 30, 2016

(87) PCT Pub. No.: WO2015/185208
PCT Pub. Date: Dec. 10, 2015

(65) Prior Publication Data

US 2017/0197984 A1 Jul. 13, 2017

(30) Foreign Application Priority Data

Jun. 2, 2014 (EP) .................................... 14382208

(51) Int. Cl.
*C07D 498/10* (2006.01)

(52) U.S. Cl.
CPC .................................. *C07D 498/10* (2013.01)

(58) Field of Classification Search
CPC .................................................... C07D 498/10
See application file for complete search history.

(56) References Cited

U.S. PATENT DOCUMENTS

| | | | | |
|---|---|---|---|---|
| 4,353,900 | A | 10/1982 | Clark | |
| 8,148,373 | B2 * | 4/2012 | Alcaraz ................ | C07D 498/10 514/235.5 |
| 8,168,783 | B2 | 5/2012 | Kokubo et al. | |
| 2009/0105290 | A1 | 4/2009 | Sundermann et al. | |
| 2017/0101420 | A1 | 4/2017 | Virgili-Bernado et al. | |

FOREIGN PATENT DOCUMENTS

| | | | |
|---|---|---|---|
| DE | 102005030051 | | 12/2006 |
| EP | 1982714 | | 10/2008 |
| WO | WO 2007/058322 | | 5/2007 |
| WO | WO 2008/155132 | | 12/2008 |
| WO | WO 2008/155132 | A1 | 12/2008 |
| WO | WO 2009/098448 | A1 | 9/2009 |
| WO | WO 2012/125613 | | 9/2012 |
| WO | WO 2012/156693 | | 11/2012 |

OTHER PUBLICATIONS

International Search Report for PCT/EP2015/001114 dated Aug. 5, 2015.
Kato, Y., Bioorganic and Medicinal Chemistry Letters, vol. 24, pp. 565-570, 2014.
Stocks, M., Bioorganic and Medicinal Chemistry Letters, vol. 20, pp. 7458-7461, 2010.
Database Registry, XP-002730855, Chemical Abstracts, May 12, 2010, Accession No. 1222524-76-6.

* cited by examiner

*Primary Examiner* — Rebecca L Anderson
(74) *Attorney, Agent, or Firm* — Hueschen and Sage

(57) ABSTRACT

The present invention relates to compounds having dual pharmacological activity towards both the sigma (σ) receptor, and the μ-opiod receptor and more particularly to diazaspiro undecane compounds having this pharmacological activity, to processes of preparation of such compounds, to pharmaceutical compositions comprising them, and to their use in therapy, in particular for the treatment of pain.

(I)

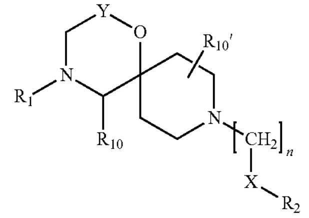

wherein
Y is

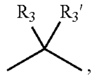

, 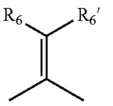 or 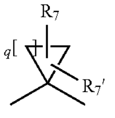

n is 1 or 2;
q is 1, 2, 3, 4, 5 or 6;
X is a bond, —C(O)O—, —C(O)$NR_8$—, —C(O)—, —O— or —C($R_4R_{4'}$)—;
$R_1$ is C(O)$R_5$ or S(O)$_2R_5$.

27 Claims, No Drawings

AMIDE DERIVATIVES OF 1-OXA-4,9-DIAZASPIRO UNDECANE COMPOUNDS HAVING MULTIMODAL ACTIVITY AGAINST PAIN

FIELD OF THE INVENTION

The present invention relates to compounds having dual pharmacological activity towards both the sigma (σ) receptor, and the μ-opiod receptor (MOR or mu-opioid) and more particularly to diazaspiro undecane derivatives having this pharmacological activity, to processes of preparation of such compounds, to pharmaceutical compositions comprising them, and to their use in therapy, in particular for the treatment of pain.

BACKGROUND OF THE INVENTION

The adequate management of pain constitutes an important challenge, since currently available treatments provide in many cases only modest improvements, leaving many patients unrelieved [Turk D C, Wilson H D, Cahana A. Treatment of chronic non-cancer pain. *Lancet* 377, 2226-2235 (2011)]. Pain affects a big portion of the population with an estimated prevalence of around 20% and its incidence, particularly in the case of chronic pain, is increasing due to the population ageing. Additionally, pain is clearly related to comorbidities, such as depression, anxiety and insomnia, which lead to important productivity losses and socio-economical burden [Goldberg D S, McGee S J. Pain as a global public health priority. *BMC Public Health.* 11, 770 (2011)]. Existing pain therapies include non-steroidal anti-inflammatory drugs (NSAIDs), opioid agonists, calcium channel blockers and antidepressants, but they are much less than optimal regarding their safety ratio. All of them show limited efficacy and a range of secondary effects that preclude their use, especially in chronic settings.

As mentioned before, there are few available therapeutic classes for the treatment of pain, and opioids are among the most effective, especially when addressing severe pain states. They act through three different types of opioid receptors (mu, kappa and gamma) which are transmembrane G-protein coupled receptors (GPCRs). Still, the main analgesic action is attributed to the activation of the μ-opioid receptor (MOR). However, the general administration of MOR agonists is limited due to their important side effects, such as constipation, respiratory depression, tolerance, emesis and physical dependence [Meldrum, M. L. (Ed.). Opioids and Pain Relief: A Historical Perspective. Progress in Pain Research and Management, Vol 25. IASP Press, Seattle, 2003]. Additionally, MOR agonists are not optimal for the treatment of chronic pain as indicated by the diminished effectiveness of morphine against chronic pain conditions. This is especially proven for the chronic pain conditions of neuropathic or inflammatory origin, in comparison to its high potency against acute pain. The finding that chronic pain can lead to MOR down-regulation may offer a molecular basis for the relative lack of efficacy of morphine in long-term treatment settings [Dickenson, A. H., Suzuki, R. *Opioids in neuropathic pain: Clues from animal studies.* Eur J Pain 9, 113-6 (2005)]. Moreover, prolonged treatment with morphine may result in tolerance to its analgesic effects, most likely due to treatment-induced MOR down-regulation, internalization and other regulatory mechanisms. As a consequence, long-term treatment can result in substantial increases in dosing in order to maintain a clinically satisfactory pain relief, but the narrow therapeutic window of MOR agonists finally results in unacceptable side effects and poor patient compliance.

The sigma-1 ($\sigma_1$) receptor was discovered 35 years ago and initially assigned to a new subtype of the opioid family, but later on and based on the studies of the enantiomers of SKF-10,047, its independent nature was established. The first link of the σ1 receptor to analgesia was established by Chien and Pasternak [Chien C C, Pasternak G W. Sigma antagonists potentiate opioid analgesia in rats. *Neurosci. Lett.* 190, 137-9 (1995)], who described it as an endogenous anti-opioid system, based on the finding that $\sigma_1$ receptor agonists counteracted opioid receptor mediated analgesia, while $\sigma_1$ receptor antagonists, such as haloperidol, potentiated it.

Many additional preclinical evidences have indicated a clear role of the $\sigma_1$ receptor in the treatment of pain [Zamanillo D, Romero L, Merlos M, Vela J M. Sigma 1 receptor: A new therapeutic target for pain. *Eur. J. Pharmacol,* 716, 78-93 (2013)]. The development of the $\sigma_1$ receptor knockout mice, which show no obvious phenotype and perceive normally sensory stimuli, was a key milestone in this endeavour. In physiological conditions the responses of the $\sigma_1$ receptor knockout mice to mechanical and thermal stimuli were found to be undistinguishable from WT ones but they were shown to possess a much higher resistance to develop pain behaviours than WT mice when hypersensitivity entered into play. Hence, in the $\sigma_1$ receptor knockout mice capsaicin did not induce mechanical hypersensitivity, both phases of formalin-induced pain were reduced, and cold and mechanical hypersensitivity were strongly attenuated after partial sciatic nerve ligation or after treatment with paclitaxel, which are models of neuropathic pain. Many of these actions were confirmed by the use of $\sigma_1$ receptor antagonists and led to the advancement of one compound, S1RA, into clinical trials for the treatment of different pain states. Compound S1RA exerted a substantial reduction of neuropathic pain and anhedonic state following nerve injury (i.e., neuropathic pain conditions) and, as demonstrated in an operant self-administration model, the nerve-injured mice, but not sham-operated mice, acquired the operant responding to obtain it (presumably to get pain relief), indicating that σ1 receptor antagonism relieves neuropathic pain and also address some of the comorbidities (i.e., anhedonia, a core symptom in depression) related to pain states.

Pain is multimodal in nature, since in nearly all pain states several mediators, signaling pathways and molecular mechanisms are implicated. Consequently, monomodal therapies fail to provide complete pain relief. Currently, combining existing therapies is a common clinical practice and many efforts are directed to assess the best combination of available drugs in clinical studies [Mao J, Gold M S, Backonja M. Combination drug therapy for chronic pain: a call for more clinical studies. *J. Pain* 12, 157-166 (2011)]. Hence, there is an urgent need for innovative therapeutics to address this unmet medical need.

As mentioned previously, opioids are among the most potent analgesics but they are also responsible for various adverse effects which seriously limit their use.

Accordingly, there is still a need to find compounds that have an alternative or improved pharmacological activity in the treatment of pain, being both effective and showing the desired selectivity, and having good “drugability” properties, i.e. good pharmaceutical properties related to administration, distribution, metabolism and excretion.

Thus, the technical problem can therefore be formulated as finding compounds that have an alternative or improved pharmacological activity in the treatment of pain. In view of the existing results of the currently available therapies and clinical practices, the present invention offers a solution by combining in a single compound binding to two different receptors relevant for the treatment of pain. This was mainly achieved by providing the compound according to the invention that bind both to the μ-opiod receptor and to the or receptor.

SUMMARY OF THE INVENTION

In this invention a family of structurally distinct diazaspiro undecane derivatives which have a dual pharmacological activity towards both the sigma (σ) receptor, and the μ-opiod receptor was identified thus solving the above problem of identifying alternative or improved pain treatments by offering such dual compounds.

The invention is in one aspect directed to a compound having a dual activity binding to the $\sigma_1$ receptor and the μ-opioid receptor for use in the treatment of pain.

As this invention is aimed at providing a compound or a chemically related series of compounds which act as dual ligands of the $\sigma_1$ receptor and the μ-opioid receptor it is a very preferred embodiment if the compound has a binding expressed as $K_i$ which is preferably <1000 nM for both receptors, more preferably <500 nM, even more preferably <100 nM.

The invention is directed in a main aspect to a compound of general formula (I), (I)

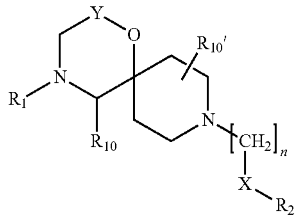

wherein $R^1$, $R^2$, $R^{10}$, R10', X, Y and n are as defined below in the detailed description.

DETAILED DESCRIPTION OF THE INVENTION

The invention is directed to a family of structurally distinct diazaspiro undecane derivatives which have a dual pharmacological activity towards both the sigma (σ) receptor, and the μ-opiod receptor thus solving the above problem of identifying alternative or improved pain treatments by offering such dual compounds.

The invention is in one aspect directed to a compound having a dual activity binding to the $\sigma_1$ receptor and the μ-opioid receptor for use in the treatment of pain.

As this invention is aimed at providing a compound or a chemically related series of compounds which act as dual ligands of the $\sigma_1$ receptor and the μ-opioid receptor it is a preferred embodiment if the compound has a binding expressed as $K_i$ which is preferably <1000 nM for both receptors, more preferably <500 nM, even more preferably <100 nM.

The applicant has surprisingly found that the problem on which the present invention is based can be solved by using a multimodal balanced analgesic approach combining two different synergistic activities in a single drug (i.e., dual ligands which are bifunctional and bind to μ-opioid receptor and to $\sigma_1$ receptor), thereby enhancing the opioid analgesia through the $\sigma_1$ activation without increasing the undesirable side effects. This supports the therapeutic value of a dual MOR/$\sigma_1$ receptor compound whereby the $\sigma_1$ receptor binding component acts as an intrinsic adjuvant of the MOR binding component.

This solution offered the advantage that the two mechanisms complement each other in order to treat pain and chronic pain using lower and better tolerated doses needed based on the potentiation of analgesia but avoiding the adverse events of μ opioid receptor agonists.

A dual compound that possess binding to both the μ-opiod receptor and to the $\sigma_1$ receptor shows a highly valuable therapeutic potential by achieving an outstanding analgesia (enhanced in respect to the potency of the opioid component alone) with a reduced side-effect profile (safety margin increased compared to that of the opioid component alone) versus existing opiod therapies.

Advantageously, the dual compounds according to the present invention would in addition show one or more the following functionalities: σ1 receptor antagonism and μ-opioid receptor agonism. It has to be noted, though, that both functionalities "antagonism" and "agonism" are also subdivided in their effect into subfunctionalities like partial agonism or inverse agonism. Accordingly, the functionalities of the dual compound should be considered within a relatively broad bandwidth.

An antagonist on one of the named receptors blocks or dampens agonist-mediated responses. Known subfunctionalities are neutral antagonists or inverse agonists.

An agonist on one of the named receptors increases the activity of the receptor above its basal level. Known subfunctionalities are full agonists, or partial agonists.

In addition, the two mechanisms complement each other since MOR agonists are only marginally effective in the treatment of neuropathic pain, while $\sigma_1$ receptor antagonists show outstanding effects in preclinical neuropathic pain models. Thus, the $\sigma_1$ receptor component adds unique analgesic actions in opioid-resistant pain. Finally, the dual approach has clear advantages over MOR agonists in the treatment of chronic pain as lower and better tolerated doses would be needed based on the potentiation of analgesia but not of the adverse events of MOR agonists.

A further advantage of using designed multiple ligands is a lower risk of drug-drug interactions compared to cocktails or multi-component drugs, thus involving simpler pharmacokinetics and less variability among patients. Additionally, this approach may improve patient compliance and broaden the therapeutic application in relation to monomechanistic drugs, by addressing more complex aetiologies. It is also seen as a way of improving the R&D output obtained using the "one drug-one target" approach, which has been questioned over the last years [Bornot A, Bauer U, Brown A, Firth M, Hellawell C, Engkvist O. Systematic Exploration of Dual-Acting Modulators from a Combined Medicinal Chemistry and Biology Perspective. J. Med. Chem, 56, 1197-1210 (2013)].

In a particular aspect, the present invention is directed to compounds of general formula (I):

(I)

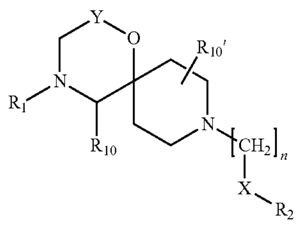

wherein

Y is

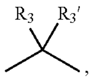
,
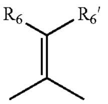
or
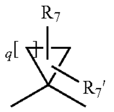

n is 1 or 2 q is 1, 2, 3, 4, 5 or 6

X is a bond, —C(O)O—, —C(O)$NR_8$—, —C(O)—, —O— or —C($R_4R_{4'}$)—;

$R_1$ is C(O)$R_5$ or S(O)$_2R_5$;

$R_2$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, or substituted or unsubstituted heterocyclyl;

$R_3$ and $R_3$' are independently selected from hydrogen, substituted or unsubstituted $C_{1-6}$ alkyl, substituted or unsubstituted $C_{2-6}$ alkenyl, substituted or unsubstituted $C_{2-6}$ alkynyl substituted or unsubstituted cycloalkyl, substituted or unsubstituted heterocyclyl, substituted or unsubstituted alkylcycloalkyl, substituted or unsubstituted alkylheterocyclyl, substituted or unsubstituted aryl, substituted or unsubstituted alkylaryl, $R_4$ is hydrogen, —$OR_8$, substituted or unsubstituted $C_{1-6}$ alkyl, substituted or unsubstituted $C_{2-6}$ alkenyl, substituted or unsubstituted $C_{2-6}$ alkynyl, —C(O)$OR_9$, —C(O)$NR_9R_{9'}$, —$NR_9$C(O)$R_{9'}$, —$NR_9R_{9'''}$, unsubstituted heterocyclyl, unsubstituted aryl and unsubstituted cycloalkyl;

$R_{4'}$ is Hydrogen, or substituted or unsubstituted $C_{1-6}$ alkyl, substituted or unsubstituted $C_{2-6}$ alkenyl or substituted or unsubstituted $C_{2-6}$ alkynyl;

$R_5$ is substituted or unsubstituted $C_{1-6}$ alkyl, substituted or unsubstituted $C_{2-6}$ alkenyl, substituted or unsubstituted $C_{2-6}$alkynyl, substituted or unsubstituted cycloalkyl, substituted or unsubstituted aryl, substituted or unsubstituted heterocyclyl, substituted or unsubstituted alkyl aryl, substituted or unsubstituted alkyl heterocyclyl and substituted or unsubstituted alkyl cycloalkyl, —$NR_8R_{8'}$;

$R_6$, $R_{6'}$ $R_7$, and $R_{7'}$ are independently selected from hydrogen, halogen, —$OR_9$, substituted or unsubstituted $C_{1-6}$ alkyl, substituted or unsubstituted $C_{2-6}$ alkenyl, substituted or unsubstituted $C_{2-6}$ alkynyl, unsubstituted heterocyclyl, unsubstituted aryl and unsubstituted cycloalkyl;

$R_8$ and $R_8$' are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;

$R_9$, $R_{9'}$ and $R_{9''}$ are independently selected from hydrogen, unsubstituted $C_{1-6}$ alkyl, unsubstituted $C_{2-6}$ alkenyl, unsubstituted $C_{2-6}$ alkynyl while $R_{9'''}$ is selected from hydrogen, unsubstituted $C_{1-6}$ alkyl, unsubstituted $C_{2-6}$ alkenyl, unsubstituted $C_{2-6}$ alkynyl and -Boc;

$R_{10}$ and $R_{10'}$ are independently selected from hydrogen, halogen, —$OR_9$, substituted or unsubstituted $C_{1-6}$ alkyl, substituted or unsubstituted $C_{2-6}$ alkenyl, substituted or unsubstituted $C_{2-6}$ alkynyl, substituted or unsubstituted —O—$C_{1-6}$ alkyl, substituted or unsubstituted —O—$C_{2-6}$ alkenyl or substituted or unsubstituted —O—$C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof, Please note that "or a corresponding salt thereof" does also mean "or a corresponding pharmaceutically acceptable salt thereof". This does apply to all below described embodiments and uses of "salt" being thus equivalent to "pharmaceutically acceptable salt".

In one embodiment the following proviso is applying: when Y is

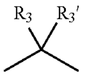

with $R_3$ and $R_{3'}$ being hydrogen, $R_1$ being C(O)$R_5$, and —$(CH_2)_n$—X—$R_2$ being alkyl, then said alkyl contains 6 or less C-atoms.

In one embodiment the following proviso is applying: when Y is

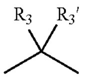

with $R_3$ and $R_{3'}$ being hydrogen, $R_1$ being C(O)$R_5$, and X not being —C($R_4R_{4'}$)—, then n would be 2.

In one embodiment one or more of the following compounds being further excluded:

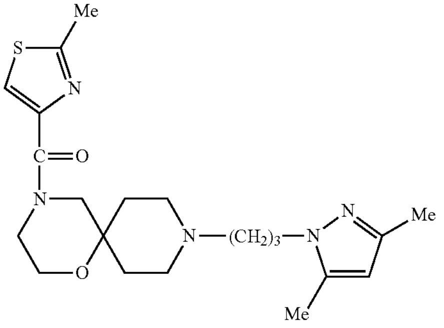
and/or

-continued

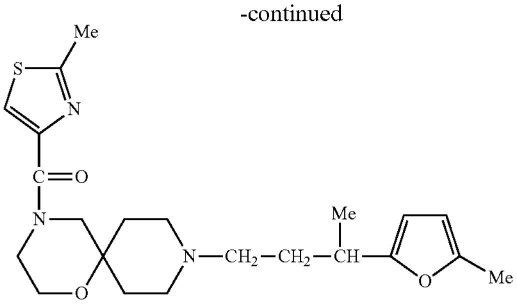

and/or

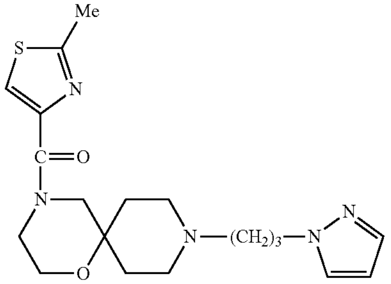

and/or

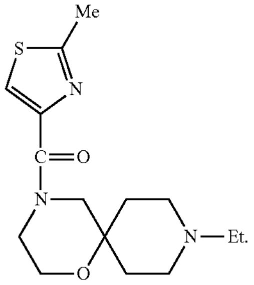 [SMILES: CCN1CCC2(CC1)CN(C(=O)c1csc(C)n1)CCO2]

In the context of this invention, alkyl is understood as meaning saturated, linear or branched hydrocarbons, which may be unsubstituted or substituted once or several times. It encompasses e.g. —$CH_3$ and —$CH_2$—$CH_3$. In these radicals, $C_{1-2}$-alkyl represents C1- or C2-alkyl, $C_{1-3}$-alkyl represents C1-, C2- or C3-alkyl, $C_{1-4}$-alkyl represents C1-, C2-, C3- or C4-alkyl, $C_{1-5}$-alkyl represents C1-, C2-, C3-, C4-, or C5-alkyl, $C_{1-6}$-alkyl represents C1-, C2-, C3-, C4-, C5- or C6-alkyl, $C_{1-7}$-alkyl represents C1-, C2-, C3-, C4-, C5-, C6- or C7-alkyl, $C_{1-8}$-alkyl represents C1-, C2-, C3-, C4-, C5-, C6-, C7- or C8-alkyl, $C_{1-10}$-alkyl represents C1-, C2-, C3-, C4-, C5-, C6-, C7-, C8-, C9- or C10-alkyl and $C_{1-18}$-alkyl represents C1-, C2-, C3-, C4-, C5-, C6-, C7-, C8-, C9-, C10-, C11-, C12-, C13-, C14-, C15-, C16-, C17- or C18-alkyl. The alkyl radicals are preferably methyl, ethyl, propyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also $CHF_2$, $CF_3$ or $CH_2OH$ etc. Preferably alkyl is understood in the context of this invention as $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl.

Alkenyl is understood as meaning unsaturated, linear or branched hydrocarbons, which may be unsubstituted or substituted once or several times. It encompasses groups like e.g. —CH═CH—$CH_3$. The alkenyl radicals are preferably vinyl (ethenyl), allyl (2-propenyl). Preferably in the context of this invention alkenyl is $C_{2-10}$-alkenyl or $C_{2-8}$-alkenyl like ethylene, propylene, butylene, pentylene, hexylene, heptylene or octylene; or is $C_{2-6}$-alkenyl like ethylene, propylene, butylene, pentylene, or hexylene; or is $C_{2-4}$-alkenyl, like ethylene, propylene, or butylenes.

Alkynyl is understood as meaning unsaturated, linear or branched hydrocarbons, which may be unsubstituted or substituted once or several times. It encompasses groups like e.g. —C≡C—$CH_3$ (1-propinyl). Preferably alkynyl in the context of this invention is $C_{2-10}$-alkynyl or $C_{2-8}$-alkynyl like ethyne, propyne, butyene, pentyne, hexyne, heptyne, or octyne; or is $C_{2-6}$-alkynyl like ethyne, propyne, butyene, pentyne, or hexyne; or is $C_{2-4}$-alkynyl like ethyne, propyne, butyene, pentyne, or hexyne.

In the context of this invention cycloalkyl is understood as meaning saturated and unsaturated (but not aromatic) cyclic hydrocarbons (without a heteroatom in the ring), which can be unsubstituted or once or several times substituted. Furthermore, $C_{3-4}$-cycloalkyl represents C3- or C4-cycloalkyl, $C_{3-5}$-cycloalkyl represents C3-, C4- or C5-cycloalkyl, $C_{3-6}$-cycloalkyl represents C3-, C4-, C5- or C6-cycloalkyl, $C_{3-7}$-cycloalkyl represents C3-, C4-, C5-, C6- or C7-cycloalkyl, $C_{3-8}$-cycloalkyl represents C3-, C4-, C5-, C6-, C7- or C8-cycloalkyl, $C_{4-5}$-cycloalkyl represents C4- or C5-cycloalkyl, $C_{4-6}$-cycloalkyl represents C4-, C5- or C6-cycloalkyl, $C_{4-7}$-cycloalkyl represents C4-, C5-, C6- or C7-cycloalkyl, $C_{5-6}$-cycloalkyl represents C5- or C6-cycloalkyl and $C_{5-7}$-cycloalkyl represents C5-, C6- or C7-cycloalkyl. Examples are cyclopropyl, 2-methylcyclopropyl, cyclopropylmethyl, cyclobutyl, cyclopentyl, cyclopentylmethyl, cyclohexyl, cycloheptyl, cyclooctyl, and also adamantly. Preferably in the context of this invention cycloalkyl is $C_{3-8}$cycloalkyl like cyclopropyl, cyclobutyl, cyclopentyl, cyclohexyl, cycloheptyl, or cyclooctyl; or is $C_{3-7}$cycloalkyl like cyclopropyl, cyclobutyl, cyclopentyl, cyclohexyl, or cycloheptyl; or is $C_{3-6}$cycloalkyl like cyclopropyl, cyclobutyl, cyclopentyl or cyclohexyl, especially cyclopentyl or cyclohexyl.

In connection with alkyl, alkenyl, alkynyl and O-alkyl—unless defined otherwise—the term substituted in the context of this invention is understood as meaning replacement of at least one hydrogen radical on a carbon atom by halogen (F, Cl, Br, I), $NR_9R_{9''''}$, $SR_9$, —$S(O)R_9$, —$S(O)_2R_9$, —$OR_9$, —$C(O)OR_9$—CN, haloalkyl, haloalkoxy or —$OC_{1-4}$alkyl being unsubstituted or substituted by one or more of $OR_9$ or halogen (F, Cl, I, Br), being $R_9$, $R_{9'}$, $R_{9''}$ and $R_{9'''}$ as defined above, and wherein when different radicals $R_1$ to $R_{10}$ are present simultaneously in Formulas I to I''' they may be identical or different. More than one replacement on the same molecule and also on the same carbon atom is possible with the same or different substituents. This includes for example 3 hydrogens being replaced on the same C atom, as in the case of $CF_3$, or at different places of the same molecule, as in the case of e.g. —CH(OH)—CH═CH—$CHCl_2$. When different radicals $R_1$ to $R_{10'}$ are present simultaneously in Formula I, I', I'' or I''' they may be identical or different.

Most preferably in connection with alky, alkenyl, alkynyl or O-alkyl, substituted is understood in the context of this invention that any alky, alkenyl, alkynyl or O-alkyl which is substituted is substituted by one or more of halogen (F, Cl, Br, I), $NR_9R_{9''''}$, $SR_9$, —$OR_9$, —$C(O)OR_9$—CN, haloalkyl, haloalkoxy or —$OC_{1-4}$alkyl being unsubstituted or substituted by one or more of $OR_9$ or halogen (F, Cl, I, Br), being $R_9$, $R_{9'}$, $R_{9''}$ and $R_{9'''}$ as defined above, and wherein when different radicals $R_1$ to $R_{10}$ are present simultaneously in Formulas I to I''' they may be identical or different.

More than one replacement on the same molecule and also on the same carbon atom is possible with the same or different substituents. This includes for example 3 hydrogens being replaced on the same C atom, as in the case of $CF_3$, or at different places of the same molecule, as in the case of e.g. —CH(OH)—CH═CH—$CHCl_2$.

In the context of this invention haloalkyl is understood as meaning an alkyl being substituted once or several times by a halogen (selected from F, Cl, Br, I). It encompasses e.g. —$CH_2Cl$, —$CH_2F$, —$CHCl_2$, —$CHF_2$, —$CCl_3$, —$CF_3$ and —$CH_2$—$CHCl_2$. Preferably haloalkyl is understood in the context of this invention as halogen-substituted $C_{1-4}$-alkyl representing halogen substituted C1-, C2-, C3- or C4-alkyl. The halogen-substituted alkyl radicals are thus preferably methyl, ethyl, propyl, and butyl. Preferred examples include —$CH_2Cl$, —$CH_2F$, —$CHCl_2$, —$CHF_2$, and —$CF_3$.

In the context of this invention haloalkoxy is understood as meaning an —O-alkyl being substituted once or several times by a halogen (selected from F, Cl, Br, I). It encompasses e.g. —$OCH_2Cl$, —$OCH_2F$, —$OCHCl_2$, —$OCHF_2$, —$OCCl_3$, —$OCF_3$ and —$OCH_2$—$CHCl_2$. Preferably haloalkyl is understood in the context of this invention as halogen-substituted —$OC_{1-4}$-alkyl representing halogen substituted C1-, C2-, C3- or C4-alkoxy. The halogen-substituted alkyl radicals are thus preferably O-methyl, O-ethyl, O-propyl, and O-butyl. Preferred examples include —$OCH_2Cl$, —$OCH_2F$, —$OCHCl_2$, —$OCHF_2$, and —$OCF_3$.

Aryl is understood as meaning ring systems with at least one aromatic ring but without heteroatoms even in only one of the rings. Examples are phenyl, naphthyl, fluoranthenyl, fluorenyl, tetralinyl or indanyl, in particular 9H-fluorenyl or anthracenyl radicals, which can be unsubstituted or once or several times substituted. Most preferably aryl is understood in the context of this invention as phenyl, naphtyl or anthracenyl, preferably is phenyl.

In the context of this invention alkyl-aryl is understood as meaning an aryl group (see above) being connected to another atom through 1 to 4 (—$CH_2$—) groups. Most preferably alkyl-aryl is benzyl, (i.e. —$CH_2$-phenyl).

In the context of this invention alkylheterocyclyl is understood as meaning an heterocyclyl group (see underneath) being connected to another atom through 1 to 4 (—$CH_2$—) groups. Most preferably alkylheterocyclyl is —$CH_2$-pyridine.

In the context of this invention alkylcycloalkyl is understood as meaning an cycloalkyl group (see above) being connected to another atom through 1 to 4 (—$CH_2$—) groups. Most preferably alkylcycloalkyl is —$CH_2$-cyclopropyl.

In a more general sense, a heterocyclyl radical or group is understood as meaning heterocyclic ring systems, with at least one saturated or unsaturated ring which contains one or more heteroatoms from the group consisting of nitrogen, oxygen and/or sulfur in the ring. A heterocyclic group can also be substituted once or several times. Examples include heteroaryls such as furan, benzofuran, thiophene, benzothiophene, pyrrole, pyridine, pyrimidine, pyrazine, quinoline, isoquinoline, phthalazine, benzo-1,2,5-thiadiazole, benzothiazole, indole, benzotriazole, benzodioxolane, benzodioxane, carbazole and quinazoline. Preferably in the context of this invention heterocyclyl is defined as a heterocyclic ring system of one or more saturated or unsaturated rings of which at least one ring contains one or more heteroatoms from the group consisting of nitrogen, oxygen and/or sulfur in the ring. Preferably it is a heterocyclic ring system of one or two saturated or unsaturated rings of which at least one ring contains one or more heteroatoms from the group consisting of nitrogen, oxygen and/or sulfur in the ring. Preferred examples include imidazole, oxadiazole, tetrazole, pyridine, pyrimidine, piperidine, piperazine, indene, 2,3-dihydroindene, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole, oxopyrrolidine, benzodioxolane, benzodioxane, carbazole and quinazoline, especially is pyridine, morpholine, thiazole, tetrahydropyrane or piperidine.

In a more specific sense, a heterocyclyl radical or group (also called heterocyclyl hereinafter) is understood as meaning heterocyclic ring systems, with at least one saturated or unsaturated ring which contains one or more heteroatoms from the group consisting of nitrogen, oxygen and/or sulfur in the ring. A heterocyclic group can also be substituted once or several times.

Examples include non-aromatic heterocyclyls such as tetrahydropyrane, oxazepane, morpholine, piperidine, pyrrolidine as well as heteroaryls such as furan, benzofuran, thiophene, benzothiophene, pyrrole, pyridine, pyrimidine, pyrazine, quinoline, isoquinoline, phthalazine, thiazole, benzothiazole, indole, benzotriazole, carbazole and quinazoline.

Subgroups inside the heterocyclyls as understood herein include heteroaryls and non-aromatic heterocyclyls.

- the heteroaryl (being equivalent to heteroaromatic radicals or aromatic heterocyclyls) is an aromatic heterocyclic ring system of one or more rings of which at least one aromatic ring contains one or more heteroatoms from the group consisting of nitrogen, oxygen and/or sulfur in the ring; preferably is an aromatic heterocyclic ring system of one or two rings of which at least one aromatic ring contains one or more heteroatoms from the group consisting of nitrogen, oxygen and/or sulfur in the ring, more preferably is selected from furan, benzofuran, thiophene, benzothiophene, pyrrole, pyridine, pyrimidine, pyrazine, quinoline, isoquinoline, phthalazine, benzothiazole, indole, benzotriazole, carbazole, quinazoline, thiazole, imidazole, pyrazole, oxazole, thiophene and benzimidazole;
- the non-aromatic heterocyclyl is a heterocyclic ring system of one or more rings of which at least one ring—with this (or these) ring(s) then not being aromatic—contains one or more heteroatoms from the group consisting of nitrogen, oxygen and/or sulfur in the ring; preferably is a heterocyclic ring system of one or two rings of which one or both rings—with this one or two rings then not being aromatic—contain/s one or more heteroatoms from the group consisting of nitrogen, oxygen and/or sulfur in the ring, more preferably is selected from oxazepam, pyrrolidine, piperidine, piperazine, tetrahydropyran, morpholine, indoline, oxopyrrolidine, benzodioxane, especially is benzodioxane, morpholine, tetrahydropyran, piperidine, oxopyrrolidine and pyrrolidine.

Preferably in the context of this invention heterocyclyl is defined as a heterocyclic ring system of one or more saturated or unsaturated rings of which at least one ring contains one or more heteroatoms from the group consisting of nitrogen, oxygen and/or sulfur in the ring. Preferably it is a heterocyclic ring system of one or two saturated or unsaturated rings of which at least one ring contains one or more heteroatoms from the group consisting of nitrogen, oxygen and/or sulfur in the ring.

Preferred examples of heterocyclyls include oxazepan, pyrrolidine, imidazole, oxadiazole, tetrazole, pyridine, pyrimidine, piperidine, piperazine, benzofuran, benzimidazole, indazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, especially is pyridine, pyrazine, indazole, benzodioxane, thiazole, benzothiazole, morpholine, tetrahydropyrane, pyrazole, imidazole, piperidine, thiophene, indole, benzimidazole, pyrrolo[2,3b] pyridine, benzoxazole, oxopyrrolidine, pyrimidine, oxazepane and pyrrolidine.

In the context of this invention oxopyrrolidine is understood as meaning pyrrolidin-2-one.

In connection with aromatic heterocyclyls (heteroaryls), non-aromatic heterocyclyls, aryls and cycloalkyls, when a ring system falls within two or more of the above cycle definitions simultaneously, then the ring system is defined first as an aromatic heterocyclyl (heteroaryl) if at least one aromatic ring contains a heteroatom. If no aromatic ring contains a heteroatom, then the ring system is defined as a non-aromatic heterocyclyl if at least one non-aromatic ring contains a heteroatom. If no non-aromatic ring contains a heteroatom, then the ring system is defined as an aryl if it contains at least one aryl cycle. If no aryl is present, then the ring system is defined as a cycloalkyl if at least one non-aromatic cyclic hydrocarbon is present.

Preferably, the aryl is a monocyclic aryl.

Preferably, the heteroaryl is a monocyclic heteroaryl.

Preferably, the non-aromatic heterocyclyl is a monocyclic non-aromatic heterocyclyl.

Preferably, the cycloalkyl is a monocyclic cycloalkyl.

In connection with aryl (including alkyl-aryl), cycloalkyl (including alkyl-cycloalkyl) or heterocyclyl (Including (alkyl-heterocyclyl), substituted is understood—unless defined otherwise—as meaning substitution of the ring-system of the aryl or alkyl-aryl, cycloalkyl or alkyl-cycloalkyl; heterocyclyl or alkyl-heterocyclyl by by one or more of halogen, —$R_9$, —$OR_9$, —$NO_2$, —$NR_9R_{9'''}$, $NR_9C(O)R_{9'}$, —$NR_9S(O)_2R_{9'}$, —$S(O)_2NR_9R_{9'}$, —$NR_9C(O)NR_{9'}R_{9''}$, —$SR_9$, —$S(O)R_9$, $S(O)_2R_{9'}$, —CN, haloalkyl, haloalkoxy, —$C(O)OR_9$, —$C(O)NR_9R_{9'}$, =O, —$OCH_2CH_2OH$, —$NR_9S(O)_2NR_{9'}R_{9''}$; $NR_xR_y$, with $R_x$ and $R_y$ independently being either H or a saturated or unsaturated, linear or branched, substituted or unsubstituted $C_{1-6}$-alkyl; a saturated or unsaturated, linear or branched, substituted or unsubstituted $C_{1-6}$-alkyl; a saturated or unsaturated, linear or branched, substituted or unsubstituted —O—$C_{1-6}$-alkyl (alkoxy); a saturated or unsaturated, linear or branched, substituted or unsubstituted —S—$C_{1-6}$-alkyl; a saturated or unsaturated, linear or branched, substituted or unsubstituted —C(O)—$C_{1-6}$-alkyl-group; a saturated or unsaturated, linear or branched, substituted or unsubstituted —C(O)—O—$C_{1-6}$-alkyl-group; a substituted or unsubstituted aryl or alkyl-aryl; a substituted or unsubstituted cycloalkyl or alkyl-cycloalkyl; a substituted or unsubstituted heterocyclyl or alkyl-heterocyclyl, being $R_9$, $R_{9'}$, $R_{9''}$ and $R_{9'''}$ as defined above, and wherein when different radicals $R_1$ to $R_{10'}$ are present simultaneously in Formulas I to I''' they may be identical or different.

Most preferably in connection with aryl (including alkyl-aryl), cycloalkyl (including alkyl-cycloalkyl) and heterocyclyl (including alkyl-heterocyclyl), substituted is understood in the context of this invention that any aryl, cycloalkyl and heterocyclyl which is substituted is substituted by one or more of halogen, —$R_9$, —$OR_9$, —$NO_2$, —$NR_9R_{9'''}$, $NR_9C(O)R_{9'}$, —$NR_9S(O)_2R_{9'}$, —$S(O)_2NR_9R_{9'}$, —$NR_9C(O)NR_{9'}R_{9''}$, —CN, haloalkyl, haloalkoxy, —$C(O)OR_9$, —$C(O)NR_9R_{9'}$, =O, —$OCH_2CH_2OH$, —$NR_9S(O)_2NR_{9'}R_{9''}$; —$OC_{1-4}$alkyl being unsubstituted or substituted by one or more of OH or halogen (F, Cl, I, Br), —CN, or —$C_{1-4}$alkyl being unsubstituted or substituted by one or more of OH or halogen (F, Cl, I, Br), being $R_9$, $R_{9'}$, $R_{9''}$ and $R_{9'''}$ as defined above, and wherein when different radicals $R_1$ to $R_{10'}$ are present simultaneously in Formulas I to I''' they may be identical or different.

Most preferably in connection with aryl (including alkyl-aryl), cycloalkyl (including alkyl-cycloalkyl) or heterocyclyl (including alkyl-heterocyclyl), substituted is understood in the context of this invention that any aryl, cycloalkyl and heterocyclyl which is substituted is substituted by one or more of halogen, —$R_9$, —$OR_9$, —$NO_2$, —$NR_9R_{9'''}$, $NR_9C(O)R_{9'}$, —$NR_9S(O)_2R_{9'}$, —$S(O)_2NR_9R_{9'}$, —$NR_9C(O)NR_{9'}R_{9''}$, —CN, haloalkyl, haloalkoxy, —$C(O)OR_9$, —$C(O)NR_9R_{9'}$, —$NR_9S(O)_2NR_{9'}R_{9''}$; —$OC_{1-4}$alkyl being unsubstituted or substituted by one or more of OH or halogen (F, Cl, I, Br), —CN, or —$C_{1-4}$alkyl being unsubstituted or substituted by one or more of OH or halogen (F, Cl, I, Br), being $R_9$, $R_{9'}$, $R_{9''}$ and $R_{9'''}$ as defined above, and wherein when different radicals $R_1$ to $R_{10'}$ are present simultaneously in Formulas I to I''' they may be identical or different.

Additionally to the above-mentioned substitutions, in connection with cycloalkyl, or heterocycly namely non-aromatic heterocyclyl, substituted is also understood—unless defined otherwise—as meaning substitution of the ring-system of the cycloalkyl or; non-aromatic heterocyclyl with

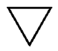

or =O.

The term "leaving group" means a molecular fragment that departs with a pair of electrons in heterolytic bond cleavage. Leaving groups can be anions or neutral molecules. Common anionic leaving groups are halides such as Cl—, Br—, and I—, and sulfonate esters, such as tosylate (TsO—) or mesylate.

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes via ionic interactions.

The term "physiologically acceptable salt" means in the context of this invention any salt that is physiologically tolerated (most of the time meaning not being toxic-especially not caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid—as an anion with at least one, preferably inorganic, cation which is physiologically tolerated-especially if used on humans and/or mammals. The salts of the alkali metals and alkaline earth metals are particularly preferred, and also those with $NH_4$, but in particular (mono)- or (di)sodium, (mono)- or (di)potassium, magnesium or calcium salts.

Physiologically acceptable salts can also be formed with anions or acids and in the context of this invention is understood as meaning salts of at least one of the compounds used according to the invention as the cation with at least one anion which are physiologically tolerated—especially if used on humans and/or mammals. By this is understood in particular, in the context of this invention, the salt formed with a physiologically tolerated acid, that is to say salts of the particular active compound with inorganic or organic acids which are physiologically tolerated—especially if used on humans and/or mammals. Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The compounds of the invention may be present in crystalline form or in the form of free compounds like a free base or acid.

Any compound that is a solvate of a compound according to the invention like a compound according to general formula I defined above is understood to be also covered by the scope of the invention. Methods of solvation are generally known within the art. Suitable solvates are pharmaceutically acceptable solvates. The term "solvate" according to this invention is to be understood as meaning any form of the active compound according to the invention in which this compound has attached to it via non-covalent binding another molecule (most likely a polar solvent). Especially preferred examples include hydrates and alcoholates, like methanolates or ethanolates.

Any compound that is a prodrug of a compound according to the invention like a compound according to general formula I defined above is understood to be also covered by the scope of the invention. The term "prodrug" is used in its broadest sense and encompasses those Derivatives that are converted in vivo to the compounds of the invention. Such Derivatives would readily occur to those skilled in the art, and include, depending on the functional groups present in the molecule and without limitation, the following Derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (April 2002).

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon or of a nitrogen by $^{15}N$-enriched nitrogen are within the scope of this invention.

The compounds of formula (I) as well as their salts or solvates of the compounds are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I) or, or of its salts. This applies also to its solvates or prodrugs.

In a further preferred embodiment of the compound according to the invention the compound is a compound according to Formula (I')

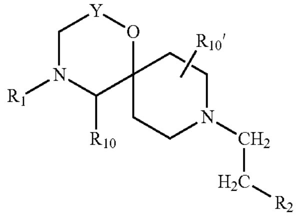

wherein

Y is

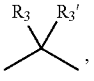
,
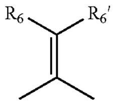
or
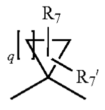

q is 1, 2, 3, 4, 5 or 6;

$R_1$ is $C(O)R_5$ or $S(O_2)R_5$;

$R_2$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, or substituted or unsubstituted heterocyclyl;

$R_3$ and $R_3'$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl and substituted or unsubstituted cycloalkyl;

$R_5$ is substituted or unsubstituted $C_{1-6}$ alkyl, substituted or unsubstituted $C_{2-6}$ alkenyl, substituted or unsubstituted $C_{2-6}$alkynyl, substituted or unsubstituted cycloalkyl, substituted or unsubstituted aryl, substituted or unsubstituted heterocyclyl, substituted or unsubstituted alkyl aryl, substituted or unsubstituted alkyl heterocyclyl and substituted or unsubstituted alkyl cycloalkyl, —$NR_8R_8$;

$R_6$, $R_{6'}$, $R_7$, and $R_{7'}$ are independently selected from hydrogen, halogen, —$OR_9$, substituted or unsubstituted $C_{1-6}$ alkyl, substituted or unsubstituted $C_{2-6}$ alkenyl, substituted or unsubstituted $C_{2-6}$ alkynyl, unsubstituted heterocyclyl, unsubstituted aryl and unsubstituted cycloalkyl;

$R_8$ and $R_8'$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;

$R_9$, $R_{9'}$ and $R_{9''}$ are independently selected from hydrogen, unsubstituted $C_{1-6}$ alkyl, unsubstituted $C_{2-6}$ alkenyl, unsubstituted $C_{2-6}$ alkynyl while $R_{9'''}$ is selected from hydrogen, unsubstituted $C_{1-6}$ alkyl, unsubstituted $C_{2-6}$ alkenyl, unsubstituted $C_{2-6}$ alkynyl and -Boc;

$R_{10}$ and $R_{10'}$ are independently selected from hydrogen, halogen, —$OR_9$, substituted or unsubstituted $C_{1-6}$ alkyl, substituted or unsubstituted $C_{2-6}$ alkenyl, substituted or unsubstituted $C_{2-6}$ alkynyl, substituted or unsubstituted —O—$C_{1-6}$ alkyl, substituted or unsubstituted —O—$C_{2-6}$ alkenyl or substituted or unsubstituted —O—$C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof, In one embodiment drawn to compounds according to Formula I' the following proviso applies:
when Y is

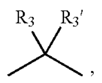

and
$-(CH_2)_2-R_2$ is alkyl, then said alkyl contains 6 or less C-atoms.

In another preferred embodiment of the compound according to the invention according to general formulas I or I' the compound is a compound according to Formula I'', (I'')

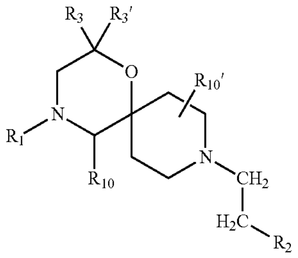

wherein
$R_1$ is $C(O)R_5$ or $S(O_2)R_5$;
$R_2$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, or substituted or unsubstituted heterocyclyl;
$R_3$ and $R_3'$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl and substituted or unsubstituted cycloalkyl;
$R_5$ is substituted or unsubstituted $C_{1-6}$ alkyl, substituted or unsubstituted $C_{2-6}$ alkenyl, substituted or unsubstituted $C_{2-6}$alkynyl, substituted or unsubstituted cycloalkyl, substituted or unsubstituted aryl, substituted or unsubstituted heterocyclyl, substituted or unsubstituted alkyl aryl, substituted or unsubstituted alkyl heterocyclyl and substituted or unsubstituted alkyl cycloalkyl, $-NR_8R_{8'}$;
$R_6$, $R_{6'}$ $R_7$, and $R_7$ are independently selected from hydrogen, halogen, $-OR_9$, substituted or unsubstituted $C_{1-6}$ alkyl, substituted or unsubstituted $C_{2-6}$ alkenyl, substituted or unsubstituted $C_{2-6}$ alkynyl, unsubstituted heterocyclyl, unsubstituted aryl and unsubstituted cycloalkyl;
$R_8$ and $R_8'$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
$R_9$, $R_{9'}$ and $R_{9''}$ are independently selected from hydrogen, unsubstituted $C_{1-6}$ alkyl, unsubstituted $C_{2-6}$ alkenyl, unsubstituted $C_{2-6}$ alkynyl while $R_{9'''}$ is selected from hydrogen, unsubstituted $C_{1-6}$ alkyl, unsubstituted $C_{2-6}$ alkenyl, unsubstituted $C_{2-6}$ alkynyl and -Boc;
$R_{10}$ and $R_{10'}$ are independently selected from hydrogen, halogen, $-OR_9$, substituted or unsubstituted $C_{1-6}$ alkyl, substituted or unsubstituted $C_{2-6}$ alkenyl, substituted or unsubstituted $C_{2-6}$ alkynyl, substituted or unsubstituted $-O-C_{1-6}$ alkyl, substituted or unsubstituted $-O-C_{2-6}$ alkenyl or substituted or unsubstituted $-O-C_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof, In one embodiment (drawn to compounds according to Formula I'') the following proviso applies:
when $-(CH_2)_2-R_2$ is alkyl, then said alkyl contains 6 or less C-atoms.

In another preferred embodiment of the compound according to the invention according to general formulas I or I' the compound is a compound according to Formula I''', (I''')

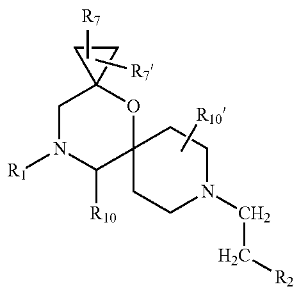

wherein
$R_1$ is $C(O)R_5$ or $S(O_2)R_5$;
$R_2$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, or substituted or unsubstituted heterocyclyl;
$R_5$ is substituted or unsubstituted $C_{1-6}$ alkyl, substituted or unsubstituted $C_{2-6}$ alkenyl, substituted or unsubstituted $C_{2-6}$alkynyl, substituted or unsubstituted cycloalkyl, substituted or unsubstituted aryl, substituted or unsubstituted heterocyclyl, substituted or unsubstituted alkyl aryl, substituted or unsubstituted alkyl heterocyclyl and substituted or unsubstituted alkyl cycloalkyl, $-NR_8R_{8'}$;
$R_6$, $R_{6'}$ $R_7$, and $R_{7'}$ are independently selected from hydrogen, halogen, $-OR_9$, substituted or unsubstituted $C_{1-6}$ alkyl, substituted or unsubstituted $C_{2-6}$ alkenyl, substituted or unsubstituted $C_{2-6}$ alkynyl, unsubstituted heterocyclyl, unsubstituted aryl and unsubstituted cycloalkyl;
$R_8$ and $R_8'$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
$R_9$, $R_{9'}$ and $R_{9''}$ are independently selected from hydrogen, unsubstituted $C_{1-6}$ alkyl, unsubstituted $C_{2-6}$ alkenyl, unsubstituted $C_{2-6}$ alkynyl while $R_{9'''}$ is selected from hydrogen, unsubstituted $C_{1-6}$ alkyl, unsubstituted $C_{2-6}$ alkenyl, unsubstituted $C_{2-6}$ alkynyl and -Boc;
$R_{10}$ and $R_{10'}$ are independently selected from hydrogen, halogen, $-OR_9$, substituted or unsubstituted $C_{1-6}$ alkyl, substituted or unsubstituted $C_{2-6}$ alkenyl, substituted or unsubstituted $C_{2-6}$ alkynyl, substituted or unsubstituted $-O-C_{1-6}$ alkyl, substituted or unsubstituted $-O-C_{2-6}$ alkenyl or substituted or unsubstituted $-O-C_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In one embodiment (EMBODIMENT DA) the compound is a compound of general formula (I),

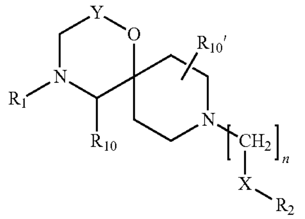

(I)

wherein

Y is

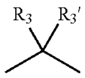
,
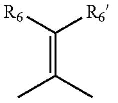
or
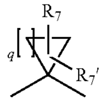

n is 1 or 2;

q is 1, 2, 3, 4, 5 or 6;

X is a bond, —C(O)O—, —C(O)$NR_8$—, —C(O)—, —O— or —C($R_4R_{4'}$)—;

$R_1$ is C(O)$R_5$ or $S(O)_2R_5$;

$R_2$ is substituted or unsubstituted $C_{1-3}$ alkyl, substituted or unsubstituted $C_{2-3}$ alkenyl, substituted or unsubstituted $C_{2-3}$ alkynyl, substituted or unsubstituted cycloalkyl, substituted or unsubstituted aryl, or substituted or unsubstituted heterocyclyl; with cycloalkyl, aryl, or heterocyclyl if substituted being substituted by substituents selected from halogen, —$R_9$, —$OR_9$, —$NO_2$, —$NR_9R_{9'''}$, $NR_9C(O)R_{9'}$, —$NR_9S(O)_2$ $R_{9'}$, —$S(O)_2NR_9R_{9'}$, —$NR_9C(O)NR_{9'}R_{9''}$, —$SR_9$, —$S(O)R_9$, $S(O)_2R_9$, —CN, haloalkyl, haloalkoxy, —C(O)$OR_9$, —C(O)$NR_9R_{9'}$, ═O, —$OCH_2CH_2OH$, —$NR_9S(O)_2NR_{9'}R_{9''}$;

$R_3$ and $R_3$' are independently selected from hydrogen, substituted or unsubstituted $C_{2-6}$ alkyl, substituted or unsubstituted $C_{2-6}$ alkenyl, substituted or unsubstituted $C_{2-6}$ alkynyl substituted or unsubstituted cycloalkyl, substituted or unsubstituted heterocyclyl, substituted or unsubstituted alkylcycloalkyl, substituted or unsubstituted alkylheterocyclyl, substituted or unsubstituted aryl, substituted or unsubstituted alkylaryl, with cycloalkyl, heterocyclyl or aryl if substituted also in alkylaryl, alkylcycloalkyl or alkylheterocyclyl being substituted by substituents selected from halogen, —$R_9$, and —$OR_9$;

$R_4$ is hydrogen, —$OR_8$, substituted or unsubstituted $C_{1-6}$ alkyl, substituted or unsubstituted $C_{2-6}$ alkenyl, substituted or unsubstituted $C_{2-6}$ alkynyl, —C(O)$OR_9$, —C(O)$NR_9R_{9'}$, —$NR_9C(O)R_{9'}$, —$NR_9R_{9'''}$, unsubstituted heterocyclyl, unsubstituted aryl and unsubstituted cycloalkyl;

$R_{4'}$ is Hydrogen, or substituted or unsubstituted $C_{1-6}$ alkyl, substituted or unsubstituted $C_{2-6}$ alkenyl or substituted or unsubstituted $C_{2-6}$ alkynyl;

$R_5$ is substituted or unsubstituted $C_{1-6}$ alkyl, substituted or unsubstituted $C_{2-6}$ alkenyl, substituted or unsubstituted $C_{2-6}$alkynyl, substituted or unsubstituted cycloalkyl, substituted or unsubstituted aryl, substituted or unsubstituted heterocyclyl, substituted or unsubstituted alkyl aryl, substituted or unsubstituted alkyl heterocyclyl and substituted or unsubstituted alkyl cycloalkyl, —$NR_8R_{8'}$, wherein said cycloalkyl, aryl or heterocyclyl if substituted also in alkylaryl, alkylcycloalkyl or alkylheterocyclyl being substituted by substituents selected from halogen, —$R_9$, —$OR_9$, —$NO_2$, —$NR_9R_{9'''}$, —$NR_9C(O)R_{9'}$, —$NR_9S(O)_2R_{9'}$, —$S(O)_2NR_9R_{9'}$, —$NR_9C(O)NR_{9'}R_{9''}$, —$SR_9$, —$S(O)R_9$, —$S(O)_2R_9$, —CN, haloalkyl, haloalkoxy, —C(O)$OR_9$ and —C(O)$NR_9R_{9'}$;

$R_6$, $R_{6'}$ $R_7$, and $R_{7'}$ are independently selected from hydrogen, halogen, —$OR_9$, substituted or unsubstituted $C_{1-6}$ alkyl, substituted or unsubstituted $C_{2-6}$ alkenyl, substituted or unsubstituted $C_{2-6}$ alkynyl, unsubstituted heterocyclyl, unsubstituted aryl and unsubstituted cycloalkyl;

$R_8$ and $R_8$' are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl, with cycloalkyl, aryl, or heterocyclyl if substituted being substituted by substituents selected from halogen, —$R_9$, —$OR_9$, —$NO_2$, —$NR_9R_{9'''}$, $NR_9C(O)R_{9'}$, —$NR_9S(O)_2R_{9'}$, —$S(O)_2NR_9R_{9'}$, —$NR_9C(O)NR_{9'}R_{9''}$, —$SR_9$, —$S(O)R_9$, —$S(O)_2R_9$, —CN, -haloalkyl, and haloalkoxy;

$R_9$, $R_{9'}$ and $R_{9''}$ are independently selected from hydrogen, unsubstituted $C_{1-6}$ alkyl, unsubstituted $C_{2-6}$ alkenyl, unsubstituted $C_{2-6}$ alkynyl while $R_{9'''}$ is selected from hydrogen, unsubstituted $C_{1-6}$ alkyl, unsubstituted $C_{2-6}$ alkenyl, unsubstituted $C_{2-6}$ alkynyl and -Boc;

$R_{10}$ and $R_{10'}$ are independently selected from hydrogen, halogen, —$OR_9$, substituted or unsubstituted $C_{1-6}$ alkyl, substituted or unsubstituted $C_{2-6}$ alkenyl, substituted or unsubstituted $C_{2-6}$ alkynyl, substituted or unsubstituted —O—$C_{1-6}$ alkyl, substituted or unsubstituted —O—$C_{2-6}$ alkenyl or substituted or unsubstituted —O—$C_{2-6}$ alkynyl;

wherein alkyl, alkenyl- or alkynyl moieties if defined for $R_2$, $R_3$, $R_{3'}$, $R_4$, $R_{4'}$, $R_5$, $R_6$, $R_{6'}$, $R_7$, $R_{7'}$, $R_8$, $R_{8'}$, $R_{10}$ and $R_{10'}$ are unsubstituted or substituted by one or more substituents selected from halogen, —$OR_9$, —$SR_9$, —CN, -haloalkyl, -haloalkoxy and —$NR_9R_{9'''}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In EMBODIMENT DA the following proviso is applying: when Y is

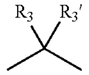

with $R_3$ and $R_{3'}$ being hydrogen, $R_1$ being C(O)$R_5$, and X not being —C($R_4R_{4'}$)—, then n would be 2.

In EMBODIMENT DA the following compounds are preferably being excluded:

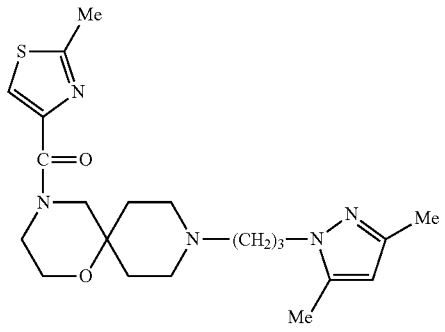

and/or

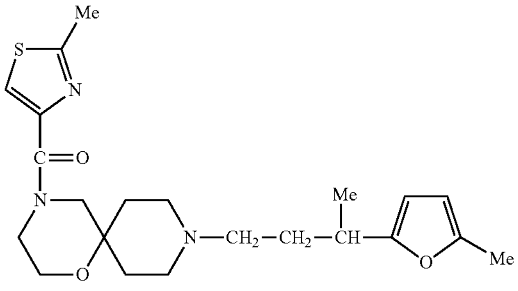

and/or

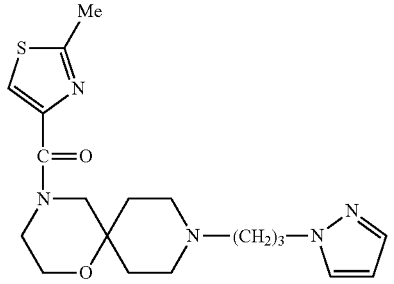

and/or

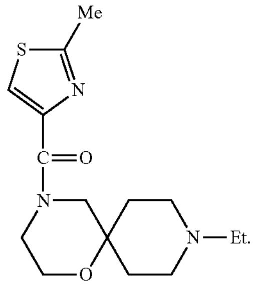 [SMILES: CCN1CCC2(CC1)CN(C(=O)c1csc(C)n1)CCO2]

In one embodiment (EMBODIMENT DB) the compound is a compound of general formula (I),

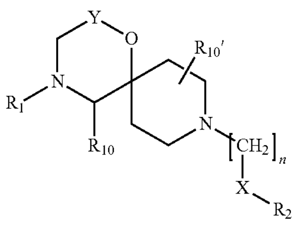

(I)

wherein

Y is

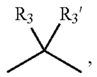, 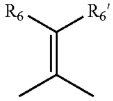 or 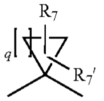

n is 1 or 2;

q is 1, 2, 3, 4, 5 or 6;

X is a bond, —C(O)O—, —C(O)$NR_8$—, —C(O)—, or —O—;

$R_1$ is C(O)$R_5$ or $S(O)_2R_5$;

$R_2$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, or substituted or unsubstituted heterocyclyl; with cycloalkyl, aryl, or heterocyclyl if substituted being substituted by substituents selected from halogen, —$R_9$, —$OR_9$, —$NO_2$, —$NR_9R_{9'''}$, $NR_9C(O)R_{9'}$, —$NR_9S(O)_2$ $R_{9'}$, —$S(O)_2NR_9R_{9'}$, —$NR_9C(O)NR_{9'}R_{9''}$, —$SR_9$, —$S(O)R_9$, $S(O)_2R_9$, —CN, haloalkyl, haloalkoxy, —C(O)$OR_9$, —C(O)$NR_9R_{9'}$, =O, —$OCH_2CH_2OH$, —$NR_9S(O)_2NR_{9'}R_{9''}$;

$R_3$ and $R_3'$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl substituted or unsubstituted cycloalkyl, substituted or unsubstituted heterocyclyl, substituted or unsubstituted alkylcycloalkyl, substituted or unsubstituted alkylheterocyclyl, substituted or unsubstituted aryl, substituted or unsubstituted alkylaryl, with cycloalkyl, heterocyclyl or aryl if substituted also in alkylaryl, alkylcycloalkyl or alkylheterocyclyl being substituted by substituents selected from halogen, —$R_9$, and —$OR_9$;

$R_4$ is hydrogen, —$OR_8$, substituted or unsubstituted $C_{1-6}$ alkyl, substituted or unsubstituted $C_{2-6}$ alkenyl, substituted or unsubstituted $C_{2-6}$ alkynyl, —C(O)$OR_9$, —C(O)$NR_9R_{9'}$, —$NR_9C(O)R_{9'}$, —$NR_9R_{9'''}$, unsubstituted heterocyclyl, unsubstituted aryl and unsubstituted cycloalkyl;

$R_{4'}$ is Hydrogen, or substituted or unsubstituted $C_{1-6}$ alkyl, substituted or unsubstituted $C_{2-6}$ alkenyl or substituted or unsubstituted $C_{2-6}$ alkynyl;

$R_5$ is substituted or unsubstituted $C_{1-6}$ alkyl, substituted or unsubstituted $C_{2-6}$ alkenyl, substituted or unsubstituted $C_{2-6}$alkynyl, substituted or unsubstituted cycloalkyl, substituted or unsubstituted aryl, substituted or unsubstituted heterocyclyl, substituted or unsubstituted alkyl aryl, substituted or unsubstituted alkyl heterocyclyl and substituted or unsubstituted alkyl cycloalkyl, —$NR_8R_{8'}$, wherein said cycloalkyl, aryl or heterocyclyl if substituted also in alkylaryl, alkylcycloalkyl or alkylheterocyclyl being substituted by substituents selected from halogen, —$R_9$, —$OR_9$, —$NO_2$, —$NR_9R_{9'''}$, —$NR_9C(O)R_{9'}$, —$NR_9S(O)_2R_{9'}$, —$S(O)_2NR_9R_{9'}$, —$NR_9C(O)NR_{9'}R_{9''}$, —$SR_9$, —$S(O)R_9$, —$S(O)_2R_9$, —CN, haloalkyl, haloalkoxy, —C(O)$OR_9$ and —C(O)$NR_9R_{9'}$;

$R_6$, $R_{6'}$ $R_7$, and $R_{7'}$ are independently selected from hydrogen, halogen, —$OR_9$, substituted or unsubstituted $C_{1-6}$ alkyl, substituted or unsubstituted $C_{2-6}$ alkenyl, substituted or unsubstituted $C_{2-6}$ alkynyl, unsubstituted heterocyclyl, unsubstituted aryl and unsubstituted cycloalkyl;

$R_8$ and $R_8'$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl, with cycloalkyl, aryl, or heterocyclyl if substituted being substituted by substituents selected from halogen, —$R_9$, —$OR_9$, —$NO_2$, —$NR_9R_{9'''}$, $NR_9C(O)R_{9'}$, —$NR_9S(O)_2R_{9'}$, —$S(O)_2NR_9R_{9'}$, —$NR_9C(O)NR_{9'}R_{9''}$, —$SR_9$, —$S(O)R_9$, —$S(O)_2R_9$, —CN, -haloalkyl, and haloalkoxy;

$R_9$, $R_{9'}$ and $R_{9''}$ are independently selected from hydrogen, unsubstituted $C_{1-6}$ alkyl, unsubstituted $C_{2-6}$ alkenyl, unsubstituted $C_{2-6}$ alkynyl while $R_{9'''}$ is selected from hydrogen, unsubstituted $C_{1-6}$ alkyl, unsubstituted $C_{2-6}$ alkenyl, unsubstituted $C_{2-6}$ alkynyl and -Boc;

$R_{10}$ and $R_{10'}$ are independently selected from hydrogen, halogen, —$OR_9$, substituted or unsubstituted $C_{1-6}$ alkyl, substituted or unsubstituted $C_{2-6}$ alkenyl, substituted or unsubstituted $C_{2-6}$ alkynyl, substituted or unsubstituted —O—$C_{1-6}$ alkyl, substituted or unsubstituted —O—$C_{2-6}$ alkenyl or substituted or unsubstituted —O—$C_{2-6}$ alkynyl;

wherein alkyl, alkenyl- or alkynyl moieties if defined for $R_2$, $R_3$, $R_{3'}$, $R_4$, $R_{4'}$, $R_5$, $R_6$, $R_{6'}$, $R_7$, $R_{7'}$, $R_8$, $R_{8'}$, $R_{10}$ and $R_{10'}$ are unsubstituted or substituted by one or more substituents selected from halogen, —$OR_9$, —$SR_9$, —CN, -haloalkyl, -haloalkoxy and —$NR_9R_{9'''}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In EMBODIMENT DB the following proviso is applying: when Y is

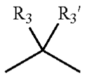

, and

—$(CH_2)_n$—X—$R_2$ is alkyl, then said alkyl contains 6 or less C-atoms.

In EMBODIMENT DB the following proviso is applying: when Y is

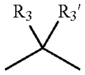

with $R_3$ and $R_{3'}$ being hydrogen, and $R_1$ being $C(O)R_5$, then n would be 2.

In EMBODIMENT DB the following compound is preferably being excluded:

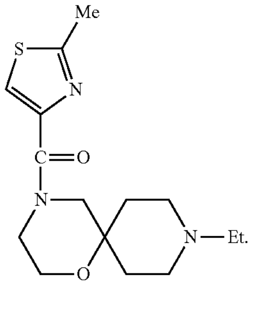

In one embodiment (EMBODIMENT DC) the compound is a compound of general formula (I),

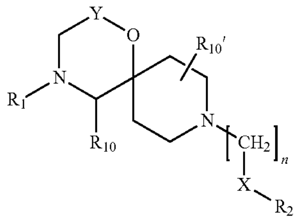

(I)

wherein

Y is

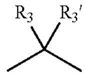

,

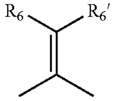

or

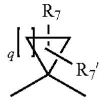

n is 1 or 2;

q is 1, 2, 3, 4, 5 or 6;

X is a bond, —C(O)O—, —$C(O)NR_8$—, —C(O)—, or —O—;

$R_1$ is $C(O)R_5$ or $S(O)_2R^5$;

$R_2$ is substituted or unsubstituted $C_{1-4}$ alkyl, substituted or unsubstituted $C_{2-4}$ alkenyl, substituted or unsubstituted $C_{2-4}$ alkynyl, substituted or unsubstituted cycloalkyl, substituted or unsubstituted aryl, or substituted or unsubstituted heterocyclyl; with cycloalkyl, aryl, or heterocyclyl if substituted being substituted by substituents selected from halogen, —$R_9$, —$OR_9$, —$NO_2$, —$NR_9R_{9'''}$, $NR_9C(O)R_{9'}$, —$NR_9S(O)_2$ $R_{9'}$, —$S(O)_2NR_9R_{9'}$, —$NR_9C(O)NR_{9'}R_{9''}$, —$SR_9$, —$S(O)R_9$, $S(O)_2R_9$, —CN, haloalkyl, haloalkoxy, —C(O)$OR_9$, —$C(O)NR_9R_{9'}$, =O, —$OCH_2CH_2OH$, —$NR_9S(O)_2NR_{9'}R_{9''}$;

$R_3$ and $R_3$' are independently selected from hydrogen, substituted or unsubstituted $C_{1-6}$ alkyl, substituted or unsubstituted $C_{2-6}$ alkenyl, substituted or unsubstituted $C_{2-6}$ alkynyl substituted or unsubstituted cycloalkyl, substituted or unsubstituted heterocyclyl, substituted or unsubstituted alkylcycloalkyl, substituted or unsubstituted alkylheterocyclyl, substituted or unsubstituted aryl, substituted or unsubstituted alkylaryl, with cycloalkyl, heterocyclyl or aryl if substituted also in alkylaryl, alkylcycloalkyl or alkylheterocyclyl being substituted by substituents selected from halogen, —$R_9$, and —$OR_9$;

$R_4$ is hydrogen, —$OR_8$, substituted or unsubstituted $C_{1-6}$ alkyl, substituted or unsubstituted $C_{2-6}$ alkenyl, substituted or unsubstituted $C_{2-6}$ alkynyl, —C(O)$OR_9$, —$C(O)NR_9R_{9'}$, —$NR_9C(O)R_{9'}$, —$NR_9R_{9'''}$, unsubstituted heterocyclyl, unsubstituted aryl and unsubstituted cycloalkyl;

$R_{4'}$ is Hydrogen, or substituted or unsubstituted $C_{1-6}$ alkyl, substituted or unsubstituted $C_{2-6}$ alkenyl or substituted or unsubstituted $C_{2-6}$ alkynyl;

$R_5$ is substituted or unsubstituted $C_{1-6}$ alkyl, substituted or unsubstituted $C_{2-6}$ alkenyl, substituted or unsubstituted $C_{2-6}$alkynyl, substituted or unsubstituted cycloalkyl, substituted or unsubstituted aryl, substituted or unsubstituted heterocyclyl, substituted or unsubstituted alkyl aryl, substituted or unsubstituted alkyl heterocyclyl and substituted or unsubstituted alkyl cycloalkyl, —$NR_8R_{8'}$, wherein said cycloalkyl, aryl or heterocyclyl if substituted also in alkylaryl, alkylcycloalkyl or alkylheterocyclyl being substituted by substituents selected from halogen, —$R_9$, —$OR_9$, —$NO_2$, —$NR_9R_{9''''}$, —$NR_9C(O)R_{9'}$, —$NR_9S(O)_2R_{9'}$, —$S(O)_2NR_9R_{9'}$, —$NR_9C(O)NR_{9'}R_{9''}$, —$SR_9$, —$S(O)R_9$, —$S(O)_2R_9$, —CN, haloalkyl, haloalkoxy, —$C(O)OR_9$ and —$C(O)NR_9R_{9'}$;

$R_6$, $R_{6'}$ $R_7$, and $R_{7'}$ are independently selected from hydrogen, halogen, —$OR_9$, substituted or unsubstituted $C_{1-6}$ alkyl, substituted or unsubstituted $C_{2-6}$ alkenyl, substituted or unsubstituted $C_{2-6}$ alkynyl, unsubstituted heterocyclyl, unsubstituted aryl and unsubstituted cycloalkyl;

$R_8$ and $R_8'$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl, with cycloalkyl, aryl, or heterocyclyl if substituted being substituted by substituents selected from halogen, —$R_9$, —$OR_9$, —$NO_2$, —$NR_9R_{9''''}$, $NR_9C(O)R_{9'}$, —$NR_9S(O)_2R_{9'}$, —$S(O)_2NR_9R_{9'}$, —$NR_9C(O)NR_{9'}R_{9''}$, —$SR_9$, —$S(O)R_9$, —$S(O)_2R_9$, —CN, -haloalkyl, and haloalkoxy;

$R_9$, $R_{9'}$ and $R_{9''}$ are independently selected from hydrogen, unsubstituted $C_{1-6}$ alkyl, unsubstituted $C_{2-6}$ alkenyl, unsubstituted $C_{2-6}$ alkynyl while $R_{9''''}$ is selected from hydrogen, unsubstituted $C_{1-6}$ alkyl, unsubstituted $C_{2-6}$ alkenyl, unsubstituted $C_{2-6}$ alkynyl and -Boc;

$R_{10}$ and $R_{10'}$ are independently selected from hydrogen, halogen, —$OR_9$, substituted or unsubstituted $C_{1-6}$ alkyl, substituted or unsubstituted $C_{2-6}$ alkenyl, substituted or unsubstituted $C_{2-6}$ alkynyl, substituted or unsubstituted —O—$C_{1-6}$ alkyl, substituted or unsubstituted —O—$C_{2-6}$ alkenyl or substituted or unsubstituted —O—$C_{2-6}$ alkynyl;

wherein alkyl, alkenyl- or alkynyl moieties if defined for $R_2$, $R_3$, $R_{3'}$, $R_4$, $R_{4'}$, $R_5$, $R_6$, $R_{6'}$, $R_7$, $R_{7'}$, $R_8$, $R_{8'}$, $R_{10}$ and $R_{10'}$ are unsubstituted or substituted by one or more substituents selected from halogen, —$OR_9$, —$SR_9$, —CN, -haloalkyl, -haloalkoxy and —$NR_9R_{9''''}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In EMBODIMENT DC the following proviso is applying: when Y is

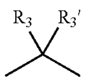

with $R_3$ and $R_{3'}$ being hydrogen, and $R_1$ being $C(O)R_5$, then n would be 2.

In EMBODIMENT DC the following compound is preferably being excluded:

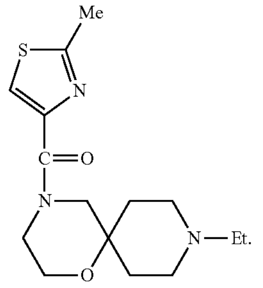

In one embodiment (EMBODIMENT DD) the compound is a compound of general formula (I),

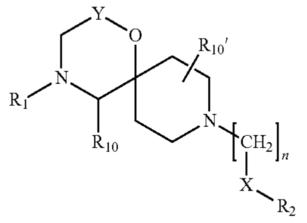

(I)

wherein Y is

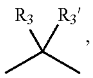
,
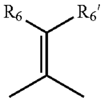
or
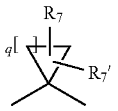

n is 2;

q is 1, 2, 3, 4, 5 or 6;

X is a bond, —C(O)O—, —$C(O)NR_8$—, —C(O)—, or —O—;

$R_1$ is $C(O)R_5$ or $S(O)_2R_5$;

$R_2$ is substituted or unsubstituted $C_{1-4}$ alkyl, substituted or unsubstituted $C_{2-4}$ alkenyl, substituted or unsubstituted $C_{2-4}$ alkynyl, substituted or unsubstituted cycloalkyl, substituted or unsubstituted aryl, or substituted or unsubstituted heterocyclyl; with cycloalkyl, aryl, or heterocyclyl if substituted being substituted by substituents selected from halogen, —$R_9$, —$OR_9$, —$NO_2$, —$NR_9R_{9''''}$, $NR_9C(O)R_{9'}$, —$NR_9S(O)_2$ $R_{9'}$, —$S(O)_2NR_9R_{9'}$, —$NR_9C(O)NR_{9'}R_{9''}$, —$SR_9$, —$S(O)R_9$, $S(O)_2R_9$, —CN, haloalkyl, haloalkoxy, —$C(O)OR_9$, —$C(O)NR_9R_{9'}$, =O, —$OCH_2CH_2OH$, —$NR_9S(O)_2NR_{9'}R_{9''}$;

$R_3$ and $R_3'$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl substituted or unsubstituted cycloalkyl, substituted or unsubstituted heterocyclyl, substituted or unsubstituted alkylcycloalkyl, substituted or unsubstituted alkylheterocyclyl, substituted or unsubstituted aryl, substituted or unsubstituted alkylaryl, with cycloalkyl, heterocyclyl or aryl if substituted also in alkylaryl, alkylcycloalkyl or alkylheterocyclyl being substituted by substituents selected from halogen, —$R_9$, and —$OR_9$;

$R_4$ is hydrogen, —$OR_8$, substituted or unsubstituted $C_{1-6}$ alkyl, substituted or unsubstituted $C_{2-6}$ alkenyl, substituted or unsubstituted $C_{2-6}$ alkynyl, —$C(O)OR_9$, —$C(O)NR_9R_{9'}$, —NR$_9$C(O)R$_{9'}$, —NR$_9$R$_{9'''}$, unsubstituted heterocyclyl, unsubstituted aryl and unsubstituted cycloalkyl;

R$_4$ is Hydrogen, or substituted or unsubstituted C$_{1-6}$ alkyl, substituted or unsubstituted C$_{2-6}$ alkenyl or substituted or unsubstituted C$_{2-6}$ alkynyl;

R$_5$ is substituted or unsubstituted C$_{1-6}$ alkyl, substituted or unsubstituted C$_{2-6}$ alkenyl, substituted or unsubstituted C$_{2-6}$alkynyl, substituted or unsubstituted cycloalkyl, substituted or unsubstituted aryl, substituted or unsubstituted heterocyclyl, substituted or unsubstituted alkyl aryl, substituted or unsubstituted alkyl heterocyclyl and substituted or unsubstituted alkyl cycloalkyl, —NR$_8$R$_{8'}$, wherein said cycloalkyl, aryl or heterocyclyl if substituted also in alkylaryl, alkylcycloalkyl or alkylheterocyclyl being substituted by substituents selected from halogen, —R$_9$, —OR$_9$, —NO$_2$, —NR$_9$R$_{9'''}$, —NR$_9$C(O)R$_{9'}$, —NR$_9$S(O)$_2$R$_{9'}$, —S(O)$_2$NR$_9$R$_{9'}$, —NR$_9$C(O)NR$_9$R$_{9''}$, —SR$_9$, —S(O)R$_9$, —S(O)$_2$R$_9$, —CN, haloalkyl, haloalkoxy, —C(O)OR$_9$ and —C(O)NR$_9$R$_{9'}$;

R$_6$, R$_{6'}$ R$_7$, and R$_{7'}$ are independently selected from hydrogen, halogen, —OR$_9$, substituted or unsubstituted C$_{1-6}$ alkyl, substituted or unsubstituted C$_{2-6}$ alkenyl, substituted or unsubstituted C$_{2-6}$ alkynyl, unsubstituted heterocyclyl, unsubstituted aryl and unsubstituted cycloalkyl;

R$_8$ and R$_{8'}$ are independently selected from hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl and substituted or unsubstituted heterocyclyl, with cycloalkyl, aryl, or heterocyclyl if substituted being substituted by substituents selected from halogen, —R$_9$, —OR$_9$, —NO$_2$, —NR$_9$R$_{9'''}$, NR$_9$C(O)R$_{9'}$, —NR$_9$S(O)$_2$R$_{9'}$, —S(O)$_2$NR$_9$R$_{9'}$, —NR$_9$C(O)NR$_9$R$_{9''}$, —SR$_9$, —S(O)R$_9$, —S(O)$_2$R$_9$, —CN, -haloalkyl, and haloalkoxy;

R$_9$, R$_{9'}$ and R$_{9''}$ are independently selected from hydrogen, unsubstituted C$_{1-6}$ alkyl, unsubstituted C$_{2-6}$ alkenyl, unsubstituted C$_{2-6}$ alkynyl while R$_{9'''}$ is selected from hydrogen, unsubstituted C$_{1-6}$ alkyl, unsubstituted C$_{2-6}$ alkenyl, unsubstituted C$_{2-6}$ alkynyl and -Boc;

R$_{10}$ and R$_{10'}$ are independently selected from hydrogen, halogen, —OR$_9$, substituted or unsubstituted C$_{1-6}$ alkyl, substituted or unsubstituted C$_{2-6}$ alkenyl, substituted or unsubstituted C$_{2-6}$ alkynyl, substituted or unsubstituted —O—C$_{1-6}$ alkyl, substituted or unsubstituted —O—C$_{2-6}$ alkenyl or substituted or unsubstituted —O—C$_{2-6}$ alkynyl;

wherein alkyl, alkenyl- or alkynyl moieties if defined for R$_2$, R$_3$, R$_{3'}$, R$_4$, R$_{4'}$, R$_5$, R$_6$, R$_{6'}$, R$_7$, R$_{7'}$, R$_8$, R$_{8'}$, R$_{10}$ and R$_{10'}$ are unsubstituted or substituted by one or more substituents selected from halogen, —OR$_9$, —SR$_9$, —CN, -haloalkyl, -haloalkoxy and —NR$_9$R$_{9'''}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the compound according to the invention according to general formulas I, I', I" or I''', wherein
R$_1$ is C(O)R$_5$ or S(O)$_2$R$_5$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the compound according to the invention according to general formulas I, I', I" or I''' wherein
R$_2$ is substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl, or substituted or unsubstituted heterocyclyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the compound according to the invention according to general formulas I, I', I" or I''', wherein
R$_3$ and R$_3$' are independently selected from hydrogen, substituted or unsubstituted C$_{1-6}$ alkyl, substituted or unsubstituted C$_{2-6}$ alkenyl, substituted or unsubstituted C$_{2-6}$ alkynyl substituted or unsubstituted cycloalkyl, substituted or unsubstituted heterocyclyl, substituted or unsubstituted alkylcycloalkyl, substituted or unsubstituted alkylheterocyclyl, substituted or unsubstituted aryl, substituted or unsubstituted alkylaryl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the compound according to the invention according to general formulas I, I', or I", wherein
R$_3$ and R$_3$' are independently selected from hydrogen, substituted or unsubstituted C$_{1-6}$ alkyl, substituted or unsubstituted C$_{2-6}$ alkenyl, substituted or unsubstituted C$_{2-6}$ alkynyl substituted or unsubstituted cycloalkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the compound according to the invention according to general formula I, R$_4$ is hydrogen, —OR$_8$, substituted or unsubstituted C$_{1-6}$ alkyl, substituted or unsubstituted C$_{2-6}$ alkenyl, substituted or unsubstituted C$_{2-6}$ alkynyl, —C(O)OR$_9$, —C(O)NR$_9$R$_{9'}$, —NR$_9$C(O)R$_{9'}$, —NR$_9$R$_{9'''}$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, the compound is a compound, wherein
R$_4$ is hydrogen, —OR$_8$, substituted or unsubstituted C$_{1-6}$ alkyl, substituted or unsubstituted C$_{2-6}$ alkenyl, substituted or unsubstituted C$_{2-6}$ alkynyl, —C(O)OR$_9$, —C(O)NR$_9$R$_{9'}$, —NR$_9$C(O)R$_{9'}$, —NR$_9$R$_{9'''}$, unsubstituted heterocyclyl, unsubstituted aryl and unsubstituted cycloalkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the compound according to the invention according to general formula I, wherein $R_4$ is Hydrogen, or substituted or unsubstituted $C_{1-6}$ alkyl, substituted or unsubstituted $C_{2-6}$ alkenyl or substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the compound according to the invention according to general formulas I, I', I'' or I''', wherein $R_5$ is substituted or unsubstituted $C_{1-6}$ alkyl, substituted or unsubstituted $C_{2-6}$ alkenyl, substituted or unsubstituted $C_{2-6}$alkynyl, substituted or unsubstituted cycloalkyl, substituted or unsubstituted aryl, substituted or unsubstituted heterocyclyl, substituted or unsubstituted alkyl aryl, substituted or unsubstituted alkyl heterocyclyl and substituted or unsubstituted alkyl cycloalkyl, —$NR_8R_{8'}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the compound according to the invention according to general formulas I, I', I'' or I''', wherein $R_6$, $R_{6'}$ $R_7$, and $R_{7'}$ are independently selected from hydrogen, halogen, —$OR_9$, substituted or unsubstituted $C_{1-6}$ alkyl, substituted or unsubstituted $C_{2-6}$ alkenyl, substituted or unsubstituted $C_{2-6}$ alkynyl, unsubstituted heterocyclyl, unsubstituted aryl and unsubstituted cycloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof;

In a further preferred embodiment of the compound according to the invention according to general formulas I, I', I'' or I''', wherein $R_8$ and $R_8$' are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof, In a further preferred embodiment of the compound according to the invention according to general formulas I, I', I'' or I''', wherein $R_9$, $R_{9'}$ and $R_{9''}$ are independently selected from hydrogen, unsubstituted $C_{1-6}$ alkyl, unsubstituted $C_{2-6}$ alkenyl, unsubstituted $C_{2-6}$ alkynyl while $R_{9'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the compound according to the invention according to general formulas I, I', I'' or I''', wherein $R_{10}$ and $R_{10'}$ are independently selected from hydrogen, halogen, —$OR_9$, substituted or unsubstituted $C_{1-6}$ alkyl, substituted or unsubstituted $C_{2-6}$ alkenyl, substituted or unsubstituted $C_{2-6}$ alkynyl, substituted or unsubstituted —O—$C_{1-6}$ alkyl, substituted or unsubstituted —O—$C_{2-6}$ alkenyl or substituted or unsubstituted —O—$C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the compound according to the invention according to general formulas I, wherein n is 1 or 2;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the compound according to the invention according to general formulas I or I', wherein q is 1, 2, 3, 4, 5 or 6;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the compound according to the invention according to general formulas I, I', I'' or I''', wherein X is a bond, —C(O)O—, —C(O)$NR_8$—, —C(O)—, —O— or —C($R_4R_{4'}$)—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the compound according to the invention according to general formulas I or I', wherein Y is

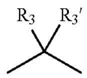

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the compound according to the invention according to general formulas I or I', wherein Y is

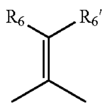

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the compound according to the invention according to general formulas I or I', wherein Y is

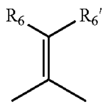

and $R_6$ and $R_{6'}$ are hydrogen optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the compound according to the invention according to general formulas I or I', wherein Y is

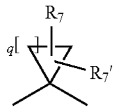

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the compound according to the invention according to general formulas I or I', wherein Y is

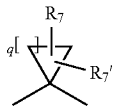

wherein q=1 and/or $R_7$ and $R_{7'}$ are hydrogen optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', I" or I'" the compound is a compound, wherein $R_1$ is $C(O)R_5$ or $S(O)_2R_5$; preferably $R_1$ is $C(O)R_5$ and/or $R_2$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, or substituted or unsubstituted heterocyclyl, wherein the aryl is selected from phenyl, naphtyl, or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline, more preferably the heterocycle is pyridine, piperidine, thiazole, morpholine;

and/or the $C_{1-6}$ alkyl is preferably selected from methyl, ethyl, propyl, butyl, pentyl or hexyl, isopropyl, or 2-methylpropyl, more preferably the $C_{1-6}$ alkyl is isopropyl;

and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or $R_3$ and $R_3'$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl substituted or unsubstituted cycloalkyl, substituted or unsubstituted heterocyclyl, substituted or unsubstituted alkylcycloalkyl, substituted or unsubstituted alkylheterocyclyl, substituted or unsubstituted aryl, substituted or unsubstituted alkylaryl, wherein the aryl is selected from phenyl, naphtyl, or anthracene; preferably is napthyl and phenyl, more preferably phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazinebenzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline,
and/or
the alkyl is $C_{1-6}$ alkyl like methyl, ethyl, propyl, butyl, pentyl, hexyl; preferably the alkyl is methyl,
and/or
the $C_{1-6}$ alkyl is preferably selected from methyl, ethyl, propyl, butyl, pentyl or hexyl, isopropyl, or 2-methylpropyl, more preferably the $C_{1-6}$ alkyl is methyl or isopropyl;
and/or
and/or
the $C_{2-6}$-alkenyl, is preferably selected from ethylene, propylene, butylene, pentylene or hexylene;
and/or
the $C_{2-6}$-alkynyl is preferably selected from ethyne, propyne, butyne, pentyne or hexyne;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably the cycloalkyl is cyclopropyl;
and/or
$R_4$ is hydrogen, $-OR_8$, substituted or unsubstituted $C_{1-6}$ alkyl, substituted or unsubstituted $C_{2-6}$ alkenyl, substituted or unsubstituted $C_{2-6}$ alkynyl, $-C(O)OR_9$, $-C(O)NR_9R_{9'}$, $-NR_9C(O)R_{9'}$, $-NR_9R_{9'''}$, unsubstituted heterocyclyl, unsubstituted aryl and unsubstituted cycloalkyl;
and/or
$R_{4'}$ is hydrogen, or substituted or unsubstituted $C_{1-6}$ alkyl, substituted or unsubstituted $C_{2-6}$ alkenyl or substituted or unsubstituted $C_{2-6}$ alkynyl; wherein
the aryl is selected from phenyl, naphtyl, or anthracene; preferably is napthyl and phenyl, more preferably phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline,
and/or
the $C_{1-6}$ alkyl is preferably selected from methyl, ethyl, propyl, butyl, pentyl, hexyl, isopropyl or 2-methylpropyl;
and/or
the $C_{2-6}$-alkenyl, is preferably selected from ethylene, propylene, butylene, pentylene or hexylene;
and/or
the $C_{2-6}$-alkynyl is preferably selected from ethyne, propyne, butyne, pentyne or hexyne;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
$R_5$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, substituted or unsubstituted alkyl-aryl, substituted or unsubstituted alkyl-heterocyclyl and substituted or unsubstituted alkyl-cycloalkyl, $-NR_8R^{8'}$, wherein
the aryl is selected from phenyl, naphtyl, or anthracene; preferably is napthyl and phenyl; more preferably is phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline, more preferably the heterocycle is pyridine, thiazole, tetrahydropyrane or piperidine;
and/or
the alkyl is $C_{1-6}$ alkyl like methyl, ethyl, propyl, butyl, pentyl or hexyl; more preferably the alkyl is methyl or ethyl;
and/or
the $C_{1-6}$ alkyl is preferably selected from methyl, ethyl, propyl, butyl, pentyl or hexyl, isopropyl, or 2-methylpropyl, more preferably the $C_{1-6}$ alkyl is methyl, ethyl or isopropyl;
and/or
the $C_{2-6}$-alkenyl, is preferably selected from ethylene, propylene, butylene, pentylene or hexylene;
and/or
the $C_{2-6}$-alkynyl is preferably selected from ethyne, propyne, butyne, pentyne or hexyne;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably the cycloalkyl is cyclopropyl;

and/or $R_6$, $R_{6'}$, $R_7$, and $R_{7'}$ are independently selected from hydrogen, halogen, —$OR_9$, substituted or unsubstituted $C_{1-6}$ alkyl, substituted or unsubstituted $C_{2-6}$ alkenyl, substituted or unsubstituted $C_{2-6}$ alkynyl, unsubstituted heterocyclyl, unsubstituted aryl and unsubstituted cycloalkyl; wherein the $C_{1-6}$ alkyl is preferably selected from methyl, ethyl, propyl, butyl, pentyl or hexyl, isopropyl, 2-methylpropyl;

and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or the aryl is selected from phenyl, naphtyl, or anthracene; preferably is napthyl and phenyl; more preferably phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline, and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably the cycloalkyl is cyclopropyl;

and/or $R_8$ and $R_8'$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl; wherein the aryl is selected from phenyl, naphtyl, or anthracene; preferably is napthyl and phenyl; more preferably is phenyl;

the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline, more preferably the heterocycle is pyridine, thiazole, tetrahydropyrane or piperidine; more preferably pyridine;

and/or the $C_{1-6}$ alkyl is preferably selected from methyl, ethyl, propyl, butyl, pentyl or hexyl, isopropyl, 2-methylpropyl; more preferably the $C_{1-6}$ alkyl is methyl, ethyl, isopropyl; more preferably methyl;

and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably the cycloalkyl is cyclopropyl;

and/or $R_9$, $R_{9'}$ and $R_{9''}$ are independently selected from hydrogen, unsubstituted $C_{1-6}$ alkyl, unsubstituted $C_{2-6}$ alkenyl, unsubstituted $C_{2-6}$ alkynyl while $R_{9'''}$ is selected from hydrogen, unsubstituted $C_{1-6}$ alkyl, unsubstituted $C_{2-6}$ alkenyl, unsubstituted $C_{2-6}$ alkynyl and -Boc; wherein the $C_{1-6}$ alkyl is preferably selected from methyl, ethyl, propyl, butyl, pentyl or hexyl, isopropyl, 2-methylpropyl; preferably methyl;

and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or $R_{10}$ and $R_{10'}$ are independently selected from hydrogen, halogen, —$OR_9$, substituted or unsubstituted $C_{1-6}$ alkyl, substituted or unsubstituted $C_{2-6}$ alkenyl, substituted or unsubstituted $C_{2-6}$ alkynyl, substituted or unsubstituted —O—$C_{1-6}$ alkyl, substituted or unsubstituted —O—$C_{2-6}$ alkenyl or substituted or unsubstituted —O—$C_{2-6}$ alkynyl; wherein the $C_{1-6}$ alkyl is preferably selected from methyl, ethyl, propyl, butyl, pentyl or hexyl, isopropyl, 2-methylpropyl;

and/or the $C_{2-6}$-alkenyl, is preferably selected from ethylene, propylene, butylene, pentylene or hexylene;

and/or the $C_{2-6}$ alkynyl is preferably selected from ethyne, propyne, butyne, pentyne or hexyne;

and/or q is 1, 2, 3, 4, 5 or 6; preferably q is 1 and/or n is 1 or 2, preferably n is 2 and/or

X is a bond, —C(O)O—, —C(O)$NR_8$—, —C(O)—, —O— or —C($R_4R_{4'}$)—; preferably X is a bond, —C(O)— or —C(O)O—;

and/or

Y is

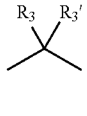
,
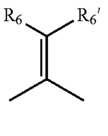
or
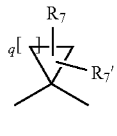

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, In another preferred embodiment of the compound according to the invention according to general formulas I, I', I'' or I''' the compound is a compound, wherein $R_1$ is $C(O)R_5$ or $S(O)_2R_5$; preferably $R_1$ is $C(O)R_5$ optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to general formulas I, I', I'' or I''' the compound is a compound, wherein $R_2$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, or substituted or unsubstituted heterocyclyl, wherein the aryl is selected from phenyl, naphtyl, or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline, more preferably the heterocycle is pyridine, piperidine, thiazole, morpholine, and/or the $C_{1-6}$ alkyl is preferably selected from methyl, ethyl, propyl, butyl, pentyl or hexyl, isopropyl, or 2-methylpropyl, more preferably the $C_{1-6}$ alkyl is isopropyl;

and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to general formulas I, I', or I'' the compound is a compound, wherein $R_3$ and $R_3'$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl substituted or unsubstituted cycloalkyl, wherein the $C_{1-6}$ alkyl is preferably selected from methyl, ethyl, propyl, butyl, pentyl, hexyl, isopropyl, or 2-methylpropyl; preferably the $C_{1-6}$ alkyl is methyl, or isopropyl, and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably the cycloalkyl is cyclopropyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to general formulas I, I', or I'' the compound is a compound, wherein $R_3$ and $R_3'$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl substituted or unsubstituted cycloalkyl, substituted or unsubstituted heterocyclyl, substituted or unsubstituted alkylcycloalkyl, substituted or unsubstituted alkylheterocyclyl, substituted or unsubstituted aryl, substituted or unsubstituted alkylaryl, wherein the aryl is selected from phenyl, naphtyl, or anthracene; preferably is napthyl and phenyl, more preferably phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline, and/or the alkyl is $C_{1-6}$ alkyl like methyl, ethyl, propyl, butyl, pentyl or hexyl; preferably the $C_{1-6}$ alkyl is methyl, and/or the $C_{1-6}$ alkyl is preferably selected from methyl, ethyl, propyl, butyl, pentyl or hexyl, isopropyl, or 2-methylpropyl, preferably the $C_{1-6}$ alkyl is methyl, or isopropyl;

and/or the $C_{2-6}$-alkenyl, is preferably selected from ethylene, propylene, butylene, pentylene or hexylene;

and/or
the $C_{2-6}$-alkynyl is preferably selected from ethyne, propyne, butyne, pentyne or hexyne;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably the cycloalkyl is cyclopropyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to general formulas I, I', or I" the compound is a compound, wherein $R_3$ and $R_3'$ are independently selected from hydrogen or unsubstituted $C_{1-6}$ alkyl.

In another preferred embodiment of the compound according to the invention according to general formulas I the compound is a compound, wherein
$R_4$ is hydrogen, —$OR_8$, substituted or unsubstituted $C_{1-6}$ alkyl, substituted or unsubstituted $C_{2-6}$ alkenyl, substituted or unsubstituted $C_{2-6}$ alkynyl, —$C(O)OR_9$, —$C(O)NR_9R_{9'}$, —$NR_9C(O)R_{9'}$, —$NR_9R_{9'''}$, wherein
the $C_{1-6}$ alkyl is preferably selected from methyl, ethyl, propyl, butyl, pentyl, hexyl, isopropyl or 2-methylpropyl;
and/or
the $C_{2-6}$-alkenyl, is preferably selected from ethylene, propylene, butylene, pentylene or hexylene;
and/or
the $C_{2-6}$-alkynyl is preferably selected from ethyne, propyne, butyne, pentyne or hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to general formulas I the compound is a compound, wherein
$R_4$ is hydrogen, —$OR_8$, substituted or unsubstituted $C_{1-6}$ alkyl, substituted or unsubstituted $C_{2-6}$ alkenyl, substituted or unsubstituted $C_{2-6}$ alkynyl, —$C(O)OR_9$, —$C(O)NR_9R_{9'}$, —$NR_9C(O)R_{9'}$, —$NR_9R_{9'''}$, unsubstituted heterocyclyl, unsubstituted aryl and unsubstituted cycloalkyl; wherein
the aryl is selected from phenyl, naphtyl, or anthracene; preferably is napthyl and phenyl, more preferably phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline,
and/or
the $C_{1-6}$ alkyl is preferably selected from methyl, ethyl, propyl, butyl, pentyl, hexyl, isopropyl or 2-methylpropyl;
and/or
the $C_{2-6}$-alkenyl, is preferably selected from ethylene, propylene, butylene, pentylene or hexylene;
and/or
the $C_{2-6}$-alkynyl is preferably selected from ethyne, propyne, butyne, pentyne or hexyne;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to general formulas I the compound is a compound, wherein
$R_{4'}$ is Hydrogen, or substituted or unsubstituted $C_{1-6}$ alkyl, substituted or unsubstituted $C_{2-6}$ alkenyl or substituted or unsubstituted $C_{2-6}$ alkynyl; wherein
the $C_{1-6}$ alkyl is preferably selected from methyl, ethyl, propyl, butyl, pentyl, hexyl, isopropyl or 2-methylpropyl;
and/or
the $C_{2-6}$-alkenyl, is preferably selected from ethylene, propylene, butylene, pentylene or hexylene;
and/or
the $C_{2-6}$-alkynyl is preferably selected from ethyne, propyne, butyne, pentyne or hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to general formulas I, I', I" or I''' the compound is a compound, wherein
$R_5$ is substituted or unsubstituted $C_{1-6}$ alkyl, substituted or unsubstituted $C_{2-6}$ alkenyl, substituted or unsubstituted $C_{2-6}$alkynyl, substituted or unsubstituted cycloalkyl, substituted or unsubstituted aryl, substituted or unsubstituted heterocyclyl, substituted or unsubstituted alkyl-aryl, substituted or unsubstituted alkyl-heterocyclyl and substituted or unsubstituted alkyl-cycloalkyl, —$NR_8R_{8'}$, wherein
the aryl is selected from phenyl, naphtyl, or anthracene; preferably is napthyl and phenyl; more preferably is phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline, more preferably the heterocycle is pyridine, thiazole, tetrahydropyrane or piperidine;

and/or the alkyl is $C_{1-6}$ alkyl like methyl, ethyl, propyl, butyl, pentyl or hexyl; more preferably the alkyl is methyl or ethyl;

and/or the $C_{1-6}$ alkyl is preferably selected from methyl, ethyl, propyl, butyl, pentyl or hexyl, isopropyl, or 2-methylpropyl, more preferably the $C_{1-6}$ alkyl is methyl, ethyl or isopropyl;

and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably the cycloalkyl is cyclopropyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof;

In another preferred embodiment of the compound according to the invention according to general formulas I, I', I" or I'" the compound is a compound, wherein $R_6$, $R_{6'}$, $R_7$, and $R_{7'}$ are independently selected from hydrogen, halogen, —$OR_9$, substituted or unsubstituted $C_{1-6}$ alkyl, substituted or unsubstituted $C_{2-6}$ alkenyl, substituted or unsubstituted $C_{2-6}$ alkynyl, unsubstituted heterocyclyl, unsubstituted aryl and unsubstituted cycloalkyl; wherein the $C_{1-6}$ alkyl is preferably selected from methyl, ethyl, propyl, butyl, pentyl or hexyl, isopropyl, 2-methylpropyl;

and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or the aryl is selected from phenyl, naphtyl, or anthracene; preferably is napthyl and phenyl; more preferably phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline, the cycloalkyl is $C_{3-8}$ cycloalkyl like cyclopropyl, cyclobutyl, cyclopentyl, cyclohexyl, cycloheptyl, or cyclooctyl; preferably is $C_{3-7}$cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably the cycloalkyl is cyclopropyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to general formulas I, I', I" or I'" the compound is a compound, wherein $R_6$, $R_{6'}$, $R_7$ and $R_{7'}$ are hydrogen.

In another preferred embodiment of the compound according to the invention according to general formulas I, I', I" or I'" the compound is a compound, wherein $R_8$ and $R_8'$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl; wherein the aryl is selected from phenyl, naphtyl, or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline, more preferably the heterocycle is pyridine, thiazole, tetrahydropyrane or piperidine; more preferably pyridine;

and/or the $C_{1-6}$ alkyl is preferably selected from methyl, ethyl, propyl, butyl, pentyl or hexyl, isopropyl, 2-methylpropyl; more preferably the $C_{1-6}$ alkyl is methyl, ethyl, isopropyl; more preferably methyl;

and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably the cycloalkyl is cyclopropyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to general formulas formulas I, I', I" or I'" the compound is a compound, wherein $R_9$, $R_{9'}$ and $R_{9''}$ are independently selected from hydrogen, unsubstituted $C_{1-6}$ alkyl, unsubstituted $C_{2-6}$ alkenyl, unsubstituted $C_{2-6}$ alkynyl while $R_{9'''}$ is selected from hydrogen, unsubstituted $C_{1-6}$ alkyl, unsubstituted $C_{2-6}$ alkenyl, unsubstituted $C_{2-6}$ alkynyl and -Boc; wherein the $C_{1-6}$ alkyl is preferably selected from methyl, ethyl, propyl, butyl, pentyl or hexyl, isopropyl, 2-methylpropyl; preferably methyl;

and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to general formulas I, I', I" or I'" the compound is a compound, wherein $R_{10}$ and $R_{10'}$ are independently selected from hydrogen, halogen, —$OR_9$, substituted or unsubstituted $C_{1-6}$ alkyl, substituted or unsubstituted $C_{2-6}$ alkenyl, substituted or unsubstituted $C_{2-6}$ alkynyl, substituted or unsubstituted —O—$C_{1-6}$ alkyl, substituted or unsubstituted —O—$C_{2-6}$ alkenyl or substituted or unsubstituted —O—$C_{2-6}$ alkynyl; wherein the $C_{1-6}$ alkyl is preferably selected from methyl, ethyl, propyl, butyl, pentyl or hexyl, isopropyl, 2-methylpropyl;

and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to general formulas I, I', I" or I'" the compound is a compound, wherein $R_{10}$ and $R_{10}'$ are hydrogen.

In another preferred embodiment of the compound according to the invention according to general formulas I, I', I" or I'" the compound is a compound, wherein q is 1, 2, 3, 4, 5 or 6; preferably q is 1 optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to general formula I the compound is a compound, wherein n is 1 or 2, preferably n is 2 optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to general formula I the compound is a compound, wherein X is a bond, —C(O)O—, —C(O)$NR_8$—, —C(O)—, —O— or —C($R_4R_{4'}$)—; preferably X is a bond;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In a preferred embodiment, $R_1$ is C(O)$R_5$.

In another preferred embodiment, $R_1$ is C(O)$R_5$ while $R_5$ is selected from substituted or unsubstituted phenyl, substituted or unsubstituted pyridine and —$NR_8R_{8'}$.

In a further preferred embodiment, $R_1$ is $S(O)_2R_5$.

In a further preferred embodiment, $R_1$ is $S(O)_2R_5$ while $R_5$ is selected from substituted or unsubstituted phenyl and unsubstituted isopropyl;

In a further preferred embodiment, $R_2$ is substituted or unsubstituted phenyl, substituted or unsubstituted pyridine, substituted or unsubstituted thiazole, unsubstituted methyl, unsubstituted isopropyl, unsubstituted O-isopropyl, substituted or unsubstituted morpholine or substituted or unsubstituted piperidine, more preferably, $R_2$ is substituted or unsubstituted phenyl or substituted or unsubstituted pyridine;

In another embodiment, $R_3$ and $R_3$' are independently selected from hydrogen, methyl and isopropyl.

In another embodiment, $R_3$ is isopropyl while $R_3$' is hydrogen.

In another embodiment, $R_3$ is methyl while $R_3$' is hydrogen.

In another embodiment, $R_3$ and $R_3$' are both hydrogen.

In another embodiment, $R_4$ and $R_4$' are independently selected from hydrogen and hydroxy, more preferably $R_4$ is hydroxy while $R_4$' is hydrogen, most preferably $R_4$ and $R_4$' are both hydrogen.

In another embodiment, $R_5$ is substituted or unsubstituted phenyl, substituted or unsubstituted cyclopropyl, substituted or unsubstituted pyridine, substituted or unsubstituted thiazole, methyltetrahydropyrane, substituted or unsubstituted piperidine, methylcyclopropyl, isopropyl, methyl, ethyl, methylphenyl and methylpyridine; most preferably $R_5$ is substituted or unsubstituted phenyl or substituted or unsubstituted pyridine.

In another embodiment, $R_5$ is —$NR_8R_{8'}$.

In another embodiment, $R_5$ is substituted or unsubstituted phenyl.

In another embodiment, $R_6$, and $R_{6'}$ are both hydrogen.

In another embodiment, $R_7$, and $R_{7'}$ are both hydrogen.

In another embodiment, $R_8$ and $R_{8'}$ are independently selected from hydrogen, methyl, phenyl, cyclopropyl and pyridine, more preferably $R_8$ is phenyl, methyl, pyridine or cyclopropyl while $R_{8'}$ is hydrogen or methyl, most preferably $R_8$ is hydrogen or methyl while $R_{8'}$ is pyridine, more preferably $R_8$ is hydrogen or methyl while $R_{8'}$ is cyclopropyl.

In another embodiment, $R_9$, $R_{9'}$ and $R_{9''}$ are independently selected from hydrogen and methyl.

In another embodiment, $R_{10}$ and $R_{10'}$ are both hydrogen.

In another embodiment, q is 1.

In another embodiment, n is 2.

In another embodiment, X is a bond.

In another embodiment, X is —C(O)—.

In another embodiment, X is —C(O)O—.

In another embodiment, X is —C($R_4R_{4'}$)—, wherein $R_4$ is OH and $R_{4'}$ is hydrogen.

In another embodiment, the halogen is fluorine, chlorine, iodine or bromine; most preferably, the halogen is fluorine or chlorine.

In another embodiment, the haloalkyl is —$CF_3$.

In another embodiment, the haloalkoxy is —$OCF_3$.

In preferred further embodiment the compounds of the general formula I are selected from

| EX | Chemical name |
|---|---|
| 1 | (2-methyl-9-phenethyl-1-oxa-4,9-diazaspiro[5.5]undecan-4-yl)(phenyl)methanone |
| 2 | (9-phenethyl-1-oxa-4,9-diazaspiro[5.5]undecan-4-yl)(phenyl)methanone |
| 3 | (2-methyl-9-phenethyl-1-oxa-4,9-diazaspiro[5.5]undecan-4-yl)(pyridin-2-yl)methanone |
| 4 | 1-(9-phenethyl-1-oxa-4,9-diazaspiro[5.5]undecan-4-yl)-2-phenylethanone |
| 5 | (9-phenethyl-1-oxa-4,9-diazaspiro[5.5]undecan-4-yl)(pyridin-3-yl)methanone |
| 6 | (9-phenethyl-1-oxa-4,9-diazaspiro[5.5]undecan-4-yl)(pyridin-4-yl)methanone |
| 7 | (4-chloropyridin-2-yl)(9-phenethyl-1-oxa-4,9-diazaspiro[5.5]undecan-4-yl)methanone |
| 8 | (2-methoxyphenyl)(9-phenethyl-1-oxa-4,9-diazaspiro[5.5]undecan-4-yl)methanone |
| 9 | (2-fluorophenyl)(9-phenethyl-1-oxa-4,9-diazaspiro[5.5]undecan-4-yl)methanone |
| 10 | 1-(2-methyl-9-phenethyl-1-oxa-4,9-diazaspiro[5.5]undecan-4-yl)ethanone |
| 11 | cyclopropyl(2-methyl-9-phenethyl-1-oxa-4,9-diazaspiro[5.5]undecan-4-yl)methanone |
| 12 | (9-phenethyl-1-oxa-4,9-diazaspiro[5.5]undecan-4-yl)(thiazol-4-yl)methanone |
| 13 | (9-phenethyl-1-oxa-4,9-diazaspiro[5.5]undecan-4-yl)(thiazol-2-yl)methanone |
| 14 | (9-phenethyl-1-oxa-4,9-diazaspiro[5.5]undecan-4-yl)(thiazol-5-yl)methanone |
| 15 | 1-(9-phenethyl-1-oxa-4,9-diazaspiro[5.5]undecan-4-yl)-2-(pyridin-3-yl)ethanone |
| 16 | 1-(9-phenethyl-1-oxa-4,9-diazaspiro[5.5]undecan-4-yl)-2-(tetrahydro-2H-pyran-4-yl)ethanone |
| 17 | (3-methoxyphenyl)(9-phenethyl-1-oxa-4,9-diazaspiro[5.5]undecan-4-yl)methanone |
| 18 | (9-phenethyl-1-oxa-4,9-diazaspiro[5.5]undecan-4-yl)(tetrahydro-2H-pyran-4-yl)methanone |
| 19 | 1-(9-phenethyl-1-oxa-4,9-diazaspiro[5.5]undecan-4-yl)-2-(pyridin-2-yl)ethanone |
| 20 | 2-cyclopropyl-1-(9-phenethyl-1-oxa-4,9-diazaspiro[5.5]undecan-4-yl)ethanone |
| 21 | (9-phenethyl-1-oxa-4,9-diazaspiro[5.5]undecan-4-yl)(5-(trifluoromethyl)pyridin-2-yl)methanone |
| 22 | (5-fluoropyridin-2-yl)(9-phenethyl-1-oxa-4,9-diazaspiro[5.5]undecan-4-yl)methanone |
| 23 | (5-chloropyridin-2-yl)(9-phenethyl-1-oxa-4,9-diazaspiro[5.5]undecan-4-yl)methanone |
| 24 | (9-phenethyl-1-oxa-4,9-diazaspiro[5.5]undecan-4-yl)(6-(trifluoromethyl)pyridin-3-yl)methanone |
| 25 | (3-fluoropyridin-2-yl)(9-phenethyl-1-oxa-4,9-diazaspiro[5.5]undecan-4-yl)methanone |
| 26 | (5-fluoropyridin-3-yl)(9-phenethyl-1-oxa-4,9-diazaspiro[5.5]undecan-4-yl)methanone |
| 27 | (2-methyl-9-phenethyl-1-oxa-4,9-diazaspiro[5.5]undecan-4-yl)(5-(trifluoromethyl)pyridin-2-yl)methanone |
| 28 | (5-fluoropyridin-2-yl)(2-methyl-9-phenethyl-1-oxa-4,9-diazaspiro[5.5]undecan-4-yl)methanone |
| 29 | (5-chloropyridin-2-yl)(2-methyl-9-phenethyl-1-oxa-4,9-diazaspiro[5.5]undecan-4-yl)methanone |
| 30 | 8-phenethyl-12-[(pyridin-2-yl)carbonyl]-4-oxa-8,12-diazadispiro[2.1.5.3]tridecane |
| 31 | 12-[(5-chloropyridin-2-yl)carbonyl]-8-phenethyl-4-oxa-8,12-diazadispiro[2.1.5.3]tridecane |
| 32 | (3-fluoropyridin-2-yl)(2-methyl-9-phenethyl-1-oxa-4,9-diazaspiro[5.5]undecan-4-yl)methanone |
| 33 | (5-fluoropyridin-3-yl)(2-methyl-9-phenethyl-1-oxa-4,9-diazaspiro[5.5]undecan-4-yl)methanone |
| 34 | (2-methyl-9-phenethyl-1-oxa-4,9-diazaspiro[5.5]undecan-4-yl)(4-(trifluoromethyl)pyridin-2-yl)methanone |
| 35 | (5-chloropyridin-3-yl)(2-methyl-9-phenethyl-1-oxa-4,9-diazaspiro[5.5]undecan-4-yl)methanone |
| 36 | (2-methyl-9-phenethyl-1-oxa-4,9-diazaspiro[5.5]undecan-4-yl)(5-(trifluoromethyl)pyridin-3-yl)methanone |
| 37 | (9-(2-(3-chloropyridin-2-yl)ethyl)-2-methyl-1-oxa-4,9-diazaspiro[5.5]undecan-4-yl)(phenyl)methanone |
| 38 | (2-methyl-9-(2-(6-(trifluoromethyl)pyridin-2-yl)ethyl)-1-oxa-4,9-diazaspiro[5.5]undecan-4-yl)(phenyl)methanone |
| 39 | (9-(2-(5-chloropyridin-2-yl)ethyl)-2-methyl-1-oxa-4,9-diazaspiro[5.5]undecan-4-yl)(phenyl)methanone |
| 40 | 6-(2-(4-benzoyl-2-methyl-1-oxa-4,9-diazaspiro[5.5]undecan-9-yl)ethyl)nicotinonitrile |
| 41 | (2-methyl-9-(2-(3-(trifluoromethyl)pyridin-2-yl)ethyl)-1-oxa-4,9-diazaspiro[5.5]undecan-4-yl)(phenyl)methanone |
| 42 | (2-methyl-9-(2-(5-(trifluoromethyl)pyridin-2-yl)ethyl)-1-oxa-4,9-diazaspiro[5.5]undecan-4-yl)(phenyl)methanone |
| 43 | (2-methyl-9-(2-(4-(trifluoromethyl)pyridin-2-yl)ethyl)-1-oxa-4,9-diazaspiro[5.5]undecan-4-yl)(phenyl)methanone |
| 44 | (2-methyl-9-(2-(3-nitropyridin-2-yl)ethyl)-1-oxa-4,9-diazaspiro[5.5]undecan-4-yl)(phenyl)methanone |
| 45 | (9-(2-(6-aminopyridin-2-yl)ethyl)-2-methyl-1-oxa-4,9-diazaspiro[5.5]undecan-4-yl)(phenyl)methanone |
| 46 | (2-methyl-9-(2-(2-nitropyridin-3-yl)ethyl)-1-oxa-4,9-diazaspiro[5.5]undecan-4-yl)(phenyl)methanone |
| 47 | (9-(2-(3-chloropyridin-2-yl)ethyl)-2-methyl-1-oxa-4,9-diazaspiro[5.5]undecan-4-yl)(2,6-difluorophenyl)methanone |

-continued

| EX | Chemical name |
|---|---|
| 48 | (9-(2-(3-chloropyridin-2-yl)ethyl)-2-methyl-1-oxa-4,9-diazaspiro[5.5]undecan-4-yl)(pyridin-2-yl)methanone |
| 49 | (9-(2-(3-chloropyridin-2-yl)ethyl)-2-methyl-1-oxa-4,9-diazaspiro[5.5]undecan-4-yl)(2-fluorophenyl)methanone |
| 50 | (9-(2-(3-chloropyridin-4-yl)ethyl)-2-methyl-1-oxa-4,9-diazaspiro[5.5]undecan-4-yl)(phenyl)methanone |
| 51 | (9-(2-(3-fluoropyridin-4-yl)ethyl)-2-methyl-1-oxa-4,9-diazaspiro[5.5]undecan-4-yl)(phenyl)methanone |
| 52 | (9-(2-(5-fluoropyridin-2-yl)ethyl)-2-methyl-1-oxa-4,9-diazaspiro[5.5]undecan-4-yl)(phenyl)methanone |
| 53 | (9-(2-(3-fluoropyridin-2-yl)ethyl)-2-methyl-1-oxa-4,9-diazaspiro[5.5]undecan-4-yl)(phenyl)methanone |
| 54 | 8-(2-(3-fluoropyridin-2-yl)ethyl)-12-[(2-fluorophenyl)carbonyl]-4-oxa-8,12-diazadispiro[2.1.5.3]tridecane |
| 55 | 1-(9-(2-(3-fluoropyridin-2-yl)ethyl)-2-methyl-1-oxa-4,9-diazaspiro[5.5]undecan-4-yl)propan-1-one |
| 56 | 8-(2-(3-fluoropyridin-2-yl)ethyl)-12-[(cyclopropyl)carbonyl]-4-oxa-8,12-diazadispiro[2.1.5.3]tridecane |
| 57 | 8-(2-(3-fluoropyridin-2-yl)ethyl)-12-[(2,6-difluorophenyl)carbonyl]-4-oxa-8,12-diazadispiro[2.1.5.3]tridecane |
| 58 | 8-(2-(3-chloropyridin-2-yl)ethyl)-12-[(2,6-difluorophenyl)carbonyl]-4-oxa-8,12-diazadispiro[2.1.5.3]tridecane |
| 59 | (2-fluorophenyl)(9-(2-(3-fluoropyridin-2-yl)ethyl)-2-methyl-1-oxa-4,9-diazaspiro[5.5]undecan-4-yl)methanone |
| 60 | (2,6-difluorophenyl)(9-(2-(3-fluoropyridin-2-yl)ethyl)-2-methyl-1-oxa-4,9-diazaspiro[5.5]undecan-4-yl)methanone |
| 61 | (9-(2-hydroxy-2-phenylethyl)-1-oxa-4,9-diazaspiro[5.5]undecan-4-yl)(phenyl)methanone |
| 62 | (9-(2-methoxyphenethyl)-1-oxa-4,9-diazaspiro[5.5]undecan-4-yl)(phenyl)methanone |
| 63 | phenyl(9-(2-(pyridin-2-yl)ethyl)-1-oxa-4,9-diazaspiro[5.5]undecan-4-yl)methanone |
| 64 | 9-phenethyl-N-phenyl-1-oxa-4,9-diazaspiro[5.5]undecane-4-carboxamide |
| 65 | cyclopropyl(9-phenethyl-1-oxa-4,9-diazaspiro[5.5]undecan-4-yl)methanone |
| 66 | (9-phenethyl-1-oxa-4,9-diazaspiro[5.5]undecan-4-yl)(pyridin-2-yl)methanone |
| 67 | N-methyl-9-phenethyl-N-phenyl-1-oxa-4,9-diazaspiro[5.5]undecane-4-carboxamide |
| 68 | (9-phenethyl-1-oxa-4,9-diazaspiro[5.5]undecan-4-yl)(piperidin-1-yl)methanone |
| 69 | phenyl(9-(3-(trifluoromethoxy)phenethyl)-1-oxa-4,9-diazaspiro[5.5]undecan-4-yl)methanone |
| 70 | phenyl(9-(2-(6-(trifluoromethyl)pyridin-3-yl)ethyl)-1-oxa-4,9-diazaspiro[5.5]undecan-4-yl)methanone |
| 71 | phenyl(9-(2-(pyridin-3-yl)ethyl)-1-oxa-4,9-diazaspiro[5.5]undecan-4-yl)methanone |
| 72 | (2-methyl-9-(2-(pyridin-3-yl)ethyl)-1-oxa-4,9-diazaspiro[5.5]undecan-4-yl)(phenyl)methanone |
| 73 | (9-(2-(6-methoxypyridin-2-yl)ethyl)-2-methyl-1-oxa-4,9-diazaspiro[5.5]undecan-4-yl)(phenyl)methanone |
| 74 | (2-methyl-9-(2-(pyridin-4-yl)ethyl)-1-oxa-4,9-diazaspiro[5.5]undecan-4-yl)(phenyl)methanone |
| 75 | 4-(2-(4-benzoyl-2-methyl-1-oxa-4,9-diazaspiro[5.5]undecan-9-yl)ethyl)benzenesulfonamide |
| 76 | (2-methyl-9-(2-(6-(trifluoromethyl)pyridin-3-yl)ethyl)-1-oxa-4,9-diazaspiro[5.5]undecan-4-yl)(phenyl)methanone |
| 77 | 4-(2-(4-benzoyl-2-methyl-1-oxa-4,9-diazaspiro[5.5]undecan-9-yl)ethyl)-N-methylbenzenesulfonamide |
| 78 | tert-butyl (4-(2-(4-(5-chloropicolinoyl)-2-methyl-1-oxa-4,9-diazaspiro[5.5]undecan-9-yl)ethyl)thiazol-2-yl)carbamate |
| 79 | tert-butyl (4-(2-(4-benzoyl-2-methyl-1-oxa-4,9-diazaspiro[5.5]undecan-9-yl)ethyl)thiazol-2-yl)carbamate |
| 80 | (2-methyl-9-(3-(trifluoromethoxy)phenethyl)-1-oxa-4,9-diazaspiro[5.5]undecan-4-yl)(pyridin-2-yl)methanone |
| 81 | (2-methyl-9-(2-nitrophenethyl)-1-oxa-4,9-diazaspiro[5.5]undecan-4-yl)(phenyl)methanone |
| 82 | (2-methyl-9-(3-nitrophenethyl)-1-oxa-4,9-diazaspiro[5.5]undecan-4-yl)(phenyl)methanone |
| 83 | 9-phenethyl-4-(phenylsulfonyl)-1-oxa-4,9-diazaspiro[5.5]undecane |
| 84 | 4-(isopropylsulfonyl)-9-phenethyl-1-oxa-4,9-diazaspiro[5.5]undecane |
| 85 | (2-methyl-9-(3-phenylpropyl)-1-oxa-4,9-diazaspiro[5.5]undecan-4-yl)(phenyl)methanone |
| 86 | (9-isopentyl-2-methyl-1-oxa-4,9-diazaspiro[5.5]undecan-4-yl)(phenyl)methanone |
| 87 | (2-methyl-9-(2-(pyridin-2-yl)ethyl)-1-oxa-4,9-diazaspiro[5.5]undecan-4-yl)(phenyl)methanone |
| 88 | (9-(2-isopropoxyethyl)-2-methyl-1-oxa-4,9-diazaspiro[5.5]undecan-4-yl)(phenyl)methanone |
| 89 | 2-(4-benzoyl-2-methyl-1-oxa-4,9-diazaspiro[5.5]undecan-9-yl)-1-morpholinoethanone |
| 90 | 2-(4-benzoyl-2-methyl-1-oxa-4,9-diazaspiro[5.5]undecan-9-yl)-1-(piperidin-1-yl)ethanone |
| 91 | 1-(9-(2-fluorophenethyl)-2-methyl-1-oxa-4,9-diazaspiro[5.5]undecan-4-yl)propan-1-one |

-continued

| EX | Chemical name |
|---|---|
| 92 | (9-(2-(5-chloropyridin-3-yl)ethyl)-2-methyl-1-oxa-4,9-diazaspiro[5.5]undecan-4-yl)(phenyl)methanone |
| 93 | (9-(2-(5-fluoropyridin-3-yl)ethyl)-2-methyl-1-oxa-4,9-diazaspiro[5.5]undecan-4-yl)(phenyl)methanone |
| 94 | 8-(2-fluorophenethyl)-12-[(pyridin-2-yl)carbonyl]-4-oxa-8,12-diazadispiro[2.1.5.3]tridecane |
| 95 | 1-(2-isopropyl-9-phenethyl-1-oxa-4,9-diazaspiro[5.5]undecan-4-yl)ethanone |
| 96 | cyclopropyl(2-isopropyl-9-phenethyl-1-oxa-4,9-diazaspiro[5.5]undecan-4-yl)methanone |
| 97 | (9-(3-nitrophenethyl)-1-oxa-4,9-diazaspiro[5.5]undecan-4-yl)(phenyl)methanone |
| 98 | (9-benzyl-2-methyl-1-oxa-4,9-diazaspiro[5.5]undecan-4-yl)(phenyl)methanone |
| 99 | (9-(2-hydroxyphenethyl)-1-oxa-4,9-diazaspiro[5.5]undecan-4-yl)(phenyl)methanone |
| 100 | (3-hydroxyphenyl)(9-phenethyl-1-oxa-4,9-diazaspiro[5.5]undecan-4-yl)methanone |
| 101 | (2-hydroxyphenyl)(9-phenethyl-1-oxa-4,9-diazaspiro[5.5]undecan-4-yl)methanone |
| 102 | (9-(2-(2-aminothiazol-4-yl)ethyl)-2-methyl-1-oxa-4,9-diazaspiro[5.5]undecan-4-yl)(5-chloropyridin-2-yl)methanone |
| 103 | (9-(2-(2-aminothiazol-4-yl)ethyl)-2-methyl-1-oxa-4,9-diazaspiro[5.5]undecan-4-yl)(phenyl)methanone |
| 104 | (9-(3-aminophenethyl)-1-oxa-4,9-diazaspiro[5.5]undecan-4-yl)(phenyl)methanone |
| 105 | (9-(2-aminophenethyl)-2-methyl-1-oxa-4,9-diazaspiro[5.5]undecan-4-yl)(phenyl)methanone |
| 106 | (9-(3-aminophenethyl)-2-methyl-1-oxa-4,9-diazaspiro[5.5]undecan-4-yl)(phenyl)methanone |
| 107 | (9-(2-(3-aminopyridin-2-yl)ethyl)-2-methyl-1-oxa-4,9-diazaspiro[5.5]undecan-4-yl)(phenyl)methanone |
| 108 | (9-(2-(2-aminopyridin-3-yl)ethyl)-2-methyl-1-oxa-4,9-diazaspiro[5.5]undecan-4-yl)(phenyl)methanone |
| 109 | 1-(3-(2-(4-benzoyl-2-methyl-1-oxa-4,9-diazaspiro[5.5]undecan-9-yl)ethyl)phenyl)urea |
| 110 | 1-(2-(2-(4-benzoyl-2-methyl-1-oxa-4,9-diazaspiro[5.5]undecan-9-yl)ethyl)phenyl)urea |
| 111 | N-(3-(2-(4-benzoyl-1-oxa-4,9-diazaspiro[5.5]undecan-9-yl)ethyl)phenyl)acetamide |
| 112 | N-(2-(2-(4-benzoyl-2-methyl-1-oxa-4,9-diazaspiro[5.5]undecan-9-yl)ethyl)phenyl)acetamide |
| 113 | N-(3-(2-(4-benzoyl-2-methyl-1-oxa-4,9-diazaspiro[5.5]undecan-9-yl)ethyl)phenyl)acetamide |
| 114 | N-(3-(2-(4-benzoyl-1-oxa-4,9-diazaspiro[5.5]undecan-9-yl)ethyl)phenyl)methanesulfonamide |
| 115 | 2-methyl-9-phenethyl-4-(phenylsulfonyl)-1-oxa-4,9-diazaspiro[5.5]undecane |
| 116 | 4-(isopropylsulfonyl)-2-methyl-9-phenethyl-1-oxa-4,9-diazaspiro[5.5]undecane |
| 117 | N,N-dimethyl-9-phenethyl-1-oxa-4,9-diazaspiro[5.5]undecane-4-carboxamide |
| 118 | N,N,2-trimethyl-9-phenethyl-1-oxa-4,9-diazaspiro[5.5]undecane-4-carboxamide |
| 119 | N-methyl-9-phenethyl-N-(pyridin-2-yl)-1-oxa-4,9-diazaspiro[5.5]undecane-4-carboxamide |
| 120 | N-cyclopropyl-9-phenethyl-1-oxa-4,9-diazaspiro[5.5]undecane-4-carboxamide |
| 121 | 9-phenethyl-N-(pyridin-3-yl)-1-oxa-4,9-diazaspiro[5.5]undecane-4-carboxamide |
| 122 | N-cyclopropyl-N-methyl-9-phenethyl-1-oxa-4,9-diazaspiro[5.5]undecane-4-carboxamide |
| 123 | N-methyl-9-phenethyl-N-(pyridin-3-yl)-1-oxa-4,9-diazaspiro[5.5]undecane-4-carboxamide |
| 124 | (R)-(2-methyl-9-phenethyl-1-oxa-4,9-diazaspiro[5.5]undecan-4-yl)(pyridin-2-yl)methanone |
| 125 | (S)-(2-methyl-9-phenethyl-1-oxa-4,9-diazaspiro[5.5]undecan-4-yl)(pyridin-2-yl)methanone |

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred further embodiment the compounds of the general formula I are selected from

| EX | Chemical name |
|---|---|
| 1 | (2-methyl-9-phenethyl-1-oxa-4,9-diazaspiro[5.5]undecan-4-yl)(phenyl)methanone |
| 2 | (9-phenethyl-1-oxa-4,9-diazaspiro[5.5]undecan-4-yl)(phenyl)methanone |
| 3 | (2-methyl-9-phenethyl-1-oxa-4,9-diazaspiro[5.5]undecan-4-yl)(pyridin-2-yl)methanone |
| 4 | 1-(9-phenethyl-1-oxa-4,9-diazaspiro[5.5]undecan-4-yl)-2-phenylethanone |
| 5 | (9-phenethyl-1-oxa-4,9-diazaspiro[5.5]undecan-4-yl)(pyridin-3-yl)methanone |
| 6 | (9-phenethyl-1-oxa-4,9-diazaspiro[5.5]undecan-4-yl)(pyridin-4-yl)methanone |
| 7 | (4-chloropyridin-2-yl)(9-phenethyl-1-oxa-4,9-diazaspiro[5.5]undecan-4-yl)methanone |
| 8 | (2-methoxyphenyl)(9-phenethyl-1-oxa-4,9-diazaspiro[5.5]undecan-4-yl)methanone |
| 9 | (2-fluorophenyl)(9-phenethyl-1-oxa-4,9-diazaspiro[5.5]undecan-4-yl)methanone |

-continued

| EX | Chemical name |
|---|---|
| 10 | 1-(2-methyl-9-phenethyl-1-oxa-4,9-diazaspiro[5.5]undecan-4-yl)ethanone |
| 11 | cyclopropyl(2-methyl-9-phenethyl-1-oxa-4,9-diazaspiro[5.5]undecan-4-yl)methanone |
| 12 | (9-phenethyl-1-oxa-4,9-diazaspiro[5.5]undecan-4-yl)(thiazol-4-yl)methanone |
| 13 | (9-phenethyl-1-oxa-4,9-diazaspiro[5.5]undecan-4-yl)(thiazol-2-yl)methanone |
| 14 | (9-phenethyl-1-oxa-4,9-diazaspiro[5.5]undecan-4-yl)(thiazol-5-yl)methanone |
| 15 | 1-(9-phenethyl-1-oxa-4,9-diazaspiro[5.5]undecan-4-yl)-2-(pyridin-3-yl)ethanone |
| 16 | 1-(9-phenethyl-1-oxa-4,9-diazaspiro[5.5]undecan-4-yl)-2-(tetrahydro-2H-pyran-4-yl)ethanone |
| 17 | (3-methoxyphenyl)(9-phenethyl-1-oxa-4,9-diazaspiro[5.5]undecan-4-yl)methanone |
| 18 | (9-phenethyl-1-oxa-4,9-diazaspiro[5.5]undecan-4-yl)(tetrahydro-2H-pyran-4-yl)methanone |
| 19 | 1-(9-phenethyl-1-oxa-4,9-diazaspiro[5.5]undecan-4-yl)-2-(pyridin-2-yl)ethanone |
| 20 | 2-cyclopropyl-1-(9-phenethyl-1-oxa-4,9-diazaspiro[5.5]undecan-4-yl)ethanone |
| 21 | (9-phenethyl-1-oxa-4,9-diazaspiro[5.5]undecan-4-yl)(5-(trifluoromethyl)pyridin-2-yl)methanone |
| 22 | (5-fluoropyridin-2-yl)(9-phenethyl-1-oxa-4,9-diazaspiro[5.5]undecan-4-yl)methanone |
| 23 | (5-chloropyridin-2-yl)(9-phenethyl-1-oxa-4,9-diazaspiro[5.5]undecan-4-yl)methanone |
| 24 | (9-phenethyl-1-oxa-4,9-diazaspiro[5.5]undecan-4-yl)(6-(trifluoromethyl)pyridin-3-yl)methanone |
| 25 | (3-fluoropyridin-2-yl)(9-phenethyl-1-oxa-4,9-diazaspiro[5.5]undecan-4-yl)methanone |
| 26 | (5-fluoropyridin-3-yl)(9-phenethyl-1-oxa-4,9-diazaspiro[5.5]undecan-4-yl)methanone |
| 27 | (2-methyl-9-phenethyl-1-oxa-4,9-diazaspiro[5.5]undecan-4-yl)(5-(trifluoromethyl)pyridin-2-yl)methanone |
| 28 | (5-fluoropyridin-2-yl)(2-methyl-9-phenethyl-1-oxa-4,9-diazaspiro[5.5]undecan-4-yl)methanone |
| 29 | (5-chloropyridin-2-yl)(2-methyl-9-phenethyl-1-oxa-4,9-diazaspiro[5.5]undecan-4-yl)methanone |
| 30 | 8-phenethyl-12-[(pyridin-2-yl)carbonyl]-4-oxa-8,12-diazadispiro[2.1.5.3]tridecane |
| 31 | 12-[(5-chloropyridin-2-yl)carbonyl]-8-phenethyl-4-oxa-8,12-diazadispiro[2.1.5.3]tridecane |
| 32 | (3-fluoropyridin-2-yl)(2-methyl-9-phenethyl-1-oxa-4,9-diazaspiro[5.5]undecan-4-yl)methanone |
| 33 | (5-fluoropyridin-3-yl)(2-methyl-9-phenethyl-1-oxa-4,9-diazaspiro[5.5]undecan-4-yl)methanone |
| 34 | (2-methyl-9-phenethyl-1-oxa-4,9-diazaspiro[5.5]undecan-4-yl)(4-(trifluoromethyl)pyridin-2-yl)methanone |
| 35 | (5-chloropyridin-3-yl)(2-methyl-9-phenethyl-1-oxa-4,9-diazaspiro[5.5]undecan-4-yl)methanone |
| 36 | (2-methyl-9-phenethyl-1-oxa-4,9-diazaspiro[5.5]undecan-4-yl)(5-(trifluoromethyl)pyridin-3-yl)methanone |
| 37 | (9-(2-(3-chloropyridin-2-yl)ethyl)-2-methyl-1-oxa-4,9-diazaspiro[5.5]undecan-4-yl)(phenyl)methanone |
| 38 | (2-methyl-9-(2-(6-(trifluoromethyl)pyridin-2-yl)ethyl)-1-oxa-4,9-diazaspiro[5.5]undecan-4-yl)(phenyl)methanone |
| 39 | (9-(2-(5-chloropyridin-2-yl)ethyl)-2-methyl-1-oxa-4,9-diazaspiro[5.5]undecan-4-yl)(phenyl)methanone |
| 40 | 6-(2-(4-benzoyl-2-methyl-1-oxa-4,9-diazaspiro[5.5]undecan-9-yl)ethyl)nicotinonitrile |
| 41 | (2-methyl-9-(2-(3-(trifluoromethyl)pyridin-2-yl)ethyl)-1-oxa-4,9-diazaspiro[5.5]undecan-4-yl)(phenyl)methanone |
| 42 | (2-methyl-9-(2-(5-(trifluoromethyl)pyridin-2-yl)ethyl)-1-oxa-4,9-diazaspiro[5.5]undecan-4-yl)(phenyl)methanone |
| 43 | (2-methyl-9-(2-(4-(trifluoromethyl)pyridin-2-yl)ethyl)-1-oxa-4,9-diazaspiro[5.5]undecan-4-yl)(phenyl)methanone |
| 44 | (2-methyl-9-(2-(3-nitropyridin-2-yl)ethyl)-1-oxa-4,9-diazaspiro[5.5]undecan-4-yl)(phenyl)methanone |
| 45 | (9-(2-(6-aminopyridin-2-yl)ethyl)-2-methyl-1-oxa-4,9-diazaspiro[5.5]undecan-4-yl)(phenyl)methanone |
| 46 | (2-methyl-9-(2-(2-nitropyridin-3-yl)ethyl)-1-oxa-4,9-diazaspiro[5.5]undecan-4-yl)(phenyl)methanone |
| 47 | (9-(2-(3-chloropyridin-2-yl)ethyl)-2-methyl-1-oxa-4,9-diazaspiro[5.5]undecan-4-yl)(2,6-difluorophenyl)methanone |
| 48 | (9-(2-(3-chloropyridin-2-yl)ethyl)-2-methyl-1-oxa-4,9-diazaspiro[5.5]undecan-4-yl)(pyridin-2-yl)methanone |
| 49 | (9-(2-(3-chloropyridin-2-yl)ethyl)-2-methyl-1-oxa-4,9-diazaspiro[5.5]undecan-4-yl)(2-fluorophenyl)methanone |
| 50 | (9-(2-(3-chloropyridin-4-yl)ethyl)-2-methyl-1-oxa-4,9-diazaspiro[5.5]undecan-4-yl)(phenyl)methanone |
| 51 | (9-(2-(3-fluoropyridin-4-yl)ethyl)-2-methyl-1-oxa-4,9-diazaspiro[5.5]undecan-4-yl)(phenyl)methanone |
| 52 | (9-(2-(5-fluoropyridin-2-yl)ethyl)-2-methyl-1-oxa-4,9-diazaspiro[5.5]undecan-4-yl)(phenyl)methanone |
| 53 | (9-(2-(3-fluoropyridin-2-yl)ethyl)-2-methyl-1-oxa-4,9-diazaspiro[5.5]undecan-4-yl)(phenyl)methanone |
| 54 | 8-(2-(3-fluoropyridin-2-yl)ethyl)-12-[(2-fluorophenyl)carbonyl]-4-oxa-8,12-diazadispiro[2.1.5.3]tridecane |
| 55 | 1-(9-(2-(3-fluoropyridin-2-yl)ethyl)-2-methyl-1-oxa-4,9-diazaspiro[5.5]undecan-4-yl)propan-1-one |

-continued

| EX | Chemical name |
|---|---|
| 56 | 8-(2-(3-fluoropyridin-2-yl)ethyl)-12-[(cyclopropyl)carbonyl]-4-oxa-8,12-diazadispiro[2.1.5.3]tridecane |
| 57 | 8-(2-(3-fluoropyridin-2-yl)ethyl)-12-[(2,6-difluorophenyl)carbonyl]-4-oxa-8,12-diazadispiro[2.1.5.3]tridecane |
| 58 | 8-(2-(3-chloropyridin-2-yl)ethyl)-12-[(2,6-difluorophenyl)carbonyl]-4-oxa-8,12-diazadispiro[2.1.5.3]tridecane |
| 59 | (2-fluorophenyl)(9-(2-(3-fluoropyridin-2-yl)ethyl)-2-methyl-1-oxa-4,9-diazaspiro[5.5]undecan-4-yl)methanone |
| 60 | (2,6-difluorophenyl)(9-(2-(3-fluoropyridin-2-yl)ethyl)-2-methyl-1-oxa-4,9-diazaspiro[5.5]undecan-4-yl)methanone |
| 61 | (9-(2-hydroxy-2-phenylethyl)-1-oxa-4,9-diazaspiro[5.5]undecan-4-yl)(phenyl)methanone |
| 62 | (9-(2-methoxyphenethyl)-1-oxa-4,9-diazaspiro[5.5]undecan-4-yl)(phenyl)methanone |
| 63 | phenyl(9-(2-(pyridin-2-yl)ethyl)-1-oxa-4,9-diazaspiro[5.5]undecan-4-yl)methanone |
| 64 | 9-phenethyl-N-phenyl-1-oxa-4,9-diazaspiro[5.5]undecane-4-carboxamide |
| 65 | cyclopropyl(9-phenethyl-1-oxa-4,9-diazaspiro[5.5]undecan-4-yl)methanone |
| 66 | (9-phenethyl-1-oxa-4,9-diazaspiro[5.5]undecan-4-yl)(pyridin-2-yl)methanone |
| 67 | N-methyl-9-phenethyl-N-phenyl-1-oxa-4,9-diazaspiro[5.5]undecane-4-carboxamide |
| 68 | (9-phenethyl-1-oxa-4,9-diazaspiro[5.5]undecan-4-yl)(piperidin-1-yl)methanone |
| 69 | phenyl(9-(3-(trifluoromethoxy)phenethyl)-1-oxa-4,9-diazaspiro[5.5]undecan-4-yl)methanone |
| 70 | phenyl(9-(2-(6-(trifluoromethyl)pyridin-3-yl)ethyl)-1-oxa-4,9-diazaspiro[5.5]undecan-4-yl)methanone |
| 71 | phenyl(9-(2-(pyridin-3-yl)ethyl)-1-oxa-4,9-diazaspiro[5.5]undecan-4-yl)methanone |
| 72 | (2-methyl-9-(2-(pyridin-3-yl)ethyl)-1-oxa-4,9-diazaspiro[5.5]undecan-4-yl)(phenyl)methanone |
| 73 | (9-(2-(6-methoxypyridin-2-yl)ethyl)-2-methyl-1-oxa-4,9-diazaspiro[5.5]undecan-4-yl)(phenyl)methanone |
| 74 | (2-methyl-9-(2-(pyridin-4-yl)ethyl)-1-oxa-4,9-diazaspiro[5.5]undecan-4-yl)(phenyl)methanone |
| 75 | 4-(2-(4-benzoyl-2-methyl-1-oxa-4,9-diazaspiro[5.5]undecan-9-yl)ethyl)benzenesulfonamide |
| 76 | (2-methyl-9-(2-(6-(trifluoromethyl)pyridin-3-yl)ethyl)-1-oxa-4,9-diazaspiro[5.5]undecan-4-yl)(phenyl)methanone |
| 77 | 4-(2-(4-benzoyl-2-methyl-1-oxa-4,9-diazaspiro[5.5]undecan-9-yl)ethyl)-N-methylbenzenesulfonamide |
| 78 | tert-butyl (4-(2-(4-(5-chloropicolinoyl)-2-methyl-1-oxa-4,9-diazaspiro[5.5]undecan-9-yl)ethyl)thiazol-2-yl)carbamate |
| 79 | tert-butyl (4-(2-(4-benzoyl-2-methyl-1-oxa-4,9-diazaspiro[5.5]undecan-9-yl)ethyl)thiazol-2-yl)carbamate |
| 80 | (2-methyl-9-(3-(trifluoromethoxy)phenethyl)-1-oxa-4,9-diazaspiro[5.5]undecan-4-yl)(pyridin-2-yl)methanone |
| 81 | (2-methyl-9-(2-nitrophenethyl)-1-oxa-4,9-diazaspiro[5.5]undecan-4-yl)(phenyl)methanone |
| 82 | (2-methyl-9-(3-nitrophenethyl)-1-oxa-4,9-diazaspiro[5.5]undecan-4-yl)(phenyl)methanone |
| 83 | 9-phenethyl-4-(phenylsulfonyl)-1-oxa-4,9-diazaspiro[5.5]undecane |
| 84 | 4-(isopropylsulfonyl)-9-phenethyl-1-oxa-4,9-diazaspiro[5.5]undecane |
| 85 | (2-methyl-9-(3-phenylpropyl)-1-oxa-4,9-diazaspiro[5.5]undecan-4-yl)(phenyl)methanone |
| 86 | (9-isopentyl-2-methyl-1-oxa-4,9-diazaspiro[5.5]undecan-4-yl)(phenyl)methanone |
| 87 | (2-methyl-9-(2-(pyridin-2-yl)ethyl)-1-oxa-4,9-diazaspiro[5.5]undecan-4-yl)(phenyl)methanone |
| 88 | (9-(2-isopropoxyethyl)-2-methyl-1-oxa-4,9-diazaspiro[5.5]undecan-4-yl)(phenyl)methanone |
| 89 | 2-(4-benzoyl-2-methyl-1-oxa-4,9-diazaspiro[5.5]undecan-9-yl)-1-morpholinoethanone |
| 90 | 2-(4-benzoyl-2-methyl-1-oxa-4,9-diazaspiro[5.5]undecan-9-yl)-1-(piperidin-1-yl)ethanone |
| 91 | 1-(9-(2-fluorophenethyl)-2-methyl-1-oxa-4,9-diazaspiro[5.5]undecan-4-yl)propan-1-one |
| 92 | (9-(2-(5-chloropyridin-3-yl)ethyl)-2-methyl-1-oxa-4,9-diazaspiro[5.5]undecan-4-yl)(phenyl)methanone |
| 93 | (9-(2-(5-fluoropyridin-3-yl)ethyl)-2-methyl-1-oxa-4,9-diazaspiro[5.5]undecan-4-yl)(phenyl)methanone |
| 94 | 8-(2-fluorophenethyl)-12-[(pyridin-2-yl)carbonyl]-4-oxa-8,12-diazadispiro[2.1.5.3]tridecane |
| 95 | 1-(2-isopropyl-9-phenethyl-1-oxa-4,9-diazaspiro[5.5]undecan-4-yl)ethanone |
| 96 | cyclopropyl(2-isopropyl-9-phenethyl-1-oxa-4,9-diazaspiro[5.5]undecan-4-yl)methanone |
| 97 | (9-(3-nitrophenethyl)-1-oxa-4,9-diazaspiro[5.5]undecan-4-yl)(phenyl)methanone |
| 98 | (9-benzyl-2-methyl-1-oxa-4,9-diazaspiro[5.5]undecan-4-yl)(phenyl)methanone |
| 99 | (9-(2-hydroxyphenethyl)-1-oxa-4,9-diazaspiro[5.5]undecan-4-yl)(phenyl)methanone |
| 100 | (3-hydroxyphenyl)(9-phenethyl-1-oxa-4,9-diazaspiro[5.5]undecan-4-yl)methanone |
| 101 | (2-hydroxyphenyl)(9-phenethyl-1-oxa-4,9-diazaspiro[5.5]undecan-4-yl)methanone |
| 102 | (9-(2-(2-aminothiazol-4-yl)ethyl)-2-methyl-1-oxa-4,9-diazaspiro[5.5]undecan-4-yl)(5-chloropyridin-2-yl)methanone |

-continued

| EX | Chemical name |
|---|---|
| 103 | (9-(2-(2-aminothiazol-4-yl)ethyl)-2-methyl-1-oxa-4,9-diazaspiro[5.5]undecan-4-yl)(phenyl)methanone |
| 104 | (9-(3-aminophenethyl)-1-oxa-4,9-diazaspiro[5.5]undecan-4-yl)(phenyl)methanone |
| 105 | (9-(2-aminophenethyl)-2-methyl-1-oxa-4,9-diazaspiro[5.5]undecan-4-yl)(phenyl)methanone |
| 106 | (9-(3-aminophenethyl)-2-methyl-1-oxa-4,9-diazaspiro[5.5]undecan-4-yl)(phenyl)methanone |
| 107 | (9-(2-(3-aminopyridin-2-yl)ethyl)-2-methyl-1-oxa-4,9-diazaspiro[5.5]undecan-4-yl)(phenyl)methanone |
| 108 | (9-(2-(2-aminopyridin-3-yl)ethyl)-2-methyl-1-oxa-4,9-diazaspiro[5.5]undecan-4-yl)(phenyl)methanone |
| 109 | 1-(3-(2-(4-benzoyl-2-methyl-1-oxa-4,9-diazaspiro[5.5]undecan-9-yl)ethyl)phenyl)urea |
| 110 | 1-(2-(2-(4-benzoyl-2-methyl-1-oxa-4,9-diazaspiro[5.5]undecan-9-yl)ethyl)phenyl)urea |
| 111 | N-(3-(2-(4-benzoyl-1-oxa-4,9-diazaspiro[5.5]undecan-9-yl)ethyl)phenyl)acetamide |
| 112 | N-(2-(2-(4-benzoyl-2-methyl-1-oxa-4,9-diazaspiro[5.5]undecan-9-yl)ethyl)phenyl)acetamide |
| 113 | N-(3-(2-(4-benzoyl-2-methyl-1-oxa-4,9-diazaspiro[5.5]undecan-9-yl)ethyl)phenyl)acetamide |
| 114 | N-(3-(2-(4-benzoyl-1-oxa-4,9-diazaspiro[5.5]undecan-9-yl)ethyl)phenyl)methanesulfonamide |
| 115 | 2-methyl-9-phenethyl-4-(phenylsulfonyl)-1-oxa-4,9-diazaspiro[5.5]undecane |
| 116 | 4-(isopropylsulfonyl)-2-methyl-9-phenethyl-1-oxa-4,9-diazaspiro[5.5]undecane |
| 117 | N,N-dimethyl-9-phenethyl-1-oxa-4,9-diazaspiro[5.5]undecane-4-carboxamide |
| 118 | N,N,2-trimethyl-9-phenethyl-1-oxa-4,9-diazaspiro[5.5]undecane-4-carboxamide |
| 119 | N-methyl-9-phenethyl-N-(pyridin-2-yl)-1-oxa-4,9-diazaspiro[5.5]undecane-4-carboxamide |
| 120 | N-cyclopropyl-9-phenethyl-1-oxa-4,9-diazaspiro[5.5]undecane-4-carboxamide |
| 121 | 9-phenethyl-N-(pyridin-3-yl)-1-oxa-4,9-diazaspiro[5.5]undecane-4-carboxamide |
| 122 | N-cyclopropyl-N-methyl-9-phenethyl-1-oxa-4,9-diazaspiro[5.5]undecane-4-carboxamide |
| 123 | N-methyl-9-phenethyl-N-(pyridin-3-yl)-1-oxa-4,9-diazaspiro[5.5]undecane-4-carboxamide |
| 124 | (R)-(2-methyl-9-phenethyl-1-oxa-4,9-diazaspiro[5.5]undecan-4-yl)(pyridin-2-yl)methanone |
| 125 | (S)-(2-methyl-9-phenethyl-1-oxa-4,9-diazaspiro[5.5]undecan-4-yl)(pyridin-2-yl)methanone |
| 126 | 8-(2-(3-fluoropyridin-2-yl)ethyl)-12-[(2,3-difluorophenyl)carbonyl]-4-oxa-8,12-diazadispiro[2.1.5.3]tridecane |
| 127 | 8-(2-(3-fluoropyridin-2-yl)ethyl)-12-[(2,4-difluorophenyl)carbonyl]-4-oxa-8,12-diazadispiro[2.1.5.3]tridecane |
| 128 | 2-(2-(12-(2-fluorobenzoyl)-4-oxa-8,12-diazadispiro[2.1.5.3]tridecan-8-yl)ethyl)nicotinonitrile |
| 129 | 8-(2-(3-fluoropyridin-2-yl)ethyl)-12-[(2,5-difluorophenyl)carbonyl]-4-oxa-8,12-diazadispiro[2.1.5.3]tridecane |
| 130 | 12-[(2-fluorophenyl)carbonyl]-8-(2-(3-methoxypyridin-2-yl)ethyl)-4-oxa-8,12-diazadispiro[2.1.5.3]tridecane |
| 131 | (2-fluorophenyl)(9-(2-(3-fluoropyridin-2-yl)ethyl)-2,2-dimethyl-1-oxa-4,9-diazaspiro[5.5]undecan-4-yl)methanone |
| 132 | 12-[(3-fluorophenyl)carbonyl]-8-(2-(3-fluoropyridin-2-yl)ethyl)-4-oxa-8,12-diazadispiro[2.1.5.3]tridecane |
| 133 | 12-[(4-fluorophenyl)carbonyl]-8-(2-(3-fluoropyridin-2-yl)ethyl)-4-oxa-8,12-diazadispiro[2.1.5.3]tridecane |
| 134 | 8-(2-(3-fluoropyridin-2-yl)ethyl)-12-[(2-methoxyphenyl)carbonyl]-4-oxa-8,12-diazadispiro[2.1.5.3]tridecane |
| 135 | 2-(8-(2-(3-fluoropyridin-2-yl)ethyl)-4-oxa-8,12-diazadispiro[2.1.5.3]tridecane-12-carbonyl)benzonitrile |
| 136 | 12-[(2-chlorophenyl)carbonyl]-8-(2-(3-fluoropyridin-2-yl)ethyl)-4-oxa-8,12-diazadispiro[2.1.5.3]tridecane |
| 137 | (2,3-difluorophenyl)(9-(2-(3-fluoropyridin-2-yl)ethyl)-2,2-dimethyl-1-oxa-4,9-diazaspiro[5.5]undecan-4-yl)methanone |
| 138 | 8-(2-(3-chloropyridin-2-yl)ethyl)-12-[(2,3-difluorophenyl)carbonyl]-4-oxa-8,12-diazadispiro[2.1.5.3]tridecane |
| 139 | 12-[(2-fluorophenyl)carbonyl]-8-(2-(6-methoxypyridin-2-yl)ethyl)-4-oxa-8,12-diazadispiro[2.1.5.3]tridecane |
| 140 | methyl 3-(12-(2,6-difluorobenzoyl)-4-oxa-8,12-diazadispiro[2.1.5.3]tridecan-8-yl)propanoate |
| 141 | 12-[(2,6-difluorophenyl)carbonyl]-8-(2-(6-methoxypyridin-2-yl)ethyl)-4-oxa-8,12-diazadispiro[2.1.5.3]tridecane |
| 142 | 8-(2,5-difluorophenethyl)-12-[(2,6-difluorophenyl)carbonyl]-4-oxa-8,12-diazadispiro[2.1.5.3]tridecane |
| 143 | (R)-(2-fluorophenyl)(9-(2-(3-fluoropyridin-2-yl)ethyl)-2-methyl-1-oxa-4,9-diazaspiro[5.5]undecan-4-yl)methanone |
| 144 | (S)-(2-fluorophenyl)(9-(2-(3-fluoropyridin-2-yl)ethyl)-2-methyl-1-oxa-4,9-diazaspiro[5.5]undecan-4-yl)methanone |
| 145 | (R)-(2,6-difluorophenyl)(9-(2-(3-fluoropyridin-2-yl)ethyl)-2-methyl-1-oxa-4,9-diazaspiro[5.5]undecan-4-yl)methanone |

-continued

| EX | Chemical name |
|---|---|
| 146 | (S)-(2,6-difluorophenyl)(9-(2-(3-fluoropyridin-2-yl)ethyl)-2-methyl-1-oxa-4,9-diazaspiro[5.5]undecan-4-yl)methanone |
| 147 | (2,3-difluorophenyl)(9-(2-(3-fluoropyridin-2-yl)ethyl)-2-methyl-1-oxa-4,9-diazaspiro[5.5]undecan-4-yl)methanone |
| 148 | (2,4-difluorophenyl)(9-(2-(3-fluoropyridin-2-yl)ethyl)-2-methyl-1-oxa-4,9-diazaspiro[5.5]undecan-4-yl)methanone |
| 149 | (2,5-difluorophenyl)(9-(2-(3-fluoropyridin-2-yl)ethyl)-2-methyl-1-oxa-4,9-diazaspiro[5.5]undecan-4-yl)methanone |
| 150 | (2-chlorophenyl)(9-(2-(3-fluoropyridin-2-yl)ethyl)-2-methyl-1-oxa-4,9-diazaspiro[5.5]undecan-4-yl)methanone |
| 151 | (3-fluorophenyl)(9-(2-(3-fluoropyridin-2-yl)ethyl)-2-methyl-1-oxa-4,9-diazaspiro[5.5]undecan-4-yl)methanone |

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another very preferred embodiment of the compound according to the invention according to general formula I' the compound is selected from compounds number 1-60, 62-87, 91-97 and 99-125;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another very preferred embodiment of the compound according to the invention according to general formula I' the compound is selected from compounds number 1-60, 62-87, 91-97 and 99-151;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to general formula I'' the compound is selected from compounds number 1-29, 32-53, 55, 59-60, 62-87, 91-93, 95-97, 99-125;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to general formula I'' the compound is selected from compounds number 1-29, 32-53, 55, 59-60, 62-87, 91-93, 95-97, 99-125, 131, 137, and 143-151;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another very preferred embodiment of the compound according to the invention according to general formula I''' the compound is selected from compounds number 30, 31, 54, 56-58 and 94;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another very preferred embodiment of the compound according to the invention according to general formula I''' the compound is selected from compounds number 30, 31, 54, 56-58, 94, 126-130, 132-136, and 138-142;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In a preferred embodiment of the compound according to the invention according to general formulas I, I', I'' or I''' wherein $R_1$ is $C(O)R_5$ or $S(O)_2R_5$;

$R_2$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, or substituted or unsubstituted heterocyclyl; with cycloalkyl, aryl, or heterocyclyl if substituted being substituted by substituents selected from halogen, $—R_9$, $—OR_9$, $—NO_2$, $—NR_9R_{9'''}$, $NR_9C(O)R_{9'}$, $—NR_9S(O)_2R_{9'}$, $—S(O)_2NR_9R_{9'}$, $—NR_9C(O)NR_{9'}R_{9''}$, $—SR_9$, $—S(O)R_9$, $S(O)_2R_9$, —CN, haloalkyl, haloalkoxy, $—C(O)OR_9$, $—C(O)NR_9R_{9'}$, =O, $—OCH_2CH_2OH$, $—NR_9S(O)_2NR_{9'}R_{9''}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another embodiment of the invention in the compound according to general formulas I, I', or I'' wherein $R_3$ and $R_3'$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl substituted or unsubstituted cycloalkyl, with cycloalkyl, heterocyclyl or aryl if substituted being substituted by substituents selected from halogen, $—R_9$, and $—OR_9$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another embodiment of the invention in the compound according to general formulas I, I', or I'' wherein $R_3$ and $R_3'$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl substituted or unsubstituted cycloalkyl, substituted or unsubstituted heterocyclyl, substituted or unsubstituted alkylcycloalkyl, substituted or unsubstituted alkylheterocyclyl, substituted or unsubstituted aryl, substituted or unsubstituted alkylaryl, with cycloalkyl, heterocyclyl or aryl if substituted (also in alkylaryl, alkylcycloalkyl or alkylheterocyclyl) being substituted by substituents selected from halogen, —$R_9$, and —$OR_9$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another embodiment of the invention in the compound according to general formulas I, I', I'' or I''' wherein $R_5$ is substituted or unsubstituted $C_{1-6}$ alkyl, substituted or unsubstituted $C_{2-6}$ alkenyl, substituted or unsubstituted $C_{2-6}$alkynyl, substituted or unsubstituted cycloalkyl, substituted or unsubstituted aryl, substituted or unsubstituted heterocyclyl, substituted or unsubstituted alkyl aryl, substituted or unsubstituted alkyl heterocyclyl and substituted or unsubstituted alkyl cycloalkyl, —$NR_8R_{8'}$, wherein said cycloalkyl, aryl or heterocyclyl if substituted (also in alkyl aryl, alkyl heterocyclyl, alkyl cycloalkyl) being substituted by substituents selected from halogen, —$R_9$, —$OR_9$, —$NO_2$, —$NR_9R_{9'''}$, —$NR_9C(O)R_{9'}$, —$NR_9S(O)_2R_{9'}$, —$S(O)_2NR_9R_{9'}$, —$NR_9C(O)NR_{9'}R_{9''}$, —$SR_9$, —$S(O)R_9$, —$S(O)_2R_{9'}$, —CN, haloalkyl, haloalkoxy, —$C(O)OR_9$ and —$C(O)NR_9R_{9'}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In a further preferred embodiment of the compound according to the invention according to general formulas I, I', I'' or I''' wherein $R_8$ and $R_8$' are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl, with cycloalkyl, aryl, or heterocyclyl if substituted being substituted by substituents selected from halogen, —$R_9$, —$OR_9$, —$NO_2$, —$NR_9R_{9'''}$, $NR_9C(O)R_{9'}$, —$NR_9S(O)_2R_{9'}$, —$S(O)_2NR_9R_{9'}$, —$NR_9C(O)NR_{9'}R_{9''}$, —$SR_9$, —$S(O)R_9$, —$S(O)_2R_9$, —CN, -haloalkyl, and haloalkoxy;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention wherein wherein alkyl, alkenyl- or alkynyl moieties if defined for $R_2$, $R_3$, $R_{3'}$, $R_4$, $R_{4'}$, $R_5$, $R_6$, $R_{6'}$, $R_7$, $R_{7'}$, $R_8$, $R_{8'}$, $R_{10}$ and $R_{10'}$ are unsubstituted or substituted by one or more substituents selected from halogen, —$OR_9$, —$SR_9$, —CN, -haloalkyl, -haloalkoxy and —$NR_9R_{9'''}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In a preferred embodiment of the compound according to the invention according to general formulas I, I', I'' or I''' wherein $R_2$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, or substituted or unsubstituted heterocyclyl; with cycloalkyl, aryl, or heterocyclyl if substituted being substituted by substituents selected from halogen, —$R_9$, —$OR_9$, —$NO_2$, —$NR_9R_{9'''}$, $NR_9C(O)R_{9'}$, —$NR_9S(O)_2$ $R_{9'}$, —$S(O)_2NR_9R_{9'}$, —$NR_9C(O)NR_{9'}R_{9''}$, —$SR_9$, —$S(O)R_9$, $S(O)_2R_9$, —CN, haloalkyl, haloalkoxy, —$C(O)OR_9$, —$C(O)NR_9R_{9'}$, =O, —$OCH_2CH_2OH$, —$NR_9S(O)_2NR_{9'}R_{9''}$; wherein the aryl is selected from phenyl, naphtyl, or anthracene; preferably is napthyl and phenyl; more preferably is phenyl; and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline, more preferably the heterocycle is pyridine, piperidine, thiazole, morpholine; and/or the $C_{1-6}$ alkyl is preferably selected from methyl, ethyl, propyl, butyl, pentyl or hexyl, isopropyl, or 2-methylpropyl, more preferably the $C_{1-6}$ alkyl is isopropyl;

and/or the is $C_{2-6}$-alkenyl, is preferably selected from ethylene, propylene, butylene, pentylene or hexylene;

and/or the is $C_{2-6}$-alkynyl is preferably selected from ethyne, propyne, butyne, pentyne or hexyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another embodiment of the invention in the compound according to general formulas I, I', or I'' wherein $R_3$ and $R_3$' are independently selected from hydrogen, substituted or unsubstituted $C_{1-6}$ alkyl, substituted or unsubstituted $C_{2-6}$ alkenyl, substituted or unsubstituted $C_{2-6}$ alkynyl substituted or unsubstituted cycloalkyl, with cycloalkyl, if substituted being substituted by substituents selected from halogen, —$R_9$, and —$OR_9$; wherein the $C_{1-6}$ alkyl is preferably selected from methyl, ethyl, propyl, butyl, pentyl, hexyl, isopropyl, or 2-methylpropyl; preferably the $C_{1-6}$ alkyl is methyl, or isopropyl, and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably the cycloalkyl is cyclopropyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another embodiment of the invention in the compound according to general formulas I, I', or I" wherein $R_3$ and $R_3'$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl substituted or unsubstituted cycloalkyl, substituted or unsubstituted heterocyclyl, substituted or unsubstituted alkylcycloalkyl, substituted or unsubstituted alkylheterocyclyl, substituted or unsubstituted aryl, substituted or unsubstituted alkylaryl, with cycloalkyl, heterocyclyl or aryl if substituted (also in alkylaryl, alkylcycloalkyl or alkylheterocyclyl) being substituted by substituents selected from halogen, $—R_9$, and $—OR_9$; wherein the aryl is selected from phenyl, naphtyl, or anthracene; preferably is napthyl and phenyl, more preferably phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline, and/or the alkyl is $C_{1-6}$ alkyl like methyl, ethyl, propyl, butyl, pentyl or hexyl; preferably the alkyl is methyl, and/or the $C_{1-6}$ alkyl is preferably selected from methyl, ethyl, propyl, butyl, pentyl or hexyl, isopropyl, or 2-methylpropyl, more preferably the $C_{1-6}$ alkyl is methyl or isopropyl;

and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably the cycloalkyl is cyclopropyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another embodiment of the invention in the compound according to general formulas I, I', I" or I'" wherein $R_5$ is substituted or unsubstituted $C_{1-6}$ alkyl, substituted or unsubstituted $C_{2-6}$ alkenyl, substituted or unsubstituted $C_{2-6}$alkynyl, substituted or unsubstituted cycloalkyl, substituted or unsubstituted aryl, substituted or unsubstituted heterocyclyl, substituted or unsubstituted alkyl aryl, substituted or unsubstituted alkyl heterocyclyl and substituted or unsubstituted alkyl cycloalkyl, $—NR_8R_{8'}$, wherein said cycloalkyl, aryl or heterocyclyl if substituted (also in alkyl aryl, alkyl heterocyclyl, alkyl cycloalkyl) being substituted by substituents selected from halogen, $—R_9$, $—OR_9$, $—NO_2$, $—NR_9R_{9'''}$, $—NR_9C(O)R_{9'}$, $—NR_9S(O)_2R_{9'}$, $—S(O)_2NR_9R_{9'}$, $—NR_9C(O)NR_{9'}R_{9''}$, $—SR_9$, $—S(O)R_9$, $—S(O)_2R_9$, —CN, haloalkyl, haloalkoxy, $—C(O)OR_9$ and $—C(O)NR_9R_{9'}$; wherein the aryl is selected from phenyl, naphtyl, or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline, more preferably the heterocycle is pyridine, thiazole, tetrahydropyrane or piperidine;

and/or the alkyl is $C_{1-6}$ alkyl like methyl, ethyl, propyl, butyl, pentyl or hexyl, more preferably the alkyl is methyl or ethyl;

and/or the $C_{1-6}$ alkyl is preferably selected from methyl, ethyl, propyl, butyl, pentyl or hexyl, isopropyl, or 2-methylpropyl, more preferably the $C_{1-6}$ alkyl is methyl, ethyl or isopropyl;

and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably the cycloalkyl is cyclopropyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In a further preferred embodiment of the compound according to the invention according to general formulas I, I', I'' or I''' wherein $R_8$ and $R_8'$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl, with cycloalkyl, aryl, or heterocyclyl if substituted being substituted by substituents selected from halogen, —$R_9$, —$OR_9$, —$NO_2$, —$NR_9R_{9'''}$, $NR_9C(O)R_{9'}$, —$NR_9S(O)_2R_{9'}$, —$S(O)_2NR_9R_{9'}$, —$NR_9C(O)NR_{9'}R_{9''}$, —$SR_9$, —$S(O)R_9$, —$S(O)_2R_9$, —CN, -haloalkyl, and haloalkoxy; wherein the aryl is selected from phenyl, naphtyl, or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline, more preferably the heterocycle is pyridine, thiazole, tetrahydropyrane or piperidine; more preferably pyridine;

and/or the $C_{1-6}$ alkyl is preferably selected from methyl, ethyl, propyl, butyl, pentyl or hexyl, isopropyl, 2-methylpropyl; more preferably the $C_{1-6}$ alkyl is methyl, ethyl, isopropyl; more preferably methyl;

and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably the cycloalkyl is cyclopropyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

As this invention is aimed at providing a compound or a chemically related series of compounds which act as dual ligands of the σ1 receptor and the μ-opiod receptor it is a very preferred embodiment in which the compounds are selected which act as dual ligands of the σ1 receptor and the μ-opiod receptor and especially compounds which have a binding expressed as $K_i$ which is preferably <1000 nM for both receptors, more preferably <500 nM, even more preferably <100 nM.

In the following the phrase "compound of the invention" is used. This is to be understood as any compound according to the invention as described above according to general formulas I, I', I'' or I'''.

The compounds of the invention represented by the above described formula (I) may include enantiomers depending on the presence of chiral centres or isomers depending on the presence of multiple bonds (e.g. Z, E). The single isomers, enantiomers or diastereoisomers and mixtures thereof fall within the scope of the present invention.

In general the processes are described below in the experimental part. The starting materials are commercially available or can be prepared by conventional methods.

As a further general remark, the use of "comprising" and "comprises" as used herein, especially when defining the steps of a process is to be understood as also disclosing "consisting of" and "consists of" respectively etc. Thus, this also includes that the steps of the respective process are then to be also understood to be limited to the steps preceded by this "comprising" or "comprises" etc.

A preferred aspect of the invention is also a process for the production of a compound according to formula I, (I)

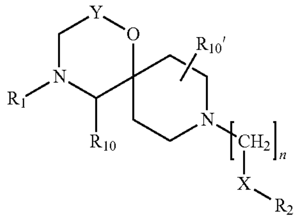

wherein $R_1$, $R_2$, $R_{10}$, $R_{10'}$, X, Y and n are as already defined above in the description, wherein a compound of formula VH or its suitable salt like the hydrochloride (VH)

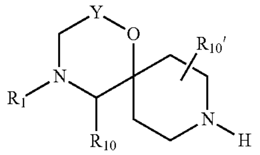

wherein $R_1$, $R_{10}$, $R_{10'}$ and Y are as already defined above in the description, is reacted with a compound according to formula VI, VII or VIII (VI)

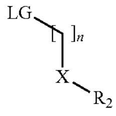

(VII)

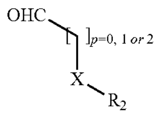

or

-continued (VIII)

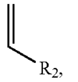

wherein $R_2$, X and n are as already defined above in the description, and wherein LG is a leaving group, leading to a compound according to formula (I).

In a first embodiment of the invention is also a process for the production of a compound according to formula VH (VH)

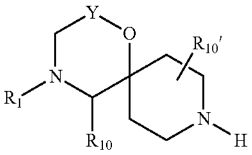

wherein $R_1$, $R_{10}$, $R_{10'}$ and Y are as already defined above in the description, by deprotection of a compound of formula VP or its suitable salt like the hydrochloride, (VP)

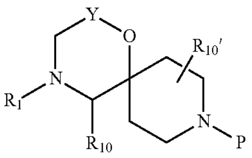

wherein P represents a suitable protecting group, preferably Boc (tert-butoxycarbonyl), and $R_1$, $R_{10}$, $R_{10'}$ and Y are as already defined above in the description;

In another embodiment of the invention is also a process for the production of a compound according to formula VA (VA)

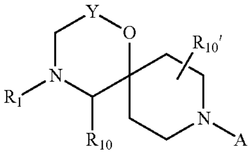

wherein A is hydrogen or P or $(CH_2)_nXR_2$, wherein P is a protecting group, and wherein $R_1$, $R_{10}$, $R_{10'}$ and Y are as already defined above in the description;

by reacting a compound of formula IIIA (IIIA)

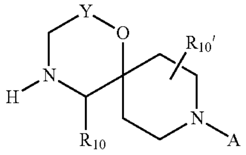

wherein A is hydrogen or P or $(CH_2)_nXR_2$, wherein P is a protecting group, and wherein $R_{10}$, $R_{10'}$ and Y are as already defined above in the description with a compound of formula IV $R_1Z$ (IV)

Wherein $R_1$ is as defined for formula (I) in the description and Z represents COOH, COW or $SO_2W$, wherein W represents halogen.

A particular embodiment is a process for the preparation of a compound of general formula IIIA (IIIA)

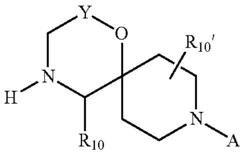

wherein A is hydrogen or P or $(CH_2)_nXR_2$, wherein P is a protecting group, and wherein $R_{10}$, $R_{10'}$ and Y are as already defined above in the description, which comprises the reduction of a compound of formula IIA (IIA)

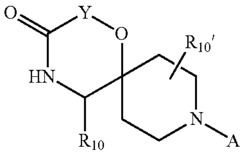

wherein A is hydrogen or P or $(CH_2)_nXR_2$, wherein P is a protecting group, and wherein $R_{10}$, $R_{10'}$ and Y are as already defined above in the description, using a suitable reducing agent such as lithium aluminium hydride, borane-tetrahydrofuran complex or borane-dimethyl sulphide complex, in a suitable solvent such as tetrahydrofuran, at a suitable temperature comprised between room temperature and the reflux temperature, preferably heating.

A particular embodiment is a process for the preparation of a compound of general formula IIIA (IIIA)

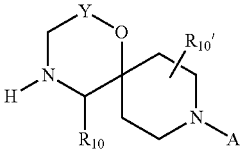

wherein A is hydrogen or P or $(CH_2)_nXR_2$, wherein P is a protecting group, and wherein $R_{10}$, $R_{10'}$ and Y are as already defined above in the description, which comprises the deprotection of a compound of formula XVIA preferably carried out by hydrogenation under hydrogen atmosphere and metal catalysis;

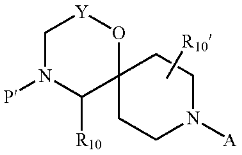

(XVIA)

wherein A is hydrogen or P or $(CH_2)_nXR_2$, wherein P and P' are protecting groups, and wherein $R_{10}$, $R_{10'}$ and Y are as already defined above in the description, A particular embodiment is a process for the preparation of a compound of general formula XVIA

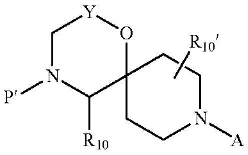

(XVIA)

wherein A is hydrogen or P or $(CH_2)_nXR_2$, wherein P and P' are protecting groups, and wherein $R_{10}$, $R_{10'}$ and Y are as already defined above in the description, which comprises the reduction of a compound of formula XVA

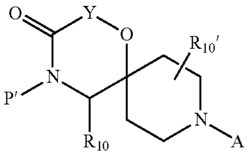

(XVA)

wherein A is hydrogen or P or $(CH_2)_nXR_2$, wherein P and P' are protecting groups, and wherein $R_{10}$, $R_{10'}$ and Y are as already defined above in the description, using a suitable reducing agent such as lithium aluminium hydride, borane-tetrahydrofuran complex or borane-dimethyl sulphide complex, in a suitable solvent such as tetrahydrofuran, at a suitable temperature comprised between room temperature and the reflux temperature, preferably heating.

Another embodiment is a process for the preparation of a compound of general formula XVA

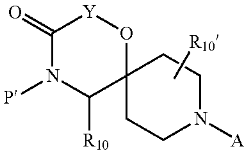

(XVA)

wherein A is hydrogen or P or $(CH_2)_nXR_2$, wherein P and P' are protecting groups, and wherein $R_{10}$, $R_{10'}$ and Y are as already defined above in the description, which comprises the cyclisation of the compound of formula XIVA

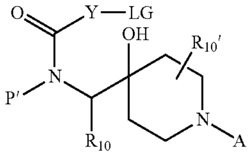

(XIVA)

wherein A is hydrogen or P or $(CH_2)_nXR_2$, wherein P and P' are protecting groups, and wherein $R_{10}$, $R_{10'}$ and Y are as already defined above in the description, in a suitable solvent, in the presence of a strong base and at a temperature comprised between −78° C. and the reflux temperature;

Another embodiment is a process for the preparation of a compound of general formula XIVA

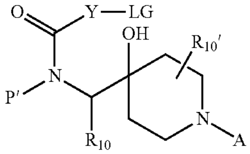

(XIVA)

wherein A is hydrogen or P or $(CH_2)_nXR_2$, wherein P and P' are protecting groups, and wherein $R_{10}$, $R_{10'}$ and Y are as already defined above in the description, which comprises reacting a compound of formula XIIA

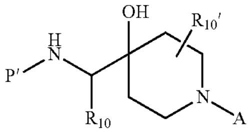

(XIIA)

wherein A is hydrogen or P or $(CH_2)_nXR_2$, wherein P and P' are protecting groups, and wherein $R_{10}$, $R_{10'}$ and Y are as already defined above in the description, with a compound of formula XIII

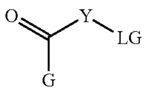

(XIII)

wherein G and LG are leaving groups, and Y is as already described above in the description;

Another particular embodiment of the invention is a process for the preparation of a compound of general formula XVbA (XVbA)

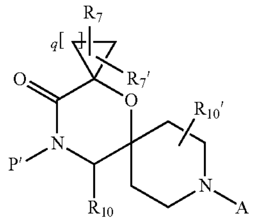

wherein A is hydrogen or P or $(CH_2)_nXR_2$, wherein P and P' are protecting groups, and wherein $R_7$, $R_{7'}$, $R_{10}$ and $R_{10'}$ are as already defined above in the description, from a compound of formula XXIIIA (XXIIIA)

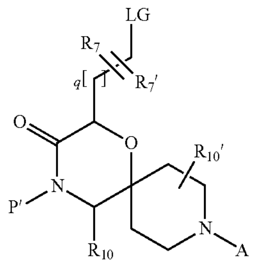

wherein A is hydrogen or P or $(CH_2)_nXR_2$, wherein P and P' are protecting groups, and wherein $R_7$, $R_{7'}$, $R_{10}$ and $R_{10'}$ are as already defined above in the description, by treatment with a strong base such as lithium diisopropylamide or potassium tert-butoxide, in an aprotic solvent such as tetrahydrofuran, at a suitable temperature, preferably cooling at 0° C.

A further embodiment of the invention is a process for for the preparation of a compound of general formula XVcA (XVcA)

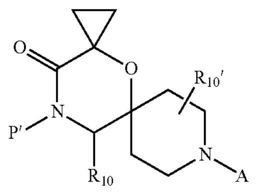

wherein A is hydrogen or P or $(CH_2)_nXR_2$, wherein P and P' are protecting groups, and and wherein $R_{10}$ and $R_{10'}$ are as already defined above in the description from a compound of formula XXIIIA (XXIIIA)

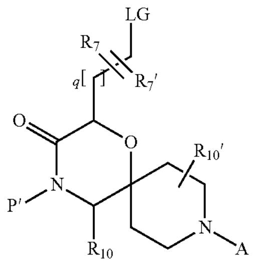

wherein A is hydrogen or P or $(CH_2)_nXR_2$, wherein P and P' are protecting groups, and wherein $R_{10}$ and $R_{10'}$ are as already defined in above in the description, when q=1 and $R_7$ and $R_{7'}$ are hydrogen, by treatment with a strong base such as lithium diisopropylamide or potassium tert-butoxide, in an aprotic solvent such as tetrahydrofuran, at a suitable temperature, preferably cooling at 0° C.

A further embodiment of the invention is a process for for the preparation of a compound of general formula XVcA (XVcA)

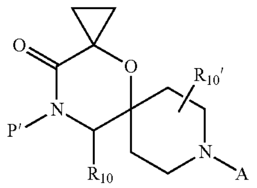

wherein A is hydrogen or P or $(CH_2)_nXR_2$, wherein P and P' are protecting groups, and wherein $R_{10}$ and $R_{10'}$ are as already defined above in the description, comprising the cyclopropanation of a compound of formula XVaA using a suitable methyl-transfer reagent such as trimethylsulfoxonium iodide or trimethylsulfonium iodide, in a suitable aprotic solvent such as dimethylsulfoxide, and in the presence of a strong base such as sodium hydride or potassium tert-butoxide, at a suitable temperature, preferably comprised between room temperature and 60° C.

(XVaA)

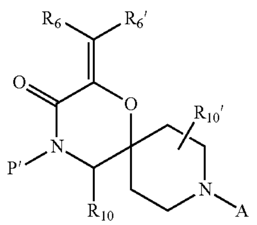

wherein A is hydrogen or P or $(CH_2)_nXR_2$, wherein P and P' are protecting groups, and wherein $R_{10}$ and $R_{10'}$ are as already defined above in the description, when $R_6$, and $R_{6'}$ are hydrogen.

A further embodiment of the invention is a process for for the preparation of a compound of general formula XVaA (XVaA)

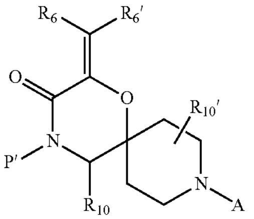

wherein A is hydrogen or P or $(CH_2)_nXR_2$, wherein P and P' are protecting groups, and wherein $R_6$, $R_{6'}$, $R_{10}$ and $R_{10'}$ are as already defined above in the description, comprising the dehydration of a compound of formula XXIA (XXIA)

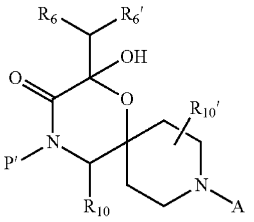

wherein A is hydrogen or P or $(CH_2)_nXR_2$, wherein P and P' are protecting groups, and wherein $R_6$, $R_{6'}$, $R_{10}$ and $R_{10'}$ are as already defined above in the description, with a dehydrating agent such as boron trifluoride diethyl etherate, in a suitable solvent such as dichloromethane, at a suitable temperature preferably at room temperature.

A further embodiment of the invention is a process for the preparation of a compound of general formula I"

(I")

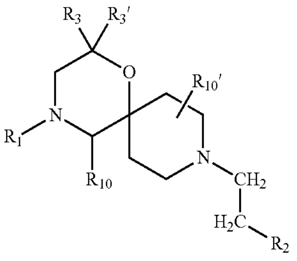

wherein $R_1$, $R_2$, $R_3$, $R_{3'}$, $R_{10}$ and $R_{10'}$ are as already defined in the description, comprising (a) reacting a compound of formula XIIx (XIIx)

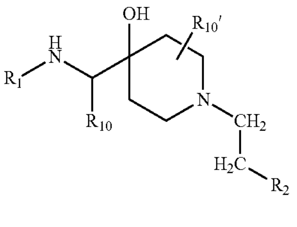

wherein $R_1$, $R_2$, $R_{10}$ and $R_{10'}$ are as defined in the description, with a compound of formula XIIIx (XIIIx)

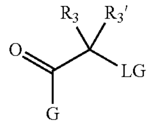

wherein $R_3$ and $R_{3'}$ are as defined in the description, and LG and G are leaving groups to obtain a compound of formula XIVx (XIVx)

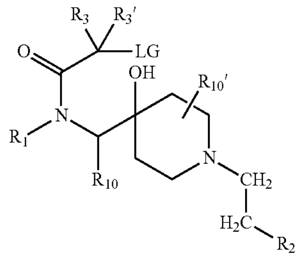

wherein $R_1$, $R_2$, $R_3$, $R_{3'}$, $R_{10}$ and $R_{10'}$ are as already defined in the preceding claims, and LG is a leaving group, (b) carrying out a cyclization of the resulting compound of formula XIVx in a suitable solvent, such as tetrahydrofuran; in the presence of a strong base such as potassium tert-butoxide or sodium hydride; and at a suitable temperature, comprised between −78° C. and the reflux temperature, preferably cooling, to obtain an compound of formula XVx (XVx)

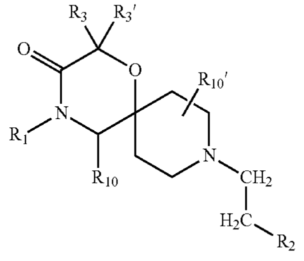

wherein $R_1$, $R_2$, $R_3$, $R_{3'}$, $R_{10}$ and $R_{10'}$ are as already defined in the preceding claims (c) and carrying out a reduction reaction by using a suitable reducing agent such as lithium aluminium hydride, borane-tetrahydrofuran complex or borane-dimethyl sulphide complex, in a suitable solvent such as tetrahydrofuran, at a suitable temperature comprised between room temperature and the reflux temperature, preferably heating, to yield a compound of formula I".

A further embodiment of the invention is a process for the preparation of a compound of general formula I'''

(I''')

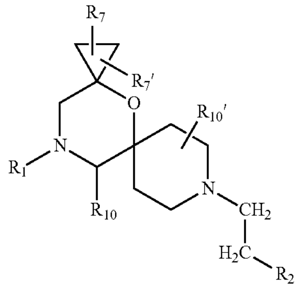

wherein $R^1$, $R^{10}$ and $R^{10'}$ are as already defined above in the preceding claims and $R^7$ and $R^{7'}$ are both hydrogen, comprising (a) the dehydration of a compound of formula XXIx (XXIx)

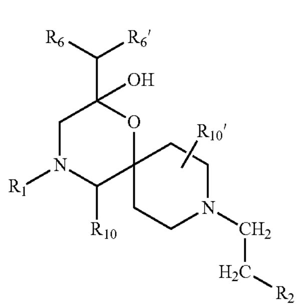

wherein $R_1$, $R_2$, $R_{10}$ and $R_{10'}$ are as already defined above in the description, and $R_6$ and $R_{6'}$ are both hydrogen, with a dehydrating agent such as boron trifluoride diethyl etherate, in a suitable solvent such as dichloromethane, at a suitable temperature preferably at room temperature, and (b) the cyclopropanation of a compound of formula XVax (XVax)

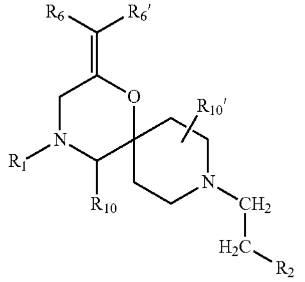

wherein $R_1$, $R_2$, $R_{10}$ and $R_{10'}$ are as already defined above in the description, and $R_6$ and $R_{6'}$ are both hydrogen, using a suitable methyl-transfer reagent such as trimethylsulfoxonium iodide or trimethylsulfonium iodide, in a suitable aprotic solvent such as dimethylsulfoxide, and in the presence of a strong base such as sodium hydride or potassium tert-butoxide, at a suitable temperature, preferably comprised between room temperature and 60° C.

The compound of formula I corresponds to the above compound of formula XVax when n=2, X is a bond and Y is

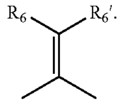

A particular embodiment is a process for the preparation of a compound of general formulas I, I', I'' or I''' wherein the hydrogen, the blocking agent P or the $—(CH_2)_n—X—R_2$ group defined as A in the above general Markush formulas may be incorporated in any step during the process.

Preparation of the hydrochloride salt: To a solution of the free base in a suitable salt, preferably in anhydrous diethyl ether, HCl was added. The solvent was evaporated to dryness to give the corresponding HCl salt.

The obtained reaction products may, if desired, be purified by conventional methods, such as crystallisation and chromatography. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form of a compound of the invention is the crystalline form, including such form in pharmaceutical composition. In the case of salts and also solvates of the compounds of the invention the additional ionic and solvent moieties must also be non-toxic. The compounds of the invention may present different polymorphic forms, it is intended that the invention encompasses all such forms.

Another aspect of the invention refers to a pharmaceutical composition which comprises a compound according to the invention as described above according to general formulas I, I', I'' or I''' or a pharmaceutically acceptable salt or stereoisomer thereof, and a pharmaceutically acceptable carrier, adjuvant or vehicle. The present invention thus provides pharmaceutical compositions comprising a compound of this invention, or a pharmaceutically acceptable salt or stereoisomers thereof together with a pharmaceutically acceptable carrier, adjuvant, or vehicle, for administration to a patient.

As a general remark, the use of "comprising" and "comprises" as used herein, especially when defining the contents of a medicament or a pharmaceutical formulation is to be understood as also disclosing "consisting of" and "consists of" respectively etc. Thus, this also includes that the contents of the respective medicament or pharmaceutical formulation are then to be also understood to be limited to the exact contents preceded by this "comprising" or "comprises" etc.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrops or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the apropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

Another aspect of the invention refers to the use of a compound of the invention or a pharmaceutically acceptable salt or isomer thereof in the manufacture of a medicament.

Another aspect of the invention refers to a compound of the invention according as described above according to general formulas I, I', I'' or I''' or a pharmaceutically acceptable salt or isomer thereof, for use as a medicament for the treatment of pain. Preferably the pain is medium to severe pain, visceral pain, chronic pain, cancer pain, migraine, inflammatory pain, acute pain or neuropathic pain, allodynia or hyperalgesia. This may include mechanical allodynia or thermal hyperalgesia.

Another aspect of the invention refers to the use of a compound of the invention in the manufacture of a medicament for the treatment or prophylaxis of pain.

In a preferred embodiment the pain is selected from medium to severe pain, visceral pain, chronic pain, cancer pain, migraine, inflammatory pain, acute pain or neuropathic pain, allodynia or hyperalgesia, also preferably including mechanical allodynia or thermal hyperalgesia.

Another aspect of this invention relates to a method of treating or preventing pain which method comprises administering to a patient in need of such a treatment a therapeutically effective amount of a compound as above defined or a pharmaceutical composition thereof. Among the pain syndromes that can be treated are medium to severe pain, visceral pain, chronic pain, cancer pain, migraine, inflammatory pain, acute pain or neuropathic pain, allodynia or hyperalgesia, whereas this could also include mechanical allodynia or thermal hyperalgesia.

The present invention is illustrated below with the aid of examples. These illustrations are given solely by way of example and do not limit the general spirit of the present invention.

EXAMPLES

General Experimental Part (Methods and Equipment of the Synthesis and Analysis)

Scheme 1

A 2-step process is described for the preparation of compounds of general formula (I) starting from a compound of formula II, as shown in the following scheme:

Scheme 1

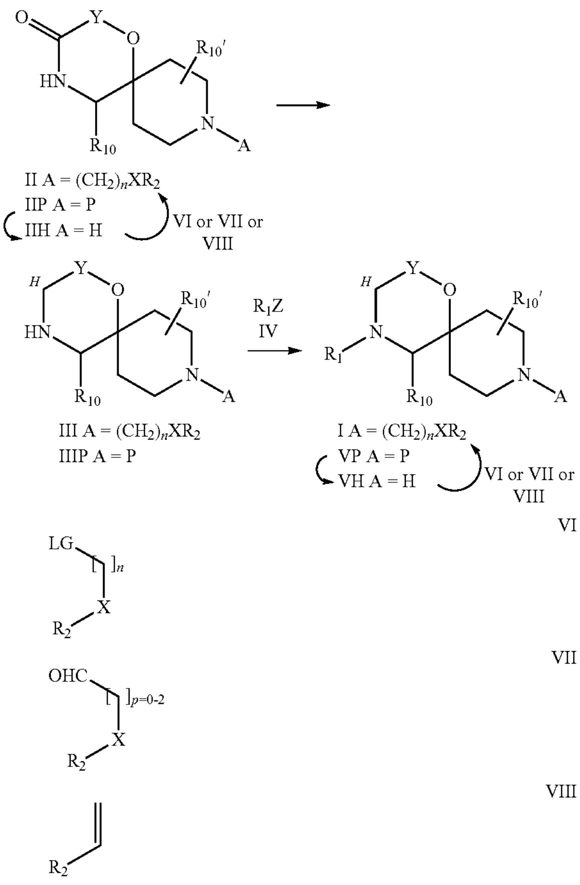

wherein $R_1$, $R_2$, $R_{10}$, $R_{10'}$, n, Y and X have the meanings as defined above for a compound of formula (I), p represents 0, 1 or 2, LG represents a leaving group such as halogen, mesylate, tosylate or triflate, P represents a suitable protecting group (preferably Boc), and P' represents another suitable protecting group (preferably 4-methoxybenzyl or benzyl) and Z represents COOH, COW or $SO_2W$ wherein W represents halogen.

The 2 step-process is carried out as described below:

Step 1: The reduction reaction of a compound of formula II to yield a compound of formula III can be performed using a suitable reducing agent such as lithium aluminium hydride, borane-tetrahydrofuran complex or borane-dimethyl sulphide complex, in a suitable solvent such as tetrahydrofuran, at a suitable temperature comprised between room temperature and the reflux temperature, preferably heating.

Step 2: A compound of formula I is prepared by reacting a compound of formula III with an acylating or sulfonylating agent of formula IV. When Z is COW or $SO_2W$, the reaction is carried out in a suitable solvent, such as dichloromethane, tetrahydrofuran, ethyl acetate or ethyl acetate-water mixtures; in the presence of an organic base such as triethylamine or diisopropylethylamine or an inorganic base such as $K_2CO_3$; and at a suitable temperature, preferably comprised between 0° C. and room temperature. Additionally, an activating agent such as 4-dimethylaminopyridine can be used.

When Z is COOH, the acylation reaction is carried out using a suitable coupling reagent such as N-(3-dimethylaminopropyl)-N'-ethylcarbodiimide (EDC), dicyclohexylcarbodiimide (DCC), N-[(dimethylamino)-1H-1,2,3-triazolo-[4,5-b]pyridin-1-ylmethylene]-N-methylmethanaminium hexafluorophosphate N-oxide (HATU) or N,N,N',N'-tetramethyl-O-(1H-benzotriazol-1-yl)uronium hexafluorophosphate (HBTU), optionally in the presence of 1-hydroxybenzotriazole, optionally in the presence of an organic base such as N-methylmorpholine or diisopropylethylamine, in a suitable solvent such as dichloromethane or dimethylformamide, and at a suitable temperature, preferably at room temperature.

Alternatively, the group $(CH_2)_nXR_2$ can be incorporated in the last step of the synthesis by reaction of a compound of formula VH with a compound of formula VI, VII or VIII, as shown in Scheme 1. A compound of formula VH is obtained by deprotection of a compound of formula VP, wherein P represents a suitable protecting group, preferably Boc (tert-butoxycarbonyl). When the protecting group is Boc, the deprotection can be conducted by adding a solution of a strong acid such as HCl, in a suitable solvent such as diethyl ether, 1,4-dioxane or methanol, or with trifluoroacetic acid in dichloromethane. A compound of formula VP is prepared from a compound of formula IIP following the same sequence described for the synthesis of compounds of formula (I).

The alkylation reaction between a compound of formula VH (or a suitable salt such as trifluoroacetate or hydrochloride) and a compound of formula VI is carried out in a suitable solvent, such as acetonitrile, dichloromethane, 1,4-dioxane or dimethylformamide, preferably in acetonitrile; in the presence of an inorganic base such as $K_2CO_3$ or $Cs_2CO_3$, or an organic base such as triethylamine or diisopropylethylamine, preferably $K_2CO_3$; at a suitable temperature comprised between room temperature and the reflux temperature, preferably heating, or alternatively, the reactions can be carried out in a microwave reactor. Additionally, an activating agent such as NaI can be used.

The reductive amination reaction between a compound of formula VH and a compound of formula VII is carried out in the presence of a reductive reagent, preferably sodium triacetoxyborohydride, in an aprotic solvent, preferably tetrahydrofuran or dichloroethane, optionally in the presence of an acid, preferably acetic acid.

The condensation reaction between a compound of general formula VH and a compound of formula VIII is preferably carried out in a suitable solvent, such as ethanol, isopropanol, n-butanol or 2-methoxyethanol, optionally in the presence of an organic base such as triethylamine or diisopropylethylamine, at a suitable temperature comprised between room temperature and the reflux temperature, preferably heating, or alternatively, the reactions can be carried out in a microwave reactor.

In a similar way, a compound of formula II can be prepared from a compound of formula IIP, by deprotection to yield a compound of formula IIH followed by reaction with a compound of formula VI, VII or VIII, following the reaction conditions described above.

The compounds of general formula IV, VI, VII and VIII wherein $R_1$, $R_2$, n, p, LG, X and Z have the meanings as defined above, are commercially available or can be prepared by conventional methods described in the bibliography.

The preparation of intermediates of general formula II, IIP, III and IIIP is described in Schemes 2 and 3 below, according to the different definitions of the group Y.

Scheme 2

The synthesis of intermediate compounds of general formula II and III is described in a general way in Scheme 2:

Scheme 2

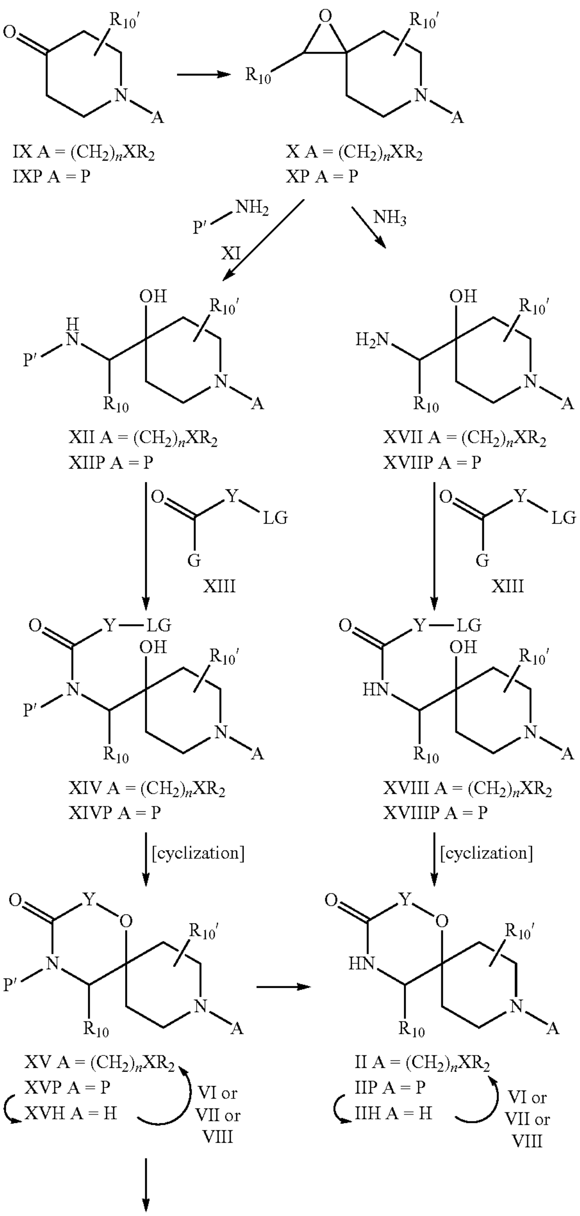

-continued

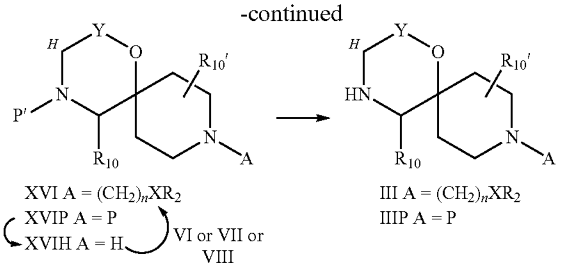

VI

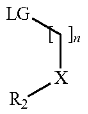

VII

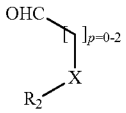

VIII

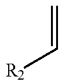

wherein $R_2$, $R_{10}$, $R_{10'}$, n, X and Y have the meanings as defined above for a compound of formula (I), p represents 0, 1 or 2, G represents a leaving group such as chloro or bromo, LG represents a leaving group such as halogen, mesylate, tosylate or triflate, P represents a suitable protecting group (preferably Boc) and P' represents another suitable protecting group (preferably 4-methoxybenzyl or benzyl).

A compound of formula II can be prepared by deprotection of a compound of formula XV wherein P' represents a suitable protecting group (preferably 4-methoxybenzyl). The deprotection reaction is carried out with cerium ammonium nitrate in a suitable solvent such as mixtures of acetonitrile-water or by heating in trifluoroacetic acid or hydrochloric acid.

Compounds of formula XV can be prepared in a 4 step-process as described below:

Step 1: When $R_{10}$=H, a compound of formula X is prepared by treating a compound of formula IX with a suitable methyl-transfer reagent such as trimethylsulfoxonium iodide or trimethylsulfonium iodide, in a suitable aprotic solvent such as dimethylsulfoxide, and in the presence of a strong base such as sodium hydride or potassium tert-butoxide, at a suitable temperature, preferably comprised between room temperature and 60° C. The compounds of formula X wherein $R_{10}$≠H can be prepared from compounds of formula IX in a two-step process, comprising an olefination under typical Wittig reaction conditions followed by an epoxidation using a suitable oxidizing agent such as a peracid (as for example m-chloroperbenzoic acid), or hydrogen peroxide (optionally in the presence of a metal catalyst).

Step 2: A compound of formula XII is prepared by reacting a compound of formula X with an amine of formula XI, in a suitable solvent such as an alcohol, preferably ethanol-water mixtures, at a suitable temperature comprised between room temperature and the reflux temperature.

Step 3: A compound of formula XIV is prepared by reacting a compound of formula XII with a compound of formula XIII. The acylation reaction is carried out in a suitable solvent, such as dichloromethane or ethyl acetate-water mixtures; in the presence of an organic base such as triethylamine or diisopropylethylamine or an inorganic base such as $K_2CO_3$; and at a suitable temperature, preferably comprised between −78° C. and room temperature.

Step 4: The intramolecular cyclization of a compound of formula XIV renders a compound of formula XV. The cyclization reaction is carried out in a suitable solvent, such as tetrahydrofuran; in the presence of a strong base such as potassium tert-butoxide or sodium hydride; and at a suitable temperature, comprised between −78° C. and the reflux temperature, preferably cooling.

Following an analogous sequence, a compound of formula II can be synthesized from a compound of formula X and ammonia.

In an alternative approach to the synthesis described in Scheme 1, a compound of formula III can be prepared from a compound of formula XV in a 2-step process that comprises the reduction of a compound of formula XV to render a compound of formula XVI under the reduction conditions described in Scheme 1, followed by deprotection to obtain a compound of formula III. In this case, P' is preferably a 4-methoxybenzyl or a benzyl group, and the deprotection reaction is preferably carried out by hydrogenation under hydrogen atmosphere and metal catalysis, preferably by the use of palladium over charcoal as catalyst in a suitable solvent such as methanol or ethanol, optionally in the presence of an acid such as acetic acid or hydrochloric acid.

Alternatively, the group $(CH_2)_nXR_2$ may be incorporated at different stages of the synthesis. Thus, a compound of formula II, III, XV or XVI can be prepared from a protected precursor of formula IIP, IIIP, XVP or XVIP, respectively, wherein P represents a suitable protecting group, by deprotection followed by reaction with a compound of formula VI, VII or VIII, under the reaction conditions described in Scheme 1.

The compounds of general formula VI, VII, VIII, IX, IXP, XI and XIII wherein $R_2$, $R_{10'}$, LG, G, P, P', X, Y, n and p have the meanings as defined above, are commercially available or can be prepared by conventional methods described in the bibliography.

Scheme 3

An alternative method for the synthesis of compounds of general formula XV wherein Y is

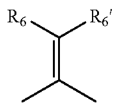

or

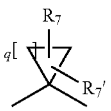

(compounds of formula XVa and XVb, respectively) is described in Scheme 3:

Compounds of formula XVa can be prepared in a 3-step process starting from a compound of formula XII:

Scheme 3

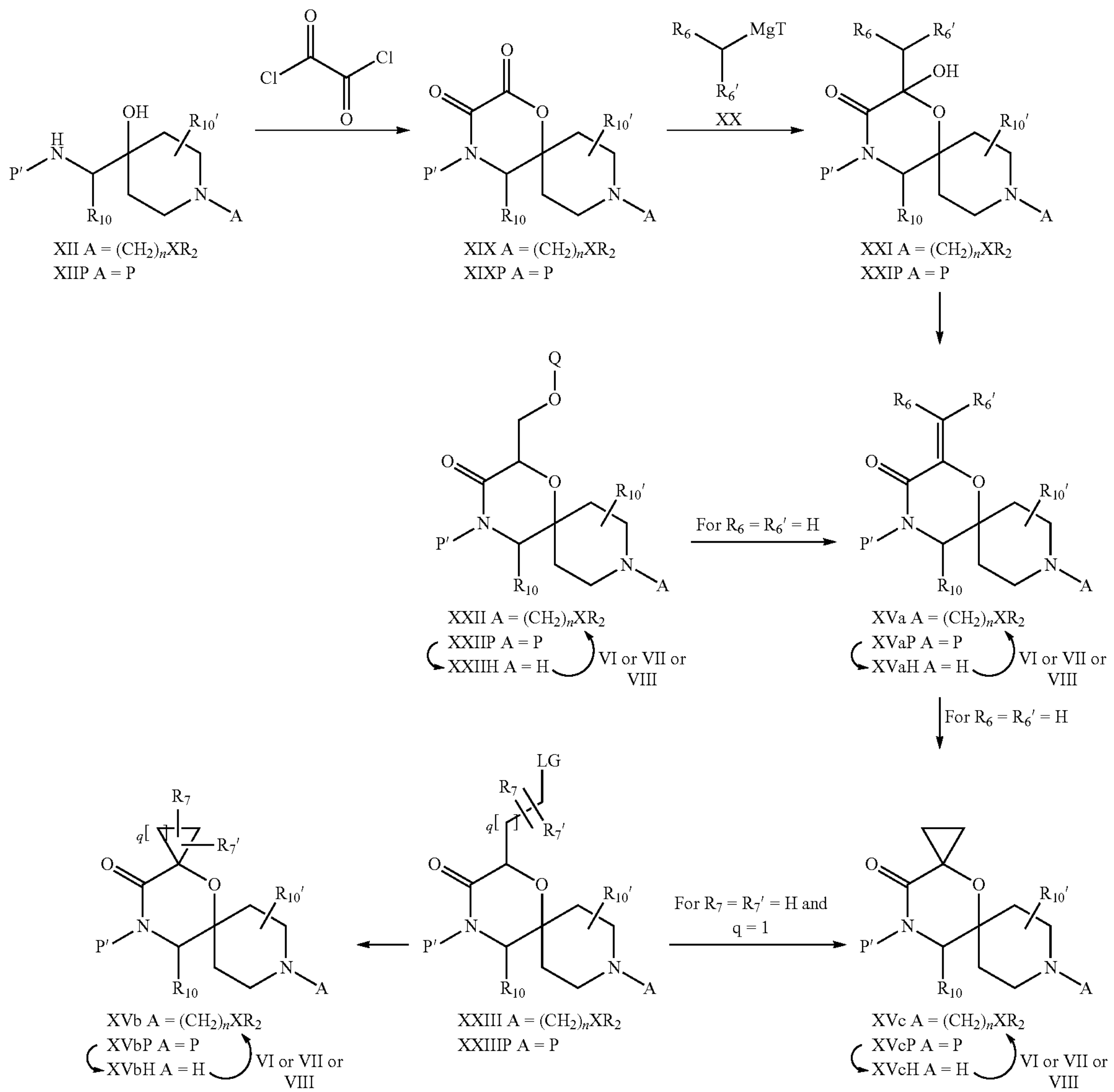

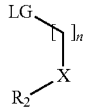

VI

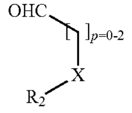

VII

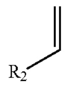

VIII wherein $R_2$, $R_6$, $R_{6'}$, $R_7$, $R_{7'}$, $R_{10}$, $R_{10'}$, X, n and q have the meanings as defined above for a compound of formula (I), p represents 0, 1 or 2, LG represents a leaving group such as halogen, mesylate, tosylate or triflate, P represents a suitable protecting group (preferably Boc), P' represents another suitable protecting group (preferably 4-methoxybenzyl or benzyl), T represents chloro, bromo or iodo and Q represents methyl or benzyl.

Step 1: A compound of formula XIX is prepared by treating a compound of formula XII with oxalyl chloride, in a suitable solvent such as dichloromethane, in the presence of a base such as triethylamine, at a suitable temperature, preferably comprised between 0° C. and room temperature. Additionally, an activating agent such as 4-dimethylaminopyridine can be used.

Step 2: A compound of formula XXI is prepared by reacting a compound of formula XIX with a Grignard reagent of formula XX, in an aprotic solvent such as tetrahydrofuran, at a suitable temperature preferably at room temperature.

Step 3: A compound of formula XVa is obtained by reacting a compound of formula XXI with a dehydrating agent such as boron trifluoride diethyl etherate, in a suitable solvent such as dichloromethane, at a suitable temperature preferably at room temperature.

Alternatively, a compound of formula XVa wherein $R_6$=$R_{6'}$=H can be prepared from a compound of formula XXII wherein Q represents methyl or benzyl. The elimination reaction is carried out in the presence of a base, such as potassium tert-butoxide, in a suitable solvent, such as tetrahydrofuran.

Compounds of formula XVc can be prepared from compounds of formula XVa wherein $R_6$=$R_{6'}$=H. The cyclopropanation reaction is carried out using a suitable methyl-transfer reagent such as trimethylsulfoxonium iodide or trimethylsulfonium iodide, in a suitable aprotic solvent such as dimethylsulfoxide, and in the presence of a strong base such as sodium hydride or potassium tert-butoxide, at a suitable temperature, preferably comprised between room temperature and 60° C. Alternatively, typical Simmons-Smith reaction conditions could be used, comprising the treatment of a compound of formula XVa with diiodomethane, a zinc source such as zinc-copper, zinc iodide or diethylzinc, in a suitable aprotic solvent, such as diethyl ether.

Alternatively, a compound of formula XVc can be prepared from a compound of formula XXIII wherein $R_7$=$R_{7'}$=H and q=1 by treatment with a strong base such as lithium diisopropylamide or potassium tert-butoxide, in an aprotic solvent such as tetrahydrofuran, at a suitable temperature, preferably cooling at 0° C. And analogously, compounds of formula XVb can be prepared from compounds of formula XXIII under the same reaction conditions.

In addition, the group $(CH_2)_nXR_2$ can be incorporated in the last step of the synthesis to prepare compounds of formula XVa, XVb and XVc from suitable protected precursors, by deprotection followed by reaction with a compound of formula VI, VII or VIII, as described in Scheme 1 for the preparation of compounds of formula I.

The compounds of general formula XXII and XXIII can be prepared by the procedures described in Scheme 2 using suitable starting materials.

The compounds of general formula VI, VII, VIII and XX wherein $R_2$, $R_6$, $R_{6'}$, LG, T, X, n and p have the meanings as defined above, are commercially available or can be prepared by conventional methods described in the bibliography.

Moreover, certain compounds of the present invention can also be obtained starting from other compounds of formula (I) by appropriate conversion reactions of functional groups, in one or several steps, using well-known reactions in organic chemistry under standard experimental conditions. As a way of example, some of these conversions include the demethylation of a methoxy group to yield an hydroxy group, the reduction of a nitro group to yield an amino group, the acylation of an amino group to yield an acylamino group and the conversion of an amino group into an ureido group.

In addition, a compound of formula I that shows chirality can also be obtained by resolution of a racemic compound of formula I either by chiral preparative HPLC or by crystallization of a diastereomeric salt or co-crystal. Alternatively, the resolution step can be carried out at a previous stage, using any suitable intermediate.

EXAMPLES

All solvents used for synthesis were p. a. quality.

The following abbreviations are used in the examples:

ACN: acetonitrile
AcOH: acetic acid
Boc: tert-butoxycarbonyl
CAN: cerium ammonium nitrate
DCM: dichloromethane
DEA: diethylamine
DIPEA: diisopropylethylamine
DMF: dimethylformamide
DMSO: dimethylsulfoxide
Eq: equivalent
EX: example
h: hour/s
HPLC: high performance liquid chromatography
INT: intermediate
LDA: lithium diisopropylamide
MeOH: methanol
MS: mass spectrometry
Min.: minutes
Quant: quantitative
Ret.: retention
r.t.: room temperature
Sat: saturated
s.m.: starting material
TFA: trifluoroacetic acid
THF: tetrahydrofuran
Wt: weight The following method was used to determine the HPLC-MS spectrums:

Column: Xbridge $C_{18}$ XP, 30×4.6 mm, 2.5 um
Temperature: 40° C.
Flow: 2.0 mL/min
Gradient: $NH_4HCO_3$ pH 8/ACN (95:5)—0.5 min—(95:5)—6.5 min—(0:100)—1 min—(0:100)
Sample dissolved aprox. 1 mg/mL in $NH_4HCO_3$ pH 8/ACN Alternatively, method B was used in some cases:

Method B:
Column: Gemini-NX 30×4.6 mm, 3 um
Temperature: 40° C.
Flow: 2.0 mL/min
Gradient: $NH_4HCO_3$ pH 8: ACN (95:5)—0.5 min—(95:5)—6.5 min—(0:100)—1 min—(0:100)
Sample dissolved aprox. 1 mg/mL in $NH_4HCO_3$ pH 8/ACN

Synthesis of Intermediates

Intermediate 1A: tert-butyl 1-oxa-6-azaspiro[2.5]octane-6-carboxylate

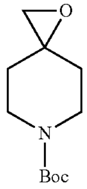 [SMILES: CC(C)(C)OC(=O)N1CCC2(CC1)CO2]

To a suspension of trimethylsulfoxonium iodide (24.3 g, 110 mmol) and NaH (4.4 g, 60 wt % in mineral oil, 110 mmol) in DMSO (140 mL), a solution of tert-butyl 4-oxopiperidine-1-carboxylate (20.0 g, 100 mmol) in DMSO (140 mL) was added dropwise. The reaction mixture was stirred at r.t. for 30 minutes, then heated at 50° C. for 1 h. After cooling to r.t., ice was slowly added, and the reaction mixture was extracted three times with ethyl acetate. The organic phases were combined, washed with water, dried over $MgSO_4$ and concentrated under vacuum to give the title compound (17.6 g, 82% yield) as a white solid. HPLC retention time: 3.31 min; MS: 158 (M+H−56).

Intermediate 1B: 6-phenethyl-1-oxa-6-azaspiro[2.5]octane

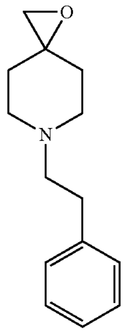 [SMILES: c1ccc(CCN2CCC3(CC2)CO3)cc1]

To a suspension of trimethylsulfoxonium iodide (13.0 g, 59 mmol) and NaH (2.36 g, 60 wt % in mineral oil, 59 mmol) in DMSO (70 mL), a solution of tert-butyl 4-oxopiperidine-1-carboxylate (10.0 g, 49 mmol) in DMSO (70 mL) was added dropwise. The reaction mixture was stirred at r.t. for 30 minutes, then heated at 50° C. for 1 h. After cooling to r.t., ice was slowly added, and the reaction mixture was extracted three times with ethyl acetate. The organic phases were combined, washed with water, dried over $MgSO_4$ and concentrated under vacuum, to give the title compound (8.24 g, 77% yield) as an oil. HPLC retention time: 3.36 min; MS: 218 (M+H).

Intermediate 2A: tert-butyl 4-(aminomethyl)-4-hydroxypiperidine-1-carboxylate

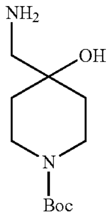

A solution of intermediate 1A (10.0 g, 46.9 mmol) in ammonia (201 mL, 7 M solution in methanol, 1.4 mol) was stirred at r.t. overnight. The solvent was removed under vacuum and the residue was purified by flash chromatography, silica gel, gradient dichloromethane to methanol:dichloromethane (1:4) to give the title compound (7.4 g, 69% yield) as a white solid. HPLC retention time: 2.15 min; MS: 131 (M+H−100).

This method was used for the preparation of intermediate 2B using suitable starting materials:

| INT | Structure | Chemical name | s.m. | Ret time (min) | MS (M + H) |
|---|---|---|---|---|---|
| 2B | 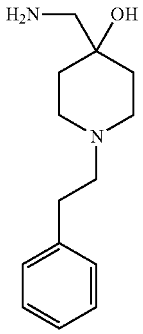 | 4-(aminomethyl)-1-phenethylpiperidin-4-ol | 1B | 2.19 | 235 |

Intermediate 2C: tert-butyl 4-hydroxy-4-(((4-methoxybenzyl)amino)methyl)piperidine-1-carboxylate

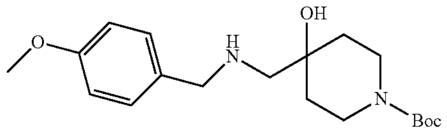 [SMILES: COc1ccc(CNCC2(O)CCN(C(=O)OC(C)(C)C)CC2)cc1]

To a solution of intermediate 1A (9.1 g, 42.5 mmol) in a mixture of ethanol:water 9:1 (200 mL), 4-methoxybenzylamine (5.6 mL, 42.5 mmol) was added. The reaction mixture was heated to 100° C. overnight in an autoclave reactor. The solvent was removed under vacuum and the residue was purified by flash chromatography, silica gel, gradient dichloromethane to methanol:dichloromethane (1:4) to give the title compound (9.4 g, 63% yield) as an oil. HPLC retention time: 3.75 min; MS: 351 (M+H).

This method was used for the preparation of intermediate 2D using suitable starting materials:

| INT | Structure | Chemical name | s.m. | Ret time (min) | MS (M + H) |
|---|---|---|---|---|---|
| 2D | 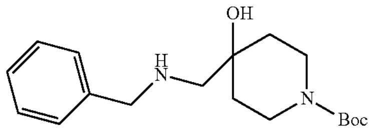 [SMILES: CC(C)(C)OC(=O)N1CCC(O)(CNCc2ccccc2)CC1] | tert-butyl 4-((benzylamino)methyl)-4-hydroxypiperidine-1-carboxylate | 1A | 3.90 | 321 |

Intermediate 3A: tert-butyl 3-oxo-1-oxa-4,9-diazaspiro[5.5]undecane-9-carboxylate

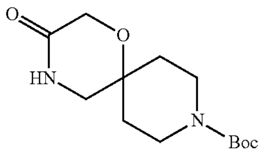 [SMILES: CC(C)(C)OC(=O)N1CCC2(CC1)CNC(=O)CO2]

Step 1. tert-Butyl 4-((2-chloroacetamido)methyl)-4-hydroxypiperidine-1-carboxylate: To a solution of intermediate 2A (1.0 g, 4.34 mmol) in ethyl acetate (9 mL), a solution of $K_2CO_3$ (1.67 g, 12.11 mmol) in water (7 mL) was added. After cooling to 0° C., chloroacetyl chloride (0.47 mL, 5.91 mmol) was added dropwise. The reaction mixture was stirred at 0° C. for 30 minutes, then the layers were separated and the aqueous phase was extracted with ethyl acetate. The organic phases were combined, dried over $MgSO_4$, filtered and concentrated to dryness to give the title compound (1.1 g). HPLC retention time: 2.90 min; MS: 207 (M+H−100).

Step 2. Title compound: To a solution of potassium tert-butoxide (7.16 mL, 1M in THF, 7.16 mmol) in a mixture of THF:tert-butanol 2.3:1 (25 mL) heated at reflux, a solution of the crude product obtained in step 1 in THF (20 mL) was added dropwise over 1 h. Then, the reaction mixture was cooled to r.t. and stirred overnight. The solvent was removed under vacuum, water was added to the residue and it was extracted with ethyl acetate. The organic phase was dried over MgSO4, filtered and concentrated under vacuum to give the title compound (0.87 g, 74% yield for the 2 steps). HPLC retention time: 2.88 min; MS: 215 (M+H−56).

This method was used for the preparation of intermediates 3B-3D using suitable starting materials:

| INT | Structure | Chemical name | s.m. | Ret time (min) | MS (M + H) |
|---|---|---|---|---|---|
| 3B | 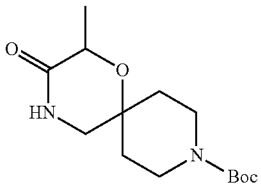 [SMILES: CC1OC2(CCN(C(=O)OC(C)(C)C)CC2)CNC1=O] | tert-butyl 2-methyl-3-oxo-1-oxa-4,9-diazaspiro [5.5] undecane-9-carboxylate | 2A | 3.16 | 229 |
| 3C | 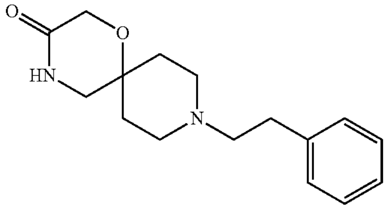 [SMILES: O=C1COC2(CCN(CCc3ccccc3)CC2)CN1] | 9-phenethyl-1-oxa-4,9-diazaspiro [5.5]undecan-3-one | 2B | 2.80 | 275 |
| 3D | 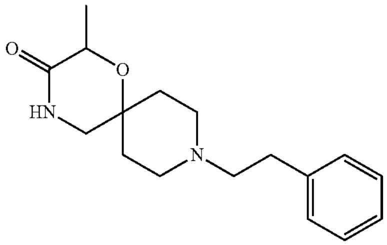 [SMILES: CC1OC2(CCN(CCc3ccccc3)CC2)CNC1=O] | 2-methyl-9-phenethyl-1-oxa-2,9-diazaspiro [5.5]undecan-3-one | 2B | 3.13 | 289 |

Intermediate 3E: tert-butyl 2-(2-chloroethyl)-4-(4-methoxybenzyl)-3-oxo-1-oxa-4,9-diazaspiro[5.5]undecane-9-carboxylate

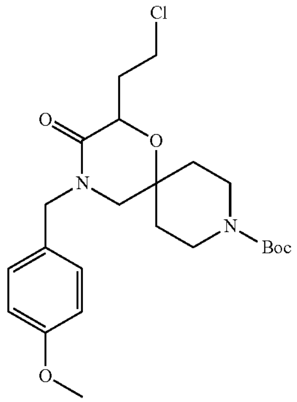 [SMILES: COc1ccc(CN2CC3(CCN(C(=O)OC(C)(C)C)CC3)OC(CCCl)C2=O)cc1]

Step 1. tert-butyl 4-((2-bromo-4-chloro-N-(4-methoxybenzyl)butanamido)methyl)-4-hydroxypiperidine-1-carboxylate: To a solution of intermediate 2C (4.71 g, 13.4 mmol) and triethylamine (4.5 mL, 32.3 mmol) in dichloromethane (200 mL), 2-bromo-4-chlorobutanoyl chloride (prepared as described in U.S. Pat. No. 6,114,541A1 (2000) Ex1) (4.43 g, 20.2 mmol) was added dropwise at 0° C. The reaction mixture was stirred at 0° C. for 3 h. Dichloromethane and $NaHCO_3$ sat solution were added and the phases were separated. The aqueous phase was back extracted with dichloromethane. The organic phases were combined, dried over $MgSO_4$, filtered and concentrated to dryness to give the title compound (8.1 g, crude product). HPLC retention time: 4.93 min; MS: 435 (M+H−100).

Step 2. Title compound: A solution of the crude product obtained in step 1 in THF (100 mL) was cooled under nitrogen to −78° C. using a dry ice/acetone bath. After addition of potassium tert-butoxide solution (20 mL, 1M in THF, 20 mmol), the reaction mixture was stirred at −78° C. for 15 minutes and then 4 h at 0° C. $NH_4Cl$ sat solution was then added, and the aqueous phase was extracted with ethyl acetate. The organic phases were combined, dried over $MgSO_4$, filtered and concentrated under vacuum to give the title compound as a crude product (4.45 g, quant yield for the 2 steps). HPLC retention time: 4.92 min; MS: 453 (M+H).

This method was used for the preparation of intermediates 3F-3H using suitable starting materials:

| INT | Structure | Chemical name | s.m. | Ret time (min) | MS (M + H) |
|---|---|---|---|---|---|
| 3F | 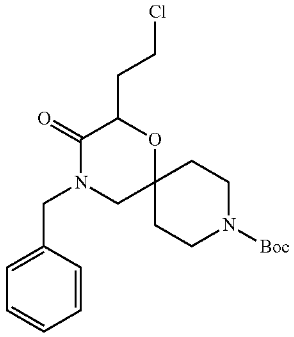 [SMILES: CC(C)(C)OC(=O)N1CCC2(CC1)CN(Cc1ccccc1)C(=O)C(CCCl)O2] | tert-butyl 4-benzyl-2-(2-chloroethyl)-3-oxo-1-oxa-4,9-diazaspiro[5.5]undecane-9-carboxylate | 2D | 5.05 | 423 |
| 3G | 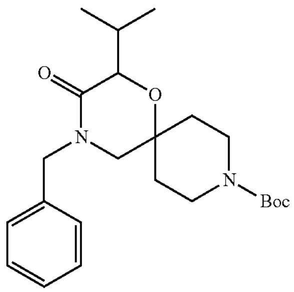 [SMILES: CC(C)C1OC2(CCN(C(=O)OC(C)(C)C)CC2)CN(Cc2ccccc2)C1=O] | tert-butyl 4-benzyl-2-isopropyl-3-oxo-1-oxa-4,9-diazaspiro[5.5]undecane-9-carboxylate | 2D | 5.28 | 403 |
| 3H | 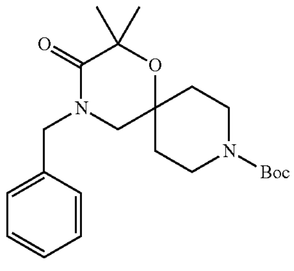 [SMILES: CC(C)(C)OC(=O)N1CCC2(CC1)CN(Cc1ccccc1)C(=O)C(C)(C)O2] | tert-butyl 4-benzyl-2,2-dimethyl-3-oxo-1-oxa-4,9-diazaspiro[5.5]undecane-9-carboxylate (1*) | 2D | 4.59 | 389 |

(1*) $NaHCO_3$ was used as base instead of triethylamine

Intermediate 3I: (R)-tert-butyl 4-(4-methoxybenzyl)-2-methyl-3-oxo-1-oxa-4,9-diazaspiro[5.5]undecane-9-carboxylate

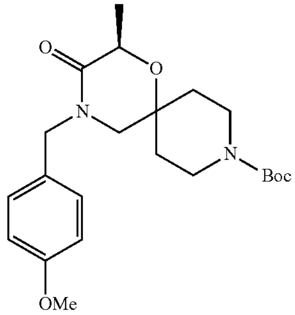 [SMILES: COc1ccc(CN2CC3(CCN(C(=O)OC(C)(C)C)CC3)O[C@H](C)C2=O)cc1]

Step 1. (S)-tert-butyl 4-((2-chloro-N-(4-methoxybenzyl) propanamido)methyl)-4-hydroxypiperidine-1-carboxylate: To a solution of intermediate 2C (3.6 g, 10.3 mmol) in ethyl acetate (50 mL), a solution of $K_2CO_3$ (3.98 g, 28.8 mmol) in water (40 mL) was added. After cooling to 0° C., a solution of (S)-2-chloropropanoyl chloride (1.77 g, 13.97 mmol) in ethyl acetate (5 mL) was added dropwise. The reaction mixture was stirred at 0° C. for 30 min, the layers were separated and the aqueous phase was extracted with ethyl acetate. The organic phases were combined, washed with cold 0.5 M HCl aqueous solution and then $NaHCO_3$ sat solution, dried over $MgSO_4$, filtered and concentrated to dryness to give the title compound (3.93 g, 87% yield). HPLC retention time: 4.52 min; MS: 341 (M+H−100).

Step 2. Title compound: A solution of the crude product obtained in step 1 (3.93 g, 8.91 mmol) in THF (60 mL) was cooled to −78° C. using a dry ice/acetone bath. After addition of potassium tert-butoxide solution (9.8 mL, 1M in THF, 9.8 mmol), the reaction mixture was stirred at −78° C. for 30 min. $NH_4Cl$ sat solution was then added, and the aqueous phase was extracted with ethyl acetate. The organic phases were combined, dried over $MgSO_4$, filtered and concentrated under vacuum to give the title compound (3.39 g, 94% yield). HPLC retention time (method B): 4.46 min; MS: 405 (M+H).

Intermediate 4A: tert-butyl 12-(4-methoxybenzyl)-13-oxo-4-oxa-8,12-diazadispiro[2.1.5.3]tridecane-8-carboxylate

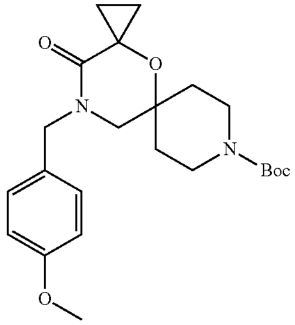 [SMILES: COc1ccc(CN2CC3(CCN(C(=O)OC(C)(C)C)CC3)OC3(CC3)C2=O)cc1]

A solution of intermediate 3E (4.45 g, 9.82 mmol) in dry THF (120 mL) was cooled to 0° C. After slow addition of LDA solution (14.7 mL, 2M in THF/n-heptane/ethylbenzene, 29.4 mmol), the reaction mixture was stirred at 0° C. for 3 hours. $NH_4Cl$ sat solution was then added, and the aqueous phase was extracted with dichloromethane. The organic phase was dried over $MgSO_4$, filtered and concentrated under vacuum. The residue was purified by flash chromatography, $C_{18}$, gradient aqueous $NH_4HCO_3$ pH 8 to acetonitrile to give the title compound (2.85 g, 69% yield). HPLC retention time: 4.60 min; MS: 417 (M+H).

This method was used for the preparation of intermediate 4B using suitable starting materials:

| INT | Structure | Chemical name | s.m. | Ret time (min) | MS (M + H) |
| --- | --- | --- | --- | --- | --- |
| 4B | 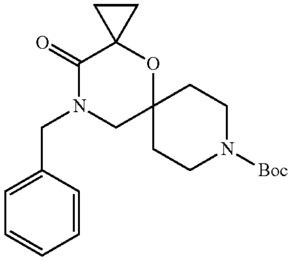 [SMILES: CC(C)(C)OC(=O)N1CCC2(CC1)CN(Cc1ccccc1)C(=O)C1(CC1)O2] | tert-butyl 12-benzyl-13-oxo-4-oxa-8,12-diazadispiro [2.1.5.3]tri-decane-8-carboxylate | 3F | 4.69 | 387 |

Intermediate 4C: 8-phenethyl-4-oxa-8,12-diazadispiro[2.1.5.3]tridecan-13-one

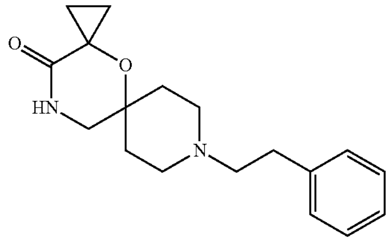 [SMILES: O=C1NCC2(CCN(CCc3ccccc3)CC2)OC12CC2]

Step 1: 12-(4-methoxybenzyl)-4-oxa-8,12-diazadispiro[2.1.5.3]tridecan-13-one trifluoroacetate: To a solution of intermediate 4A (1.5 g, 3.6 mmol) in dichloromethane (36 mL), trifluoroacetic acid (2.8 mL, 36 mmol) was added, and the reaction mixture was stirred at r.t. for 4 h. The solvent was evaporated to give the title compound as a crude product (1.55 g, 73 wt %, quant yield), that was used in the following step without further purification. HPLC retention time: 2.43 min; MS: 317.0 (M+H).

Step 2: 12-(4-methoxybenzyl)-8-phenethyl-4-oxa-8,12-diazadispiro[2.1.5.3]tridecan-13-one: A mixture of the crude product obtained in step 1 (1.55 g, 73 wt %, 3.61 mmol), (2-bromoethyl)benzene (0.59 mL, 4.33 mmol), sodium iodide (0.325 g, 2.17 mmol) and $K_2CO_3$ (2.49 g, 18 mmol) in acetonitrile (36 mL) was stirred in a sealed tube at 80° C. overnight. Water was added and the reaction mixture was extracted with ethyl acetate. The organic phases were combined, dried over $MgSO_4$, filtered and concentrated to dryness. The residue was purified by flash chromatography, silica gel, gradient dichloromethane to methanol:dichloromethane (1:4) to give the title compound (1.17 g, 77% yield).

HPLC retention time: 4.54 min; MS: 421.1 (M+H).

Step 3: Title compound: A mixture of the product obtained in step 2 (0.170 g, 0.404 mmol) and CAN (0.568 g, 1.21 mmol) in a mixture of acetonitrile:water 1:1 (5 mL) was stirred at r.t. for 7 hours. $Na_2CO_3$ sat solution was added to the reaction mixture and it was extracted with ethyl acetate. The organic phases were combined, washed with brine, dried over $MgSO_4$, filtered and concentrated to dryness. The residue was purified eluting through an acidic ion exchange resin cartridge (SCX), to give the title compound (106 mg, 88% yield). HPLC retention time: 3.31 min; MS: 301 (M+H).

Intermediate 4D: tert-butyl 13-oxo-4-oxa-8,12-diazadispiro[2.1.5.3]tridecane-8-carboxylate

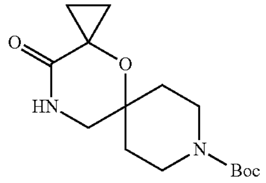 [SMILES: CC(C)(C)OC(=O)N1CCC2(CC1)CNC(=O)C1(CC1)O2]

Step 1. 4-oxa-8,12-diazadispiro[2.1.5.3]tridecan-13-one trifluoroacetate: A solution of intermediate 4A (1.78 g, 4.26 mmol) in TFA (20 mL) was stirred in a sealed tube at 80° C. for 4 days. The reaction mixture was concentrated to dryness and water was added to the residue. The acidic aqueous phase was washed with ethyl ether, that was discarded. The aqueous layer was evaporated to dryness to give the title compound (1.17 g, 88% yield). HPLC retention time: 0.33 min; MS: 197 (M+H).

Step 2. Title compound: A solution of the crude product obtained in step 1 and di-tert-butyl dicarbonate (1.40 g, 6.40 mmol) in a mixture of 1,4-dioxane (40 mL) and 1M NaOH aqueous solution (10 mL) was stirred at r.t. overnight. Water was added and the resulting mixture was extracted with ethyl acetate. The organic phases were combined, dried over $MgSO_4$, filtered and concentrated to dryness. The residue was purified by flash chromatography, silica gel, gradient dichloromethane to methanol:dichloromethane (1:4) to give the title compound (0.872 g, 78% yield). HPLC retention time: 3.29 min; MS: 297 (M+H).

Intermediate 5A: tert-butyl 1-oxa-4,9-diazaspiro[5.5]undecane-9-carboxylate

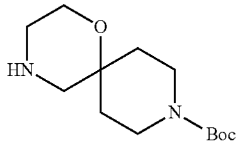 [SMILES: CC(C)(C)OC(=O)N1CCC2(CC1)CNCCO2]

To a solution of intermediate 3A (1.50 g, 5.55 mmol) in THF (19 mL), borane-dimethyl sulfide complex (1.67 mL, 16.6 mmol) was added dropwise at r.t. The reaction mixture was stirred at 55° C. for 2 h, then it was cooled to r.t. MeOH was carefully added and the solvent was concentrated under vacuum. The residue was dissolved in methanol (20 mL), N,N-dimethylethylenediamine (3.0 mL, 28.3 mmol) was added and the mixture was stirred under reflux overnight. After cooling to r.t., the volatiles were removed under vacuum, and the residue was purified by flash chromatography, silica gel, gradient dichloromethane to methanol:dichloromethane (1:4) to give the title compound (0.928 g, 65% yield). HPLC retention time: 2.91 min; MS: 257 (M+H).

This method was used for the preparation of intermediates 5B-5E using suitable starting materials:

| INT | Structure | Chemical name | s.m. | Ret time (min) | MS (M + H) |
|---|---|---|---|---|---|
| 5B | 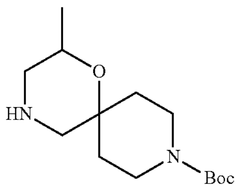 [SMILES: CC1CNCC2(CCN(C(=O)OC(C)(C)C)CC2)O1] | tert-butyl 2-methyl-1-oxa-4,9-diazaspiro[5.5]undecane-9-carboxylate | 3B | 3.17 | 271 |
| 5C | 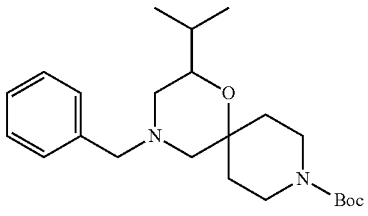 [SMILES: CC(C)C1CN(Cc2ccccc2)CC2(CCN(C(=O)OC(C)(C)C)CC2)O1] | tert-butyl 4-benzyl-2-isopropyl-1-oxa-4,9-diazaspiro[5.5]undecane-9-carboxylate | 3G | 6.53 | 389 |
| 5D | 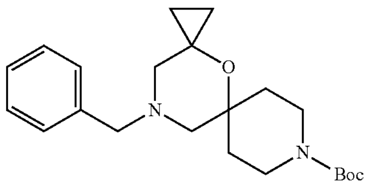 [SMILES: CC(C)(C)OC(=O)N1CCC2(CC1)CN(Cc1ccccc1)CC1(CC1)O2] | tert-butyl 12-benzyl-4-oxa-8,12-diazadispiro[2.1.5.3]tri-decane-8-carboxylate | 4B | 5.80 | 373 |

Intermediate 5F: tert-butyl 2-isopropyl-1-oxa-4,9-diazaspiro[5.5]undecane-9-carboxylate acetate

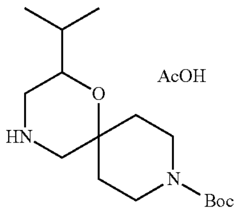 [SMILES: "AcOH" ; CC(C)C1CNCC2(CCN(C(=O)OC(C)(C)C)CC2)O1]

A mixture of intermediate 5C (0.263 g, 0.677 mmol), AcOH (0.077 mL, 1.35 mmol) and palladium hydroxide (52 mg, 20% wt on carbon) in methanol (8 mL) was stirred under 3 bars of $H_2$ at r.t. for 1 day. The solids were filtered off and the solvent was removed under vacuum to give the title compound as a crude product (0.322 g, quant yield), used in the next step without further purification. HPLC retention time: 3.99 min; MS: 299 (M+H−56).

This method was also used for the alternative preparation of intermediate 5E using Intermediate 5D as starting material.

Intermediate 5G: 9-phenethyl-1-oxa-4,9-diazaspiro[5.5]undecane

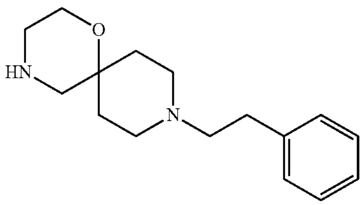 [SMILES: c1ccc(CCN2CCC3(CC2)CNCCO3)cc1]

To a solution of intermediate 3C (1.25 g, 4.56 mmol) in THF (25 mL), lithium aluminium hydride solution (18.2 mL, 1M in THF, 18.2 mmol) was added dropwise. The reaction mixture was stirred at 50° C. overnight, then 1M NaOH aqueous solution was added, and the aqueous phase was extracted with dichloromethane. The organic phases were combined, dried over $MgSO_4$, filtered and concentrated under vacuum to give the title compound (1.10 g, 84% yield). HPLC retention time: 2.67 min; MS: 261 (M+H).

This method was used for the preparation of intermediate 5H using suitable starting materials:

| INT | Structure | Chemical name | s.m. | Ret time (min) | MS (M + H) |
| --- | --- | --- | --- | --- | --- |
| 5H | 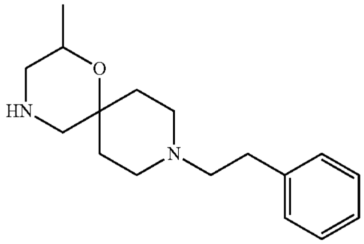 [SMILES: CC1CNCC2(CCN(CCc3ccccc3)CC2)O1] | 2-methyl-9-phenethyl-1-oxa-4,9-diazaspiro[5.5]undecane | 3D | 3.00 | 275 |

Intermediate 5I: 8-phenethyl-4-oxa-8,12-diazadispiro[2.1.5.3]tridecane

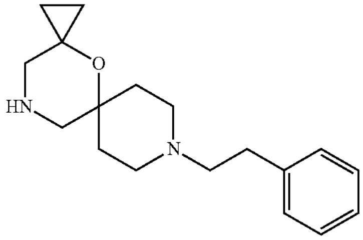 [SMILES: c1ccc(CCN2CCC3(CC2)CNCC2(CC2)O3)cc1]

To a solution of intermediate 4C (0.200 g, 0.67 mmol) in THF (7 mL) at 0° C., lithium aluminium hydride solution (2.66 mL, 1M in THF, 2.66 mmol) was added dropwise. The reaction mixture was stirred at 80° C. for 1.5 h, then NaOH 1M aqueous solution was added, and the aqueous phase was extracted with dichloromethane. The organic phases were combined, dried over $MgSO_4$, filtered and concentrated under vacuum to give the title compound (0.170 g, 89% yield). HPLC retention time: 3.07 min; MS: 287 (M+H).

Intermediate 5J: tert-butyl 4-benzyl-2,2-dimethyl-1-oxa-4,9-diazaspiro[5.5]undecane-9-carboxylate

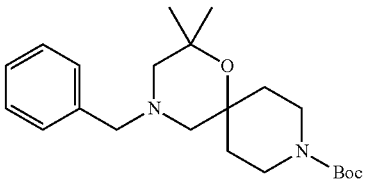 [SMILES: CC(C)(C)OC(=O)N1CCC2(CC1)CN(Cc1ccccc1)CC(C)(C)O2]

Intermediate 5J was prepared following the procedure described for Intermediate 5A, using Intermediate 3H as starting material. HPLC retention time: 6.12 min; MS: 375 (M+H).

Intermediate 5K: tert-butyl 2,2-dimethyl-1-oxa-4,9-diazaspiro[5.5]undecane-9-carboxylate

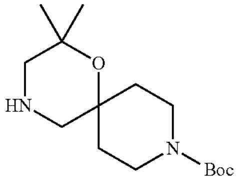 [SMILES: CC(C)(C)OC(=O)N1CCC2(CC1)CNCC(C)(C)O2]

Intermediate 5K was prepared following the procedure described for Intermediate 5F, using Intermediate 5J as starting material. HPLC retention time: 3.58 min; MS: 285 (M+H).

Intermediate 5L: (R)-tert-butyl 4-(4-methoxybenzyl)-2-methyl-1-oxa-4,9-diazaspiro[5.5]undecane-9-carboxylate

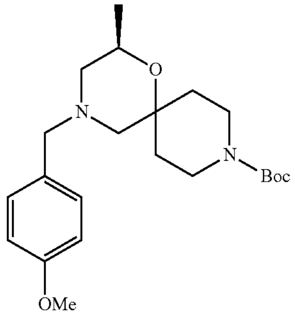 [SMILES: COc1ccc(CN2C[C@@H](C)OC3(CCN(C(=O)OC(C)(C)C)CC3)C2)cc1]

Intermediate 5L was prepared following the procedure described for Intermediate 5A, using Intermediate 3I as starting material and borane-tetrahydrofuran complex instead of borane-dimethyl sulfide complex as the reducing agent. HPLC retention time (method B): 5.57 min; MS: 391 (M+H).

Intermediate 5M: (R)-tert-butyl 2-methyl-1-oxa-4,9-diazaspiro[5.5]undecane-9-carboxylate acetate

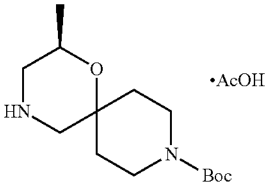 [SMILES: "·AcOH" ; C[C@@H]1CNCC2(CCN(C(=O)OC(C)(C)C)CC2)O1]

Intermediate 5M was prepared following the procedure described for Intermediate 5F, using Intermediate 5L as starting material and 10% Palladium on activated charcoal as the hydrogenation catalyst. HPLC retention time (method B): 3.10 min; MS: 271 (M+H).

Intermediate 6A: tert-butyl 4-benzoyl-1-oxa-4,9-diazaspiro[5.5]undecane-9-carboxylate

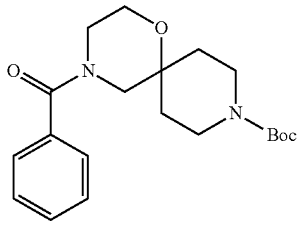 [SMILES: CC(C)(C)OC(=O)N1CCC2(CC1)CN(C(=O)c1ccccc1)CCO2]

To a solution of intermediate 5A (1.68 g, 6.55 mmol) in dichloromethane (65 mL) at 0° C., benzoyl chloride (0.84 mL, 7.21 mmol) and triethylamine (1.09 mL, 7.86 mmol) were added dropwise. The reaction mixture was stirred at rt for 2 h, then $NaHCO_3$ sat solution was added and it was extracted with dichloromethane. The organic phases were combined, dried over $MgSO_4$, filtered and concentrated to dryness. The residue was purified by flash chromatography, silica gel, gradient dichloromethane to methanol:dichloromethane (1:4) to give the title compound (2.22 g, 94% yield). HPLC retention time: 4.01 min; MS: 361 (M+H).

This method was used for the preparation of intermediates 6B-6K using suitable starting materials:

| INT | Structure | Chemical name | s.m. | Ret time (min) | MS (M + H) |
|---|---|---|---|---|---|
| 6B | 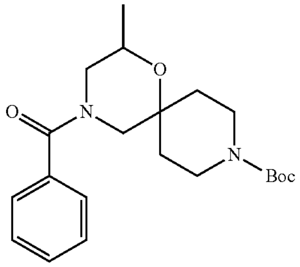 [SMILES: CC1CN(C(=O)c2ccccc2)CC2(CCN(C(=O)OC(C)(C)C)CC2)O1] | tert-butyl 4-benzoyl-2-methyl-1-oxa-4,9-diazaspiro[5.5]undecane-9-carboxylate | 5B | 4.33 | 375 |
| 6C | 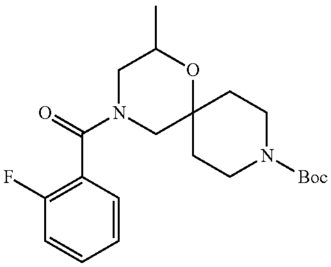 [SMILES: CC1CN(C(=O)c2ccccc2F)CC2(CCN(C(=O)OC(C)(C)C)CC2)O1] | tert-butyl 4-(2-fluoro-benzoyl)-2-methyl-1-oxa-4,9-diazaspiro[5.5]undecane-9-carboxylate | 5B | 4.49 | 393 |
| 6D | 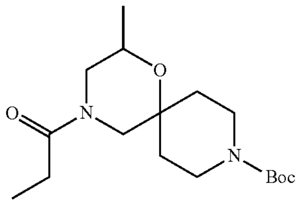 [SMILES: CCC(=O)N1CC(C)OC2(CCN(C(=O)OC(C)(C)C)CC2)C1] | tert-butyl 2-methyl-4-propionyl-1-oxa-4,9-diazaspiro[5.5]undecane-9-carboxylate | 5B | 3.87 | 327 |

-continued

| INT | Structure | Chemical name | s.m. | Ret time (min) | MS (M + H) |
|---|---|---|---|---|---|
| 6E | 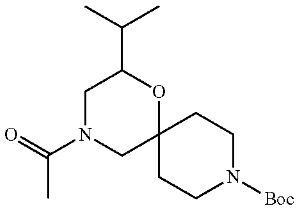 [SMILES: CC(=O)N1CC(C(C)C)OC2(CCN(C(=O)OC(C)(C)C)CC2)C1] | tert-butyl 4-acetyl-2-isopropyl-1-oxa-4,9-diazaspiro [5.5]undecane-9-carboxylate | 5F | 4.38 | 341 |
| 6F | 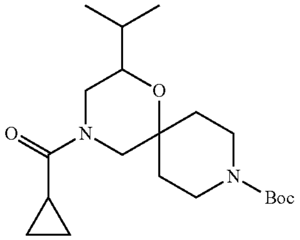 [SMILES: CC(C)C1CN(C(=O)C2CC2)CC2(CCN(C(=O)OC(C)(C)C)CC2)O1] | tert-butyl 4-(cyclopro-panecarbonyl)-2-isopropyl-1-oxa-4,9-diazaspiro [5.5]undecane-9-carboxylate | 5F | 4.84 | 367 |
| 6G | 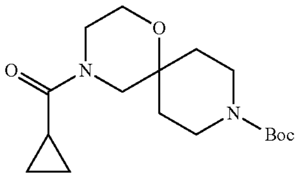 [SMILES: CC(C)(C)OC(=O)N1CCC2(CC1)CN(C(=O)C1CC1)CCO2] | tert-butyl 4-(cyclopro-panecarbonyl)-1-oxa-4,9-diazaspiro [5.5]undecane-9-carboxylate | 5A | 3.58 | 325 |
| 6H | 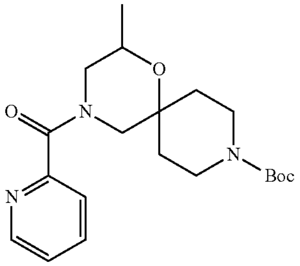 [SMILES: CC1CN(C(=O)c2ccccn2)CC2(CCN(C(=O)OC(C)(C)C)CC2)O1] | tert-butyl 2-methyl-4-picolinoyl-1-oxa-4,9-diazaspiro [5.5]undecane-9-carboxylate | 5B | 3.72 | 320 (M + H − 56) |
| 6I | 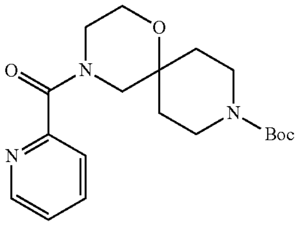 [SMILES: CC(C)(C)OC(=O)N1CCC2(CC1)CN(C(=O)c1ccccn1)CCO2] | tert-butyl 4-picolinoyl-1-oxa-4,9-diazaspiro [5.5]undecane-9-carboxylate | 5A | 3.43 | 306 (M + H − 56) |
| 6J | 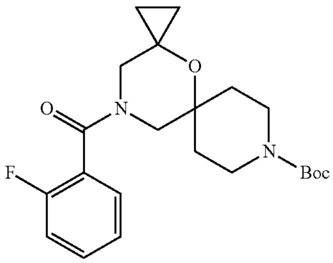 [SMILES: CC(C)(C)OC(=O)N1CCC2(CC1)CN(C(=O)c1ccccc1F)CC1(CC1)O2] | tert-butyl 12-(2-fluoro-benzoyl)-4-oxa-8,12-diazadispiro [2.1.5.3]tri-decane-8-carboxylate | 5E | 4.56 | 405 |

-continued

| INT | Structure | Chemical name | s.m. | Ret time (min) | MS (M + H) |
|---|---|---|---|---|---|
| 6K | 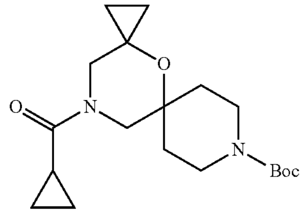 [SMILES: CC(C)(C)OC(=O)N1CCC2(CC1)CN(C(=O)C1CC1)CC1(CC1)O2] | tert-butyl 12-(cyclo-propanoyl)-4-oxa-8,12-diazadispiro[2.1.5.3]tri-decane-8-carboxylate | 5E | 3.97 | 351 |

Intermediate 6L: tert-butyl 4-(5-chloropicolinoyl)-2-methyl-1-oxa-4,9-diazaspiro[5.5]undecane-9-carboxylate

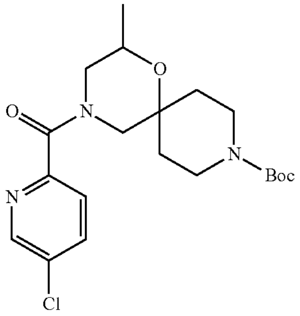 [SMILES: CC1CN(C(=O)c2ccc(Cl)cn2)CC2(CCN(C(=O)OC(C)(C)C)CC2)O1]

A mixture of intermediate 5B (0.381 g, 1.41 mmol), N-(3-dimethylaminopropyl)-N-ethylcarbodiimide hydrochloride (0.324 g, 1.69 mmol), 1-hydroxybenzotriazole (0.228 g, 1.69 mmol) and 5-chloropyridine-2-carboxylic acid (0.222 g, 1.41 mmol) in dichloromethane (12 mL) was stirred at r.t. overnight. The reaction mixture was diluted with water and the phases were separated. The organic phase was washed with 1M NaOH aqueous solution, dried over $MgSO_4$, filtered and concentrated to dryness. The residue was purified by flash chromatography, silica gel, gradient dichloromethane to methanol:dichloromethane (1:4) to give the title compound (0.442 g, 76% yield). HPLC retention time: 4.39 min; MS: 354 (M+H−56).

This method was used for the preparation of intermediates 6M-6O using suitable starting materials:

| INT | Structure | Chemical name | s.m. | Ret time (min) | MS (M + H) |
|---|---|---|---|---|---|
| 6M | 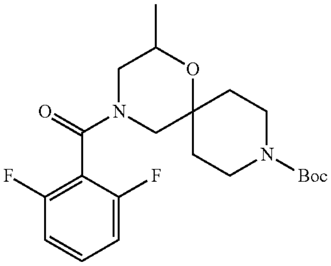 [SMILES: CC1CN(C(=O)c2c(F)cccc2F)CC2(CCN(C(=O)OC(C)(C)C)CC2)O1] | tert-butyl 4-(2,6-difluoro-benzoyl)-2-methyl-1-oxa-4,9-diazaspiro[5.5]undecane-9-carboxylate | 5B | 4.59 | 311 (M + H − 100) |
| 6N | 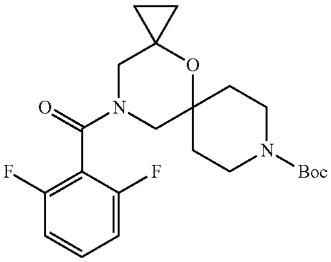 [SMILES: CC(C)(C)OC(=O)N1CCC2(CC1)CN(C(=O)c1c(F)cccc1F)CC1(CC1)O2] | tert-butyl 12-(2,6-difluoro-benzoyl)-4-oxa-8,12-diazadispiro[2.1.5.3]tri-decane-8-carboxylate | 5E | 4.53 | 423 |

-continued

| INT | Structure | Chemical name | s.m. | Ret time (min) | MS (M + H) |
|---|---|---|---|---|---|
| 6O | 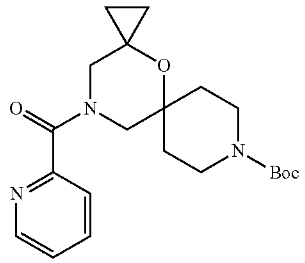 [SMILES: CC(C)(C)OC(=O)N1CCC2(CC1)CN(C(=O)c1ccccn1)CC1(CC1)O2] | tert-butyl 12-picolinyl-4-oxa-8,12-diazadispiro [2.1.5.3]tri-decane-8-carboxylate | 5E | 3.9 | 332 (M + H − 56) |

Intermediates 6P to 6AC were prepared according to the procedure described for Intermediate 6A, using suitable starting materials:

| INT | Structure | Chemical name | s.m. | Ret time (min) | MS (M + H) |
|---|---|---|---|---|---|
| 6P | 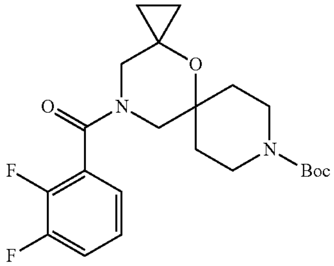 [SMILES: CC(C)(C)OC(=O)N1CCC2(CC1)CN(C(=O)c1cccc(F)c1F)CC1(CC1)O2] | tert-butyl 4-benzoyl-2-methyl-1-oxa-4,9-diazaspiro [5.5]undecane-9-carboxylate | 5E | 4.33 | 375 |
| 6Q | 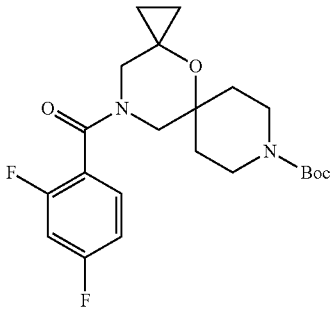 [SMILES: CC(C)(C)OC(=O)N1CCC2(CC1)CN(C(=O)c1ccc(F)cc1F)CC1(CC1)O2] | tert-butyl 12-(2,4-difluoro-benzoyl)-4-oxa-8,12-diazadispiro [2.1.5.3]tri-decane-8-carboxylate | 5E | 4.57 | 423 |
| 6R | 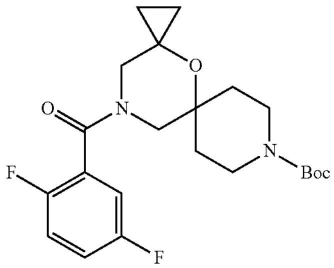 [SMILES: CC(C)(C)OC(=O)N1CCC2(CC1)CN(C(=O)c1cc(F)ccc1F)CC1(CC1)O2] | tert-butyl 12-(2,5-difluoro-benzoyl)-4-oxa-8,12-diazadispiro [2.1.5.3]tri-decane-8-carboxylate | 5E | 4.46 | 423 |

-continued

| INT | Structure | Chemical name | s.m. | Ret time (min) | MS (M + H) |
|---|---|---|---|---|---|
| 6S | 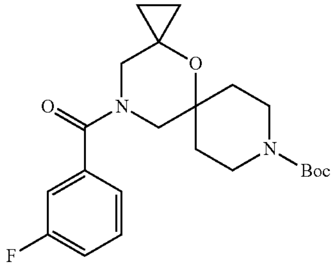 [SMILES: CC(C)(C)OC(=O)N1CCC2(CC1)CN(C(=O)c1cccc(F)c1)CC1(CC1)O2] | tert-butyl 12-(3-fluoro-benzoyl)-4-oxa-8,12-diazadispiro[2.1.5.3]tri-decane-8-carboxylate | 5E | 4.45 | 405 |
| 6T | 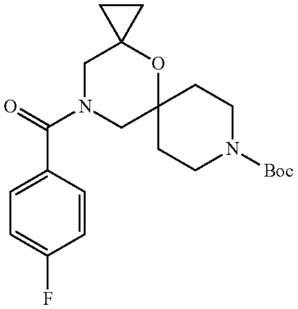 [SMILES: CC(C)(C)OC(=O)N1CCC2(CC1)CN(C(=O)c1ccc(F)cc1)CC1(CC1)O2] | tert-butyl 12-(4-fluoro-benzoyl)-4-oxa-8,12-diazadispiro[2.1.5.3]tri-decane-8-carboxylate | 5E | 4.42 | 405 |
| 6U | 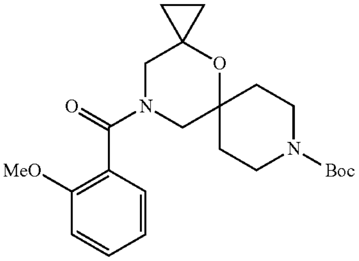 [SMILES: COc1ccccc1C(=O)N1CC2(CCN(C(=O)OC(C)(C)C)CC2)OC2(CC2)C1] | tert-butyl 12-(2-methoxy-benzoyl)-4-oxa-8,12-diazadispiro[2.1.5.3]tri-decane-8-carboxylate | 5E | 4.3 | 417 |
| 6V | 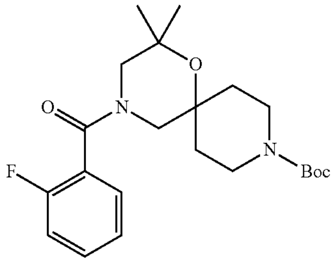 [SMILES: CC(C)(C)OC(=O)N1CCC2(CC1)CN(C(=O)c1ccccc1F)CC(C)(C)O2] | tert-butyl 4-(2-fluoro-benzoyl)-2,2-dimethyl-1-oxa-4,9-diazaspiro[5.5]undecane-9-carboxylate | 5K | 4.67 | 407 |
| 6W | 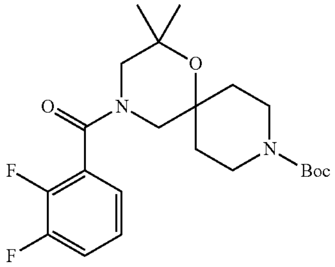 [SMILES: CC(C)(C)OC(=O)N1CCC2(CC1)CN(C(=O)c1cccc(F)c1F)CC(C)(C)O2] | tert-butyl 4-(2,3-difluoro-benzoyl)-2,2-dimethyl-1-oxa-4,9-diazaspiro[5.5]undecane-9-carboxylate | 5K | 4.76 | 425 |

-continued

| INT | Structure | Chemical name | s.m. | Ret time (min) | MS (M + H) |
|---|---|---|---|---|---|
| 6X | 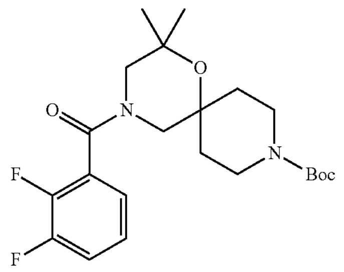 [SMILES: CC(C)(C)OC(=O)N1CCC2(CC1)CN(C(=O)c1cccc(F)c1F)CC(C)(C)O2] | tert-butyl 4-(2,3-difluoro-benzoyl)-2-methyl-1-oxa-4,9-diazaspiro[5.5]undecane-9-carboxylate | 5B | 4.55 (method B) | 411.1 |
| 6Y | 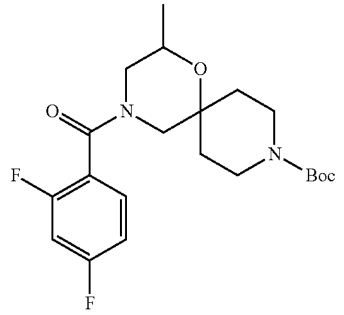 [SMILES: CC1CN(C(=O)c2ccc(F)cc2F)CC2(CCN(C(=O)OC(C)(C)C)CC2)O1] | tert-butyl 4-(2,4-difluoro-benzoyl)-2-methyl-1-oxa-4,9-diazaspiro[5.5]undecane-9-carboxylate | 5B | 4.52 (method B) | 411.1 |
| 6Z | 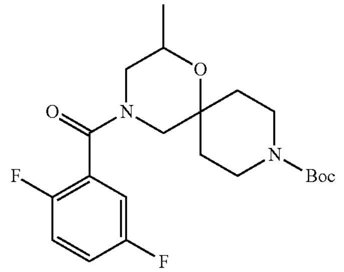 [SMILES: CC1CN(C(=O)c2cc(F)ccc2F)CC2(CCN(C(=O)OC(C)(C)C)CC2)O1] | tert-butyl 4-(2,5-difluoro-benzoyl)-2-methyl-1-oxa-4,9-diazaspiro[5.5]undecane-9-carboxylate | 5B | 4.52 (method B) | 411.2 |
| 6AA | 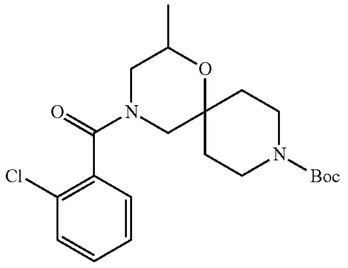 [SMILES: CC1CN(C(=O)c2ccccc2Cl)CC2(CCN(C(=O)OC(C)(C)C)CC2)O1] | tert-butyl 4-(2-chloro-benzoyl)-2-methyl-1-oxa-4,9-diazaspiro[5.5]undecane-9-carboxyalte | 5B | 4.56 (method B) | 409.1 |
| 6AB | 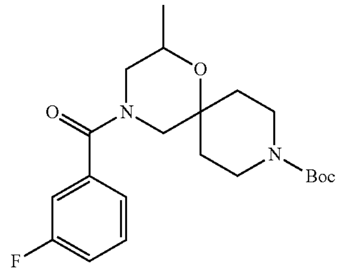 [SMILES: CC1CN(C(=O)c2cccc(F)c2)CC2(CCN(C(=O)OC(C)(C)C)CC2)O1] | tert-butyl 4-(3-fluoro-benzoyl)-2-methyl-1-oxa-4,9-diazaspiro[5.5]undecane-9-carboxylate | 5B | 4.43 (method B) | 393.2 |

-continued

| INT | Structure | Chemical name | s.m. | Ret time (min) | MS (M + H) |
|---|---|---|---|---|---|
| 6AC | 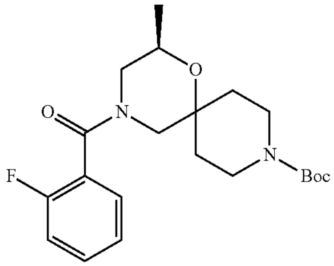 [SMILES: C[C@@H]1CN(C(=O)c2ccccc2F)CC2(CCN(C(=O)OC(C)(C)C)CC2)O1] | (R)-tert-butyl 4-(2-fluorobenzoyl)-2-methyl-1-oxa-4,9-diazaspiro[5.5]undecane-9-carboxylate | 5M | 4.42 (method B) | 393.1 |

Intermediates 6AD and 6AE were prepared according to the procedure described for Intermediate 6L, using suitable starting materials:

| INT | Structure | Chemical name | s.m. | Ret time (min) | MS (M + H) |
|---|---|---|---|---|---|
| 6AD | 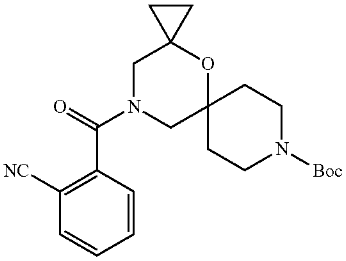 [SMILES: CC(C)(C)OC(=O)N1CCC2(CC1)CN(C(=O)c1ccccc1C#N)CC1(CC1)O2] | tert-butyl 12-(2-cyanobenzoyl)-4-oxa-8,12-diazadispiro[2.1.5.3]tridecane-8-carboxylate | 5E | 4.15 | 356.1 (M + H − 56) |
| 6AE | 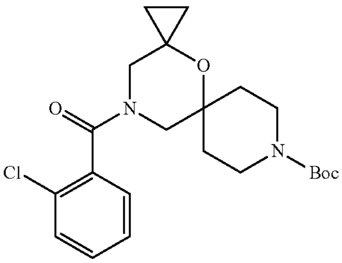 [SMILES: CC(C)(C)OC(=O)N1CCC2(CC1)CN(C(=O)c1ccccc1Cl)CC1(CC1)O2] | tert-butyl 12-(2-chlorobenzoyl)-4-oxa-8,12-diazadispiro[2.1.5.3]tridecane-8-carboxylate | 5E | 4.56 | 421.1 |

Intermediate 7A: tert-butyl 4-(phenylsulfonyl)-1-oxa-4,9-diazaspiro[5.5]undecane-9-carboxylate

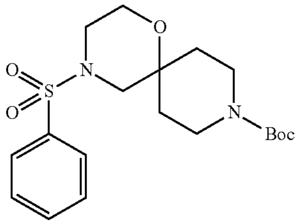 [SMILES: CC(C)(C)OC(=O)N1CCC2(CC1)CN(S(=O)(=O)c1ccccc1)CCO2]

To a solution of intermediate 5A (0.150 g, 0.585 mmol) in dichloromethane (6 mL) cooled at 0° C., benzenesulfonyl chloride (0.083 mL, 0.644 mmol) and triethylamine (0.122 mL, 0.878 mmol) were added dropwise. The reaction mixture was stirred at rt overnight, then water was added and it was extracted with dichloromethane. The organic phases were combined, dried over $MgSO_4$, filtered and concentrated to dryness to give the title compound (0.225 g, 97% yield). HPLC retention time: 4.55 min; MS: 297 (M+H−100).

This method was used for the preparation of intermediates 7B-7D using suitable starting materials:

| INT | Structure | Chemical name | s.m. | Ret time (min) | MS (M + H) |
|---|---|---|---|---|---|
| 7B | 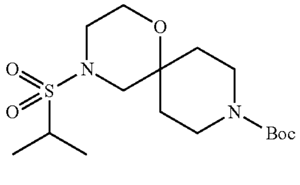 [SMILES: CC(C)S(=O)(=O)N1CCOC2(CCN(C(=O)OC(C)(C)C)CC2)C1] | tert-butyl 4-(isopropyl-sulfonyl)-1-oxa-4,9-diazaspiro[5.5] undecane-9-carboxylate | 5A | 4.00 | 263 (M + H − 100) |
| 7C | 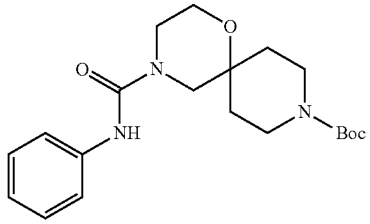 [SMILES: CC(C)(C)OC(=O)N1CCC2(CC1)CN(C(=O)Nc1ccccc1)CCO2] | tert-butyl 4-(phenyl-carbamoyl)-1-oxa-4,9-diazaspiro[5.5] undecane-9-carboxylate (*1) | 5A | 4.01 | 320 (M + H − 56) |
| 7D | 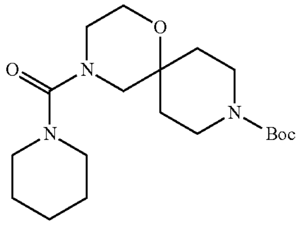 [SMILES: CC(C)(C)OC(=O)N1CCC2(CC1)CN(C(=O)N1CCCCC1)CCO2] | tert-butyl 4-(piperidine-1-carbonyl)-1-oxa-4,9-diazaspiro[5.5] undecane-9-carboxylate (*2) | 5A | 4.18 | 312 (M + H − 56) |

*1: Phenyl isocyanate was used as electrophile

*2: 1-Piperidinecarbonyl chloride was used as electrophile and DIPEA was used as base instead of triethylamine.

Intermediate 7E: tert-butyl 4-(methyl(phenyl)carbamoyl)-1-oxa-4,9-diazaspiro[5.5]undecane-9-carboxylate

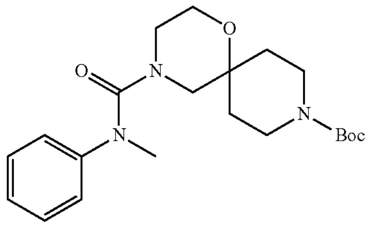 [SMILES: CN(C(=O)N1CCOC2(CCN(C(=O)OC(C)(C)C)CC2)C1)c1ccccc1]

A solution of intermediate 7C (0.120 g, 0.320 mmol) in dry DMF (1.2 mL) was added to a mixture of NaH (15 mg, 60 wt % in mineral oil, 0.383 mmol) in dry DMF (0.5 mL) cooled at 0° C. The reaction mixture was stirred at 0° C. for 30 minutes, then iodomethane (0.040 mL, 0.639 mmol) was added and the resulting mixture was stirred at r.t. overnight. Water was added to the reaction mixture and it was extracted with dichloromethane. The organic phases were combined, dried over $MgSO_4$, filtered and concentrated to dryness. The residue was purified by flash chromatography, silica gel, gradient dichloromethane to methanol:dichloromethane (1:4) to give the title compound (45 mg, 36% yield). HPLC retention time: 4.39 min; MS: 334 (M+H−56).

SYNTHESIS OF EXAMPLES

Example 1: (2-methyl-9-phenethyl-1-oxa-4,9-diazaspiro[5.5]undecan-4-yl)(phenyl)methanone hydrochloride

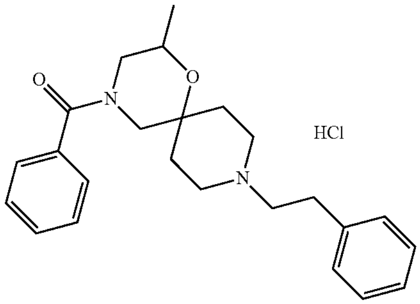 [SMILES: CC1CN(C(=O)c2ccccc2)CC2(CCN(CCc3ccccc3)CC2)O1 ; Cl]

HCl

Step 1. Title compound: To a solution of intermediate 5H (0.142 g, 0.518 mmol) and triethylamine (0.173 mL, 1.242 mmol) in dichloromethane (6 mL), benzoyl chloride (0.173 mL, 1.242 mmol) was added dropwise at 0° C. The reaction mixture was stirred at 0° C. for 2 h. $NaHCO_3$ sat solution was added and the aqueous phase was extracted with dichlorometane. The organic phases were combined, washed with brine, dried over $MgSO_4$, filtered and concentrated to dryness. The residue was purified by flash chromatography, silica gel, gradient dichloromethane to methanol:dichloromethane (1:9) to give the title compound as its free base (131 mg, 67% yield).

Step 2. Preparation of the hydrochloride salt: To a solution of the free base (28 mg, 0.074 mmol) in anhydrous diethyl ether (1 mL), HCl (2M solution in diethyl ether, 0.041 mL, 0.081 mmol) was added. The solvent was evaporated to dryness to give the corresponding HCl salt (26 mg, 86% yield).

HPLC retention time: 4.27 min; MS: 379.2 (M+H).

This method was used for the preparation of examples 2-11 using suitable starting materials:

| EX | Structure | Chemical name | Ret time (min | MS (M + H) |
|---|---|---|---|---|
| 2 | 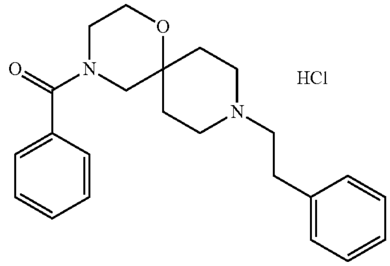 [SMILES: O=C(c1ccccc1)N1CCOC2(CCN(CCc3ccccc3)CC2)C1 ; Cl] HCl | (9-phenethyl-1-oxa-4,9-diazaspiro[5.5]undecan-4-yl)(phenyl)methanone hydrochloride | 3.91 | 365.2 |
| 3 | 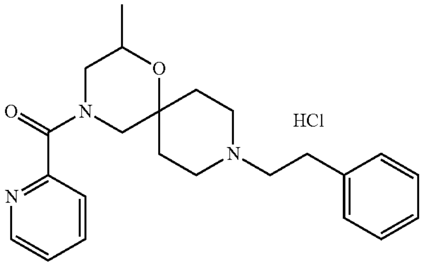 [SMILES: CC1CN(C(=O)c2ccccn2)CC2(CCN(CCc3ccccc3)CC2)O1 ; Cl] HCl | (2-methyl-9-phenethyl-1-oxa-4,9-diazaspiro[5.5]undecan-4-yl)(pyridin-2-yl)methanone hydrochloride | 3.64 | 380.2 |
| 4 | 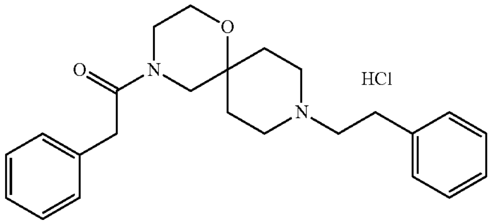 [SMILES: O=C(Cc1ccccc1)N1CCOC2(CCN(CCc3ccccc3)CC2)C1 ; Cl] HCl | 1-(9-phenethyl-1-oxa-4,9-diazaspiro[5.5]undecan-4-yl)-2-phenylethanone hydrochloride | 4.03 | 379.2 |

-continued

| EX | Structure | Chemical name | Ret time (min | MS (M + H) |
|---|---|---|---|---|
| 5 | 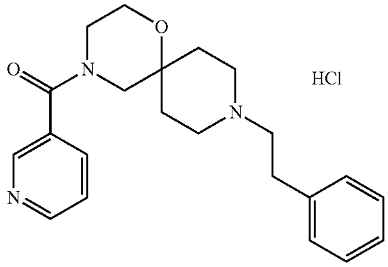 [SMILES: O=C(c1cccnc1)N1CCOC2(CCN(CCc3ccccc3)CC2)C1 ; Cl] HCl | (9-phenethyl-1-oxa-4,9-diazaspiro[5.5]undecan-4-yl)(pyridin-3-yl)methanone hydrochloride | 3.24 | 366.2 |
| 6 | 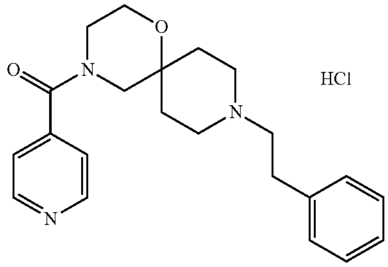 [SMILES: O=C(c1ccncc1)N1CCOC2(CCN(CCc3ccccc3)CC2)C1 ; Cl] HCl | (9-phenethyl-1-oxa-4,9-diazaspiro[5.5]undecan-4-yl)(pyridin-4-yl)methanone hydrochloride | 3.26 | 366.2 |
| 7 | 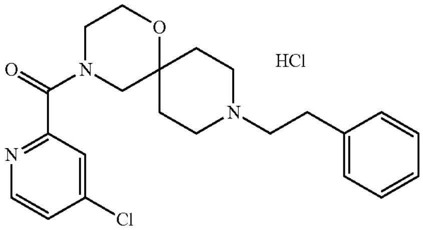 [SMILES: O=C(c1cc(Cl)ccn1)N1CCOC2(CCN(CCc3ccccc3)CC2)C1 ; Cl] HCl | (4-chloropyridin-2-yl)(9-phenethyl-1-oxa-4,9-diazaspiro[5.5]undecan-4-yl)methanone hydrochloride | 3.81 | 400.1 |
| 8 | 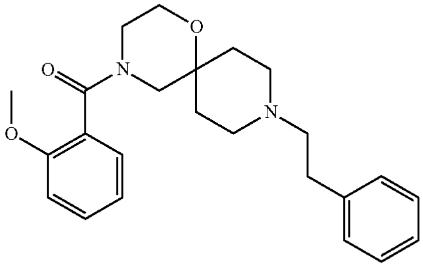 [SMILES: COc1ccccc1C(=O)N1CCOC2(CCN(CCc3ccccc3)CC2)C1] | (2-methoxyphenyl)(9-phenethyl-1-oxa-4,9-diazaspiro[5.5]undecan-4-yl)methanone | 3.91 | 395.2 |
| 9 | 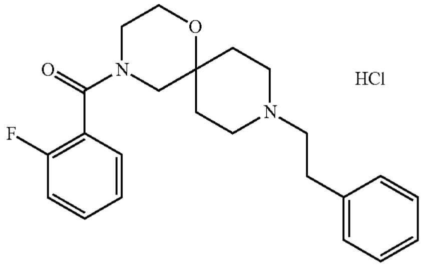 [SMILES: O=C(c1ccccc1F)N1CCOC2(CCN(CCc3ccccc3)CC2)C1 ; Cl] HCl | (2-fluorophenyl)(9-phenethyl-1-oxa-4,9-diazaspiro[5.5]undecan-4-yl)methanone hydrochloride | 4.01 | 383.2 |

-continued

| EX | Structure | Chemical name | Ret time (min | MS (M + H) |
|---|---|---|---|---|
| 10 | 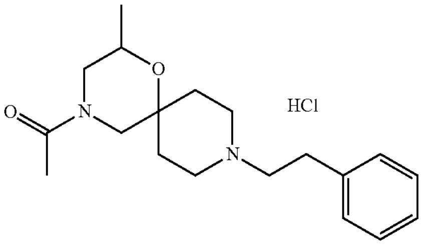 [SMILES: CC(=O)N1CC(C)OC2(CCN(CCc3ccccc3)CC2)C1 ; Cl] HCl | 1-(2-methyl-9-phenethyl-1-oxa-4,9-diazaspiro[5.5]undecan-4-yl)ethanone hydrochloride | 3.42 | 317.2 |
| 11 | 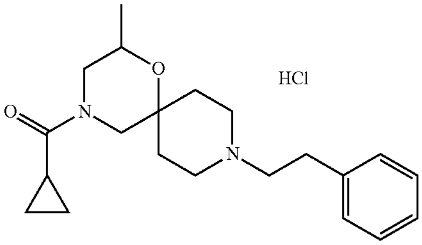 [SMILES: CC1CN(C(=O)C2CC2)CC2(CCN(CCc3ccccc3)CC2)O1 ; Cl] HCl | cyclopropyl(2-methyl-9-phenethyl-1-oxa-4,9-diazaspiro[5.5]undecan-4-yl)methanone hydrochloride | 3.81 | 343.2 |

Where indicated, the hydrochloride salts were prepared as described in example 1

Example 12: (9-phenethyl-1-oxa-4,9-diazaspiro[5.5]undecan-4-yl)(thiazol-4-yl)methanone

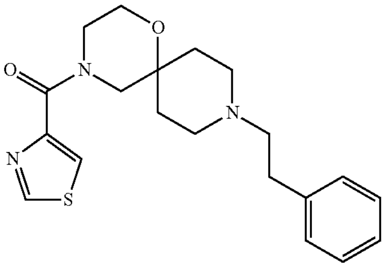 [SMILES: O=C(c1cscn1)N1CCOC2(CCN(CCc3ccccc3)CC2)C1]

To a solution of intermediate 5G (0.085 g, 0.327 mmol) in dichloromethane (3 mL), 1-hydroxybenzotriazole (0.053 g, 0.392 mmol), N-(3-dimethylaminopropyl)-N-ethylcarbodiimide hydrochloride (0.075 g, 0.392 mmol) and thiazole-4-carboxylic acid (0.042 g, 0.327 mmol) were subsequently added. The reaction mixture was stirred at r.t. overnight. Water and dichloromethane were added and the phases were separated. The organic phase was washed with 1M NaOH aqueous solution, dried over $MgSO_4$, filtered and concentrated to dryness. The residue was purified by flash chromatography, silica gel, gradient dichloromethane to methanol:dichloromethane (1:4) to give the title compound (71 mg, 58% yield). HPLC retention time: 3.35 min; MS: 372.1 (M+H).

This method was used for the preparation of examples 13-36 using suitable starting materials:

| EX | Structure | Chemical name | Ret time (min | MS (M + H) |
|---|---|---|---|---|
| 13 | 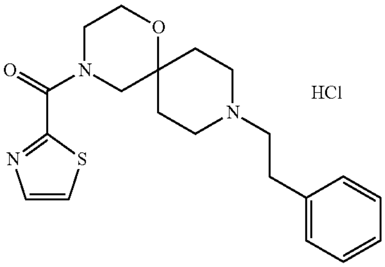 [SMILES: O=C(c1nccs1)N1CCOC2(CCN(CCc3ccccc3)CC2)C1 ; Cl] HCl | (9-phenethyl-1-oxa-4,9-diazaspiro[5.5]undecan-4-yl)(thiazol-2-yl)methanone hydrochloride | 3.8 | 372.1 |

-continued

| EX | Structure | Chemical name | Ret time (min | MS (M + H) |
|---|---|---|---|---|
| 14 | 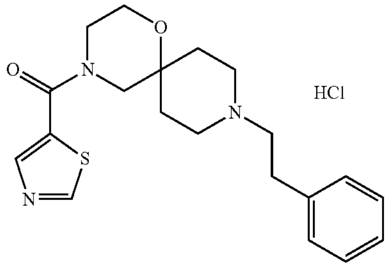 [SMILES: O=C(c1cncs1)N1CCOC2(CCN(CCc3ccccc3)CC2)C1 ; Cl] HCl | (9-phenethyl-1-oxa-4,9-diazaspiro[5.5]undecan-4-yl)(thiazol-5-yl)methanone hydrochloride | 3.33 | 372.1 |
| 15 | 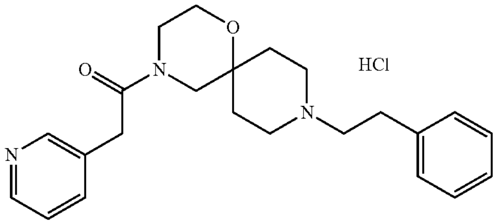 [SMILES: O=C(Cc1cccnc1)N1CCOC2(CCN(CCc3ccccc3)CC2)C1 ; Cl] HCl | 1-(9-phenethyl-1-oxa-4,9-diazaspiro[5.5]undecan-4-yl)-2-(pyridin-3-yl)ethanone hydrochloride | 3.26 | 380.2 |
| 16 | 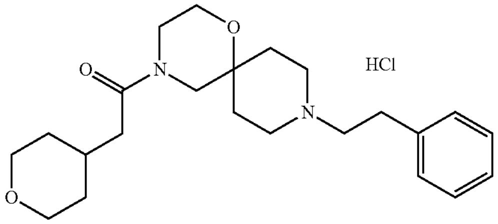 [SMILES: O=C(CC1CCOCC1)N1CCOC2(CCN(CCc3ccccc3)CC2)C1 ; Cl] HCl | 1-(9-phenethyl-1-oxa-4,9-diazaspiro[5.5]undecan-4-yl)-2-(tetrahydro-2H-pyran-4-yl)ethanone hydrochloride | 3.4 | 387.2 |
| 17 | 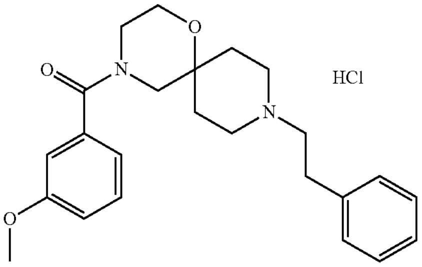 [SMILES: COc1cccc(C(=O)N2CCOC3(CCN(CCc4ccccc4)CC3)C2)c1 ; Cl] HCl | (3-methoxyphenyl)(9-phenethyl-1-oxa-4,9-diazaspiro[5.5]undecan-4-yl)methanone hydrochloride | 4.02 | 395.2 |
| 18 | 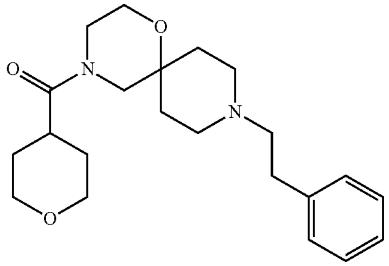 [SMILES: O=C(C1CCOCC1)N1CCOC2(CCN(CCc3ccccc3)CC2)C1] | (9-phenethyl-1-oxa-4,9-diazaspiro[5.5]undecan-4-yl)(tetrahydro-2H-pyran-4-yl)methanone | 3.29 | 373.2 |
| 19 | 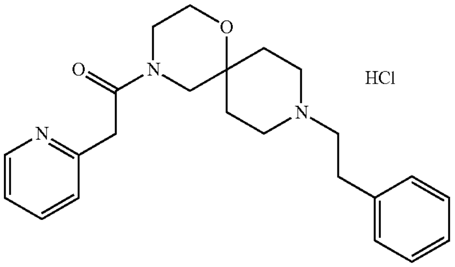 [SMILES: O=C(Cc1ccccn1)N1CCOC2(CCN(CCc3ccccc3)CC2)C1 ; Cl] HCl | 1-(9-phenethyl-1-oxa-4,9-diazaspiro[5.5]undecan-4-yl)-2-(pyridin-2-yl)ethanone hydrochloride | 3.32 | 380.2 |

-continued

| EX | Structure | Chemical name | Ret time (min | MS (M + H) |
|---|---|---|---|---|
| 20 | 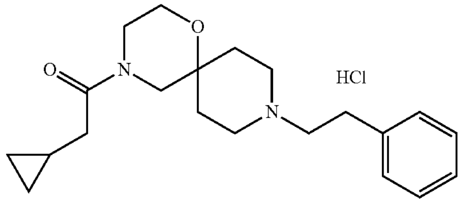 [SMILES: O=C(CC1CC1)N1CCOC2(CCN(CCc3ccccc3)CC2)C1 ; Cl] HCl | 2-cyclopropyl-1-(9-phenethyl-1-oxa-4,9-diazaspiro[5.5]undecan-4-yl)ethanone hydrochloride | 3.62 | 343.2 |
| 21 | 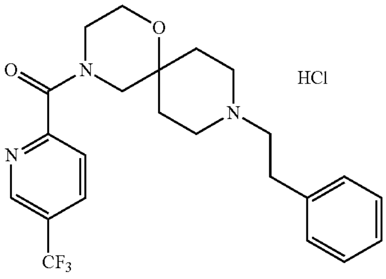 [SMILES: O=C(c1ccc(C(F)(F)F)cn1)N1CCOC2(CCN(CCc3ccccc3)CC2)C1 ; Cl] HCl | (9-phenethyl-1-oxa-4,9-diazaspiro[5.5]undecan-4-yl)(5-(trifluoromethyl)pyridin-2-yl)methanone hydrochloride | 4.23 | 434.2 |
| 22 | 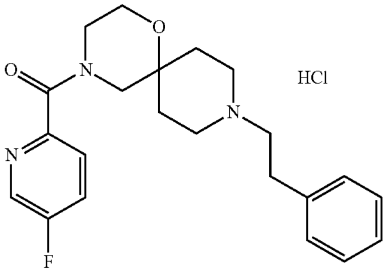 [SMILES: O=C(c1ccc(F)cn1)N1CCOC2(CCN(CCc3ccccc3)CC2)C1 ; Cl] HCl | (5-fluoropyridin-2-yl)(9-phenethyl-1-oxa-4,9-diazaspiro[5.5]undecan-4-yl)methanone hydrochloride | 3.65 | 384.2 |
| 23 | 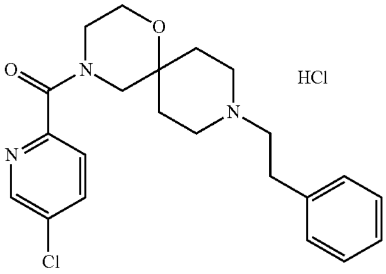 [SMILES: O=C(c1ccc(Cl)cn1)N1CCOC2(CCN(CCc3ccccc3)CC2)C1 ; Cl] HCl | (5-chloropyridin-2-yl)(9-phenethyl-1-oxa-4,9-diazaspiro[5.5]undecan-4-yl)methanone hydrochloride | 3.94 | 400.2 |
| 24 | 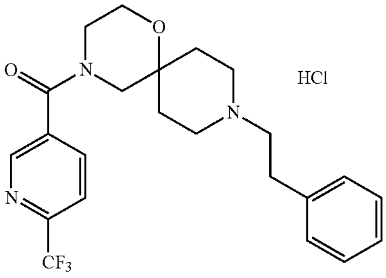 [SMILES: O=C(c1ccc(C(F)(F)F)nc1)N1CCOC2(CCN(CCc3ccccc3)CC2)C1 ; Cl] HCl | (9-phenethyl-1-oxa-4,9-diazaspiro[5.5]undecan-4-yl)(6-(trifluoromethyl)pyridin-3-yl)methanone hydrochloride | 4.14 | 434.2 |

-continued

| EX | Structure | Chemical name | Ret time (min | MS (M + H) |
|---|---|---|---|---|
| 25 | 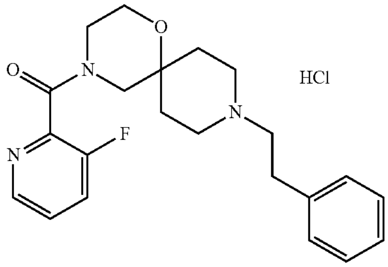 [SMILES: O=C(c1ncccc1F)N1CCOC2(CCN(CCc3ccccc3)CC2)C1 ; Cl] HCl | (3-fluoropyridin-2-yl)(9-phenethyl-1-oxa-4,9-diazaspiro[5.5]undecan-4-yl)methanone hydrochloride | 3.45 | 384.2 |
| 26 | 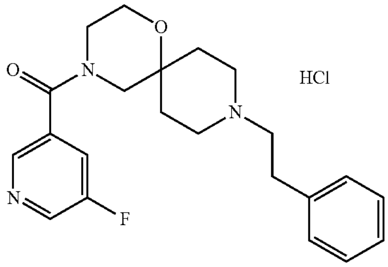 [SMILES: O=C(c1cncc(F)c1)N1CCOC2(CCN(CCc3ccccc3)CC2)C1 ; Cl] HCl | (5-fluoropyridin-3-yl)(9-phenethyl-1-oxa-4,9-diazaspiro[5.5]undecan-4-yl)methanone hydrochloride | 3.53 | 384.2 |
| 27 | 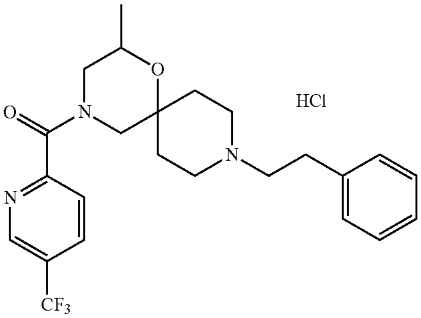 [SMILES: CC1CN(C(=O)c2ccc(C(F)(F)F)cn2)CC2(CCN(CCc3ccccc3)CC2)O1 ; Cl] HCl | (2-methyl-9-phenethyl-1-oxa-4,9-diazaspiro[5.5]undecan-4-yl)(5-(trifluoromethyl)pyridin-2-yl)methanone hydrochloride | 4.23 | 448 |
| 28 | 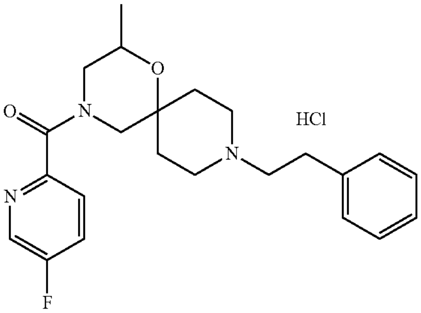 [SMILES: CC1CN(C(=O)c2ccc(F)cn2)CC2(CCN(CCc3ccccc3)CC2)O1 ; Cl] HCl | (5-fluoropyridin-2-yl)(2-methyl-9-phenethyl-1-oxa-4,9-diazaspiro[5.5]undecan-4-yl)methanone hydrochloride | 3.72 | 398 |
| 29 | 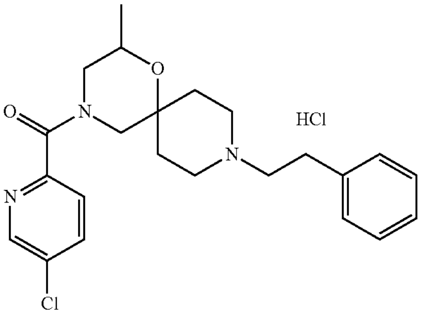 HCl | (5-chloropyridin-2-yl)(2-methyl-9-phenethyl-1-oxa-4,9-diazaspiro[5.5]undecan-4-yl)methanone hydrochloride | 4.26 | 414 |

-continued

| EX | Structure | Chemical name | Ret time (min | MS (M + H) |
|---|---|---|---|---|
| 30 | 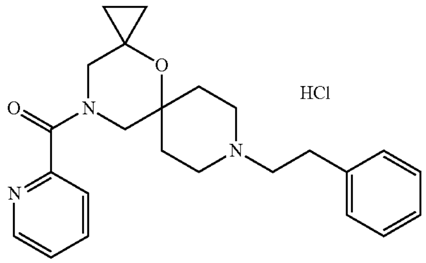 [SMILES: O=C(c1ccccn1)N1CC2(CCN(CCc3ccccc3)CC2)OC2(CC2)C1 ; Cl] | 8-phenethyl-12-[(pyridin-2-yl)carbonyl]-4-oxa-8,12-diazadispiro[2.1.5.3]tri-decane hydrochloride | 3.77 | 392.2 |
| 31 | 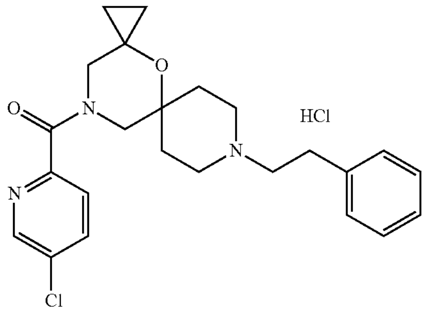 [SMILES: O=C(c1ccc(Cl)cn1)N1CC2(CCN(CCc3ccccc3)CC2)OC2(CC2)C1 ; Cl] | 12-[(5-chloropyridin-2-yl)carbonyl]-8-phenethyl-4-oxa-8,12-diazadispiro [2.1.5.3]tridecane hydrochloride | 4.36 | 426.2 |
| 32 | 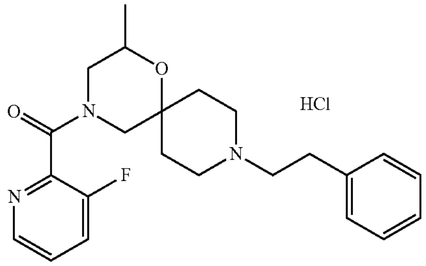 [SMILES: CC1CN(C(=O)c2ncccc2F)CC2(CCN(CCc3ccccc3)CC2)O1 ; Cl] | (3-fluoropyridin-2-yl)(2-methyl-9-phenethyl-1-oxa-4,9-diazaspiro[5.5]undecan-4-yl)methanone hydrochloride | 3.8 | 398.2 |
| 33 | 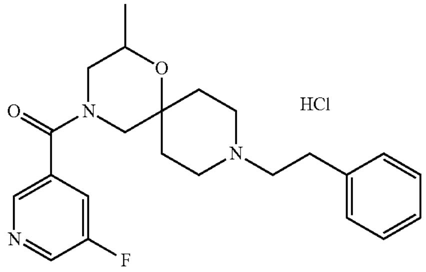 [SMILES: CC1CN(C(=O)c2cncc(F)c2)CC2(CCN(CCc3ccccc3)CC2)O1 ; Cl] | (5-fluoropyridin-3-yl)(2-methyl-9-phenethyl-1-oxa-4,9-diazaspiro[5.5]undecan-4-yl)methanone hydrochloride | 3.89 | 398.2 |
| 34 | 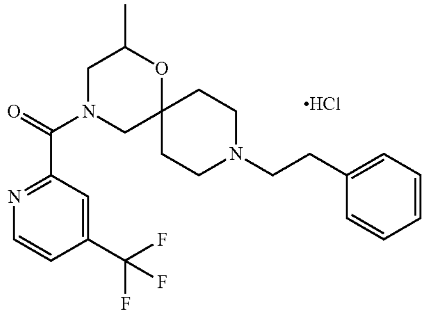 [SMILES: CC1CN(C(=O)c2cc(C(F)(F)F)ccn2)CC2(CCN(CCc3ccccc3)CC2)O1 ; Cl] | (2-methyl-9-phenethyl-1-oxa-4,9-diazaspiro[5.5]undecan-4-yl)(4-(trifluoromethyl)pyridin-2-yl)methanone hydrochloride | 4.49 | 448.2 |

-continued

| EX | Structure | Chemical name | Ret time (min | MS (M + H) |
|---|---|---|---|---|
| 35 | 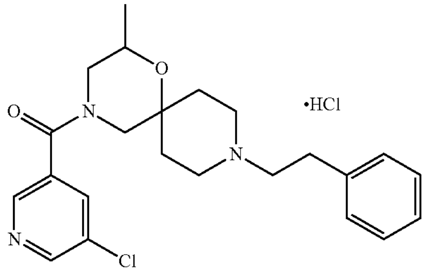 [SMILES: CC1CN(C(=O)c2cncc(Cl)c2)CC2(CCN(CCc3ccccc3)CC2)O1 ; Cl] •HCl | (5-chloropyridin-3-yl)(2-methyl-9-phenethyl-1-oxa-4,9-diazaspiro[5.5]undecan-4-yl)methanone hydrochloride | 4.06 | 414.2 |
| 36 | 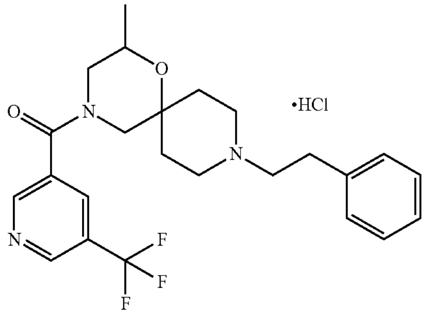 [SMILES: CC1CN(C(=O)c2cncc(C(F)(F)F)c2)CC2(CCN(CCc3ccccc3)CC2)O1 ; Cl] •HCl | (2-methyl-9-phenethyl-1-oxa-4,9-diazaspiro[5.5]undecan-4-yl)(5-(trifluoromethyl)pyridin-3-yl)methanone hydrochloride | 4.33 | 448.2 |

Where indicated, the hydrochloride salts were prepared as described in example 1

Example 37: (9-(2-(3-chloropyridin-2-yl)ethyl)-2-methyl-1-oxa-4,9-diazaspiro[5.5]undecan-4-yl)(phenyl)methanone hydrochloride

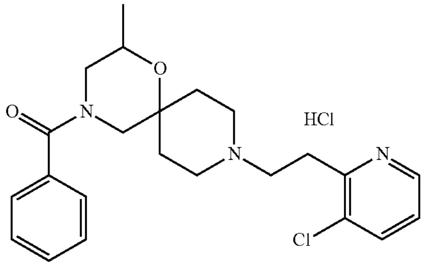 [SMILES: CC1CN(C(=O)c2ccccc2)CC2(CCN(CCc3ncccc3Cl)CC2)O1 ; Cl]

HCl

Step 1: (2-methyl-1-oxa-4,9-diazaspiro[5.5]undecan-4-yl)(phenyl)methanone trifluoroacetate. To a solution of intermediate 6B (1.35 g, 3.59 mmol) in dichloromethane (13 mL), trifluoroacetic acid (2.8 mL, 35.9 mmol) was added, and the reaction mixture was heated to reflux for 2 h. The solvent was evaporated to give the title compound as a crude product (1.9 g, 72 wt %, quant yield), that was used in the following step without further purification. HPLC retention time: 2.13 min; MS: 275 (M+H).

Step 2: (2-methyl-1-oxa-4,9-diazaspiro[5.5]undecan-4-yl)(phenyl)methanone. The crude product obtained in step 1 (0.100 g, 72 wt %, 0.26 mmol) was dissolved in dichloromethane and it was washed with 1M NaOH aqueous solution. The combined aqueous phases were back-extracted with dichloromethane. The organic phases were combined, washed with water, dried over $MgSO_4$, filtered and concentrated under vacuum to give the title compound (0.050 g, 70% yield for the two steps).

Step 3: Title compound: A solution of the compound obtained in step 2 (0.050 g, 0.182 mmol) and 3-chloro-2-vinylpyridine (described in Angewandte Chemie-International Edition; vol. 52; nb. 37; (2013); p. 9755-9758) (0.033 g, 0.237 mmol) in 2-methoxyethanol (1 mL) was heated at 120° C. in a sealed tube under argon for 2 days. The reaction mixture was cooled to r.t. and the solvent was evaporated. The residue was purified by flash chromatography, silica gel, gradient dichloromethane to methanol:dichloromethane (1:4) to give the title compound as its free base (19 mg, 25% yield).

The previous compound was converted to its hydrochloride salt as described in example 1.

HPLC retention time: 3.77 min; MS: 414 (M+H).

This method was used for the preparation of examples 38-60 using suitable starting materials:

| EX | Structure | Chemical name | Ret time (min | MS (M + H) |
|---|---|---|---|---|
| 38 | 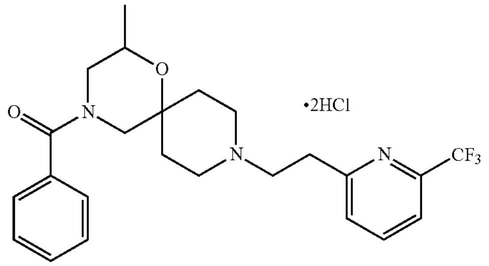 [SMILES: CC1CN(C(=O)c2ccccc2)CC2(CCN(CCc3cccc(C(F)(F)F)n3)CC2)O1 ; "·2HCl"] | (2-methyl-9-(2-(6-(trifluoromethyl)pyridin-2-yl)ethyl)-1-oxa-4,9-diazaspiro[5.5]undecan-4-yl)(phenyl)methanone dihydrochloride | 4.22 | 448.2 |
| 39 | 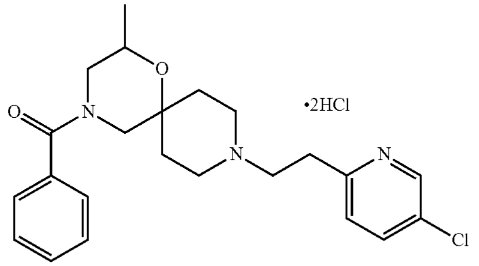 [SMILES: CC1CN(C(=O)c2ccccc2)CC2(CCN(CCc3ccc(Cl)cn3)CC2)O1 ; "·2HCl"] | (9-(2-(5-chloropyridin-2-yl)ethyl)-2-methyl-1-oxa-4,9-diazaspiro[5.5]undecan-4-yl)(phenyl)methanone dihydrochloride | 3.87 | 414.1 |
| 40 | 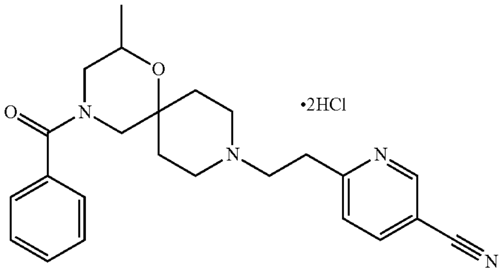 [SMILES: CC1CN(C(=O)c2ccccc2)CC2(CCN(CCc3ccc(C#N)cn3)CC2)O1 ; "·2HCl"] | 6-(2-(4-benzoyl-2-methyl-1-oxa-4,9-diazaspiro[5.5]undecan-9-yl)ethyl)nicotinonitrile dihydrochloride | 3.48 | 405.2 |
| 41 | 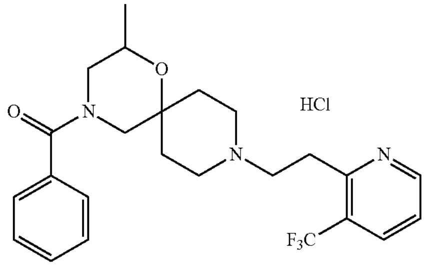 [SMILES: CC1CN(C(=O)c2ccccc2)CC2(CCN(CCc3ncccc3C(F)(F)F)CC2)O1 ; Cl] | (2-methyl-9-(2-(3-(trifluoromethyl)pyridin-2-yl)ethyl)-1-oxa-4,9-diazaspiro[5.5]undecan-4-yl)(phenyl)methanone hydrochloride | 4.07 | 448.2 |
| 42 | 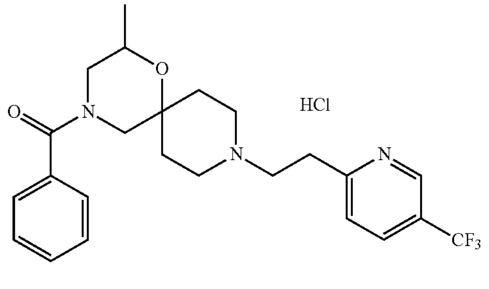 [SMILES: CC1CN(C(=O)c2ccccc2)CC2(CCN(CCc3ccc(C(F)(F)F)cn3)CC2)O1 ; Cl] | (2-methyl-9-(2-(5-(trifluoromethyl)pyridin-2-yl)ethyl)-1-oxa-4,9-diazaspiro[5.5]undecan-4-yl)(phenyl)methanone hydrochloride | 4.15 | 448.2 |

-continued

| EX | Structure | Chemical name | Ret time (min | MS (M + H) |
| --- | --- | --- | --- | --- |
| 43 | 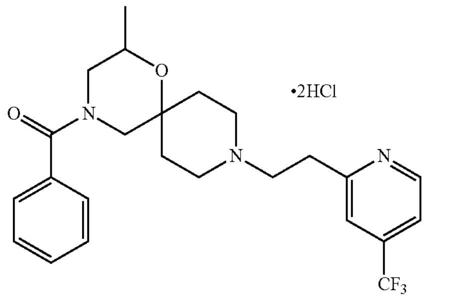 [SMILES: CC1CN(C(=O)c2ccccc2)CC2(CCN(CCc3cc(C(F)(F)F)ccn3)CC2)O1 ; "·2HCl"] | (2-methyl-9-(2-(4-(trifluoromethyl)pyridin-2-yl)ethyl)-1-oxa-4,9-diazaspiro[5.5]undecan-4-yl)(phenyl)methanone dihydrochloride | 4.15 | 448.2 |
| 44 | 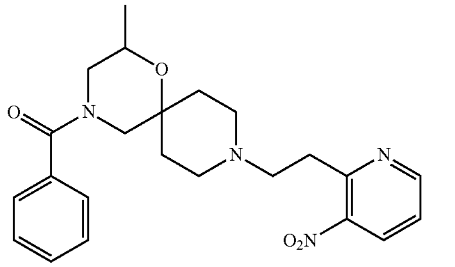 [SMILES: CC1CN(C(=O)c2ccccc2)CC2(CCN(CCc3ncccc3[N+](=O)[O-])CC2)O1] | (2-methyl-9-(2-(3-nitropyridin-2-yl)ethyl)-1-oxa-4,9-diazaspiro[5.5]undecan-4-yl)(phenyl)methanone | 3.67 | 425.2 |
| 45 | 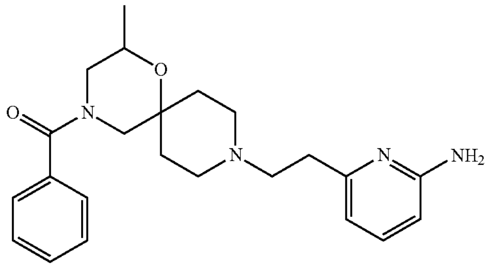 [SMILES: CC1CN(C(=O)c2ccccc2)CC2(CCN(CCc3cccc(N)n3)CC2)O1] | (9-(2-(6-aminopyridin-2-yl)ethyl)-2-methyl-1-oxa-4,9-diazaspiro[5.5]undecan-4-yl)(phenyl)methanone | 3.21 | 395.2 |
| 46 | 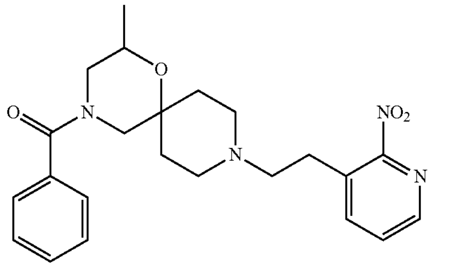 [SMILES: CC1CN(C(=O)c2ccccc2)CC2(CCN(CCc3cccnc3[N+](=O)[O-])CC2)O1] | (2-methyl-9-(2-(2-nitropyridin-3-yl)ethyl)-1-oxa-4,9-diazaspiro[5.5]undecan-4-yl)(phenyl)methanone | 3.78 | 425.2 |
| 47 | 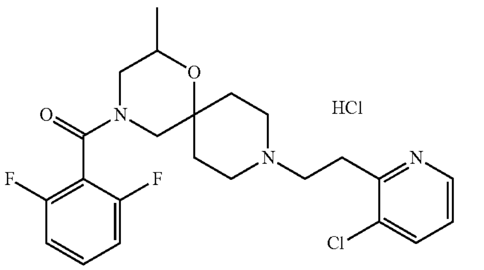 [SMILES: CC1CN(C(=O)c2c(F)cccc2F)CC2(CCN(CCc3ncccc3Cl)CC2)O1 ; Cl] | (9-(2-(3-chloropyridin-2-yl)ethyl)-2-methyl-1-oxa-4,9-diazaspiro[5.5]undecan-4-yl)(2,6-difluorophenyl)methanone hydrochloride | 4.02 | 450.1 |

-continued

| EX | Structure | Chemical name | Ret time (min | MS (M + H) |
|---|---|---|---|---|
| 48 | 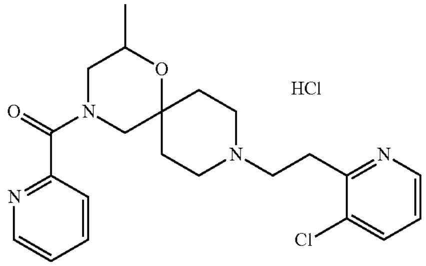 [SMILES: CC1CN(C(=O)c2ccccn2)CC2(CCN(CCc3ncccc3Cl)CC2)O1 ; Cl] HCl | (9-(2-(3-chloropyridin-2-yl)ethyl)-2-methyl-1-oxa-4,9-diazaspiro[5.5]undecan-4-yl)(pyridin-2-yl)methanone hydrochloride | 3.28 | 415.1 |
| 49 | 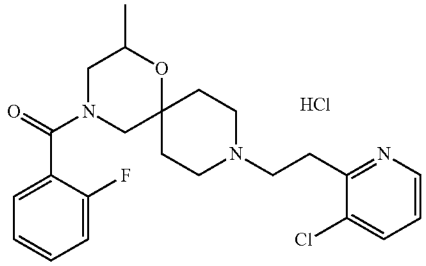 [SMILES: CC1CN(C(=O)c2ccccc2F)CC2(CCN(CCc3ncccc3Cl)CC2)O1 ; Cl] HCl | (9-(2-(3-chloropyridin-2-yl)ethyl)-2-methyl-1-oxa-4,9-diazaspiro[5.5]undecan-4-yl)(2-fluorophenyl)methanone hydrochloride | 3.91 | 432.1 |
| 50 | 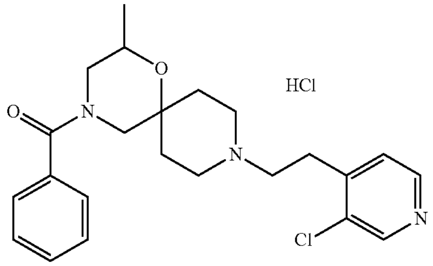 [SMILES: CC1CN(C(=O)c2ccccc2)CC2(CCN(CCc3ccncc3Cl)CC2)O1 ; Cl] HCl | (9-(2-(3-chloropyridin-4-yl)ethyl)-2-methyl-1-oxa-4,9-diazaspiro[5.5]undecan-4-yl)(phenyl)methanone hydrochloride | 3.78 | 414.2 |
| 51 | 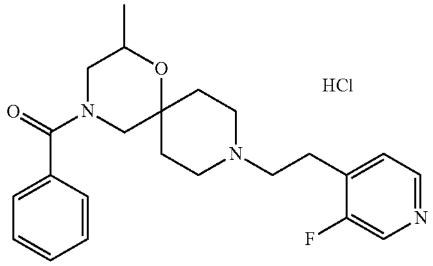 [SMILES: CC1CN(C(=O)c2ccccc2)CC2(CCN(CCc3ccncc3F)CC2)O1 ; Cl] HCl | (9-(2-(3-fluoropyridin-4-yl)ethyl)-2-methyl-1-oxa-4,9-diazaspiro[5.5]undecan-4-yl)(phenyl)methanone hydrochloride | 3.56 | 398.2 |
| 52 | 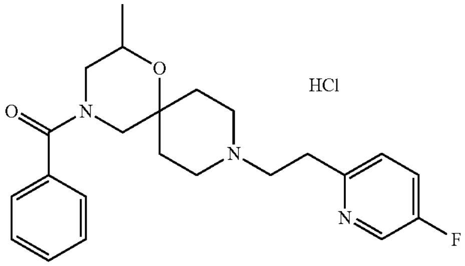 [SMILES: CC1CN(C(=O)c2ccccc2)CC2(CCN(CCc3ccc(F)cn3)CC2)O1 ; Cl] HCl | (9-(2-(5-fluoropyridin-2-yl)ethyl)-2-methyl-1-oxa-4,9-diazaspiro[5.5]undecan-4-yl)(phenyl)methanone hydrochloride | 3.57 | 398.2 |

-continued

| EX | Structure | Chemical name | Ret time (min | MS (M + H) |
| --- | --- | --- | --- | --- |
| 53 | 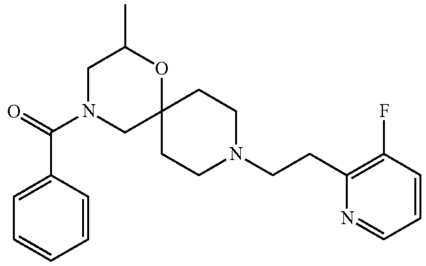 [SMILES: CC1CN(C(=O)c2ccccc2)CC2(CCN(CCc3ncccc3F)CC2)O1] | (9-(2-(3-fluoropyridin-2-yl)ethyl)-2-methyl-1-oxa-4,9-diazaspiro[5.5]undecan-4-yl)(phenyl)methanone | 3.65 | 398.2 |
| 54 | 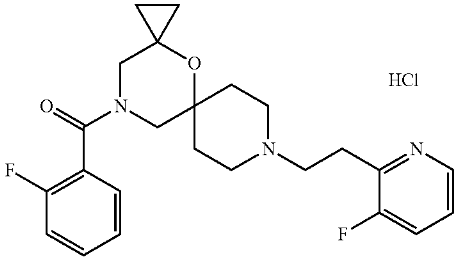 [SMILES: O=C(c1ccccc1F)N1CC2(CCN(CCc3ncccc3F)CC2)OC2(CC2)C1 ; Cl] HCl | 8-(2-(3-fluoropyridin-2-yl)ethyl)-12-[(2-fluorophenyl)carbonyl]-4-oxa-8,12-diazadispiro[2.1.5.3]tri-decane hydrochloride | 3.66 | 428.2 |
| 55 | 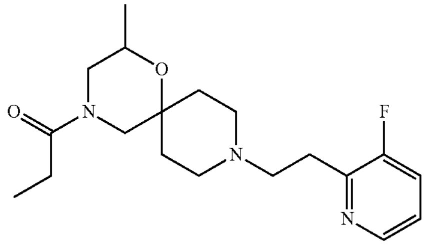 [SMILES: CCC(=O)N1CC(C)OC2(CCN(CCc3ncccc3F)CC2)C1] | 1-(9-(2-(3-fluoropyridin-2-yl)ethyl)-2-methyl-1-oxa-4,9-diazaspiro[5.5]undecan-4-yl)propan-1-one | 3.1 | 350.2 |
| 56 | 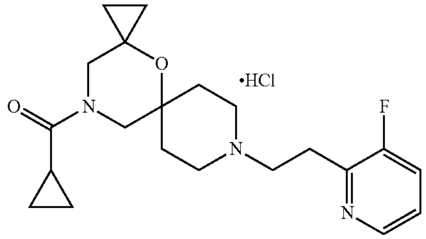 [SMILES: O=C(C1CC1)N1CC2(CCN(CCc3ncccc3F)CC2)OC2(CC2)C1 ; Cl] •HCl | 8-(2-(3-fluoropyridin-2-yl)ethyl)-12-[(cyclopropyl)carbonyl]-4-oxa-8,12-diazadispiro[2.1.5.3]tri-decane hydrochloride | 3.18 | 374.2 |
| 57 | 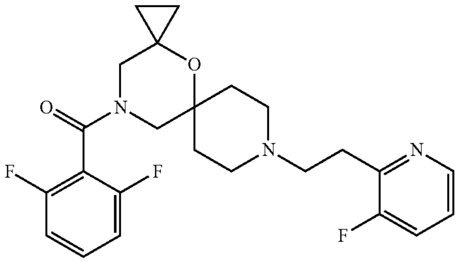 [SMILES: O=C(c1c(F)cccc1F)N1CC2(CCN(CCc3ncccc3F)CC2)OC2(CC2)C1] | 8-(2-(3-fluoropyridin-2-yl)ethyl)-12-[(2,6-difluorophenyl)carbonyl]-4-oxa-8,12-diazadispiro[2.1.5.3]tri-decane | 3.72 | 446.2 |

-continued

| EX | Structure | Chemical name | Ret time (min | MS (M + H) |
|---|---|---|---|---|
| 58 | 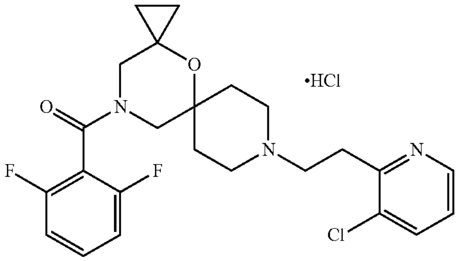 [SMILES: O=C(c1c(F)cccc1F)N1CC2(CCN(CCc3ncccc3Cl)CC2)OC2(CC2)C1 ; Cl] •HCl | 8-(2-(3-chloropyridin-2-yl)ethyl)-12-[(2,6-difluorophenyl)carbonyl]-4-oxa-8,12-diazadispiro[2.1.5.3]tridecane hydrochloride | 3.89 | 462.1 |
| 59 | 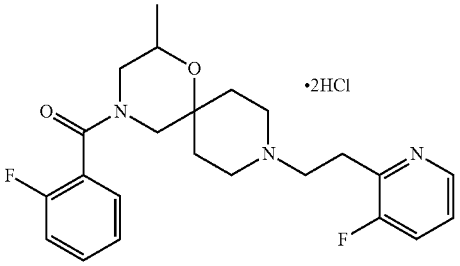 [SMILES: CC1CN(C(=O)c2ccccc2F)CC2(CCN(CCc3ncccc3F)CC2)O1 ; "·2HCl"] •2HCl | (2-fluorophenyl)(9-(2-(3-fluoropyridin-2-yl)ethyl)-2-methyl-1-oxa-4,9-diazaspiro[5.5]undecan-4-yl)methanone dihydrochloride | 3.55 | 416.2 |
| 60 | 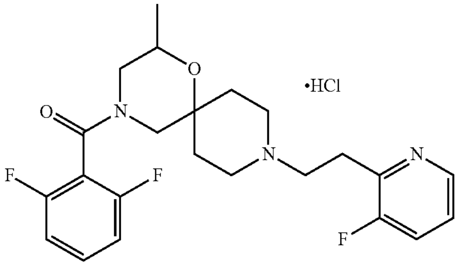 [SMILES: CC1CN(C(=O)c2c(F)cccc2F)CC2(CCN(CCc3ncccc3F)CC2)O1 ; Cl] •HCl | (2,6-difluorophenyl)(9-(2-(3-fluoropyridin-2-yl)ethyl)-2-methyl-1-oxa-4,9-diazaspiro[5.5]undecan-4-yl)methanone hydrochloride | 3.64 | 434.2 |

Where indicated, the hydrochloride salts were prepared as described in example 1

Example 61: (9-(2-hydroxy-2-phenylethyl)-1-oxa-4,9-diazaspiro[5.5]undecan-4-yl)(phenyl)methanone hydrochloride

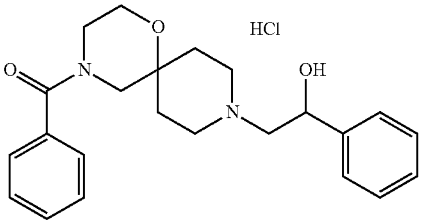 [SMILES: O=C(c1ccccc1)N1CCOC2(CCN(CC(O)c3ccccc3)CC2)C1 ; Cl]

Step 1: phenyl(1-oxa-4,9-diazaspiro[5.5]undecan-4-yl)methanone trifluoroacetate. To a solution of intermediate 6A (2.22 g, 6.16 mmol) in dichloromethane (22 mL), trifluoroacetic acid (4.2 mL. 54.4 mmol) was added, and the reaction mixture was heated to reflux for 2 h. The solvent was evaporated to give the title compound as a crude product (4.43 g, 52 wt %, quant yield). HPLC retention time: 1.73 min; MS: 261.1 (M+H).

Step 2: phenyl(1-oxa-4,9-diazaspiro[5.5]undecan-4-yl)methanone. The crude product obtained in step 1 (0.6 g, 52 wt %) was dissolved in dichloromethane and it was washed with 1M NaOH aqueous solution. The combined aqueous phases were back extracted with dichloromethane. The organic phases were combined, washed with water, dried over $MgSO_4$, filtered and concentrated under vacuum to give the title compound (0.150 g, 69% yield for the two steps).

Step 3: Title compound: A mixture of the compound obtained in step 2 (0.075 g, 0.288 mmol), 2-phenyloxirane (0.033 mL, 0.288 mmol) and lithium perchlorate (0.037 g, 0.346 mmol) in DMF (1.5 mL) was heated at 80° C. in a sealed tube for 3 days. Water was added. and the reaction mixture was extracted with ethyl acetate. The organic phases were combined, washed with water and brine, dried over $MgSO_4$, filtered and concentrated to dryness. The residue was purified by flash chromatography, silica gel, gradient dichloromethane to methanol:dichloromethane (1:4) to give the title compound as its free base (21 mg, 19% yield).

The previous compound was converted to its hydrochloride salt as described in example 1.

HPLC retention time: 3.47 min; MS: 381.2 (M+H).

Example 62: (9-(2-methoxyphenethyl)-1-oxa-4,9-diazaspiro[5.5]undecan-4-yl)(phenyl)methanone

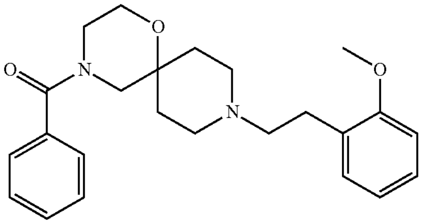 [SMILES: COc1ccccc1CCN1CCC2(CC1)CN(C(=O)c1ccccc1)CCO2]

A mixture of the crude product obtained in step 1 of example 61 (0.300 g, 65 wt %, 0.521 mmol). 1-(2-bromoethyl)-2-methoxybenzene (0.118 g, 0.547 mmol), sodium iodide (0.047 g, 0.313 mmol) and $K_2CO_3$ (0.360 g, 2.60 mmol) in acetonitrile (4 mL) was stirred in a sealed tube at 80° C. overnight. Water was added and the reaction mixture was extracted with ethyl acetate. The organic phases were combined, washed with brine, dried over $MgSO_4$, filtered and concentrated to dryness. The residue was purified by flash chromatography, silica gel, gradient dichloromethane to methanol:dichloromethane (1:4) to give the title compound (155 mg, 76% yield).

HPLC retention time: 3.89 min; MS: 395.2 (M+H).

This method was used for the preparation of examples 63-97 using suitable starting materials:

| EX | Structure | Chemical name | Ret time (min) | MS (M + H) |
|---|---|---|---|---|
| 63 | 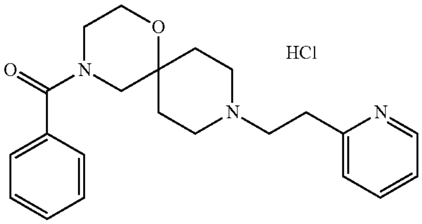 [SMILES: O=C(c1ccccc1)N1CCOC2(CCN(CCc3ccccn3)CC2)C1 ; Cl] HCl | phenyl(9-(2-(pyridin-2-yl)ethyl)-1-oxa-4,9-diazaspiro[5.5]undecan-4-yl)methanone hydrochloride | 3.01 | 366.2 |
| 64 | 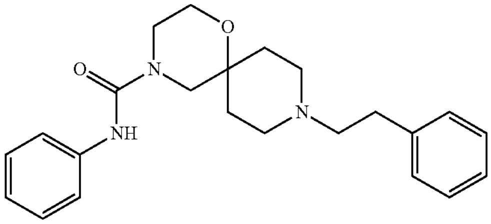 [SMILES: O=C(Nc1ccccc1)N1CCOC2(CCN(CCc3ccccc3)CC2)C1] | 9-phenethyl-N-phenyl-1-oxa-4,9-diazaspiro[5.5]undecane-4-carboxamide | 3.84 | 380.2 |
| 65 | 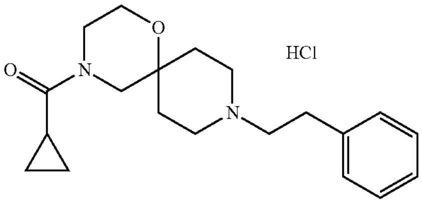 [SMILES: O=C(C1CC1)N1CCOC2(CCN(CCc3ccccc3)CC2)C1 ; Cl] HCl | cyclopropyl(9-phenethyl-1-oxa-4,9-diazaspiro[5.5]undecan-4-yl)methanone hydrochloride | 3.44 | 329.2 |
| 66 | 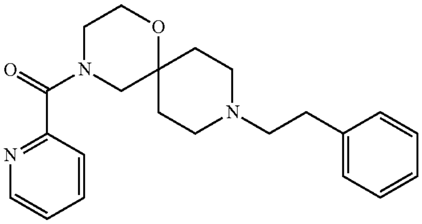 [SMILES: O=C(c1ccccn1)N1CCOC2(CCN(CCc3ccccc3)CC2)C1] | (9-phenethyl-1-oxa-4,9-diazaspiro[5.5]undecan-4-yl)(pyridin-2-yl)methanone | 3.34 | 366.2 |
| 67 | 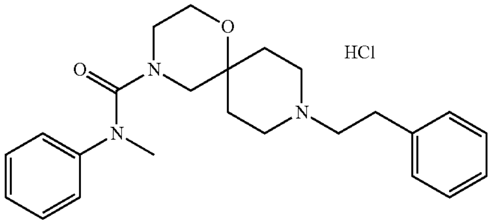 [SMILES: CN(C(=O)N1CCOC2(CCN(CCc3ccccc3)CC2)C1)c1ccccc1 ; Cl] HCl | N-methyl-9-phenethyl-N-phenyl-1-oxa-4,9-diazaspiro[5.5]undecane-4-carboxamide hydrochloride | 4.22 | 394.2 |

-continued

| EX | Structure | Chemical name | Ret time (min) | MS (M + H) |
|---|---|---|---|---|
| 68 | 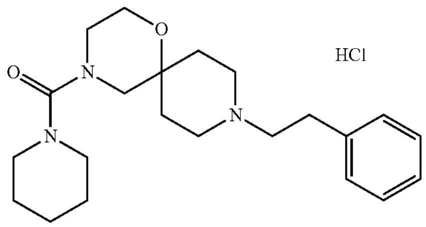 [SMILES: O=C(N1CCCCC1)N1CCOC2(CCN(CCc3ccccc3)CC2)C1 ; Cl] HCl | (9-phenethyl-1-oxa-4,9-diazaspiro[5.5]undecan-4-yl)(piperidin-1-yl)methanone hydrochloride | 3.95 | 372.2 |
| 69 | 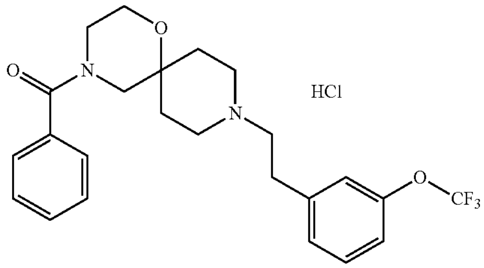 [SMILES: O=C(c1ccccc1)N1CCOC2(CCN(CCc3cccc(OC(F)(F)F)c3)CC2)C1 ; Cl] HCl | phenyl(9-(3-(trifluoromethoxy)phenethyl)-1-oxa-4,9-diazaspiro[5.5]undecan-4-yl)methanone hydrochloride | 4.64 | 449.2 |
| 70 | 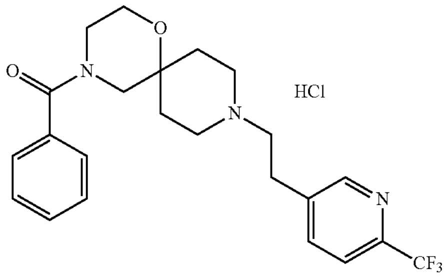 [SMILES: O=C(c1ccccc1)N1CCOC2(CCN(CCc3ccc(C(F)(F)F)nc3)CC2)C1 ; Cl] HCl | phenyl(9-(2-(6-(trifluoromethyl)pyridin-3-yl)ethyl)-1-oxa-4,9-diazaspiro[5.5]undecan-4-yl)methanone hydrochloride | 3.86 | 434.2 |
| 71 | 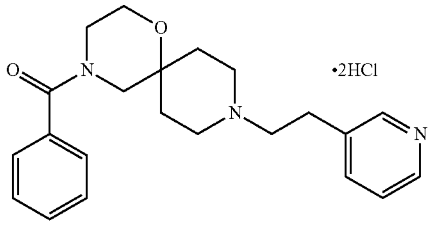 [SMILES: O=C(c1ccccc1)N1CCOC2(CCN(CCc3cccnc3)CC2)C1 ; "·2HCl"] •2HCl | phenyl(9-(2-(pyridin-3-yl)ethyl)-1-oxa-4,9-diazaspiro[5.5]undecan-4-yl)methanone dihydrochloride | 2.98 | 366 |
| 72 | 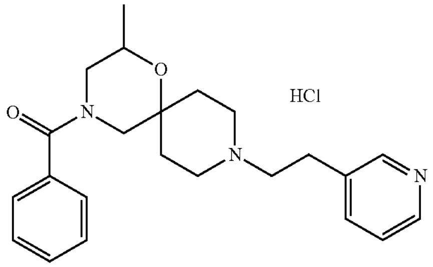 [SMILES: CC1CN(C(=O)c2ccccc2)CC2(CCN(CCc3cccnc3)CC2)O1 ; Cl] HCl | (2-methyl-9-(2-(pyridin-3-yl)ethyl)-1-oxa-4,9-diazaspiro[5.5]undecan-4-yl)(phenyl)methanone hydrochloride | 3.27 | 380.1 |

-continued

| EX | Structure | Chemical name | Ret time (min) | MS (M + H) |
|---|---|---|---|---|
| 73 | 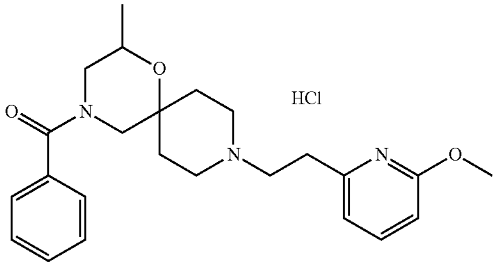 [SMILES: COc1cccc(CCN2CCC3(CC2)CN(C(=O)c2ccccc2)CC(C)O3)n1 ; Cl] HCl | (9-(2-(6-methoxypyridin-2-yl)ethyl)-2-methyl-1-oxa-4,9-diazaspiro[5.5]undecan-4-yl)(phenyl)methanone hydrochloride | 3.88 | 410.1 |
| 74 | 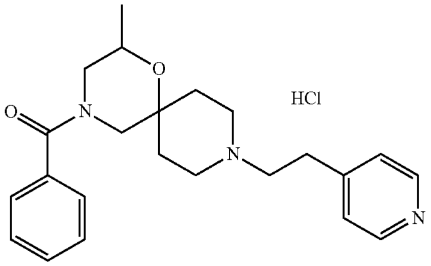 [SMILES: CC1CN(C(=O)c2ccccc2)CC2(CCN(CCc3ccncc3)CC2)O1 ; Cl] HCl | (2-methyl-9-(2-(pyridin-4-yl)ethyl)-1-oxa-4,9-diazaspiro[5.5]undecan-4-yl)(phenyl)methanone hydrochloride | 3.27 | 380.1 |
| 75 | 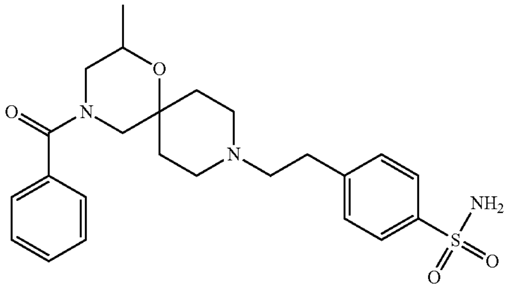 [SMILES: CC1CN(C(=O)c2ccccc2)CC2(CCN(CCc3ccc(S(N)(=O)=O)cc3)CC2)O1] | 4-(2-(4-benzoyl-2-methyl-1-oxa-4,9-diazaspiro[5.5]undecan-9-yl)ethyl)benzene-sulfonamide | 3.31 | 458 |
| 76 | 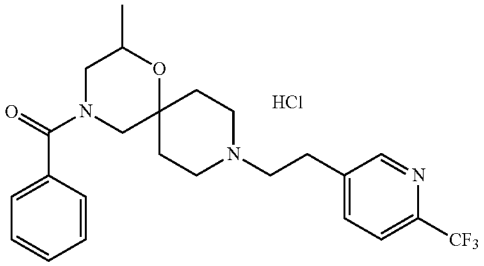 [SMILES: CC1CN(C(=O)c2ccccc2)CC2(CCN(CCc3ccc(C(F)(F)F)nc3)CC2)O1 ; Cl] HCl | (2-methyl-9-(2-(6-(trifluoromethyl)pyridin-3-yl)ethyl)-1-oxa-4,9-diazaspiro[5.5]undecan-4-yl)(phenyl)methanone hydrochloride | 4.09 | 448.1 |
| 77 | 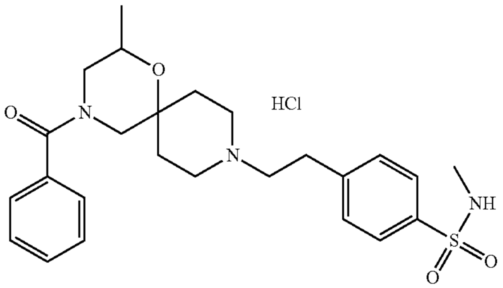 [SMILES: CNS(=O)(=O)c1ccc(CCN2CCC3(CC2)CN(C(=O)c2ccccc2)CC(C)O3)cc1 ; Cl] HCl | 4-(2-(4-benzoyl-2-methyl-1-oxa-4,9-diazaspiro[5.5]undecan-9-yl)ethyl)-N-methylbenzene-sulfonamide hydrochloride | 3.52 | 472 |

-continued

| EX | Structure | Chemical name | Ret time (min) | MS (M + H) |
|---|---|---|---|---|
| 78 | 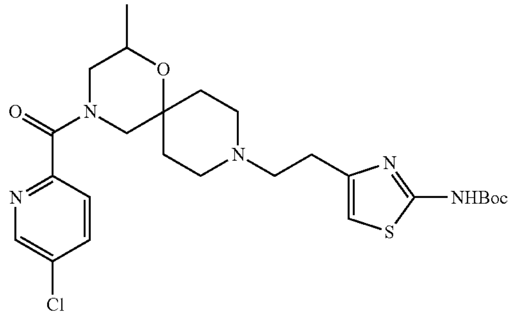 [SMILES: CC1CN(C(=O)c2ccc(Cl)cn2)CC2(CCN(CCc3csc(NC(=O)OC(C)(C)C)n3)CC2)O1] | tert-butyl (4-(2-(4-(5-chloropicolinoyl)-2-methyl-1-oxa-4,9-diazaspiro[5.5]undecan-9-yl)ethyl)thiazol-2-yl)carbamate | 4.28 | 536 |
| 79 | 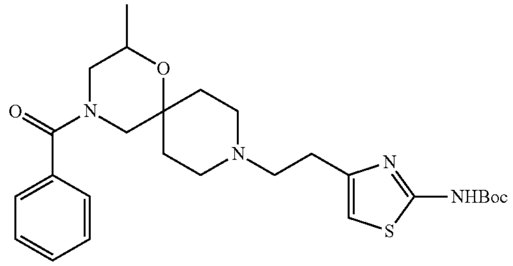 [SMILES: CC1CN(C(=O)c2ccccc2)CC2(CCN(CCc3csc(NC(=O)OC(C)(C)C)n3)CC2)O1] | tert-butyl (4-(2-(4-benzoyl-2-methyl-1-oxa-4,9-diazaspiro[5.5]undecan-9-yl)ethyl)thiazol-2-yl)carbamate | 4.22 | 501.1 |
| 80 | 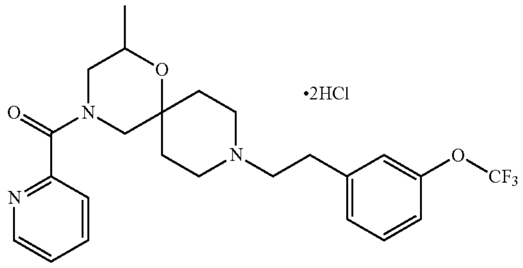 [SMILES: CC1CN(C(=O)c2ccccn2)CC2(CCN(CCc3cccc(OC(F)(F)F)c3)CC2)O1] | (2-methyl-9-(3-(trifluoromethoxy)phenethyl)-1-oxa-4,9-diazaspiro[5.5]undecan-4-yl)(pyridin-2-yl)methanone dihydrochloride | 4.45 | 464.2 |
| 81 | 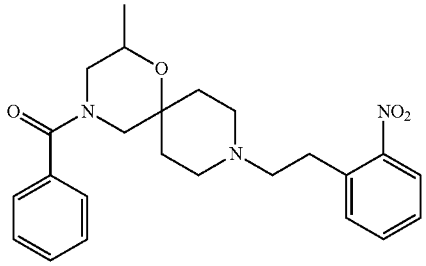 [SMILES: CC1CN(C(=O)c2ccccc2)CC2(CCN(CCc3ccccc3[N+](=O)[O-])CC2)O1] | (2-methyl-9-(2-nitrophenethyl)-1-oxa-4,9-diazaspiro[5.5]undecan-4-yl)(phenyl)methanone | 4.26 | 424.2 |
| 82 | 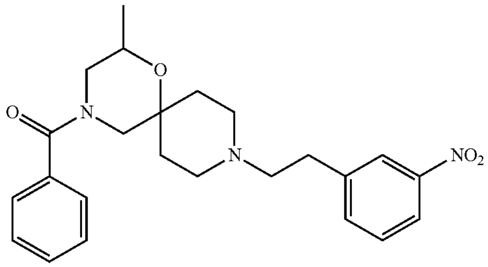 [SMILES: CC1CN(C(=O)c2ccccc2)CC2(CCN(CCc3cccc([N+](=O)[O-])c3)CC2)O1] | (2-methyl-9-(3-nitrophenethyl)-1-oxa-4,9-diazaspiro[5.5]undecan-4-yl)(phenyl)methanone | 4.28 | 424.2 |

-continued

| EX | Structure | Chemical name | Ret time (min) | MS (M + H) |
|---|---|---|---|---|
| 83 | 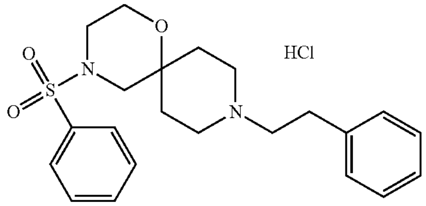 [SMILES: O=S(=O)(c1ccccc1)N1CCOC2(CCN(CCc3ccccc3)CC2)C1 ; Cl] HCl | 9-phenethyl-4-(phenylsulfonyl)-1-oxa-4,9-diazaspiro[5.5]undecane hydrochloride | 4.42 | 401.1 |
| 84 | 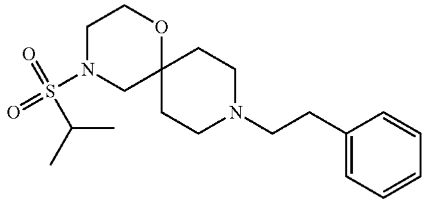 [SMILES: CC(C)S(=O)(=O)N1CCOC2(CCN(CCc3ccccc3)CC2)C1] | 4-(isopropylsulfonyl)-9-phenethyl-1-oxa-4,9-diazaspiro[5.5]undecane | 3.84 | 367.2 |
| 85 | 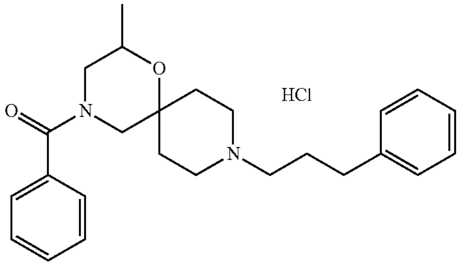 [SMILES: CC1CN(C(=O)c2ccccc2)CC2(CCN(CCCc3ccccc3)CC2)O1 ; Cl] HCl | (2-methyl-9-(3-phenylpropyl)-1-oxa-4,9-diazaspiro[5.5]undecan-4-yl)(phenyl)methanone hydrochloride | 4.39 | 393.2 |
| 86 | 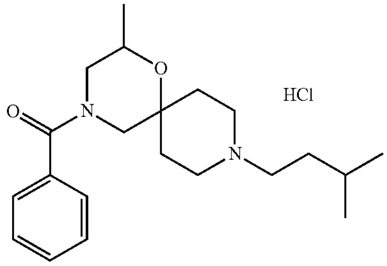 [SMILES: CC(C)CCN1CCC2(CC1)CN(C(=O)c1ccccc1)CC(C)O2 ; Cl] HCl | (9-isopentyl-2-methyl-1-oxa-4,9-diazaspiro[5.5]undecan-4-yl)(phenyl)methanone hydrochloride | 3.93 | 345.2 |
| 87 | 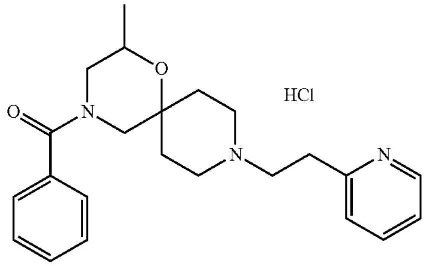 [SMILES: CC1CN(C(=O)c2ccccc2)CC2(CCN(CCc3ccccn3)CC2)O1 ; Cl] HCl | (2-methyl-9-(2-(pyridin-2-yl)ethyl)-1-oxa-4,9-diazaspiro[5.5]undecan-4-yl)(phenyl)methanone hydrochloride | 3.3 | 380.2 |
| 88 | 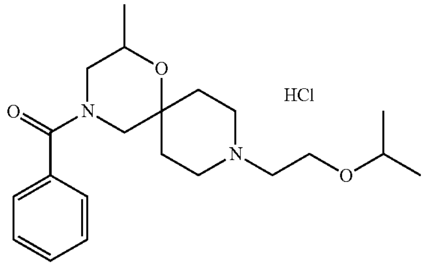 [SMILES: CC(C)OCCN1CCC2(CC1)CN(C(=O)c1ccccc1)CC(C)O2 ; Cl] HCl | (9-(2-isopropoxyethyl)-2-methyl-1-oxa-4,9-diazaspiro[5.5]undecan-4-yl)(phenyl)methanone hydrochloride | 3.58 | 361.2 |

-continued

| EX | Structure | Chemical name | Ret time (min) | MS (M + H) |
|---|---|---|---|---|
| 89 | 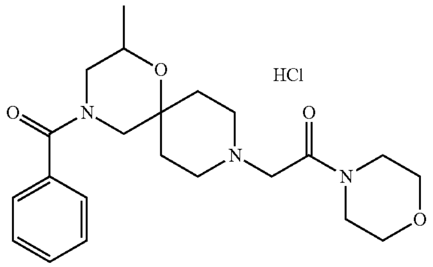 [SMILES: CC1CN(C(=O)c2ccccc2)CC2(CCN(CC(=O)N3CCOCC3)CC2)O1 ; Cl] | 2-(4-benzoyl-2-methyl-1-oxa-4,9-diazaspiro[5.5]undecan-9-yl)-1-morpholinoethanone hydrochloride | 2.97 | 402.2 |
| 90 | 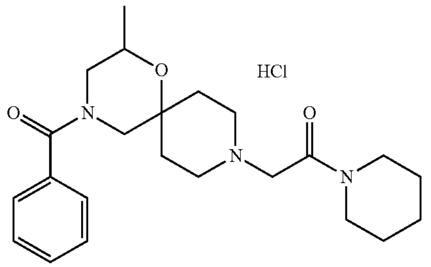 [SMILES: CC1CN(C(=O)c2ccccc2)CC2(CCN(CC(=O)N3CCCCC3)CC2)O1 ; Cl] | 2-(4-benzoyl-2-methyl-1-oxa-4,9-diazaspiro[5.5]undecan-9-yl)-1-(piperidin-1-yl)ethanone hydrochloride | 3.57 | 400.2 |
| 91 | 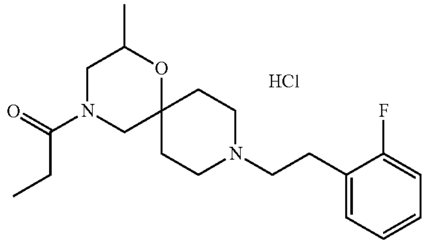 [SMILES: CCC(=O)N1CC(C)OC2(CCN(CCc3ccccc3F)CC2)C1 ; Cl] | 1-(9-(2-fluorophenethyl)-2-methyl-1-oxa-4,9-diazaspiro[5.5]undecan-4-yl)propan-1-one hydrochloride | 3.89 | 349.2 |
| 92 | 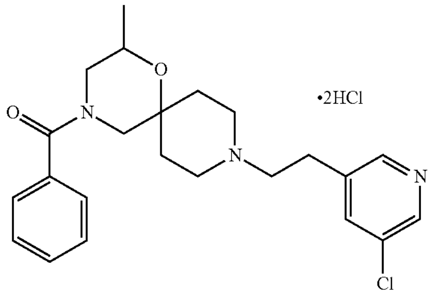 [SMILES: CC1CN(C(=O)c2ccccc2)CC2(CCN(CCc3cncc(Cl)c3)CC2)O1 ; "·2HCl"] | (9-(2-(5-chloropyridin-3-yl)ethyl)-2-methyl-1-oxa-4,9-diazaspiro[5.5]undecan-4-yl)(phenyl)methanone dihydrochloride | 3.9 | 414.2 |
| 93 | 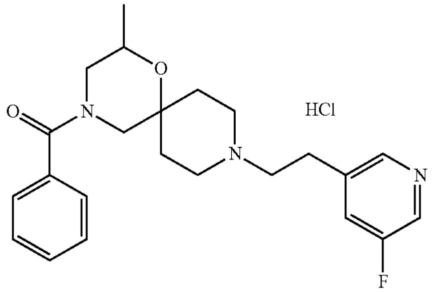 [SMILES: CC1CN(C(=O)c2ccccc2)CC2(CCN(CCc3cncc(F)c3)CC2)O1 ; Cl] | (9-(2-(5-fluoropyridin-3-yl)ethyl)-2-methyl-1-oxa-4,9-diazaspiro[5.5]undecan-4-yl)(phenyl)methanone hydrochloride | 3.52 | 398.2 |

-continued

| EX | Structure | Chemical name | Ret time (min) | MS (M + H) |
|---|---|---|---|---|
| 94 | 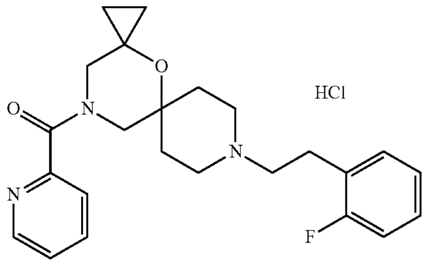 [SMILES: O=C(c1ccccn1)N1CC2(CCN(CCc3ccccc3F)CC2)OC2(CC2)C1 ; Cl] HCl | 8-(2-fluorophenethyl)-12-[(pyridin-2-yl)carbonyl]-4-oxa-8,12-diazadispiro[2.1.5.3]tri-decane hydrochloride | 3.98 | 410.2 |
| 95 | 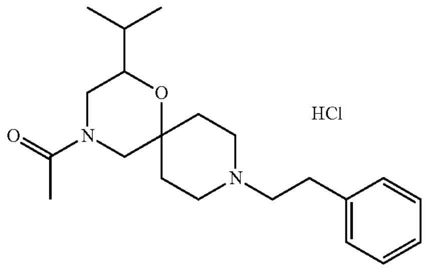 [SMILES: CC(=O)N1CC(C(C)C)OC2(CCN(CCc3ccccc3)CC2)C1 ; Cl] HCl | 1-(2-isopropyl-9-phenethyl-1-oxa-4,9-diazaspiro[5.5]undecan-4-yl)ethanone hydrochloride | 4.2 | 345.2 |
| 96 | 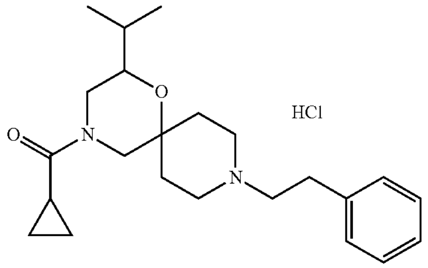 [SMILES: CC(C)C1CN(C(=O)C2CC2)CC2(CCN(CCc3ccccc3)CC2)O1 ; Cl] HCl | cyclopropyl(2-isopropyl-9-phenethyl-1-oxa-4,9-diazaspiro[5.5]undecan-4-yl)methanone hydrochloride | 4.64 | 371.2 |
| 97 | 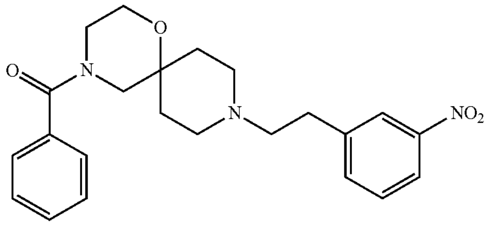 [SMILES: O=C(c1ccccc1)N1CCOC2(CCN(CCc3cccc([N+](=O)[O-])c3)CC2)C1] | (9-(3-nitrophenethyl)-1-oxa-4,9-diazaspiro[5.5]undecan-4-yl)(phenyl)methanone (1*) | 3.9 | 410.2 |

(1*) DIPEA was used as base instead of $K_2CO_3$

Where indicated, the hydrochloride salts were prepared as described in example 1

Example 98: (9-benzyl-2-methyl-1-oxa-4,9-diazaspiro[5.5]undecan-4-yl)(phenyl)methanone hydrochloride

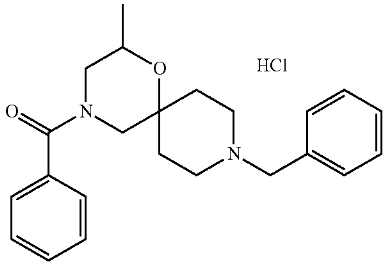 [SMILES: CC1CN(C(=O)c2ccccc2)CC2(CCN(Cc3ccccc3)CC2)O1 ; Cl]

To a solution of the crude product obtained in step 1 of example 37 (0.150 g, 60 wt %, 0.232 mmol) and benzaldehyde (0.031 mL, 0.301 mmol) in THF (1.6 mL), acetic acid (0.029 mL, 0.514) was added. The reaction mixture was stirred for 15 min., then sodium triacetoxyborohydride (0.245 g, 1.160 mmol) was added in 4 portions over 5 h. The resulting mixture was stirred at r.t. overnight. Water was added and it was extracted with ethyl acetate. The organic phases were combined, dried over $MgSO_4$, filtered and concentrated to dryness. The residue was purified by flash chromatography, silica gel, gradient dichloromethane to methanol:dichloromethane (1:4) to give the title compound as its free base (84 mg, 100% yield).

To a solution of the free base (84 mg, 0.23 mmol) in anhydrous diethyl ether (3 mL), HCl (2M solution in diethyl ether, 0.119 mL, 0.23 mmol) was added. The solids were filtered and dried under vacuum to give the corresponding HCl salt (54 mg, 56% yield).

HPLC retention time: 4.25 min; MS: 365.2 (M+H).

Example 99: (9-(2-hydroxyphenethyl)-1-oxa-4,9-diazaspiro[5.5]undecan-4-yl)(phenyl)methanone

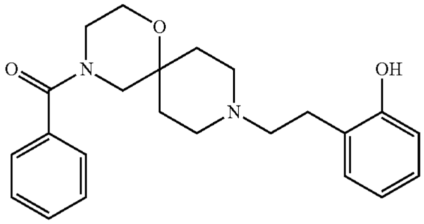 [SMILES: O=C(c1ccccc1)N1CCOC2(CCN(CCc3ccccc3O)CC2)C1]

To a solution of example 62 (0.118 g, 0.299 mmol) in dichloromethane (3 mL), boron tribromide solution (0.90 mL, 1M in dichloromethane, 0.90 mmol) was added dropwise at −78° C. The reaction mixture was allowed to warm to −10° C. over 1 h, then it was stirred at −10° C. for 1 h and 2 h at 0° C. Then, 8M NaOH aqueous solution was added until pH 8-9 and it was extracted with dichloromethane. The organic phases were combined, washed with brine, dried over $MgSO_4$, filtered and concentrated to dryness. The residue was purified by flash chromatography, silica gel, gradient dichloromethane to methanol:dichloromethane (1:4) to give the title compound (0.045 g, 39% yield). HPLC retention time: 3.84 min; MS: 381.2 (M+H).

This method was used for the preparation of examples 100-101 starting from the corresponding examples described above:

| EX | Structure | Chemical name | Ret time (min | MS (M + H) |
|---|---|---|---|---|
| 100 | 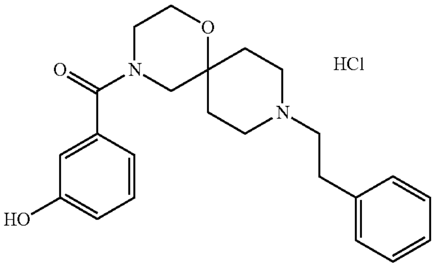 [SMILES: O=C(c1cccc(O)c1)N1CCOC2(CCN(CCc3ccccc3)CC2)C1 ; Cl] | (3-hydroxyphenyl)(9-phenethyl-1-oxa-4,9-diazaspiro[5.5]undecan-4-yl)methanone hydrochloride | 3.52 | 381.2 |
| 101 | 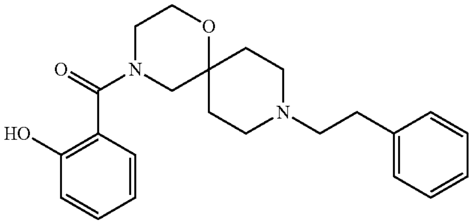 [SMILES: O=C(c1ccccc1O)N1CCOC2(CCN(CCc3ccccc3)CC2)C1] | (2-hydroxyphenyl)(9-phenethyl-1-oxa-4,9-diazaspiro[5.5]undecan-4-yl)methanone | 3.53 | 381.2 |

Where indicated, the hydrochloride salts were prepared as described in example 1

Example 102: (9-(2-(2-aminothiazol-4-yl)ethyl)-2-methyl-1-oxa-4,9-diazaspiro[5.5]undecan-4-yl)(5-chloropyridin-2-yl)methanone hydrochloride

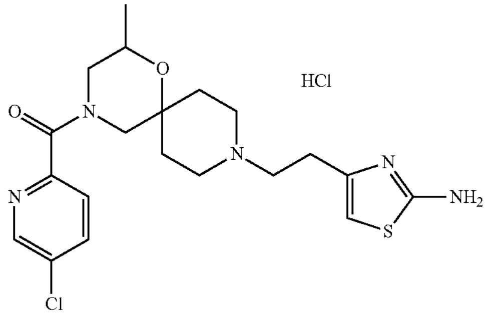 [SMILES: CC1CN(C(=O)c2ccc(Cl)cn2)CC2(CCN(CCc3csc(N)n3)CC2)O1 ; Cl]

To a solution of example 78 (0.086 g, 0.160 mmol) in dichloromethane (2.5 mL), trifluoroacetic acid (0.45 mL, 5.86 mmol) was added. The reaction mixture was stirred at r.t. overnight, and then the solvent was evaporated. The residue was purified by flash chromatography, $C_{18}$, gradient aqueous $NH_4HCO_3$ pH 8 to acetonitrile, and then it was filtered through an acidic ion-exchange resin (SCX cartridge), to give the title compound as its free base (0.021 g, 33% yield).

The previous compound was converted to its hydrochloride salt as described in example 1.

HPLC retention time: 3.11 min; MS: 436.1 (M+H).

This method was used for the preparation of example 103 starting from the corresponding example described above:

| EX | Structure | Chemical name | Ret time (min | MS (M + H) |
|---|---|---|---|---|
| 103 | 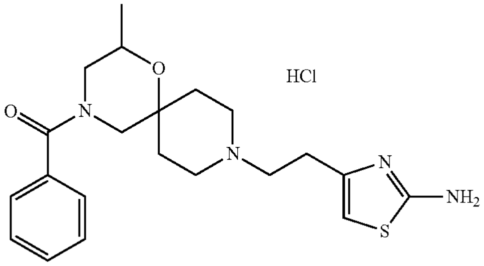 [SMILES: CC1CN(C(=O)c2ccccc2)CC2(CCN(CCc3csc(N)n3)CC2)O1 ; Cl] | (9-(2-(2-aminothiazol-4-yl)ethyl)-2-methyl-1-oxa-4,9-diazaspiro[5.5]undecan-4-yl)(phenyl)methanone hydrochloride | 3.08 | 401 |

The hydrochloride salt was prepared as described in example 1

Example 104: (9-(3-aminophenethyl)-1-oxa-4,9-diazaspiro[5.5]undecan-4-yl)(phenyl)methanone

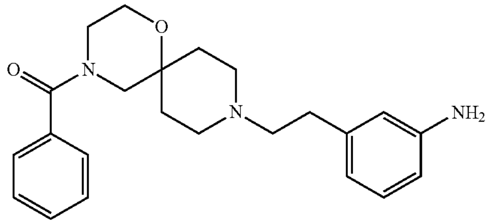

A mixture of example 97 (0.175 g, 0.427 mmol) and palladium (18 mg, 10% wt on charcoal) in methanol (3.3 mL) was stirred at r.t. under 4 bars of $H_2$ overnight. Then, the solids were filtered off and the solvent was removed under vacuum to give the title compound (0.137 g, 85% yield). HPLC retention time: 3.10 min; MS: 380.2 (M+H).

This method was used for the preparation of examples 105-108 starting from the corresponding examples described above:

| EX | Structure | Chemical name | Ret time (min | MS (M + H) |
|---|---|---|---|---|
| 105 | 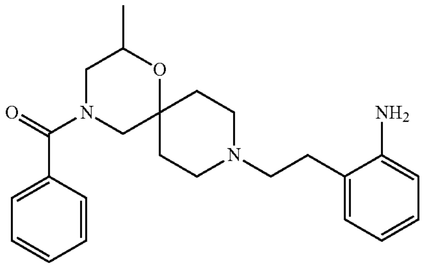 | (9-(2-aminophenethyl)-2-methyl-1-oxa-4,9-diazaspiro[5.5]undecan-4-yl)(phenyl)methanone | 3.72 | 394.2 |
| 106 | 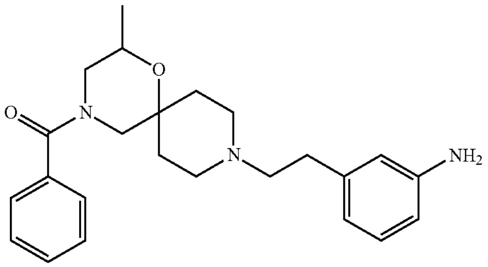 | (9-(3-aminophenethyl)-2-methyl-1-oxa-4,9-diazaspiro[5.5]undecan-4-yl)(phenyl)methanone | 3.49 | 394.2 |
| 107 | 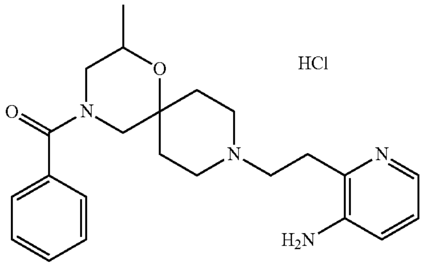 [SMILES: CC1CN(C(=O)c2ccccc2)CC2(CCN(CCc3ncccc3N)CC2)O1 ; Cl] HCl | (9-(2-(3-aminopyridin-2-yl)ethyl)-2-methyl-1-oxa-4,9-diazaspiro[5.5]undecan-4-yl)(phenyl)methanone hydrochloride | 2.89 | 395.2 |
| 108 | 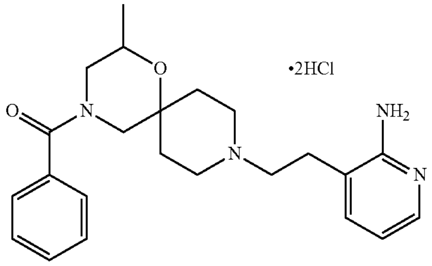 [SMILES: CC1CN(C(=O)c2ccccc2)CC2(CCN(CCc3cccnc3N)CC2)O1] •2HCl | (9-(2-(2-aminopyridin-3-yl)ethyl)-2-methyl-1-oxa-4,9-diazaspiro[5.5]undecan-4-yl)(phenyl)methanone dihydrochloride | 3.35 | 395.2 |

Where indicated, the hydrochloride salts were prepared as described in example 1

Example 109: 1-(3-(2-(4-benzoyl-2-methyl-1-oxa-4,9-diazaspiro[5.5]undecan-9-yl)ethyl)phenyl)urea hydrochloride

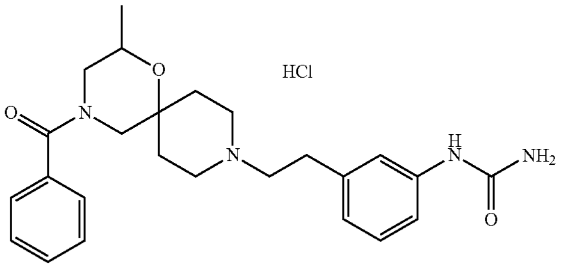 [SMILES: CC1CN(C(=O)c2ccccc2)CC2(CCN(CCc3cccc(NC(N)=O)c3)CC2)O1 ; Cl]

To a solution of example 106 (0.041 g, 0.104 mmol) in a mixture of acetic acid/water 1:1.5 (0.6 mL), potassium cyanate (0.013 g, 0.156 mmol) was added, and the reaction mixture was stirred at r.t. overnight. $NaHCO_3$ sat solution was then added, and the aqueous phase was extracted with ethyl acetate. The organic phases were combined, washed with water, dried over $MgSO_4$, filtered and concentrated under vacuum. The residue was purified by flash chromatography, silica gel, gradient dichloromethane to methanol: dichloromethane (1:4) to give the title compound as its free base (0.016 g, 36% yield).

The previous compound was converted to its hydrochloride salt as described in example 1.

HPLC retention time: 3.21 min; MS: 437.2 (M+H).

This method was used for the preparation of example 110 starting from the corresponding example described above:

| EX | Structure | Chemical name | Ret time (min | MS (M + H) |
|---|---|---|---|---|
| 110 | 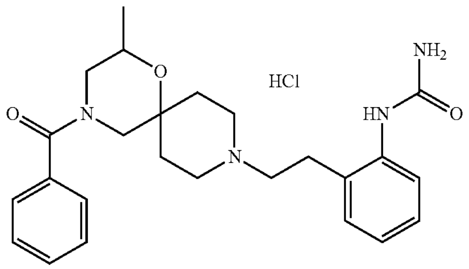 [SMILES: CC1CN(C(=O)c2ccccc2)CC2(CCN(CCc3ccccc3NC(N)=O)CC2)O1 ; Cl] | 1-(2-(2-(4-benzoyl-2-methyl-1-oxa-4,9-diazaspiro[5.5]undecan-9-yl)ethyl)phenyl)urea hydrochloride | 3.26 | 437.2 |

Example 111: N-(3-(2-(4-benzoyl-1-oxa-4,9-diazaspiro[5.5]undecan-9-yl)ethyl)phenyl)acetamide

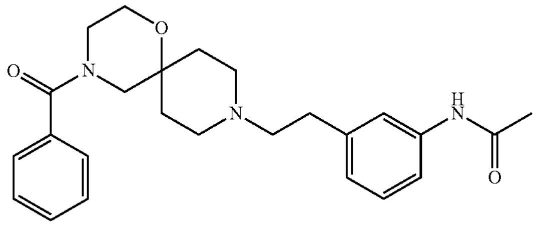 [SMILES: CC(=O)Nc1cccc(CCN2CCC3(CC2)CN(C(=O)c2ccccc2)CCO3)c1]

To a solution of example 104 (0.067 g, 0.175 mmol) and triethylamine (0.037 mL, 0.263 mmol) in dichloromethane (1.8 mL), acetyl chloride (0.014 mL, 0.193 mmol) was added dropwise at 0° C. The reaction mixture was stirred at r.t. overnight. $NaHCO_3$ sat solution was added and the aqueous phase was extracted with dichlorometane. The organic phases were combined, dried over $MgSO_4$, filtered and concentrated to dryness. The residue was purified by flash chromatography, silica gel, gradient dichloromethane to methanol:dichloromethane (1:4) to give the title compound (60 mg, 81% yield). HPLC retention time: 3.09 min; MS: 422.2 (M+H).

This method was used for the preparation of examples 112-113 starting from the corresponding examples described above:

| EX | Structure | Chemical name | Ret time (min | MS (M + H) |
|---|---|---|---|---|
| 112 | 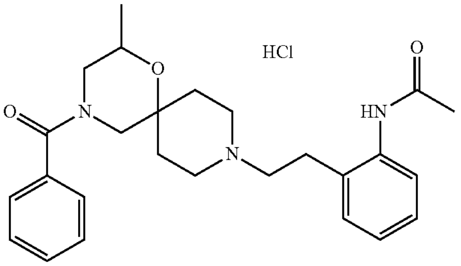 [SMILES: CC(=O)Nc1ccccc1CCN1CCC2(CC1)CN(C(=O)c1ccccc1)CC(C)O2 ; Cl] HCl | N-(2-(2-(4-benzoyl-2-methyl-1-oxa-4,9-diazaspiro[5.5]undecan-9-yl)ethyl)phenyl)acetamide hydrochloride | 3.43 | 436.2 |
| 113 | 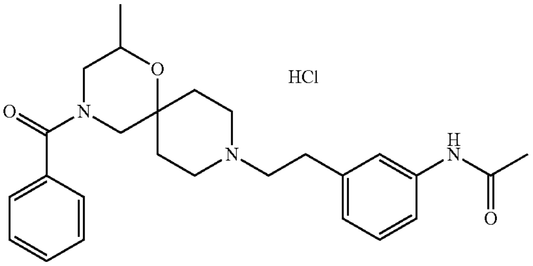 [SMILES: CC(=O)Nc1cccc(CCN2CCC3(CC2)CN(C(=O)c2ccccc2)CC(C)O3)c1 ; Cl] HCl | N-(3-(2-(4-benzoyl-2-methyl-1-oxa-4,9-diazaspiro[5.5]undecan-9-yl)ethyl)phenyl)acetamide hydrochloride | 3.42 | 436.2 |

The hydrochloride salts were prepared as described in example 1

Example 114: N-(3-(2-(4-benzoyl-1-oxa-4,9-diazaspiro[5.5]undecan-9-yl)ethyl)phenyl)methanesulfonamide

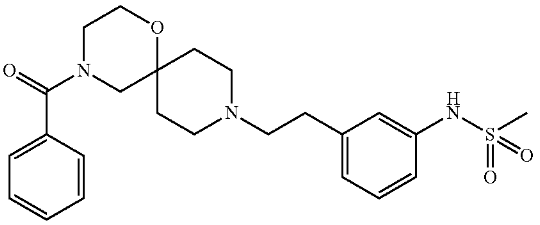 [SMILES: CS(=O)(=O)Nc1cccc(CCN2CCC3(CC2)CN(C(=O)c2ccccc2)CCO3)c1]

To a solution of example 104 (0.067 g, 0.175 mmol) and triethylamine (0.037 mL, 0.263 mmol) in dichloromethane (2 mL), methanesulfonyl chloride (0.015 mL, 0.193 mmol) was added dropwise at 0° C. The reaction mixture was stirred at r.t. overnight. $NaHCO_3$ sat solution was added and the aqueous phase was extracted with dichlorometane. The organic phases were combined, dried over $MgSO_4$, filtered and concentrated to dryness. The residue was dissolved in dichloromethane (2 mL), then additional triethylamine (0.024 mL, 0.175 mmol) and methanesulfonyl chloride (0.007 mL, 0.090 mmol) were added dropwise at 0° C. The reaction mixture was again stirred at r.t. overnight. $NaHCO_3$ sat solution was added and the aqueous phase was extracted with dichlorometane. The organic phases were combined, dried over $MgSO_4$, filtered and concentrated to dryness. The residue was purified by flash chromatography, silica gel, gradient dichloromethane to methanol:dichloromethane (1:4) to give the title compound (46 mg, 58% yield). HPLC retention time: 3.30 min; MS: 458.2 (M+H).

Example 115: 2-methyl-9-phenethyl-4-(phenylsulfonyl)-1-oxa-4,9-diazaspiro[5.5]undecane hydrochloride

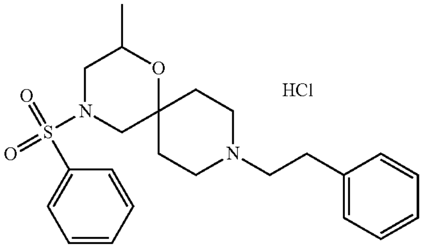 [SMILES: CC1CN(S(=O)(=O)c2ccccc2)CC2(CCN(CCc3ccccc3)CC2)O1 ; Cl]

HCl

To a solution of intermediate 5H (0.100 g, 0.364 mmol) and triethylamine (0.076 mL, 0.547 mmol) in dichloromethane (3.5 mL) cooled at 0° C., benzenesulfonyl chloride (0.051 mL, 0.40 mmol) was added dropwise. The reaction mixture was allowed to warm and stirred at r.t. overnight. Water was added and the aqueous phase was extracted with dichlorometane. The organic phases were combined, dried over $MgSO_4$, filtered and concentrated to dryness. The residue was purified by flash chromatography, silica gel, gradient dichloromethane to methanol:dichloromethane (1:4) to give the title compound as its free base (104 mg, 69% yield).

The previous compound was converted to its hydrochloride salt as described in example 1.

HPLC retention time: 4.81 min; MS: 415.2 (M+H).

This method was used for the preparation of example 116 using suitable starting materials:

| EX | Structure | Chemical name | Ret time (min | MS (M + H) |
|---|---|---|---|---|
| 116 | 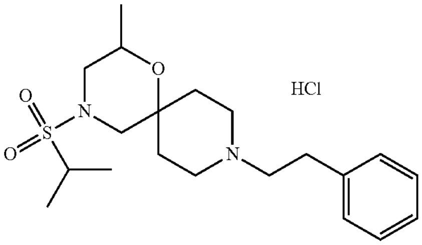 [SMILES: CC1CN(S(=O)(=O)C(C)C)CC2(CCN(CCc3ccccc3)CC2)O1 ; Cl] HCl | 4-(isopropylsulfonyl)-2-methyl-9-phenethyl-1-oxa-4,9-diazaspiro[5.5]undecane hydrochloride | 4.23 | 381.2 |

Example 117: N,N-dimethyl-9-phenethyl-1-oxa-4,9-diazaspiro[5.5]undecane-4-carboxamide

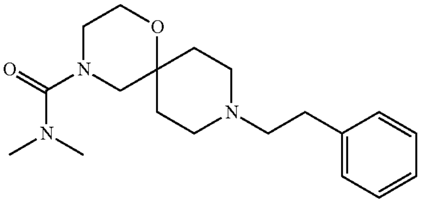 [SMILES: CN(C)C(=O)N1CCOC2(CCN(CCc3ccccc3)CC2)C1]

To a solution of intermediate 5G (0.075 g, 0.29 mmol) and triethylamine (0.060 mL, 0.43 mmol) in dichloromethane (3 mL) cooled at 0° C., dimethylcarbamic chloride (0.032 mL, 0.34 mmol) was added dropwise. The reaction mixture was allowed to reach r.t. and stirred overnight. $NaHCO_3$ sat solution was added and the aqueous phase was extracted with dichlorometane. The organic phases were combined, washed with brine, dried over $MgSO_4$, filtered and concentrated to dryness. The residue was purified by flash chromatography, silica gel, gradient dichloromethane to methanol:dichloromethane (1:4) to give the title compound (63 mg, 66% yield).

HPLC retention time: 3.33 min; MS: 332.2 (M+H).

This method was used for the preparation of example 118 using suitable starting materials:

| EX | Structure | Chemical name | Ret time (min | MS (M + H) |
|---|---|---|---|---|
| 118 | 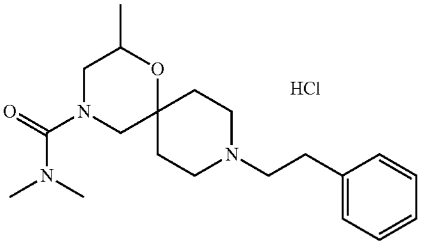 [SMILES: CC1CN(C(=O)N(C)C)CC2(CCN(CCc3ccccc3)CC2)O1 ; Cl] HCl | N,N,2-trimethyl-9-phenethyl-1-oxa-4,9-diazaspiro[5.5]undecane-4-carboxamide hydrochloride | 3.65 | 346.2 |

The hydrochloride salt was prepared as described in example 1

Example 119: N-methyl-9-phenethyl-N-(pyridin-2-yl)-1-oxa-4,9-diazaspiro[5.5]undecane-4-carboxamide hydrochloride

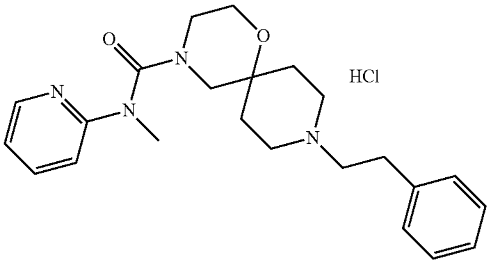 [SMILES: CN(C(=O)N1CCOC2(CCN(CCc3ccccc3)CC2)C1)c1ccccn1 ; Cl]

To a solution of 2-(methylamino)pyridine (0.033 mL, 0.317 mmol) in chloroform (3.6 mL), triethylamine (0.36 mL, 2.59 mmol) and a solution of triphosgene (94 mg, 0.317 mmol) in chloroform (3.6 mL) were added under a nitrogen atmosphere. The reaction mixture was stirred at r.t. for 1 h., then a solution of intermediate 5G (0.075 g, 0.288 mmol) in chloroform (3.6 mL) was added. The resulting mixture was heated to reflux for 1 h, then the solvent was evaporated. The residue was purified by flash chromatography, silica gel, gradient dichloromethane to methanol:dichloromethane (1:4) to give the title compound as its free base (60 mg, 53% yield).

The previous compound was converted to its hydrochloride salt as described in example 1.

HPLC retention time: 3.57 min; MS: 395.2 (M+H).

Example 120: N-cyclopropyl-9-phenethyl-1-oxa-4,9-diazaspiro[5.5]undecane-4-carboxamide

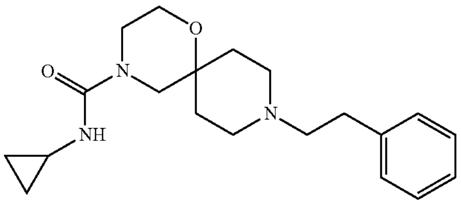 [SMILES: O=C(NC1CC1)N1CCOC2(CCN(CCc3ccccc3)CC2)C1]

To a solution of intermediate 5G (0.050 g, 0.131 mmol) in chloroform (1.8 mL) cooled at 0° C., triethylamine (0.060 mL, 0.432 mmol) and a solution of 4-nitrophenyl chloroformate (0.087 g, 0.432 mmol) in chloroform (0.5 mL) were added under a nitrogen atmosphere. The reaction mixture was stirred at 0° C. for 1 h., then a solution of cyclopropylamine (0.022 mL, 0.317 mmol) in chloroform (3.6 mL) was added. The resulting mixture was stirred at r.t. overnight. Then water was added and it was extracted with dichloromethane. The organic phases were combined, dried over $MgSO_4$, filtered and concentrated to dryness. The residue was purified by flash chromatography, silica gel, gradient dichloromethane to methanol:dichloromethane (1:4) to give the title compound (64 mg, 65% yield). HPLC retention time: 3.10 min; MS: 344.2 (M+H).

This method was used for the preparation of example 121 using suitable starting materials:

| EX | Structure | Chemical name | Ret time (min | MS (M + H) |
|---|---|---|---|---|
| 121 | 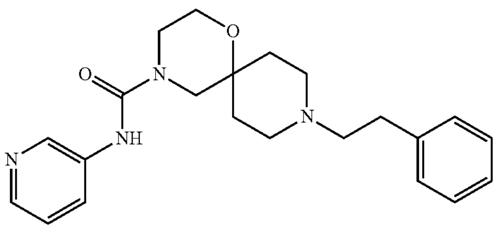 [SMILES: O=C(Nc1cccnc1)N1CCOC2(CCN(CCc3ccccc3)CC2)C1] | 9-phenethyl-N-(pyridin-3-yl)-1-oxa-4,9-diazaspiro[5.5]undecane-4-carboxamide | 3.28 | 381.2 |

Example 122: N-cyclopropyl-N-methyl-9-phenethyl-1-oxa-4,9-diazaspiro[5.5]undecane-4-carboxamide hydrochloride

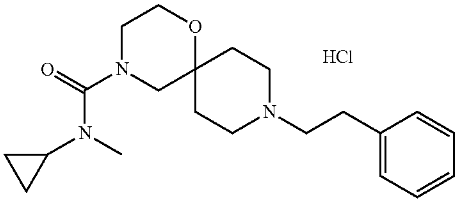 [SMILES: CN(C(=O)N1CCOC2(CCN(CCc3ccccc3)CC2)C1)C1CC1 ; Cl]

To a suspension of NaH (8 mg, 60 wt % in mineral oil, 0.205 mmol) in dry DMF (0.2 mL) cooled at 0° C., example 120 (64 mg, 0.186 mmol) was added. The reaction mixture was stirred at 0° C. for 30 minutes, then iodomethane (0.012 mL, 0.186 mmol) was added and the resulting mixture was stirred at r.t. overnight. Water was added to the reaction mixture and it was extracted with dichloromethane. The organic phases were combined, dried over $MgSO_4$, filtered and concentrated to dryness. The residue was purified by flash chromatography, silica gel, gradient dichloromethane to methanol:dichloromethane (1:4) to give the title compound as its free base (12 mg, 18% yield).

The previous compound was converted to its hydrochloride salt as described in example 1.

HPLC retention time: 3.61 min; MS: 358.2 (M+H).

This method was used for the preparation of example 123 starting from the corresponding example described above:

| EX | Structure | Chemical name | Ret time (min | MS (M + H) |
|---|---|---|---|---|
| 123 | 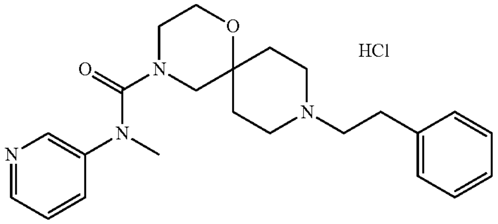 [SMILES: CN(C(=O)N1CCOC2(CCN(CCc3ccccc3)CC2)C1)c1cccnc1 ; Cl] HCl | N-methyl-9-phenethyl-N-(pyridin-3-yl)-1-oxa-4,9-diazaspiro[5.5]undecane-4-carboxamide hydrochloride | 3.29 | 395.2 |

Examples 124 and 125: (R)-(2-methyl-9-phenethyl-1-oxa-4,9-diazaspiro[5.5]undecan-4-yl)(pyridin-2-yl) methanone hydrochloride and (S)-(2-methyl-9-phenethyl-1-oxa-4,9-diazaspiro[5.5]undecan-4-yl)(pyridin-2-yl)methanone hydrochloride Ex 124

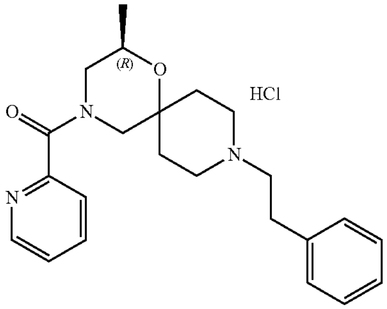

HCl

-continued

Ex 125

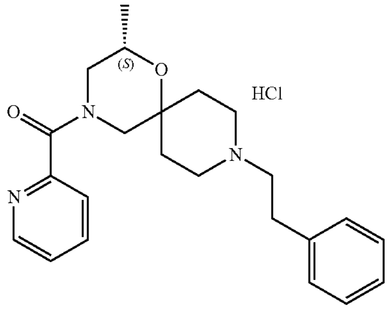

HCl

Starting from example 3, a chiral preparative HPLC separation (column: Chiralcel ODH; temperature: ambient; flow: 0.8 mL/min; eluent: n-Heptane/EtOH 90/10 v/v) was carried out obtaining examples 124 and 125 as the free bases. Their hydrochloride salts were prepared as described in example 1

HPLC retention time: 3.65 min; MS: 380.2 (M+H)

Examples 126 to 138 were prepared according to the procedure described in Example 37, using suitable starting materials:

| EX | Structure | Chemical name | Ret time (min | MS (M + H) |
|---|---|---|---|---|
| 126 | 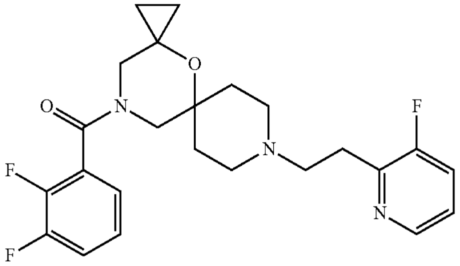 [SMILES: O=C(c1cccc(F)c1F)N1CC2(CCN(CCc3ncccc3F)CC2)OC2(CC2)C1] | 8-(2-(3-fluoropyridin-2-yl)ethyl)-12-[(2,3-difluorophenyl)carbonyl]-4-oxa-8,12-diazadispiro[2.1.5.3]tridecane | 3.71 | 446.2 |
| 127 | 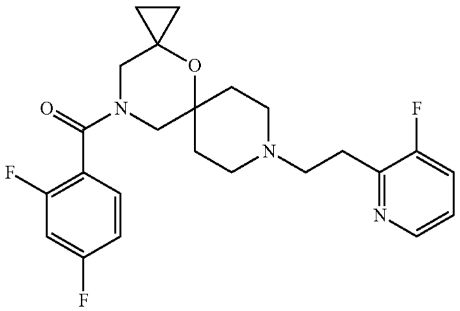 [SMILES: O=C(c1ccc(F)cc1F)N1CC2(CCN(CCc3ncccc3F)CC2)OC2(CC2)C1] | 8-(2-(3-fluoropyridin-2-yl)ethyl)-12-[(2,4-difluorophenyl)carbonyl]-4-oxa-8,12-diazadispiro[2.1.5.3]tridecane | 3.69 | 446.2 |

-continued

| EX | Structure | Chemical name | Ret time (min | MS (M + H) |
|---|---|---|---|---|
| 128 | 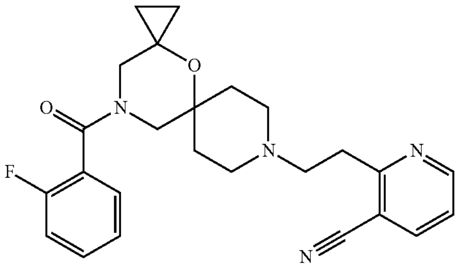 [SMILES: N#Cc1cccnc1CCN1CCC2(CC1)CN(C(=O)c1ccccc1F)CC1(CC1)O2] | 2-(2-(12-(2-fluorobenzoyl)-4-oxa-8,12-diazadispiro[2.1.5.3]tridecan-8-yl)ethyl)nicotinonitrile | 3.52 | 435.2 |
| 129 | 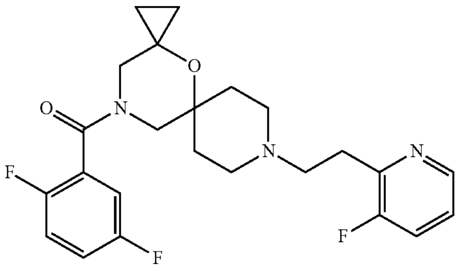 [SMILES: O=C(c1cc(F)ccc1F)N1CC2(CCN(CCc3ncccc3F)CC2)OC2(CC2)C1] | 8-(2-(3-fluoropyridin-2-yl)ethyl)-12-[(2,5-difluorophenyl)carbonyl]-4-oxa-8,12-diazadispiro[2.1.5.3]tridecane | 3.72 | 446.2 |
| 130 | 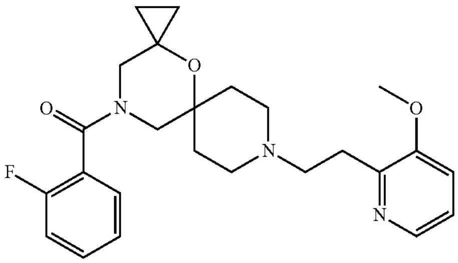 [SMILES: COc1cccnc1CCN1CCC2(CC1)CN(C(=O)c1ccccc1F)CC1(CC1)O2] | 12-[(2-fluorophenyl)carbonyl]-8-(2-(3-methoxypyridin-2-yl)ethyl)-4-oxa-8,12-diazadispiro[2.1.5.3]tridecane | 3.53 | 440.2 |
| 131 | 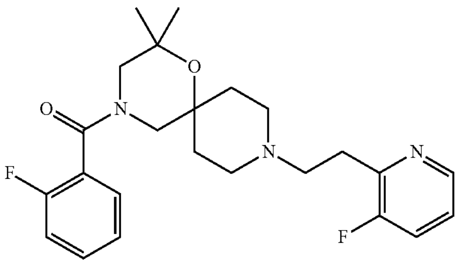 [SMILES: CC1(C)CN(C(=O)c2ccccc2F)CC2(CCN(CCc3ncccc3F)CC2)O1] | (2-fluorophenyl)(9-(2-(3-fluoropyridin-2-yl)ethyl)-2,2-dimethyl-1-oxa-4,9-diazaspiro[5.5]undecan-4-yl)methanone | 3.77 | 430.2 |
| 132 | 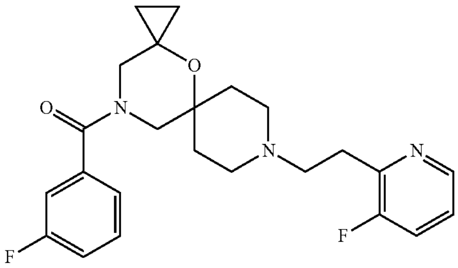 [SMILES: O=C(c1cccc(F)c1)N1CC2(CCN(CCc3ncccc3F)CC2)OC2(CC2)C1] | 12-[(3-fluorophenyl)carbonyl]-8-(2-(3-fluoropyridin-2-yl)ethyl)-4-oxa-8,12-diazadispiro[2.1.5.3]tridecane | 3.6 | 428.2 |

-continued

| EX | Structure | Chemical name | Ret time (min | MS (M + H) |
|---|---|---|---|---|
| 133 | 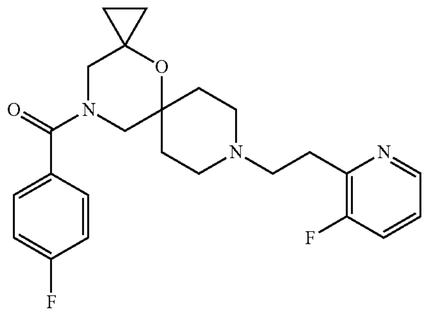 [SMILES: O=C(c1ccc(F)cc1)N1CC2(CCN(CCc3ncccc3F)CC2)OC2(CC2)C1] | 12-[(4-fluorophenyl)carbonyl]-8-(2-(3-fluoropyridin-2-yl)ethyl)-4-oxa-8,12-diazadispiro[2.1.5.3]tridecane | 3.64 | 428.2 |
| 134 | 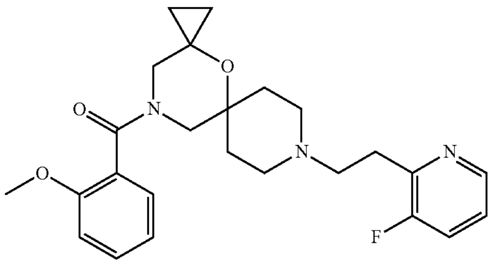 [SMILES: COc1ccccc1C(=O)N1CC2(CCN(CCc3ncccc3F)CC2)OC2(CC2)C1] | 8-(2-(3-fluoropyridin-2-yl)ethyl)-12-[(2-methoxyphenyl)carbonyl]-4-oxa-8,12-diazadispiro[2.1.5.3]tridecane | 3.58 | 440.2 |
| 135 | 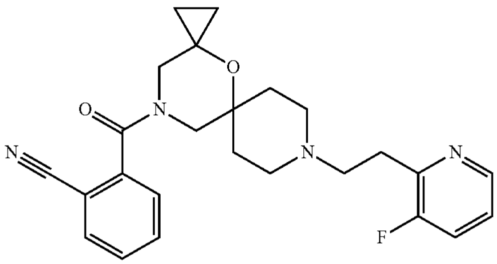 [SMILES: N#Cc1ccccc1C(=O)N1CC2(CCN(CCc3ncccc3F)CC2)OC2(CC2)C1] | 2-(8-(2-(3-fluoropyridin-2-yl)ethyl)-4-oxa-8,12-diazadispiro[2.1.5.3]tridecane-12-carbonyl)benzonitrile | 3.43 | 435.2 |
| 136 | 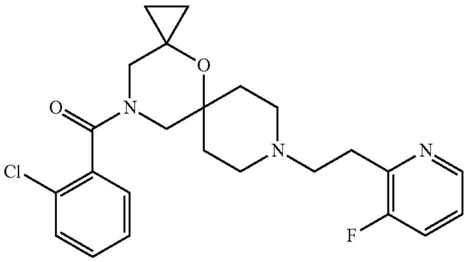 [SMILES: O=C(c1ccccc1Cl)N1CC2(CCN(CCc3ncccc3F)CC2)OC2(CC2)C1] | 12-[(2-chlorophenyl)carbonyl]-8-(2-(3-fluoropyridin-2-yl)ethyl)-4-oxa-8,12-diazadispiro[2.1.5.3]tridecane | 3.74 | 444.1 |
| 137 | 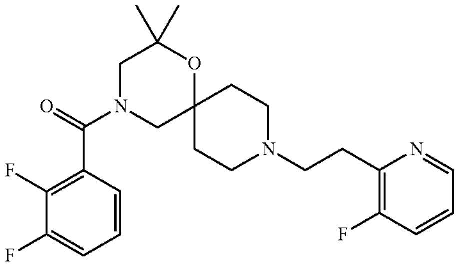 [SMILES: CC1(C)CN(C(=O)c2cccc(F)c2F)CC2(CCN(CCc3ncccc3F)CC2)O1] | (2,3-difluorophenyl)(9-(2-(3-fluoropyridin-2-yl)ethyl)-2,2-dimethyl-1-oxa-4,9-diazaspiro[5.5]undecan-4-yl)methanone | 4.00 (method B) | 448.2 |

-continued

| EX | Structure | Chemical name | Ret time (min | MS (M + H) |
|---|---|---|---|---|
| 138 | 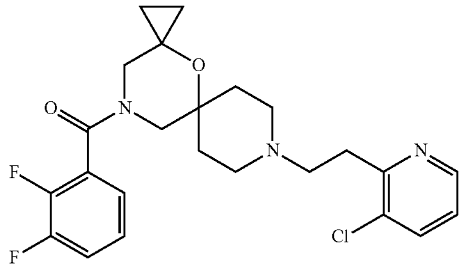 [SMILES: O=C(c1cccc(F)c1F)N1CC2(CCN(CCc3ncccc3Cl)CC2)OC2(CC2)C1] | 8-(2-(3-chloropyridin-2-yl)ethyl)-12-[(2,3-difluorophenyl)carbonyl]-4-oxa-8,12-diazadispiro[2.1.5.3]tridecane | 4.01 | 462.1 |

Examples 139 to 142 were prepared according to the procedure described in Example 62, using suitable starting materials:

| EX | Structure | Chemical name | Ret time (min) | MS (M + H) |
|---|---|---|---|---|
| 139 | 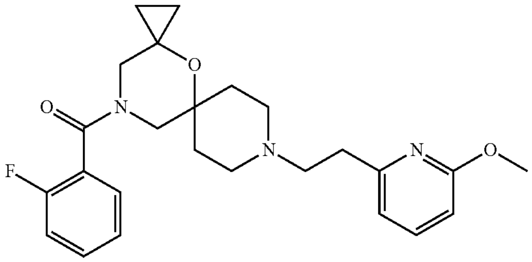 [SMILES: COc1cccc(CCN2CCC3(CC2)CN(C(=O)c2ccccc2F)CC2(CC2)O3)n1] | 12-[(2-fluorophenyl)carbonyl]-8-(2-(6-methoxypyridin-2-yl)ethyl)-4-oxa-8,12-diazadispiro[2.1.5.3]tridecane | 3.98 | 440.2 |
| 140 | 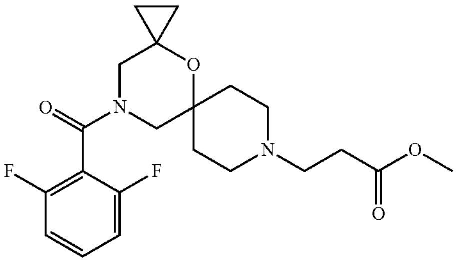 [SMILES: COC(=O)CCN1CCC2(CC1)CN(C(=O)c1c(F)cccc1F)CC1(CC1)O2] | methyl 3-(12-(2,6-difluorobenzoyl)-4-oxa-8,12-diazadispiro[2.1.5.3]tridecan-8-yl)propanoate | 3.43 | 409.1 |
| 141 | 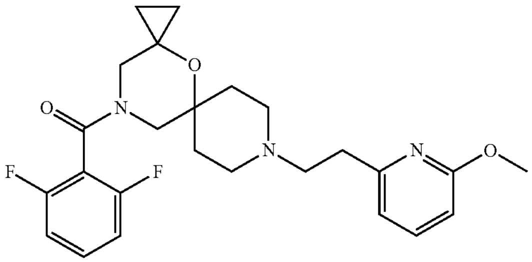 [SMILES: COc1cccc(CCN2CCC3(CC2)CN(C(=O)c2c(F)cccc2F)CC2(CC2)O3)n1] | 12-[(2,6-difluorophenyl)carbonyl]-8-(2-(6-methoxypyridin-2-yl)ethyl)-4-oxa-8,12-diazadispiro[2.1.5.3]tridecane | 4.17 | 458.2 |

-continued

| EX | Structure | Chemical name | Ret time (min) | MS (M + H) |
| --- | --- | --- | --- | --- |
| 142 | 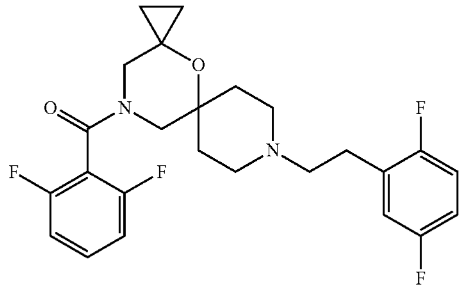 [SMILES: O=C(c1c(F)cccc1F)N1CC2(CCN(CCc3cc(F)ccc3F)CC2)OC2(CC2)C1] | 8-(2,5-difluorophenethyl)-12-[(2,6-difluorophenyl)carbonyl]-4-oxa-8,12-diazadispiro[2.1.5.3]tridecane | 4.81 (method B) | 463.2 |

Examples 143 and 144: (R)-(2-fluorophenyl)(9-(2-(3-fluoropyridin-2-yl)ethyl)-2-methyl-1-oxa-4,9-diazaspiro[5.5]undecan-4-yl)methanone and (S)-(2-fluorophenyl)(9-(2-(3-fluoropyridin-2-yl)ethyl)-2-methyl-1-oxa-4,9-diazaspiro[5.5]undecan-4-yl) methanone Ex 143

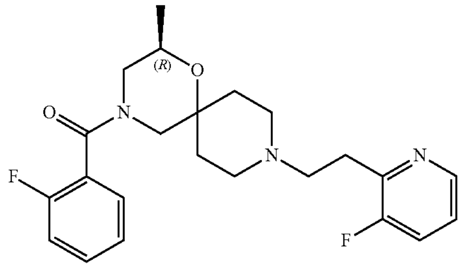

Ex 144

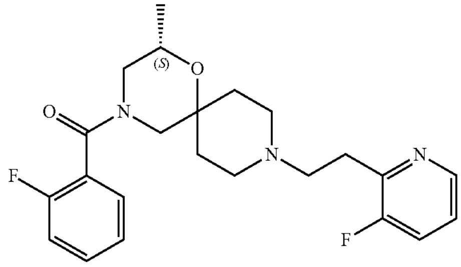

Starting from example 59, a chiral preparative HPLC separation (column: Chiralpak IC; temperature: ambient; flow: 11 mL/min; eluent: n-Heptane/(EtOH+0.33% DEA) 70/30 v/v) was carried out obtaining examples 143 and 144.

HPLC retention time: 3.55 min; MS: 416.2 (M+H)

Alternative Method for the Synthesis of Example 143: (R)-(2-fluorophenyl)(9-(2-(3-fluoropyridin-2-yl)ethyl)-2-methyl-1-oxa-4,9-diazaspiro[5.5]undecan-4-yl)methanone

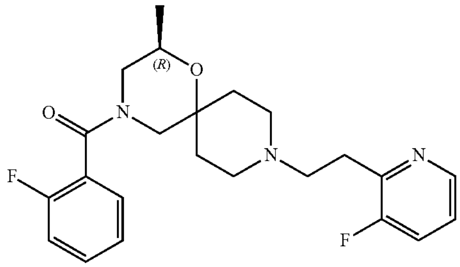

Example 143 was also prepared according to the procedure described in Example 37, using intermediate 6AC as starting material, ethanol as the reaction solvent and heating the reaction mixture at 90° C.

Examples 145 and 146: (R)-(2,6-difluorophenyl)(9-(2-(3-fluoropyridin-2-yl)ethyl)-2-methyl-1-oxa-4,9-diazaspiro[5.5]undecan-4-yl)methanone and (S)-(2,6-difluorophenyl)(9-(2-(3-fluoropyridin-2-yl)ethyl)-2-methyl-1-oxa-4,9-diazaspiro[5.5]undecan-4-yl) methanone Ex 145

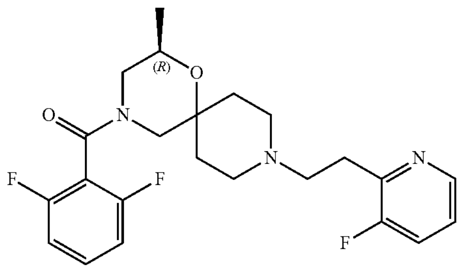

-continued

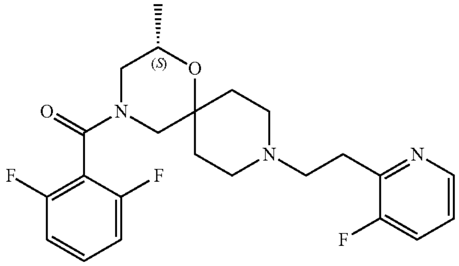

Ex 146

Starting from example 60, a chiral preparative HPLC separation (column: Chiralpak IA; temperature: ambient; flow: 10 mL/min; eluent: n-Heptane/(EtOH+0.33% DEA) 70/30 v/v) was carried out obtaining examples 145 and 146.

HPLC retention time: 3.64 min; MS: 434.2 (M+H)

Examples 147 to 151 were prepared according to the procedure described in Example 37, using suitable starting materials, ethanol as the solvent and heating at 90° C.:

| EX | Structure | Chemical name | Ret time (min) | MS (M + H) |
|---|---|---|---|---|
| 147 | 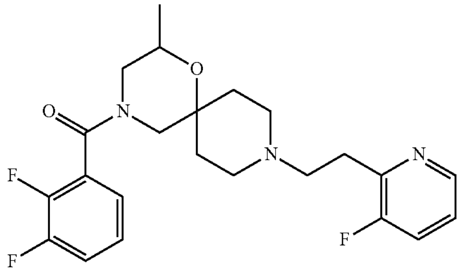 [SMILES: CC1CN(C(=O)c2cccc(F)c2F)CC2(CCN(CCc3ncccc3F)CC2)O1] | (2,3-difluorophenyl)(9-(2-(3-fluoropyridin-2-yl)ethyl)-2-methyl-1-oxa-4,9-diazaspiro[5.5]undecan-4-yl)methanone | 3.73 (method B) | 434.2 |
| 148 | 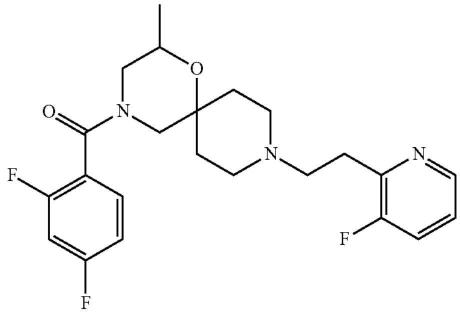 [SMILES: CC1CN(C(=O)c2ccc(F)cc2F)CC2(CCN(CCc3ncccc3F)CC2)O1] | (2,4-difluorophenyl)(9-(2-(3-fluoropyridin-2-yl)ethyl)-2-methyl-1-oxa-4,9-diazaspiro[5.5]undecan-4-yl)methanone | 3.70 (method B) | 434.2 |
| 149 | 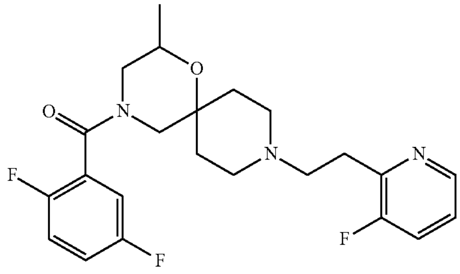 [SMILES: CC1CN(C(=O)c2cc(F)ccc2F)CC2(CCN(CCc3ncccc3F)CC2)O1] | (2,5-difluorophenyl)(9-(2-(3-fluoropyridin-2-yl)ethyl)-2-methyl-1-oxa-4,9-diazaspiro[5.5]undecan-4-yl)methanone | 3.70 (method B) | 434.2 |
| 150 | 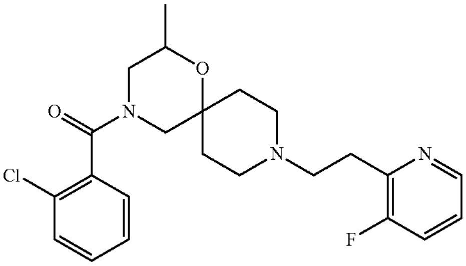 [SMILES: CC1CN(C(=O)c2ccccc2Cl)CC2(CCN(CCc3ncccc3F)CC2)O1] | (2-chlorophenyl)(9-(2-(3-fluoropyridin-2-yl)ethyl)-2-methyl-1-oxa-4,9-diazaspiro[5.5]undecan-4-yl)methanone | 3.72 (method B) | 432.2 |

-continued

| EX | Structure | Chemical name | Ret time (min) | MS (M + H) |
|---|---|---|---|---|
| 151 | 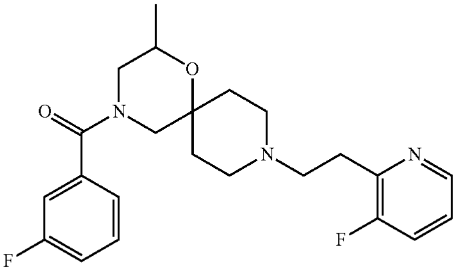 [SMILES: CC1CN(C(=O)c2cccc(F)c2)CC2(CCN(CCc3ncccc3F)CC2)O1] | (3-fluorophenyl)(9-(2-(3-fluoropyridin-2-yl)ethyl)-2-methyl-1-oxa-4,9-diazaspiro[5.5]undecan-4-yl)methanone | 3.61 (method B) | 416.2 |

Biological Activity

Pharmacological Study

Human $\sigma_1$ Receptor Radioligand Assay

To investigate binding properties of test compounds to human $\sigma_1$ receptor, transfected HEK-293 membranes and [$^3$H](+)-pentazocine (Perkin Elmer, NET-1056), as the radioligand, were used. The assay was carried out with 7 μg of membrane suspension, 5 nM of [$^3$H](+)-pentazocine in either absence or presence of either buffer or 10 μM Haloperidol for total and non-specific binding, respectively. Binding buffer contained Tris-HCl 50 mM at pH 8. Plates were incubated at 37° C. for 120 minutes. After the incubation period, the reaction mix was then transferred to MultiScreen HTS, FC plates (Millipore), filtered and plates were washed 3 times with ice-cold 10 mM Tris-HCL (pH7.4). Filters were dried and counted at approximately 40% efficiency in a MicroBeta scintillation counter (Perkin-Elmer) using EcoScint liquid scintillation cocktail Human μ-Opioid Receptor Radioligand Assay To investigate binding properties of test compounds to human μ-opioid receptor, transfected CHO-K1 cell membranes and [$^3$H]-DAMGO (Perkin Elmer, ES-542-C), as the radioligand, were used. The assay was carried out with 20 μg of membrane suspension, 1 nM of [$^3$H]-DAMGO in either absence or presence of either buffer or 10 μM Naloxone for total and non-specific binding, respectively. Binding buffer contained Tris-HCl 50 mM, MgCl2 5 mM at pH 7.4. Plates were incubated at 27° C. for 60 minutes. After the incubation period, the reaction mix was then transferred to MultiScreen HTS, FC plates (Millipore), filtered and plates were washed 3 times with ice-cold 10 mM Tris-HCL (pH 7.4). Filters were dried and counted at approximately 40% efficiency in a MicroBeta scintillation counter (Perkin-Elmer) using EcoScint liquid scintillation cocktail.

Results:

As this invention is aimed at providing a compound or a chemically related series of compounds which act as dual ligands of the $\sigma_1$ receptor and the μ-opioid receptor it is a very preferred embodiment in which the compounds are selected which act as dual ligands of the $\sigma_1$ receptor and the μ-opiod receptor and especially compounds which have a binding expressed as $K_i$ which is preferably <1000 nM for both receptors, more preferably <500 nM, even more preferably <100 nM.

The following scale has been adopted for representing the binding to the the $\sigma_1$ receptor and the μ-opiod receptor expressed as $K_i$:

+ Both $K_i$-μ and Ki-$\sigma_1$>=500 nM

++ One $K_i$<500 nM while the other $K_i$ is >=500 nM

+++ Both $K_i$-μ and $K_i$-$\sigma_1$<500 nM

++++ Both $K_i$-μ and $K_i$-$\sigma_1$<100 nM

All compounds prepared in the present application exhibit binding to the $\sigma_1$ receptor and the μ-opioid receptor, in particular the following binding results are shown:

| EX | μ and $\sigma_1$ dual binding |
|---|---|
| 1 | ++++ |
| 2 | ++++ |
| 3 | +++ |
| 4 | ++ |
| 5 | ++ |
| 6 | + |
| 7 | + |
| 8 | +++ |
| 9 | ++++ |
| 10 | + |
| 11 | +++ |
| 12 | ++ |
| 13 | ++ |
| 14 | ++ |
| 15 | ++ |
| 16 | ++ |
| 17 | +++ |
| 18 | + |
| 19 | ++ |
| 20 | ++ |
| 21 | +++ |
| 22 | +++ |
| 23 | +++ |
| 24 | + |
| 25 | ++ |
| 26 | ++ |
| 27 | ++++ |
| 28 | ++++ |
| 29 | ++++ |
| 30 | +++ |
| 31 | ++++ |
| 32 | ++ |
| 33 | +++ |
| 34 | +++ |
| 35 | +++ |
| 36 | ++ |
| 37 | +++ |
| 38 | ++ |
| 39 | +++ |
| 40 | + |
| 41 | ++ |
| 42 | ++ |
| 43 | +++ |
| 44 | + |
| 45 | + |
| 46 | + |
| 47 | +++ |
| 48 | ++ |
| 49 | +++ |
| 50 | ++++ |

-continued

| EX | μ and $\sigma_1$ dual binding |
|---|---|
| 51 | +++ |
| 52 | +++ |
| 53 | +++ |
| 54 | ++++ |
| 55 | + |
| 56 | + |
| 57 | +++ |
| 58 | +++ |
| 59 | + |
| 60 | + |
| 61 | + |
| 62 | +++ |
| 63 | ++ |
| 64 | + |
| 65 | +++ |
| 66 | + |
| 67 | ++++ |
| 68 | +++ |
| 69 | ++++ |
| 70 | ++ |
| 71 | + |
| 72 | +++ |
| 73 | +++ |
| 74 | +++ |
| 75 | + |
| 76 | +++ |
| 77 | + |
| 78 | + |
| 79 | + |
| 80 | ++ |
| 81 | + |
| 82 | + |
| 83 | ++ |
| 84 | +++ |
| 85 | +++ |
| 86 | + |
| 87 | ++ |
| 88 | + |
| 89 | + |
| 90 | + |
| 91 | ++ |
| 92 | ++++ |
| 93 | +++ |
| 94 | +++ |
| 95 | + |
| 96 | +++ |
| 97 | + |
| 98 | +++ |
| 99 | +++ |
| 100 | +++ |
| 101 | +++ |
| 102 | ++ |
| 103 | ++ |
| 104 | + |
| 105 | + |
| 106 | + |
| 107 | + |
| 108 | +++ |
| 109 | ++ |
| 110 | ++ |
| 111 | ++ |
| 112 | ++ |
| 113 | +++ |
| 114 | ++ |
| 115 | +++ |
| 116 | +++ |
| 117 | ++ |
| 118 | + |
| 119 | ++ |
| 120 | + |
| 121 | + |
| 122 | +++ |
| 123 | + |
| 124 | ++ |
| 125 | +++ |

-continued

| EX | μ and $\sigma_1$ dual binding |
|---|---|
| 126 | +++ |
| 127 | +++ |
| 128 | +++ |
| 129 | ++++ |
| 130 | ++ |
| 131 | +++ |
| 132 | +++ |
| 133 | ++++ |
| 134 | + |
| 135 | ++ |
| 136 | +++ |
| 137 | +++ |
| 138 | ++++ |
| 139 | +++ |
| 140 | + |
| 141 | +++ |
| 142 | ++++ |
| 143 | ++ |
| 144 | ++ |
| 145 | ++ |
| 146 | ++ |
| 147 | + |
| 148 | + |
| 149 | + |
| 150 | + |
| 151 | + |

The invention claimed is:

1. A compound of formula (I), (I)

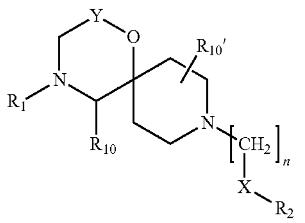

wherein

Y is

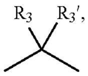, 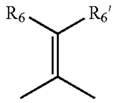 or 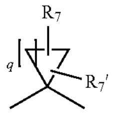 ;

n is 1 or 2;

q is 1, 2, 3, 4, 5or 6;

X is a bond, —C(O)O—, —C(O)$NR_8$—, —C(O)—, —O— or —C($R_4R_4$)—;

$R_1$ is C(O)$R_5$ or S(O)$_2R_5$;

$R_2$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, or substituted or unsubstituted heterocyclyl; with cycloalkyl, aryl, or heterocyclyl, if substituted, being substituted by substituents selected from the group consisting of halogen, —$R_9$, —$OR_9$, —$NO_2$, —$NR_9R_{9'''}$, $NR_9C(O)R_{9'}$, —$NR_9S(O)_2R_{9'}$, —$S(O)_2NR_9R_{9'}$, —$NR_9C(O)NR_{9'}R_{9''}$—, —$SR_9$, —$S(O)R_9$, $S(O)_2R_9$, —CN, haloalkyl, haloalkoxy, —C(O)O$R_9$, —C(O)N$R_9R_{9'}$, =O, —O$CH_2CH_2$OH, —N$R_9$S$(O)_2$N$R_9R_{9''}$;

$R_3$ and $R_3$' are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl substituted or unsubstituted cycloalkyl, substituted or unsubstituted heterocyclyl, substituted or unsubstituted alkylcycloalkyl, substituted or unsubstituted alkylheterocyclyl, substituted or unsubstituted aryl, substituted or unsubstituted alkylaryl, with cycloalkyl, heterocyclyl or aryl, if substituted, also in alkylaryl, alkylcycloalkyl or alkylheterocyclyl, being substituted by substituents selected from the group consisting of halogen, —$R_9$, and —O$R_9$;

$R_4$ is hydrogen, —O$R_8$, substituted or unsubstituted $C_{1-6}$ alkyl, substituted or unsubstituted $C_{2-6}$ alkenyl, substituted or unsubstituted $C_{2-6}$ alkynyl, —C(O)O$R_9$, —C(O)N$R_9R_{9'}$, —N$R_9$C(O)$R_{9'}$, —N$R_9R_{9''''}$, unsubstituted heterocyclyl, unsubstituted aryl or unsubstituted cycloalkyl;

$R_{4'}$ is hydrogen, or substituted or unsubstituted $C_{1-6}$ alkyl, substituted or unsubstituted $C_{2-6}$ alkenyl or substituted or unsubstituted $C_{2-6}$ alkynyl;

$R_5$ is substituted or unsubstituted $C_{1-6}$ alkyl, substituted or unsubstituted $C_{2-6}$ alkenyl, substituted or unsubstituted $C_{2-6}$alkynyl, substituted or unsubstituted cycloalkyl, substituted or unsubstituted aryl, substituted or unsubstituted heterocyclyl, substituted or unsubstituted alkyl aryl, substituted or unsubstituted alkyl heterocyclyl and substituted or unsubstituted alkyl cycloalkyl, —N$R_8R_{8'}$, wherein the cycloalkyl, aryl or heterocyclyl, if substituted, also in alkylaryl, alkylcycloalkyl or alkylheterocyclyl, being substituted by substituents selected from the group consisting of halogen, —$R_9$, —O$R_9$, —$NO_2$, —N$R_9R_{9''''}$, —N$R_9$C(O)$R_{9'}$, —N$R_9$S$(O)_2R_{9'}$, —S$(O)_2$N$R_9R_{9'}$, —N$R_9$C(O)N$R_{9'}R_{9''}$, —S$R_9$, —S(O) $R_9$, —S$(O)_2R_9$, —CN, haloalkyl, haloalkoxy, —C(O) O$R_9$ and —C(O)N$R_9R_{9'}$;

$R_6$, $R_{6'}$ $R_7$, and $R_{7'}$ are independently selected from the group consisting of hydrogen, halogen, —O$R_9$, substituted or unsubstituted $C_{1-6}$ alkyl, substituted or unsubstituted $C_{2-6}$ alkenyl, substituted or unsubstituted $C_{2-6}$ alkynyl unsubstituted heterocyclyl, unsubstituted aryl and unsubstituted cycloalkyl;

$R_8$ and $R_8$' are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl, with cycloalkyl, aryl, or heterocyclyl if substituted, being substituted by substituents selected from the group consisting of halogen, —$R_9$, —O$R_9$, —$NO_2$, —N$R_9R_{9''''}$, N$R_9$C(O)$R_{9'}$, —N$R_9$S$(O)_2R_{9'}$, —S$(O)_2$ N$R_9R_{9'}$, —N$R_9$C(O)N$R_{9'}R_{9''}$, —S$R_9$, —S(O)$R_9$, —S$(O)_2$R, —CN, -haloalkyl, and haloalkoxy;

$R_9$, $R_{9'}$ and $R_{9''}$, are independently selected from the group consisting of hydrogen, unsubstituted $C_{1-6}$ alkyl, unsubstituted $C_{2-6}$ alkenyl, and unsubstituted $C_2$a alkynyl;

$R_{9'''}$ is selected from the group consisting of hydrogen, unsubstituted $C_{1-6}$ alkyl, unsubstituted $C_{2-6}$ alkenyl, unsubstituted $C_{2-6}$ alkynyl and -Boc;

$R_{10}$ and $R_{10'}$ are independently selected from the group consisting of hydrogen, halogen, —O$R_9$, substituted or unsubstituted $C_{1-6}$ alkyl, substituted or unsubstituted $C_{2-6}$ alkenyl, substituted or unsubstituted $C_{2-6}$ alkynyl, substituted or unsubstituted —O— $C_{1-6}$ alkyl, substituted or unsubstituted —O— $C_{2-6}$ alkenyl and substituted or unsubstituted —O— $C_{2-6}$ alkynyl;

wherein the alkyl, alkenyl or alkynyl moieties as defined for $R_2$, $R_3$, $R_{3'}$, $R_4$, $R_{4'}$, $R_5$, $R_6$, $R_{6'}$, $R_7$, $R_{7'}$, $R_8$, $R_{8'}$, $R_{10}$ and $R_{10'}$ are unsubstituted or substituted by one or more substituents selected from the group consisting of halogen, —O$R_9$, —S$R_9$, —CN, -haloalkyl, -haloalkoxy and —N$R_9R_{9''''}$;

optionally as a stereoisomer, including enantiomers and diastereomers, a racemate or in form of a mixture of at least two stereoisomers, including enantiomers and/or diastereomers, in any mixing ratio, or a corresponding salt thereof, or a corresponding solvate thereof, with the following provisos applying:

when Y is

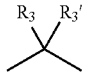

with $R_3$ and $R_{3'}$ being hydrogen, $R_1$ being C(O)$R_5$, and —$(CH_2)_n$—X—$R_2$ is alkyl, then said alkyl contains 6 or less C-atoms; and when Y is

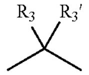

with $R_3$ and $R_{3'}$ being hydrogen, $R_1$ being C(O)$R_5$, and X not being —C($R_4R_{4'}$)—, then n is 2;

the following compounds are excluded from formula (I):

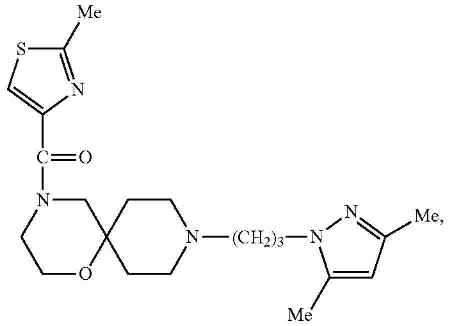

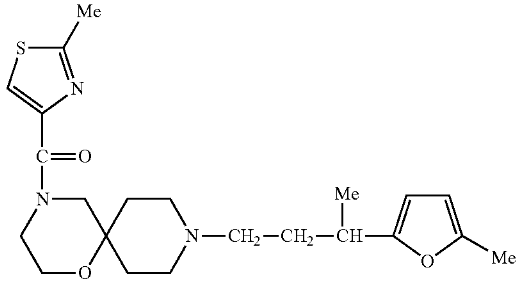

and

-continued

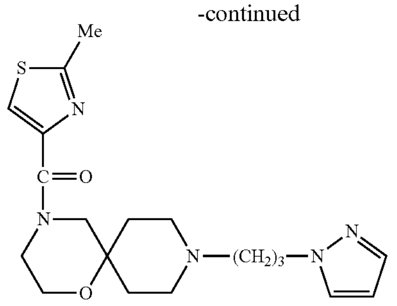

2. The compound according to claim 1, wherein $R_3$ and $R_3'$ are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl and substituted or unsubstituted cycloalkyl, with cycloalkyl, if substituted, being substituted by substituents selected from halogen, —$R_9$, and —$OR_9$;

and $R_4$ is hydrogen, —$OR_8$, substituted or unsubstituted $C_{1-6}$ alkyl, substituted or unsubstituted $C_{2-6}$ alkenyl, substituted or unsubstituted $C_{2-6}$ alkynyl, —C(O)$OR_9$, —C(O)$NR_9R_9'$, —$NR_9C(O)R_{9''}$, or —$NR_9R_{9'''}$;

optionally as a stereoisomer, including enantiomers and diastereomers, a racemate or in form of a mixture of at least two stereoisomers, including enantiomers and/or diastereomers, in any mixing ratio, or a corresponding salt thereof, or a corresponding solvate thereof.

3. The compound according to claim 1, wherein $R_2$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, or substituted or unsubstituted heterocyclyl; with cycloalkyl, aryl, or heterocyclyl, if substituted, being substituted by substituents selected from the group consisting of halogen, —$R_9$, —$OR_9$, —$NO_2$, —$NR_9R_{9'''}$, $NR_9C(O)R_{9'}$, —$NR_9SO2R_{9'}$, —$S(O)_2NR_9R_{9'}$, —$NR_9C(O)NR_{9'}R_{9''}$, —$SR_9$, —$S(O)R_9$, $S(O)_2R_9$, —CN, haloalkyl, haloalkoxy, —C(O)$OR_9$, —C(O)$NR_9R_{9'}$, =O, —$OCH_2CH_2OH$, —$NR_9S(O)_2NR_{9'}R_{9''}$;

$R_9$, $R_{9'}$, and $R_{9''}$ are independently selected from the group consisting of hydrogen, unsubstituted $C_{1-6}$ alkyl, unsubstituted $C_{2-6}$ alkenyl, and unsubstituted $C_{2-6}$ alkynyl;

$R_{9'''}$ is selected from the group consisting of hydrogen, unsubstituted $C_{1-6}$ alkyl, unsubstituted $C_{2-6}$ alkenyl, unsubstituted $C_{2-6}$ alkynyl and -Boc;

wherein the aryl is phenyl, naphthyl, or anthracene;

the heterocyclyl is a heterocyclic ring system of one or more saturated or unsaturated rings of which at least one ring contains one or more heteroatoms selected from the group consisting of nitrogen, oxygen and sulfur, and the cycloalkyl is $C_{3-8}$ cycloalkyl;

optionally as a stereoisomer, including enantiomers and diastereomers, a racemate or in form of a mixture of at least two stereoisomers, including enantiomers and/or diastereomers, in any mixing ratio, or a corresponding salt thereof, or a corresponding solvate thereof.

4. The compound according to claim 3, wherein the $C_{1-6}$ alkyl is isopropyl; the $C_{2-6}$ alkenyl is ethenyl, propenyl, butenyl, pentenyl, or hexenyl; the $C_{2-6}$ alkynyl is ethynyl, propynyl, butynyl, pentynyl, or hexynyl; the cycloalkyl is cyclopropyl, cyclobutyl, cyclopentyl, or cyclohexyl; the aryl is phenyl; and the heterocyclyl is pyridine, piperidine, thiazole, or morpholine.

5. The compound according to claim 1, wherein $R_3$ and $R_3'$ are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted heterocyclyl, substituted or unsubstituted alkylcycloalkyl, substituted or unsubstituted alkylheterocyclyl, substituted or unsubstituted aryl, substituted or unsubstituted alkylaryl, with cycloalkyl, heterocyclyl or aryl, if substituted, also in alkylaryl, alkylcycloalkyl or alkylheterocyclyl, being substituted by substituents selected from the group consisting of halogen, —$R_9$, and —$OR_9$;

$R_9$, and $R_{9'}$ are independently selected from the group consisting of hydrogen, unsubstituted $C_{1-6}$ alkyl, unsubstituted $C_{2-6}$ alkenyl, and unsubstituted $C_{2-6}$ alkynyl;

wherein the aryl is phenyl, naphthyl, or anthracene;

the heterocyclyl is a heterocyclic ring system of one or more saturated or unsaturated rings of which at least one ring contains one or more heteroatoms selected from the group consisting of nitrogen, oxygen and sulfur;

the alkyl is $C_{1-6}$ alkyl;

and the cycloalkyl is $C_{3-8}$ cycloalkyl;

optionally as a stereoisomer, including enantiomers and diastereomers, a racemate or in form of a mixture of at least two stereoisomers, including enantiomers and/or diastereomers, in any mixing ratio, or a corresponding salt thereof, or a corresponding solvate thereof.

6. The compound according to claim 5, wherein the $C_{1-6}$ alkyl is methyl or isopropyl; the $C_{2-6}$ alkenyl is ethenyl, propenyl, butenyl, pentenyl, or hexenyl; the $C_{2-6}$ is ethynyl, propynyl, butynyl, pentynyl, or hexynyl; the cycloalkyl is cyclopropyl; the aryl is phenyl; and the heterocyclyl is imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole or quinazoline.

7. The compound according to claim 5, wherein $R_3$ and $R_{3'}$ are independently selected from the group consisting of hydrogen and unsubstituted $C_{1-6}$ alkyl.

8. The compound according to claim 1, wherein

X is a bond, —C(O)O—, —C(O)$NR_8$—, —C(O)—, —O— or —C($R_4R_{4'}$)—, wherein $R_4$ is hydrogen, —$OR_8$, substituted or unsubstituted $C_{1-6}$ alkyl, substituted or unsubstituted $C_{2-6}$ alkenyl, substituted or unsubstituted $C_{2-6}$ alkynyl, —$COOR_9$, —$CONR_9R_9'$, —$NR_9COR_{9'}$, or —$NR_9R_{9'''}$;

$R_{4'}$ is hydrogen, or substituted or unsubstituted $C_{1-6}$ alkyl, substituted or unsubstituted $C_{2-6}$ alkenyl or substituted or unsubstituted $C_{2-6}$ alkynyl;

$R_8$ and $R_8'$ are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl, $R_9$, $R_{9'}$ and $R_{9''}$ are independently selected from the group consisting of hydrogen, unsubstituted $C_{1-6}$ alkyl, unsubstituted $C_{2-6}$ alkenyl, and unsubstituted $C_{2-6}$ alkynyl;

$R_{9'''}$ is selected from the group consisting of hydrogen, unsubstituted $C_{1-6}$ alkyl, unsubstituted $C_{2-6}$ alkenyl, unsubstituted $C_{2-6}$ alkynyl and -Boc;

wherein the aryl is phenyl, naphthyl, or anthracene;

and the heterocyclyl is a heterocyclic ring system of one or more saturated or unsaturated rings of which at least one ring contains one or more heteroatoms selected from the group consisting of nitrogen, oxygen and sulfur;

optionally as a stereoisomer, including enantiomers and diastereomers, a racemate or in form of a mixture of at least two stereoisomers, including enantiomers and/or diastereomers, in any mixing ratio, or a corresponding salt thereof, or a corresponding solvate thereof.

9. The compound according to claim 8, wherein the $C_{1-6}$ alkyl is methyl, ethyl, propyl, butyl, pentyl, hexyl, isopropyl, or 2-methylpropyl; the $C_{2-6}$ alkenyl is ethenyl, propenyl, butenyl, pentenyl, or hexenyl; the $C_{2-6}$ alkynyl is ethynyl, propynyl, butynyl, pentynyl, or hexynyl; the aryl is phenyl; and the heterocyclyl is imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole or quinazoline.

10. The compound according to claim 1, wherein $R_5$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, substituted or unsubstituted alkyl aryl, substituted or unsubstituted alkyl heterocyclyl, substituted or unsubstituted alkyl cycloalkyl, or —$NR_8R_{8'}$, wherein the cycloalkyl, aryl or heterocyclyl groups, if substituted, also in alkyl aryl, alkyl heterocyclyl, alkyl cycloalkyl, are substituted by substituents selected from the group consisting of halogen, —$R_9$, —$OR_9$, —$NO_2$, —$NR_9R_{9'''}$, —$NR_9C(O)R_{9'}$, —$NR_9S(O)_2R_{9'}$, —$S(O)_2NR_9R_{9'}$, —$NR_9C(O)NR_9'R_{9''}$, —$SR_9$, —$S(O)R_9$, —$S(O)_2R_9$, —CN, haloalkyl, haloalkoxy, —$C(O)OR_9$ and —$C(O)NR_9R_{9'}$;

$R_8$ and $R_8'$ are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;

$R_9$, $R_{9'}$ and $R_{9''}$ are independently selected from the group consisting of hydrogen, unsubstituted $C_{1-6}$ alkyl, unsubstituted $C_{2-6}$ alkenyl, and unsubstituted $C_{2-6}$ alkynyl;

$R_{9'''}$ is selected from the group consisting of hydrogen, unsubstituted $C_{1-6}$ alkyl, unsubstituted $C_{2-6}$ alkenyl, unsubstituted $C_{2-6}$ alkynyl and -Boc;

wherein the aryl is phenyl, naphthyl, or anthracene;

the heterocyclyl is a heterocyclic ring system of one or more saturated or unsaturated rings of which at least one ring contains one or more heteroatoms from the group consisting of nitrogen, oxygen and sulfur;

the alkyl is $C_{1-6}$ alkyl;

and the cycloalkyl is $C_{3-8}$ cycloalkyl;

optionally as a stereoisomer, including enantiomers and diastereomers, a racemate or in form of a mixture of at least two stereoisomers, including enantiomers and/or diastereomers, in any mixing ratio, or a corresponding salt thereof, or a corresponding solvate thereof.

11. The compound according to claim 10, wherein the $C_{1-6}$ alkyl is methyl, ethyl, or isopropyl; the $C_{2-6}$ alkenyl is ethenyl, propenyl, butenyl, pentenyl, or hexenyl; the $C_{2-6}$ alkynyl is ethynyl, propynyl, butynyl, pentynyl, or hexynyl; the cycloalkyl is cyclopropyl; the aryl is phenyl; and the heterocyclyl is pyridine, thiazole, tetrahydropyran or piperidine.

12. The compound according to claim 1, wherein $R_6$, $R_{6'}$ $R_7$, and $R_{7'}$ are independently selected from the group consisting of hydrogen, halogen, —$OR_9$, substituted or unsubstituted $C_{1-6}$ alkyl, substituted or unsubstituted $C_{2-6}$ alkenyl, substituted or unsubstituted $C_{2-6}$ alkynyl, unsubstituted heterocyclyl, unsubstituted aryl and unsubstituted cycloalkyl;

$R_9$, $R_{9'}$ and $R_{9''}$ are independently selected from the group consisting of hydrogen, unsubstituted $C_{1-6}$ alkyl, unsubstituted $C_{2-6}$ alkenyl, unsubstituted $C_{2-6}$ alkynyl;

$R_{9'''}$ is selected from hydrogen, unsubstituted $C_{1-6}$ alkyl, unsubstituted $C_{2-6}$ alkenyl, unsubstituted $C_{2-6}$ alkynyl and -Boc;

wherein the aryl is phenyl, naphthyl, or anthracene;

the heterocyclyl is a heterocyclic ring system of one or more saturated or unsaturated rings of which at least one ring contains one or more heteroatoms selected from the group consisting of nitrogen, oxygen and sulfur;

and the cycloalkyl is $C_{3-8}$ cycloalkyl;

optionally as a stereoisomer, including enantiomers and diastereomers, a racemate or in form of a mixture of at least two stereoisomers, including enantiomers and/or diastereomers, in any mixing ratio, or a corresponding salt thereof, or a corresponding solvate thereof.

13. The compound of claim 12, wherein the $C_{1-6}$ alkyl is methyl; the $C_{2-6}$ alkenyl is ethenyl, propenyl, butenyl, pentenyl, or hexenyl; the $C_{2-6}$ alkynyl is ethynyl, propynyl, butynyl, pentynyl, or hexynyl; the cycloalkyl is cyclopropyl; the aryl is phenyl; and the heterocyclyl is imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyran, morpholine, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole or quinazoline.

14. The compound of claim 12, wherein $R_6$, $R_{6'}$ $R_7$, and $R_{7'}$ are hydrogen.

15. The compound according to claim 1, wherein $R_{10}$ and $R_{10'}$ are independently selected from the group consisting of hydrogen, halogen, —$OR_9$, substituted or unsubstituted $C_{1-6}$ alkyl, substituted or unsubstituted $C_{2-6}$ alkenyl, substituted or unsubstituted $C_{2-6}$ alkynyl, substituted or unsubstituted —O— $C_{1-6}$ alkyl, substituted or unsubstituted —O—$C_{2-6}$ alkenyl or substituted or unsubstituted —O—$C_{2-6}$ alkynyl.

16. The compound according to claim 15, wherein the $C_{1-6}$ alkyl is methyl, ethyl, propyl, butyl, pentyl, hexyl, isopropyl, or 2-methylpropyl; the $C_{2-6}$ alkenyl is ethenyl, propenyl, butenyl, pentenyl, or hexenyl; and the $C_{2-6}$ alkynyl is ethynyl, propynyl, butynyl, pentynyl, or hexynyl.

17. The compound according to claim 15, wherein $R_{10}$ and $R_{10'}$ are hydrogen.

18. The compound according to claim 1, wherein the compound of formula I is a compound of formula I'

(I')

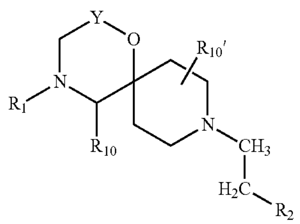

wherein

Y is

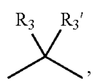, 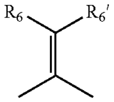 or 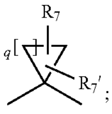;

q is 1, 2, 3, 4, 5 or 6;

$R_1$ is $C(O)R_5$ or $S(O_2)R_5$;

$R_2$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, or substituted or unsubstituted heterocyclyl, with cycloalkyl, aryl, or heterocyclyl, if substituted, being substituted by substituents selected from the group consisting of halogen, —$R_9$, —$OR_9$, —$NO_2$, —$NR_9R_{9''''}$, —$NR_9C(O)R_{9'}$, —$NR_9S(O)_2R_{9'}$, —$S(O)_2NR_9R_{9'}$, —$NR_9C(O)NR_{9'}R_{9''}$, —$SR_9$, —$S(O)R_9$, $S(O)_2R_9$, —CN, haloalkyl, haloalkoxy, —$C(O)OR_9$, —$C(O)NR_9R_{9'}$, =O, —$OCH_2CH_2OH$, —$NR_9S(O)_2NR_{9'}R_{9''}$;

$R_3$ and $R_3'$ are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, and substituted or unsubstituted cycloalkyl, with cycloalkyl, if substituted, being substituted by substituents selected from the group consisting of halogen, —$R_9$, and —$OR_9$;

$R_5$ is substituted or unsubstituted $C_{1-6}$ alkyl, substituted or unsubstituted $C_{2-6}$ alkenyl, substituted or unsubstituted $C_{2-6}$alkynyl, substituted or unsubstituted cycloalkyl, substituted or unsubstituted aryl, substituted or unsubstituted heterocyclyl, substituted or unsubstituted alkyl aryl, substituted or unsubstituted alkyl heterocyclyl, substituted or unsubstituted alkyl cycloalkyl, or —$NR_8R_{8'}$, wherein the cycloalkyl, aryl or heterocyclyl, if substituted, also in alkylaryl, alkylcycloalkyl or alkylheterocyclyl, being substituted by substituents selected from the group consisting of halogen, —$R_9$, —$OR_9$, —$NO_2$, $NR_9R_{9''''}$, —$NR_9C(O)R_{9'}$, —$NR_9S(O)_2R_{9'}$, —$S(O)_2NR_9R_{9'}$, —$NR_9C(O)NR_{9'}R_{9''}$, —$SR_9$, —$S(O)R_9$, —$S(O)_2R_9$, —CN, haloalkyl, haloalkoxy, —$C(O)OR_9$ and —$C(O)NR_9R_{9'}$;

$R_6$, $R_{6'}$ $R_7$, and $R_{7'}$ are independently selected from the group consisting of hydrogen, halogen, —$OR_9$, substituted or unsubstituted $C_{1-6}$ alkyl, substituted or unsubstituted $C_{2-6}$ alkenyl, substituted or unsubstituted $C_{2-6}$ alkynyl, unsubstituted heterocyclyl, unsubstituted aryl and unsubstituted cycloalkyl;

$R_8$ and $R_8'$ are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl, with cycloalkyl, aryl, or heterocyclyl if substituted, being substituted by substituents selected from the group consisting of halogen, —$R_9$, —$OR_9$, —$NO_2$, —$NR_9R_{9''''}$, $NR_9C(O)R_{9'}$, —$NR_9S(O)_2R_{9'}$, —$S(O)_2NR_9R_{9'}$, —$NR_9C(O)NR_{9'}R_{9''}$, —$SR_9$, —$S(O)R_9$, —$S(O)_2R_9$, —CN, -haloalkyl, and haloalkoxy;

$R_9$, $R_{9'}$ and $R_{9''}$ are independently selected from the group consisting of hydrogen, unsubstituted $C_{1-6}$ alkyl, unsubstituted $C_{2-6}$ alkenyl, unsubstituted $C_{2-6}$ alkynyl;

$R_{9''''}$ is selected from the group consisting of hydrogen, unsubstituted $C_{1-6}$ alkyl, unsubstituted $C_{2-6}$ alkenyl, unsubstituted $C_{2-6}$ alkynyl and -Boc;

$R_{10}$ and $R_{10'}$ are independently selected from the group consisting of hydrogen, halogen, —$OR_9$, substituted or unsubstituted $C_{1-6}$ alkyl, substituted or unsubstituted $C_{2-6}$ alkenyl, substituted or unsubstituted $C_{2-6}$ alkynyl, substituted or unsubstituted —O— $C_{1-6}$ alkyl, substituted or unsubstituted —O—$C_{2-6}$ alkenyl, and substituted or unsubstituted —O—$C_{2-6}$ alkynyl;

wherein the alkyl, alkenyl or alkynyl moieties as defined for $R_2$, $R_3$, $R_{3'}$, $R_5$, $R_6$, $R_{6'}$, $R_7$, $R_{7'}$, $R_8$, $R_{8'}$, $R_{10}$ and $R_{10'}$ are unsubstituted or substituted by one or more substituents selected from the group consisting of halogen, —$OR_9$, —$SR_9$, —CN, -haloalkyl, -haloalkoxy and —$NR_9R_{9''''}$;

optionally as a stereoisomer, including enantiomers and diastereomers, a racemate or in form of a mixture of at least two stereoisomers, including enantiomers and/or diastereomers, in any mixing ratio, or a corresponding salt thereof, or a corresponding solvate thereof, with the following proviso applying:

when Y is

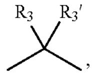, and $(CH_2)_2$—$R_2$ is alkyl, then said alkyl contains 6 or less C-atoms.

19. The compound according to claim 1, wherein the compound of formula I is a compound of formula I"

(I'')

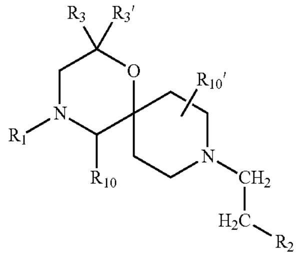

wherein $R_1$ is $C(O)R_5$ or $S(O_2)R_5$;

$R_2$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, or substituted or unsubstituted heterocyclyl, with cycloalkyl, aryl, or heterocyclyl, if substituted, being substituted by substituents selected from the group consisting of halogen, $—R_9$, $—OR_9$, $—NO_2$, $—NR_9R_{9''''}$, $NR_9C(O)R_{9'}$, $—NR_9S(O)_2R_{9'}$, $—S(O)_2NR_9R_{9'}$, $—NR_9C(O)NR_{9'}R_{9''}$, $—SR_9$, $—S(O)R_9$, $S(O)_2R_9$, —CN, haloalkyl, haloalkoxy, $—C(O)OR_9$, $—C(O)NR_9R_{9'}$, =O, $—OCH_2CH_2OH$, $—NR_9S(O)_2NR_{9'}R_{9''}$;

$R_3$ and $R_3'$ are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl and substituted or unsubstituted cycloalkyl, with cycloalkyl, if substituted, being substituted by substituents selected from the group consisting of halogen, $—R_9$, and $—OR_9$;

$R_5$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, substituted or unsubstituted alkyl aryl, substituted or unsubstituted alkyl heterocyclyl and substituted or unsubstituted alkyl cycloalkyl, or $—NR_8R_8$, wherein the cycloalkyl, aryl or heterocyclyl, if substituted, also in alkylaryl, alkylcycloalkyl or alkylheterocyclyl, being substituted by substituents selected from the group consisting of halogen, $—R_9$, $—OR_9$, $—NO_2$, $—NR_9R_{9''''}$, $—NR_9C(O)R_{9'}$, $—NR_9S(O)_2R_{9'}$, $—S(O)_2NR_9R_{9'}$, $—NR_9C(O)NR_{9'}R_{9''}$, $—SR_9$, $—S(O)R_9$, $—S(O)_2R_9$, —CN, haloalkyl, haloalkoxy, $—C(O)OR_9$ and $—C(O)NR_9R_{9''}$;

$R_8$ and $R_8'$ are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl, with cycloalkyl, aryl, or heterocyclyl if substituted, being substituted by substituents selected from the group consisting of halogen, $—R_9$, $—OR_9$, $—NO_2$, $—NR_9R_{9''''}$, $NR_9C(O)R_{9'}$, $—NR_9S(O)_2R_{9'}$, $—S(O)_2NR_9R_{9'}$, $—NR_9C(O)NR_{9'}R_{9''}$, $—SR_9$, $—S(O)R_9$, $—S(O)_2R_9$, —CN, -haloalkyl, and haloalkoxy;

$R_9$, $R_{9'}$ and $R_{9''}$ are independently selected from the group consisting of hydrogen, unsubstituted $C_{1-6}$ alkyl, unsubstituted $C_{2-6}$ alkenyl, and unsubstituted $C_{2-6}$ alkynyl;

$R_{9''''}$ is selected from the group consisting of hydrogen, unsubstituted $C_{1-6}$ alkyl, unsubstituted $C_{2-6}$ alkenyl, unsubstituted $C_{2-6}$ alkynyl and -Boc;

$R_{10}$ and $R_{10'}$ are independently selected from the group consisting of hydrogen, halogen, $—OR_9$, substituted or unsubstituted $C_{1-6}$ alkyl, substituted or unsubstituted $C_{2-6}$ alkenyl, substituted or unsubstituted $C_{2-6}$ alkynyl, substituted or unsubstituted $—O—C_{1-6}$ alkyl, substituted or unsubstituted $—O—C_{2-6}$ alkenyl, and substituted or unsubstituted $—O—C_{2-6}$ alkynyl;

wherein the alkyl, alkenyl or alkynyl moieties as defined for $R_2$, $R_3$, $R_{3'}$, $R_5$, $R_8$, $R_{8'}$, $R_{10}$ and $R_{10'}$ are unsubstituted or substituted by one or more substituents selected from the group consisting of halogen, $—OR_9$, $—SR_9$, —CN, -haloalkyl, -haloalkoxy and $—NR_9R_{9''''}$;

optionally as a stereoisomer, including enantiomers and diastereomers, a racemate or in form of a mixture of at least two stereoisomers, including enantiomers and/or diastereomers, in any mixing ratio, or a corresponding salt thereof, or a corresponding solvate thereof, with the following proviso applying:

when $—(CH_2)_2—R_2$ is alkyl, then said alkyl contains 6 or less C-Atoms.

20. The compound according to claim 5, wherein the compound of formula I is a compound of formula I'''

(I''')

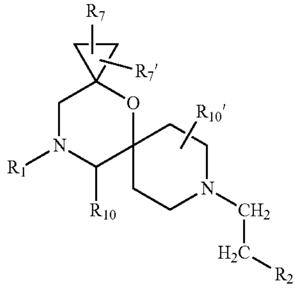

wherein $R_1$ is $C(O)R_5$ or $S(O_2)R_5$;

$R_2$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, or substituted or unsubstituted heterocyclyl, with cycloalkyl, aryl, or heterocyclyl, if substituted, being substituted by substituents selected from the croup consisting of halogen, $—R_9$, $—OR_9$, $—NO_2$, $—NR_9R_{9''''}$, $NR_9C(O)R_{9'}$, $—NR_9S(O)_2R_{9'}$, $—S(O)_2NR_9R_{9'}$, $—NR_9C(O)NR_{9'}R_{9''}$, $—SR_9$, $—S(O)R_9$, $S(O)_2R_9$, —CN, haloalkyl, haloalkoxy, $—C(O)OR_9$, $—C(O)NR_9R_{9'}$, =O, $—OCH_2CH_2OH$, $—NR_9S(O)_2NR_{9'}R_{9''}$;

$R_5$ is substituted or unsubstituted $C_{1-6}$ alkyl, substituted or unsubstituted $C_{2-6}$ alkenyl, substituted or unsubstituted $C_{2-6}$alkynyl, substituted or unsubstituted cycloalkyl, substituted or unsubstituted aryl, substituted or unsubstituted heterocyclyl, substituted or unsubstituted alkyl aryl, substituted or unsubstituted alkyl heterocyclyl and substituted or unsubstituted alkyl cycloalkyl, or $—NR_8R_{8'}$, wherein the cycloalkyl, aryl or heterocyclyl, if substituted, also in alkylaryl, alkylcycloalkyl or alkylheterocyclyl, being substituted by substituents selected from the group consisting of halogen, $—R_9$, $—OR_9$, $—NO_2$, $—NR_9R_{9''''}$, $—NR_9C(O)R_{9'}$, $—NR_9S(O)_2R_{9'}$, —$S(O)_2NR_9R_{9'}$, —$NR_9C(O)NR_{9'}R_{9''}$, —$SR_9$, —$S(O)R_9$, —$S(O)_2R_9$, —CN, haloalkyl, haloalkoxy, —$C(O)OR_9$ and —$C(O)NR_9R_{9'}$;

$R_7$ and $R_{7'}$ are independently selected from the group consisting of hydrogen, halogen, —$OR_9$, substituted or unsubstituted $C_{1-6}$ alkyl, substituted or unsubstituted $C_{2-6}$ alkenyl, substituted or unsubstituted $C_{2-6}$ alkynyl, unsubstituted heterocyclyl, unsubstituted aryl, and unsubstituted cycloalkyl;

$R_8$ and $R_8'$ are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, and substituted or unsubstituted heterocyclyl, with cycloalkyl, aryl, or heterocyclyl if substituted, being substituted by substituents selected from the group consisting of halogen, —$R_9$, —$OR_9$, —$NO_2$, —$NR_9R_{9'''}$, $NR_9C(O)R_{9'}$, —$NR_9S(O)_2R_{9'}$, —$S(O)_2NR_9R_{9'}$, —$NR_9C(O)NR_{9'}R_{9''}$, —$SR_9$, —$S(O)R_9$, —$S(O)_2R_9$, —CN, -haloalkyl, and haloalkoxy;

$R_9$, $R_{9'}$ and $R_{9''}$ are independently selected from the group consisting of hydrogen, unsubstituted $C_{1-6}$ alkyl, unsubstituted $C_{2-6}$ alkenyl, and unsubstituted $C_{2-6}$ alkynyl;

$R_{9'''}$ is selected from the group consisting of hydrogen, unsubstituted $C_{1-6}$ alkyl, unsubstituted $C_{2-6}$ alkenyl, unsubstituted $C_{2-6}$ alkynyl and -Boc;

$R_{10}$ and $R_{10'}$ are independently selected from the group consisting of hydrogen, halogen, —$OR_9$, substituted or unsubstituted $C_{1-6}$ alkyl, substituted or unsubstituted $C_{2-6}$ alkenyl, substituted or unsubstituted $C_{2-6}$ alkynyl, substituted or unsubstituted —O—$C_{1-6}$ alkyl, substituted or unsubstituted —O—$C_{2-6}$ alkenyl or substituted or unsubstituted —O—$C_{2-6}$ alkynyl;

wherein the alkyl, alkenyl or alkynyl moieties as defined for $R_2$, $R_5$, $R_7$, $R_{7'}$, $R_8$, $R_{8'}$, $R_{10}$ and $R_{10'}$ are unsubstituted or substituted by one or more substituents selected from the group consisting of halogen, —$OR_9$, —$SR_9$, —CN, -haloalkyl, -haloalkoxy and —$NR_9R_{9'''}$;

optionally as a stereoisomer, including enantiomers and diastereomers, a racemate or in form of a mixture of at least two stereoisomers, including enantiomers and/or diastereomers, in any mixing ratio, or a corresponding salt thereof, or a corresponding solvate thereof.

21. The compound according to claim 1, which is selected from the group consisting of:

(2-methyl-9-phenethyl-1-oxa-4,9-diazaspiro[5.5]undecan-4-yl)(phenyl)methanone (9-phenethyl-1-oxa-4,9-diazaspiro[5.5]undecan-4-yl)(phenyl)methanone (2-methyl-9-phenethyl-1-oxa-4,9-diazaspiro[5.5]undecan-4-yl)(pyridin-2-yl)methanone 1-(9-phenethyl-1-oxa-4,9-diazaspiro[5.5]undecan-4-yl)-2-phenylethanone (9-phenethyl-1-oxa-4,9-diazaspiro[5.5]undecan-4-yl)(pyridin-3-yl)methanone (9-phenethyl-1-oxa-4,9-diazaspiro[5.5]undecan-4-yl)(pyridin-4-yl)methanone (4-chloropyridin-2-yl)(9-phenethyl-1-oxa-4,9-diazaspiro[5.5]undecan-4-yl)methanone (2-methoxyphenyl)(9-phenethyl-1-oxa-4,9-diazaspiro[5.5]undecan-4-yl)methanone (2-fluorophenyl)(9-phenethyl-1-oxa-4,9-diazaspiro[5.5]undecan-4-yl)methanone 1-(2-methyl-9-phenethyl-1-oxa-4,9-diazaspiro[5.5]undecan-4-yl)ethanone cyclopropyl(2-methyl-9-phenethyl-1-oxa-4,9-diazaspiro[5.5]undecan-4-yl)methanone (9-phenethyl-1-oxa-4,9-diazaspiro[5.5]undecan-4-yl)(thiazol-4-yl)methanone (9-phenethyl-1-oxa-4,9-diazaspiro[5.5]undecan-4-yl)(thiazol-2-yl)methanone (9-phenethyl-1-oxa-4,9-diazaspiro[5.5]undecan-4-yl)(thiazol-5-yl)methanone 1-(9-phenethyl-1-oxa-4,9-diazaspiro[5.5]undecan-4-yl)-2-(pyridin-3-yl)ethanone 1-(9-phenethyl-1-oxa-4,9-diazaspiro[5.5]undecan-4-yl)-2-(tetrahydro-2H-pyran-4-yl)ethanone (3-methoxyphenyl)(9-phenethyl-1-oxa-4,9-diazaspiro[5.5]undecan-4-yl)methanone (9-phenethyl-1-oxa-4,9-diazaspiro[5.5]undecan-4-yl)(tetrahydro-2H-pyran-4-yl)methanone 1-(9-phenethyl-1-oxa-4,9-diazaspiro[5.5]undecan-4-yl)-2-(pyridin-2-yl)ethanone 2-cyclopropyl-1-(9-phenethyl-1-oxa-4,9-diazaspiro[5.5]undecan-4-yl)ethanone (9-phenethyl-1-oxa-4,9-diazaspiro[5.5]undecan-4-yl)(5-(trifluoromethyl)pyridin-2-yl)methanone (5-fluoropyridin-2-yl)(9-phenethyl-1-oxa-4,9-diazaspiro[5.5]undecan-4-yl)methanol (5-chloropyridin-2-yl)(9-phenethyl-1-oxa-4,9-diazaspiro[5.5]undecan-4-yl)methanone (9-phenethyl-1-oxa-4,9-diazaspiro[5.5]undecan-4-yl)(6-(trifluoromethyl)pyridin-3-yl)methanone (3-fluoropyridin-2-yl)(9-phenethyl-1-oxa-4,9-diazaspiro[5.5]undecan-4-yl)methanone (5-fluoropyridin-3-yl)(9-phenethyl-1-oxa-4,9-diazaspiro[5.5]undecan-4-yl)methanone (2-methyl-9-phenethyl-1-oxa-4,9-diazaspiro[5.5]undecan-4-yl)(5-(trifluoromethyl)pyridin-2-yl)methanone (5-fluoropyridin-2-yl)(2-methyl-9-phenethyl-1-oxa-4,9-diazaspiro[5.5]undecan-4-yl)methanone (5-chloropyridin-2-yl)(2-methyl-9-phenethyl-1-oxa-4,9-diazaspiro[5.5]undecan-4-yl)methanone 8-phenethyl-12-[(pyridin-2-yl)carbonyl]-4-oxa-8,12-diazadispiro[2.1.5.3]tridecane 12-[(5-chloropyridin-2-yl)carbonyl]-8-phenethyl-4-oxa-8,12-diazadispiro[2.1.5.3]tridecane (3-fluoropyridin-2-yl)(2-methyl-9-phenethyl-1-oxa-4,9-diazaspiro[5.5]undecan-4-yl)methanone (5-fluoropyrid in-3-yl)(2-methyl-9-phenethyl-1-oxa-4,9-diazaspiro[5.5]undecan-4-yl)methanone (2-methyl-9-phenethyl-1-oxa-4,9-diazaspiro[5.5]undecan-4-yl)(4-(trifluoromethyl)pyridin-2-yl)methanone (5-chloropyridin-3-yl)(2-methyl-9-phenethyl-1-oxa-4,9-diazaspiro[5.5]undecan-4-yl)methanone (2-methyl-9-phenethyl-1-oxa-4,9-diazaspiro[5.5]undecan-4-yl)(5-(trifluoromethyl)pyridin-3-yl)methanone (9-(2-(3-chloropyridin-2-yl)ethyl)-2-methyl-1-oxa-4,9-diazaspiro[5.5]undecan-4-yl)(phenyl)methanone (2-methyl-9-(2-(6-(trifluoromethyl)pyridin-2-yl)ethyl)-1-oxa-4,9-diazaspiro[s 0.5]undecan-4-yl)(phenyl)methanone (9-(2-(5-chloropyridin-2-yl)ethyl)-2-methyl-1-oxa-4,9-diazaspiro[5.5]undecan-4-yl)(phenyl)methanone 6-(2-(4-benzoyl-2-methyl-1-oxa-4,9-diazaspiro[5.5]undecan-9-yl)ethyl)nicotinonitrile (2-methyl-9-(2-(3-(trifluoromethyl)pyridin-2-yl)ethyl)-1-oxa-4,9-diazaspiro[5.5]undecan-4-yl)(phenyl)methanone (2-methyl-9-(2-(5-(trifluoromethyl)pyridin-2-yl)ethyl)-1-oxa-4,9-diazaspiro[5.5]undecan-4-yl)(phenyl)methanone (2-methyl-9-(2-(4-(trifluoromethyl)pyridin-2-yl)ethyl)-1-oxa-4,9-diazaspiro[5.5]undecan-4-yl)(phenyl)methanone (2-methyl-9-(2-(3-nitropyridin-2-yl)ethyl)-1-oxa-4,9-diazaspiro[5.5]undecan-4-yl)(phenyl)methanone (9-(2-(6-aminopyridin-2-yl)ethyl)-2-methyl-1-oxa-4,9-diazaspiro[5.5]undecan-4-yl)(phenyl)methanone (2-methyl-9-(2-(2-nitropyridin-3-yl)ethyl)-1-oxa-49-diazaspiro[5.5]undecan-4-yl)(phenyl)methanone (9-(2-(3-chloropyridin-2-yl)ethyl)-2-methyl-1-oxa-4,9-diazaspiro[5.5]undecan-4-yl)(2,6-difluorophenyl)methanone (9-(2-(3-chloropyridin-2-yl)ethyl)-2-methyl-1-oxa-4,9-diazaspiro[5.5]undecan-4-yl)(pyridin-2-yl)methanone (9-(2-(3-chloropyridin-2-yl)ethyl)-2-methyl-1-oxa-4,9-diazaspiro[5.5]undecan-4-Yl)(2-fluorophenyl)methanone (9-(2-(3-chloropyridin-4-yl)ethyl)-2-methyl-1-oxa-4,9-diazaspiro[5.5]undecan-4-yl)(phenyl)methanone (9-(2-(3-fluoropyridin-4-yl)ethyl)-2-methyl-1-oxa-4,9-diazaspiro[5.5]undecan-4-yl)(phenyl)methanone (9-(2-(5-fluoropyridin-2-yl)ethyl)-2-methyl-1-oxa-4,9-diazaspiro[5.5]undecan-4-yl)(phenyl)methanone (9-(2-(3-fluoropyridin-2-yl)ethyl)-2-methyl-1-oxa-4,9-diazaspiro[5.5]undecan-4-yl)(phenyl)methanone 8-(2-(3-fluoropyridin-2-yl)ethyl)-12-[(2-fluorophenyl)carbonyl]-4-oxa-8,12-diazadispiro[2.1.5.3]tridecane 1-(9-(2-(3-fluoropyridin-2-yl)ethyl)-2-methyl-1-oxa-4,9-diazaspiro[5.5]undecan-4-yl)propan-1-one 8-(2-(3-fluoropyridin-2-yl)ethyl)-12-[(cyclopropyl)carbonyl]-4-oxa-8,12-diazadispiro[2.1.5.3]tridecane 8-(2-(3-fluoropyridin-2-yl)ethyl)-12-[(2,6-difluorophenyl)carbonyl]-4-oxa-8,12-diazadispiro[2.1.5.3]tridecane 8-(2-(3-chloropyridin-2-yl)ethyl)-12-[(2,6-difluorophenyl)carbonyl]-4-oxa-8,12-diazadispiro[2.1.5.3]tridecane (2-fluorophenyl)(9-(2-(3-fluoropyridin-2-yl)ethyl)-2-methyl-1-oxa-4,9-diazaspiro[5.5]undecan-4-yl)methanone (2,6-difluorophenyl)(9-(2-(3-fluoropyridin-2-yl)ethyl)-2-methyl-1-oxa-4,9-diazaspiro[5.5]undecan-4-yl)methanone (9-(2-hydroxy-2-phenylethyl)-1-oxa-4,9-diazaspiro[5.5]undecan-4-yl)(phenyl)methanone (9-(2-methoxyphenethyl)-1-oxa-4,9-diazaspiro[5.5]undecan-4-yl)(phenyl)methanone phenyl(9-(2-(pyridin-2-yl)ethyl)-1-oxa-4,9-diazaspiro[5.5]undecan-4-yl)methanone 9-phenethyl-N-phenyl-1-oxa-4,9-diazaspiro[5.5]undecane-4-carboxamide cyclopropyl(9-phenethyl-1-oxa-4,9-diazaspiro[5.5]undecan-4-yl)methanone (9-phenethyl-1-oxa-4,9-diazaspiro[5.5]undecan-4-yl)(pyridin-2-yl)methanone N-methyl-9-phenethyl-N-phenyl-1-oxa-4,9-diazaspiro[5.5]undecane-4-carboxamide (9-phenethyl-1-oxa-4,9-diazaspiro[5.5]undecan-4-yl)(piperidin-1-yl)methanone phenyl(9-(3-(trifluoromethoxy)phenethyl)-1-oxa-4,9-diazaspiro[5.5]undecan-4-yl)methanone phenyl(9-(2-(6-(trifluoromethyl)pyridin-3-yl)ethyl)-1-oxa-4,9-diazaspiro[5.5]undecan-4-yl)methanone phenyl(9-(2-(pyridin-3-yl)ethyl)-1-oxa-4,9-diazaspiro[5.5]undecan-4-yl)methanone (2-methyl-9-(2-(pyridin-3-yl)ethyl)-1-oxa-4,9-diazaspiro[5.5]undecan-4-yl)(phenyl)methanone (9-(2-(6-methoxypyridin-2-yl)ethyl)-2-methyl-1-oxa-4,9-diazaspiro[5.5]undecane-4-yl)(phenyl)methanone (2-methyl-9-(2-(pyridin-4-yl)ethyl)-1-oxa-4,9-diazaspiro[5.5]undecane-4-yl)(phenyl)methanone 4-(2-(4-benzoyl-2-methyl-1-oxa-4,9-diazaspiro[5.5]undecan-9-yl)ethyl)benzenesulfonamide (2-methyl-9-(2-(6-(trifluoromethyl)pyridin-3-yl)ethyl)-1-oxa-4-diazaspiro[5.5]undecan-4-yl)(phenyl)methanone 4-(2-(4-benzoyl-2-methyl-1-oxa-4,9-diazaspiro[5.5]undecan-9-yl)ethyl)-N-methylbenzenesulfonamide tert-butyl (4-(2-(4-(5-chloropicolinoyl)-2-methyl-1-oxa-4,9-diazaspiro[5.5]undecan-9-yl)ethyl)thiazol-2-yl)carbamate tert-butyl (4-(2-(4-benzoyl-2-methyl-1-oxa-4,9-diazaspiro[5.5]undecan-9-yl)ethyl)thiazol-2-yl)carbamate (2-methyl-9-(3-(trifluoromethoxy)phenethyl)-1-oxa-4,9-diazaspiro[5.5]undecan-4-yl)(pyridin-2-yl)methanone (2-methyl-9-(2-nitrophenethyl)-1-oxa-49-diazaspiro[5.5]undecan-4-yl)(Phenyl)methanone (2-methyl-9-(3-nitrophenethyl)-1-oxa-4,9-diazaspiro[5.5]undecan-4-yl)(Phenyl)methanone 9-phenethyl-4-(phenylsulfonyl)-1-oxa-4,9-diazaspiro[5.5]undecane 4-(isopropylsulfonyl)-9-phenethyl-1-oxa-4,9-diazaspiro[5.5]undecane (2-methyl-9-(3-phenylpropyl)-1-oxa-4,9-diazaspiro[5.5]undecan-4-yl)(phenyl)methanone (9-isopentyl-2-methyl-1-oxa-4,9-diazaspiro[5.5]undecan-4-yl)(phenyl)methanone (2-methyl-9-(2-(pyridin-2-yl)ethyl)-1-oxa-4,9-diazaspiro[5.5]undecan-4-yl)(phenyl)methanone (9-(2-isopropoxyethyl)-2-methyl-1-oxa-4,9-diazaspiro[5.5]undecan-4-yl)(phenyl)methanone 2-(4-benzoyl-2-methyl-1-oxa-4,9-diazaspiro[5.5]undecan-9-yl)-1-morpholinoethanone 2-(4-benzoyl-2-methyl-1-oxa-4,9-diazaspiro[5.5]undecan-9-yl)-1-(piperidin-1-yl)ethanone 1-(9-(2-fluorophenethyl)-2-methyl-1-oxa-4,9-diazaspiro[5.5]undecan-4-yl)propan-1-one (9-(2-(5-chloropyridin-3-yl)ethyl)-2-methyl-1-oxa-4,9-diazaspiro[5.5]undecan-4-yl)(phenyl)methanone (9-(2-(5-fluoropyrid in-3-yl)ethyl)-2-methyl-1-oxa-4,9-diazaspiro[5.5]undecan-4-yl)(phenyl)methanone 8-(2-fluorophenethyl)-12-[(pyridin-2-yl)carbonyl]-4-oxa-8,12-diazadispiro[2.1.5.3]tridecane 1-(2-isopropyl-9-phenethyl-1-oxa-4,9-diazaspiro[5.5]undecan-4-yl)ethanone cyclopropyl(2-isopropyl-9-phenethyl-1-oxa-4,9-diazaspiro[5.5]undecan-4-yl)methanone (9-(3-nitrophenethyl)-1-oxa-4,9-diazaspiro[5.5]undecan-4-yl)(phenyl)methanone (9-benzyl-2-methyl-1-oxa-4,9-diazaspiro[5.5]undecan-4-yl)(phenyl)methanone (9-(2-hydroxyphenethyl)-1-oxa-4,9-diazaspiro[5.5]undecan-4-yl)(phenyl)methanone (3-hydroxyphenyl) (9-phenethyl-1-oxa-4,9-diazaspiro[5.5]undecan-4-yl)methanone (2-hydroxyphenyl)(9-phenethyl-1-oxa-4,9-diazaspiro[5.5]undecan-4-yl)methanone (9-(2-(2-aminothiazol-4-yl)ethyl)-2-methyl-1-oxa-4,9-diazaspiro[5.5]undecan-4-yl)(5-chloropyridin-2-yl)methanone (9-(2-(2-aminothiazol-4-yl)ethyl)-2-methyl-1-oxa-4,9-diazaspiro[5.5]undecan-4-yl)(phenyl)methanone (9-(3-aminophenethyl)-1-oxa-4,9-diazaspiro[5.5]undecan-4-yl)(phenyl)methanone (9-(2-aminophenethyl)-2-methyl-1-oxa-4,9-diazaspiro[5.5]undecan-4-yl)(phenyl)methanone
(9-(3-aminophenethyl)-2-methyl-1-oxa-4,9-diazaspiro[5.5]undecan-4-yl)(phenyl)methanone
(9-(2-(3-aminopyridin-2-yl)ethyl)-2-methyl-1-oxa-4,9-diazaspiro[5.5]undecan-4-yl)(phenyl)methanone
(9-(2-(2-aminopyridin-3-yl)ethyl)-2-methyl-1-oxa-4,9-diazaspiro[5.5]undecan-4-yl)(phenyl)methanone
1-(3-(2-(4-benzoyl-2-methyl-1-oxa-4,9-diazaspiro[5.5]undecan-9-yl)ethyl)phenyl)urea
1-(2-(2-(4-benzoyl-2-methyl-1-oxa-4,9-diazaspiro[5.5]undecan-9-yl)ethyl)phenyl)urea
N-(3-(2-(4-benzoyl-1-oxa-4,9-diazaspiro[5.5]undecan-9-yl)ethyl)phenyl)acetamide
N-(2-(2-(4-benzoyl-2-methyl-1-oxa-4,9-diazaspiro[5.5]undecan-9-yl)ethyl)phenyl)acetamide
N-(3-(2-(4-benzoyl-2-methyl-1-oxa-4,9-diazaspiro[5.5]undecan-9-yl)ethyl)phenyl)acetamide
N-(3-(2-(4-benzoyl-1-oxa-4,9-diazaspiro[5.5]undecan-9-yl)ethyl)phenyl)methanesulfonamide
2-methyl-9-phenethyl-4-(phenylsulfonyl)-1-oxa-4,9-diazaspiro[5.5]undecane
4-(isopropylsulfonyl)-2-methyl-9-phenethyl-1-oxa-4,9-diazaspiro[5.5]undecan
N,N-dimethyl-9-phenethyl-1-oxa-4,9-diazaspiro[5.5]undecane-4-carboxamide
N,N,2-trimethyl-9-phenethyl-1-oxa-4,9-diazaspiro[5.5]undecane-4-carboxamide
N-methyl-9-phenethyl-N-(pyridin-2-yl)-1-oxa-4,9-diazaspiro[5.5]undecane-4-carboxamide
N-cyclopropyl-9-phenethyl-1-oxa-4,9-diazaspiro[5.5]undecane-4-carboxamide
9-phenethyl-N-(pyridin-3-yl)-1-oxa-4,9-diazaspiro[5.5]undecane-4-carboxamide
N-cyclopropyl-N-methyl-9-phenethyl-1-oxa-4,9-diazaspiro[5.5]undecane-4-carboxamide
N-methyl-9-phenethyl-N-(pyridin-3-yl)-1-oxa-4,9-diazaspiro[5.5]undecane-4-carboxamide
(R)-(2-methyl-9-phenethyl-1-oxa-4,9-diazaspiro[5.5]undecan-4-yl)(pyridin-2-yl)methanone
(S)-(2-methyl-9-phenethyl-1-oxa-4,9-diazaspiro[5.5]undecan-4-yl)(pyridin-2-yl)methanone
8-(2-(3-fluoropyridin-2-yl)ethyl)-12-[(2,3-difluorophenyl)carbonyl]-4-oxa-8,12-diazadispiro[2.1.5.3]tridecane
8-(2-(3-fluoropyridin-2-yl)ethyl)-12-[(2,4-difluorophenyl)carbonyl]-4-oxa-8,12-diazadispiro[2.1.5.3]tridecane
2-(2-(12-(2-fluorobenzoyl)-4-oxa-8,12-diazadispiro[2.1.5.3]tridecan-8-yl)ethyl)nicotinonitrile
8-(2-(3-fluoropyridin-2-yl)ethyl)-12-[(2,5-difluorophenyl)carbonyl]-4-oxa-8,12-diazadispiro[2.1.5.3]tridecane
12-[(2-fluorophenyl)carbonyl]-8-(2-(3-methoxypyrid in-2-yl)ethyl)-4-oxa-8,12-diazadispiro[2.1.5.3]tridecane
(2-fluorophenyl)(9-(2-(3-fluoropyridin-2-yl)ethyl)-2,2-dimethyl-1-oxa-4,9-diazaspiro[5.5]undecan-4-yl)methanone
12-[(3-fluorophenyl)carbonyl]-8-(2-(3-fluoropyridin-2-yl)ethyl)-4-oxa-8,12-diazadispiro[2.1.5.3]tridecane
12-[(4-fluorophenyl)carbonyl]-8-(2-(3-fluoropyridin-2-yl)ethyl)-4-oxa-8,12-diazadispiro[2.1.5.3]tridecane
8-(2-(3-fluoropyridin-2-yl)ethyl)-12-[(2-methoxyphenyl)carbonyl]-4-oxa-8,12-diazadispiro[2.1.5.3]tridecane
2-(8-(2-(3-fluoropyridin-2-yl)ethyl)-4-oxa-8,12-diazadispiro[2.1.5.3]tridecane-12-carbonyl)benzonitrile
12-[(2-chlorophenyl)carbonyl]-8-(2-(3-fluoropyridin-2-yl)ethyl)-4-oxa-8,12-diazadispiro[2.1.5.3]tridecane
(2,3-difluorophenyl)(9-(2-(3-fluoropyridin-2-yl)ethyl)-2,2-dimethyl-1-oxa-4,9-diazaspiro[5.5]undecan-4-yl)methanone
8-(2-(3-chloropyridin-2-yl)ethyl)-12-[(2,3-difluorophenyl)carbonyl]-4-oxa-8,12-diazadispiro[2.1.5.3]tridecane
12-[(2-fluorophenyl)carbonyl]-8-(2-(6-methoxypyridin-2-yl)ethyl)-4-oxa-8,12-diazadispiro[2.1.5.3]tridecane
methyl 3-(12-(2,6-difluorobenzoyl)-4-oxa-8,12-diazadispiro[2.1.5.3]tridecan-8-yl)propanoate
12-[(2,6-difluorophenyl)carbonyl]-8-(2-(6-methoxypyridin-2-yl)ethyl)-4-oxa-8,12-diazadispiro[2.1.5.3]tridecane
8-(2,5-difluorophenethyl)-12-[(2,6-difluorophenyl)carbonyl]-4-oxa-8,12-diazadispiro[2.1.5.3]tridecane
(R)-(2-fluorophenyl)(9-(2-(3-fluoropyridin-2-yl)ethyl)-2-methyl-1-oxa-4,9-diazaspiro[5.5]undecan-4-yl)methanone
(S)-(2-fluorophenyl)(9-(2-(3-fluoropyrid in-2-yl)ethyl)-2-methyl-1-oxa-4,9-diazaspiro[5.5]undecan-4-yl)methanone
(R)-(2,6-difluorophenyl)(9-(2-(3-fluoropyridin-2-yl)ethyl)-2-methyl-1-oxa-4,9-diazaspiro[5.5]undecan-4-yl)methanone
(S)-(2,6-difluorophenyl)(9-(2-(3-fluoropyrid in-2-yl)ethyl)-2-methyl-1-oxa-4,9-diazaspiro[5.5]undecan-4-yl)methanone
(2,3-difluorophenyl)(9-(2-(3-fluoropyridin-2-yl)ethyl)-2-methyl-1-oxa-4,9-diazaspiro[5.5]undecan-4-yl)methanone
(2,4-difluorophenyl)(9-(2-(3-fluoropyridin-2-yl)ethyl)-2-methyl-1-oxa-4,9-diazaspiro[5.5]undecan-4-yl)methanone
(2,5-difluorophenyl)(9-(2-(3-fluoropyridin-2-yl)ethyl)-2-methyl-1-oxa-4,9-diazaspiro[5.5]undecan-4-yl)methanone
(2-chlorophenyl)(9-(2-(3-fluoropyrid in-2-yl)ethyl)-2-methyl-1-oxa-4,9-diazaspiro[5.5]undecan-4-yl)methanone
(3-fluorophenyl)(9-(2-(3-fluoropyridin-2-yl)ethyl)-2-methyl-1-oxa-4,9-diazaspiro[5.5]undecan-4-yl)methanone, optionally as a stereoisomer, including enantiomers and diastereomers, a racemate or in form of a mixture of at least two of the stereoisomers, including enantiomers and/or diastereomers, in any mixing ratio, or a corresponding salt thereof.

22. A process for the production of a compound of formula I according to claim 1, (I)

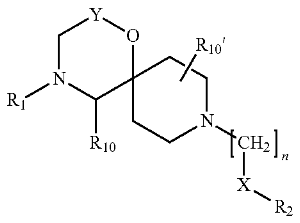

wherein a compound of formula VH or its suitable salt, (VH)

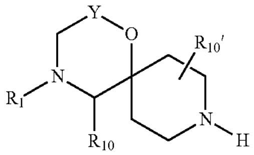

is reacted with a compound according to formula VI, VII or VIII (VI)

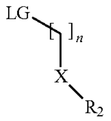

(VII)

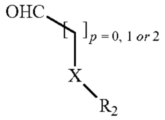

or (VIII)

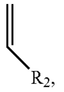

wherein LG is a leaving group.

23. A process for the preparation of a compound of formula I" according to claim 19

(I")

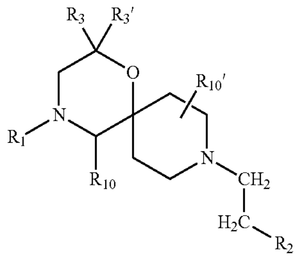

comprising (a) reacting a compound of formula XIIx (XIIx)

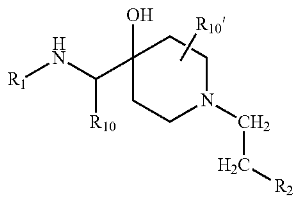

with a compound of formula XIIIx (XIIIx)

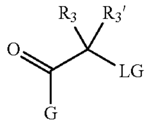

wherein LG and G are leaving groups to obtain a compound of formula XIVx (XIVx)

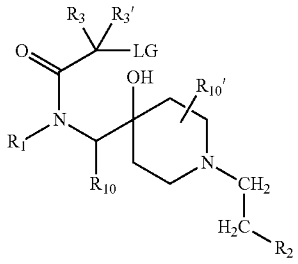

wherein LG is a leaving group, (b) carrying out a cyclization of the resulting compound of formula XIVx in a suitable A solvent; in the presence of a strong base; and at a suitable temperature, comprised between −78° C. and the reflux temperature, such as cooling, to obtain a compound of formula XVx (XVx)

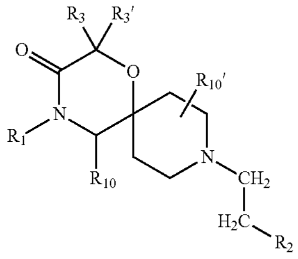

(c) and carrying out a reduction reaction by using a suitable reducing agent in a suitable solvent, at a suitable temperature comprised between room temperature and the reflux temperature, to yield a compound of formula I".

24. A process for the preparation of a compound of formula I''' according to claim 20

(I''')

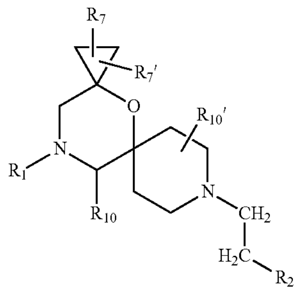

wherein $R_1$, $R_{10}$ and $R_{10'}$ are as defined in claim 20 and $R_7$ and $R_{7'}$ are both hydrogen, comprising (a) dehydration of a compound of formula XXIx (XXIx)

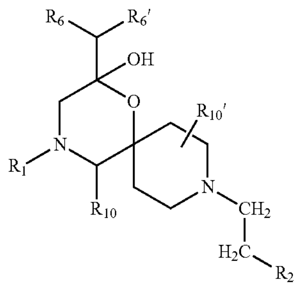

wherein $R_6$ and $R_{6'}$ are both hydrogen, with a dehydrating agent, in a suitable solvent, at a suitable temperature, and (b) cyclopropanation of the resulting compound of formula XVax (XVax)

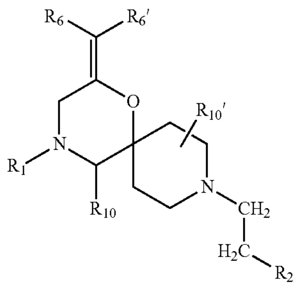

wherein $R_6$ and $R_{6'}$ are both hydrogen, using a suitable methyl-transfer reagent, in a suitable aprotic solvent, and in the presence of a strong base, at a suitable temperature.

25. A pharmaceutical composition which comprises the compound according to claim 1, or a pharmaceutically acceptable salt thereof, and a pharmaceutically acceptable carrier, adjuvant or vehicle.

26. A method of treating pain in a subject in need thereof, comprising administration of an effective amount of the compound according to claim 1.

27. The method according to claim 26, wherein the pain is selected from the group consisting of medium to severe pain, visceral pain, chronic pain, cancer pain, migraine, inflammatory pain, acute pain or neuropathic pain, allodynia and hyperalgesia.

* * * * *

UNITED STATES PATENT AND TRADEMARK OFFICE

CERTIFICATE OF CORRECTION

PATENT NO. : 10,065,971 B2
APPLICATION NO. : 15/315095
DATED : September 4, 2018
INVENTOR(S) : Marina Virgili-Bernado et al.

It is certified that error appears in the above-identified patent and that said Letters Patent is hereby corrected as shown below:

On the Title Page

Item (87), PCT Pub. No.: “WO2015/185208” should read -- WO2015/185208 A1 --

Item (30), under Foreign Application Priority Data: “14382208” should read -- 14382208.8 --

In the Claims

Column 183, Line 57: “$-S(O)_2R$,” should read -- $-S(O)_2R_9$, --

Column 183, Line 60: “$C_2a$” should read -- $C_{2-6}$ --

Column 185, Line 45: “$-NR_9S(O)_2NR_{9''}R_{9''}$;” should read -- $-NR_9S(O)_2NR_{9'}R_{9''}$; --

Column 189, Line 23 (in the formula): “$CH_3$” should read -- $CH_2$ --

Column 192, Line 25: “claim 5” should read -- claim 1 --

Column 194, Line 24: “methanol” should read -- methanone --

Column 194, Line 45: “fluoropyrid in” should read -- fluoropyridin --

Column 194, Line 55: “[s 0.5]” should read -- [5.5] --

Column 195, Line 08: “-49-” should read -- -4,9- --

Column 195, Line 16: “4-Yl” should read -- 4-yl --

Column 195, Line 47: start a new line with “phenyl(9-”

Signed and Sealed this
Twenty-third Day of October, 2018

Andrei Iancu
*Director of the United States Patent and Trademark Office*

Column 196, Line 02: “undecane-4” should read -- undecan-4 --

Column 196, Line 04: “undecane-4” should read -- undecan-4 --

Column 196, Line 08: “oxa-4-” should read -- oxa-4,9- --

Column 196, Line 19: “-49-” should read -- -4,9- --

Column 196, Line 20: “Phenyl” should read -- phenyl --

Column 196, Line 22: “Phenyl” should read -- phenyl --

Column 196, Line 43: “fluoropyrid in” should read -- fluoropyridin --

Column 196, Line 48: start a new line with “cyclopropyl”

Column 198, Line 28: “fluoropyrid in” should read -- fluoropyridin --

Column 198, Line 41: “fluoropyrid in” should read -- fluoropyridin --

Column 200, Line 37: delete “A”